United States Patent
Kobayashi et al.

(10) Patent No.: US 6,525,042 B1
(45) Date of Patent: Feb. 25, 2003

(54) SULFONYL DERIVATIVES

(75) Inventors: Syozo Kobayashi, Tokyo (JP); Satoshi Komoriya, Tokyo (JP); Masayuki Ito, Tokyo (JP); Tsutomu Nagata, Tokyo (JP); Akiyoshi Mochizuki, Tokyo (JP); Noriyasu Haginoya, Tokyo (JP); Takayasu Nagahara, Tokyo (JP); Haruhiko Horino, Tokoyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/508,680

(22) PCT Filed: Sep. 30, 1998

(86) PCT No.: PCT/JP98/04411
§ 371 (c)(1),
(2), (4) Date: Mar. 28, 2000

(87) PCT Pub. No.: WO99/16747
PCT Pub. Date: Apr. 8, 1999

(30) Foreign Application Priority Data

Sep. 30, 1997 (JP) ............................................. 9-267117

(51) Int. Cl.$^7$ .................... C07D 243/02; C07D 245/02; C07D 207/335; A61K 31/495; A61K 31/55

(52) U.S. Cl. ............ 514/212.03; 514/218; 514/252.13; 514/255.02; 540/460; 540/424; 540/526; 544/359; 544/360; 544/385; 548/543

(58) Field of Search .............................. 540/460, 524, 540/520; 544/359, 360, 385; 548/543; 514/212.03, 218, 252.13, 255.02

(56) References Cited

U.S. PATENT DOCUMENTS 5,731,315 A    3/1998   Ewing et al. ................ 544/335

FOREIGN PATENT DOCUMENTS

| JP | 6-509076 | 10/1934 |
|---|---|---|
| WO | WO 96/10022 | 4/1996 |
| WO | WO 96/40679 | 12/1996 |
| WO | WO 97/06802 | 2/1997 |
| WO | WO 97/29104 | 8/1997 |
| WO | WO 98/06705 | 2/1998 |
| WO | WO 98/21188 | 5/1998 |
| WO | WO 98/25611 | 6/1998 |
| WO | WO 98/54164 | 12/1998 |
| WO | WO 99/16751 | 4/1999 |
| WO | WO 99/37304 | 7/1999 |
| WO | WO 99/40075 | 8/1999 |
| WO | WO 99/57099 | 11/1999 |
| WO | WO 99/57112 | 11/1999 |

OTHER PUBLICATIONS

Rauch et al., Ann. Intern. Med. 34(3): 224–38, 2001. PubMed Abstract provided.*
Van Aken et al., Clin. Appl. Thromb. Hemost. 7(3): 195–204, 2001. PubMed Abstract provided.*

* cited by examiner

*Primary Examiner*—Richard L. Raymond
*Assistant Examiner*—Venkataraman Balasubramanian
(74) *Attorney, Agent, or Firm*—Oblon, Spivak, McClelland, Maier & Neustadt, P.C.

(57) ABSTRACT

Sulfonyl derivatives represented by general formula (I), salts of the same, and solvates of both: and application of them as drugs: [wherein $R^1$ is hydrogen, hydroxyl, nitro or the like; $R^2$ and $R^3$ are each independently hydrogen, halogeno or the like; $R^4$ and $R^5$ are each dependently hydrogen, halogeno or the like; $Q^1$ is an optionally substituted saturated or unsaturated 5- or 6-membered cyclic hydrocarbon group or the like; $Q^2$ is a single bond, oxygen or the like; $Q^3$ is, e.g., a group represented by formula (a): $T^1$ is carbonyl or the like; and $X^1$ and $X^2$ are each independently methylidyne or nitrogen]. These compounds exhibit potent Fxa inhibiting activities and serve as excellent anticoagulants which speedily exert satisfactory and persistent anti-thrombotic effects through oral administration and little cause adverse effects.

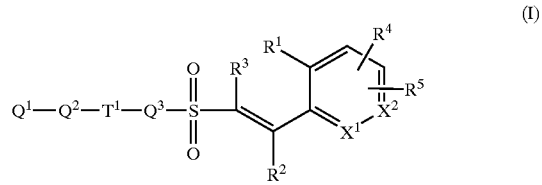

(I)

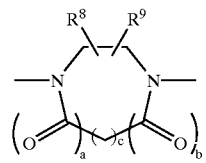

(a)

12 Claims, No Drawings

SULFONYL DERIVATIVES

TECHNICAL FIELD

The present invention relates to a novel, orally-administrable sulfonyl derivative or salt thereof which inhibits an activated coagulation factor (which will hereinafter be abbreviated as "FXa"), thereby exhibiting strong anticoagulant action; and a coagulation suppressor or preventive and/or remedy for thrombosis or embolism which comprises the derivative or salt as an effective ingredient.

BACKGROUND ART

Exasperation of coagulation capacity is an important factor for unstable angina, cerebral infarction, cerebral embolism, myocardial infarction, pulmonary infarction, pulmonary embolism, Buerger's disease, deep vein thrombosis, disseminated intravascular coagulation syndrome, thrombus formation after valve replacement, reocclusion after revascularization or formation of thrombus upon extracorporeal circulation. There is accordingly a demand for an excellent anticoagulant which is excellent in dose-responsiveness, has long-lasting effects, has a low risk of hemorrhage, has less side effects and exhibits rapid and sufficient effects even by oral administration (Thrombosis Research, 68, 507–512, 1992).

Studies on anticoagulants based on various acting mechanisms suggest that a FXa inhibitor has a possibility of becoming an excellent anticoagulant. The coagulation system is a series of reactions wherein a large amount of a thrombus is produced through an amplification step due to a multi-stage enzymatic reaction and induces the formation of insoluble fibrin. In the intrinsic system, after the multi-stage reaction following the activation of a contact factor, activated Factor IX activates factor X on a phospholipid membrane in the presence of activated Factor VIII and a calcium ion, while in the extrinsic system, activated Factor VII activates Factor X in the presence of a tissue factor. In other words, the activation of Factor X into FXa in the coagulation system is an essential reaction in the formation of thrombin. Activated Factor X (FXa) in each system carries out limited proteolysis of prothrombin, thereby forming thrombin. The resulting thrombin activates the coagulation factors on the upstream side, whereby the formation of thrombin is amplified further. As described above, the coagulation system upstream of FXa is separated into intrinsic and extrinsic systems so that the inhibition of the enzyme of the coagulation system upstream of FXa does not suppress the production of FXa sufficiently, inevitably resulting in the production of thrombin. Furthermore, the coagulation occurs as a self-amplifying reaction so that the suppression of the coagulation system can be accomplished more efficiently by the inhibition of FXa which exists upstream of the thrombin than by the inhibition of the thrombin formed (Thrombosis Research, 15, 617–629(1979)).

Another merit of the FXa inhibitor is that an effective dose in a thrombus model is largely different from the dose for extending the bleeding time in an experimental hemorrhage model. From the experimental result, the FXa inhibitor is presumed to be an anticoagulant with a low risk of hemorrhage.

As a FXa inhibitor, various compounds are reported. In general, antithrombin III or antithrombin III-dependent penta-saccharide is known to have no inhibitory action against a prothrombinase complex which plays a practical role in the thrombus formation in vivo (Thrombosis Research, 68, 507–512(1992); Journal of Clinical Investigation, 71, 1383–1389(1983); Mebio, August issue, 1992–1997) and moreover, it does not exhibit effectiveness in oral administration. Although tick anticoagulant peptide (TAP) (Science, 248, 593–596(1990)) or antistacin (AST) (Journal of Biological Chemistry, 263, 10162–10167(1988)) isolated from a tick or leech which is a bloodsucker inhibits FXa and exhibits anti-thrombus effects on the models of from venous thrombus to arterial thrombus, it is not effective when orally administered because it is a high-molecular peptide. From such a viewpoint, a low-molecular FXa inhibitor which directly inhibits a coagulation factor without depending on antithrombin III has been developed.

An object of the present invention is to provide, as an excellent anticoagulant, a novel compound which has strong FXa inhibitory action, exhibits prompt, sufficient and long-lasting anti-thrombus effects even by the oral administration and has less side effects.

DISCLOSURE OF THE INVENTION

With the forgoing in view, the present inventors have carried out an extensive investigation on the synthesis of a novel FXa inhibitor and its pharmacological action. As a result, it has been found that a novel sulfonyl derivative, salt thereof or solvate thereof exhibits strong FXa inhibitory action and strong anticoagulant action, inhibits FXa strongly, promptly and continuously by the oral administration, exhibits anti-coagulant action and anti-thrombus action, is highly safe and is useful as a preventive or remedy for various diseases caused by a thrombus or embolus, thus leading to completion of the present invention. The present invention provides a sulfonyl derivative represented by the following formula (I):

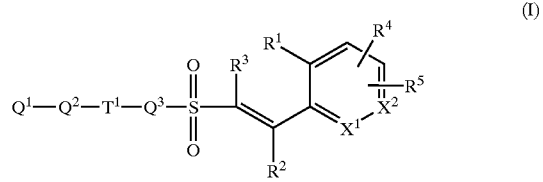

[wherein:

R$^1$ represents a hydrogen atom, a hydroxyl group, a nitro group, a cyano group, a halogen atom, an alkyl group, a hydroxyalkyl group, an alkoxyl group, an alkoxyalkyl group, a carboxyl group, a carboxyalkyl group, an alkylcarbonyl group, an alkoxycarbonyl group, an alkoxycarbonylalkyl group, an alkylcarbonyloxy group or a group A$^1$-B$^1$— (in which A$^1$ represents an amino group which may have one or two substituents, a saturated or unsaturated 5- or 6-membered cyclic hydrocarbon group which may have a substituent or a saturated or unsaturated 5- or 6-membered heterocyclic group which may have a substituent and B$^1$ represents a single bond, a carbonyl group, an alkylene group, a carbonylalkyl group, a carbonylalkyloxy group or an alkylenecarbonyloxy group), R$^2$ and R$^3$ each independently represents a hydrogen atom, a halogen atom, an alkyl group, a hydroxyalkyl group or an alkoxyalkyl group or R$^2$ or R$^3$ may be coupled together with R$^1$ to form a C$_{1-3}$ alkylene or alkenylene group, R$^4$ and R$^5$ each independently represents a hydrogen atom, a hydroxyl group, a halogen atom, an alkyl group or an alkoxyl group (with the proviso that R$^4$ and R$^5$ do not represent a hydrogen atom at the same time), $Q^1$ represents a saturated or unsaturated 5- or 6-membered cyclic hydrocarbon group which may have a substituent, a saturated or unsaturated 5- or 6-membered heterocyclic group which may have a substituent or a saturated or unsaturated bicyclic or tricyclic fused ring group which may have a substituent, $Q^2$ represents a single bond, an oxygen atom, a sulfur atom, a linear or branched $C_{1-6}$ alkylene group, a linear or branched $C_{2-6}$ alkenylene group, a linear or branched $C_{2-6}$ alkynylene group, a group —N($R^6$)—CO— (in which $R^6$ represents a hydrogen atom or an alkyl group), a group —N($R^7$)—($CH_2$)$_m$— (in which $R^7$ represents a hydrogen atom or an alkyl group and m stands for an integer of 0 to 6) or a group of the following formula:

(which represents a divalent, saturated or unsaturated 5- or 6-membered cyclic hydrocarbon group which may have a substituent, a divalent, saturated or unsaturated 5- or 6-membered heterocyclic group which may have a substituent or a divalent, saturated or unsaturated dicyclic fused ring group which may have a substituent and ←C means the bonding of the carbon atom of this group to $Q^1$), $Q^3$ represents any one of the following groups:

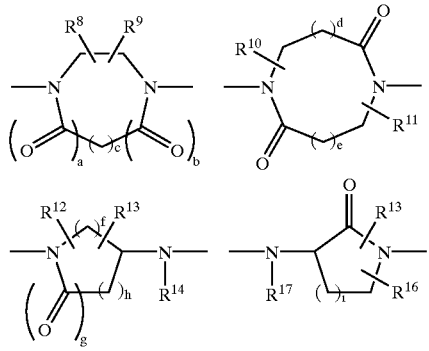

(in which when the carbon atom to which each of $R^8$, $R^9$, $R^{10}$, $R^{11}$, $R^{12}$, $R^{13}$, $R^{15}$ and $R^{16}$ has been bonded is not adjacent to a nitrogen atom, $R^8$, $R^9$, $R^{10}$, $R^{11}$, $R^{12}$, $R^{13}$, $R^{15}$ and $R^{16}$ each independently represents:

a hydrogen atom,
a hydroxyl group,
an alkyl group,
an alkoxyl group,
an alkoxyalkyl group,
an alkoxyalkyloxy group,
a hyroxyalkyl group,
a hydroxyalkyloxy group,
a hydroxyalkylcarbonyl group,
a hydroxyalkylsulfonyl group,
a formyl group,
a formylalkyl group,
a formylalkylcarbonyl group,
a formylalkylsulfonyl group,
an alkylcarbonyl group,
an alkylsulfonyl group,
an alkylcarbonylalkyl group,
an alkylsulfonylalkyl group,
a carboxyl group,
a carboxyalkyl group,
a carboxyalkyloxy group,
a carboxyalkylcarbonyl group,
a carboxyalkylsulfonyl group,
a carboxyalkylcarbonylalkyl group,
a carboxyalkylsulfonylalkyl group ,
an alkoxycarbonyl group,
an alkoxycarbonylalkyl group,
an alkoxycarbonylalkyloxy group,
an alkoxycarbonylalkylcarbonyl group,
an alkoxycarbonylalkylsulfonyl group,
an amino group which may have one or two substituents,
an aminoalkyl group in which the amino moiety may have one or two substituents,
an aminoalkyloxy group in which the amino moiety may have one or two substituents,
an aminoalkylcarbonyl group in which the amino moiety may have one or two substituents,
an aminoalkylcarbonyloxy group in which the amino moiety may have one or two substituents,
an aminocarbonyl group in which the amino moiety may have one or two substituents,
an aminocarbonylalkyl group in which the amino moiety may have one or two substituents,
an aminocarbonylalkyloxy group in which the amino moiety may have one or two substituents or
a group $A^2$-$B^2$— (in which $A^2$ represents a saturated or unsaturated 5- or 6-membered cyclic hydrocarbon group which may have a substituent or a saturated or unsaturated 5- or 6-membered heterocyclic group which may have a substituent and $B^2$ represents a single bond, a carbonyl group or an alkylene group), when the carbon atom to which each of $R^8$, $R^9$, $R^{10}$, $R^{11}$, $R^{12}$, $R^{13}$, $R^{15}$ and $R^{16}$ has been bonded is adjacent to a nitrogen atom, $R^8$, $R^9$, $R^{10}$, $R^{11}$, $R^{12}$, $R^{13}$, $R^{15}$ and $R^{16}$ each independently represents:

a hydrogen atom,
an alkyl group,
a hydroxyalkyl group,
a hydroxyalkylcarbonyl group,
a hydroxyalkylsulfonyl group,
a formyl group,
a formylalkyl group,
a formylalkylcarbonyl group,
a formylalkylsulfonyl group,
an alkylcarbonyl group,
an alkylsulfonyl group,
an alkylcarbonylalkyl group,
an alkylsulfonylalkyl group,
a carboxyl group,
a carboxyalkyl group,
a carboxyalkylcarbonyl group,
a carboxyalkylsulfonyl group,
a carboxyalkylcarbonylalkyl group,
a carboxyalkylsulfonylalkyl group,
an alkoxyalkyl group,
an alkoxycarbonyl group,
an alkoxycarbonylalkyl group,
an alkoxycarbonylalkylcarbonyl group,
an alkoxycarbonylalkylsulfonyl group,
an aminoalkyl group in which the amino moiety may have one or two substituents,
an aminoalkylcarbonyl group in which the amino moiety may have one or two substituents, an aminocarbonyl group in which the amino moiety may have one or two substituents, an aminocarbonylalkyl group in which the amino moiety may have one or two substituents or a group $A^3$-$B^3$— (in which $A^3$ represents a saturated or unsaturated 5- or 6-membered cyclic hydrocarbon group which may have a substituent or a saturated or unsaturated 5- or 6-membered heterocyclic group which may have a substituent and $B^3$ represents a single bond, a carbonyl group or an alkylene group), $R^8$ and $R^9$, $R^{10}$ and $R^{11}$, $R^{12}$ and $R^{13}$, and $R^{15}$ and $R^{16}$ may each be coupled together with a carbon atom which constitutes the ring and represent a saturated or unsaturated 5- to 7-membered cyclic hydrocarbon group which may have a substituent or a saturated or unsaturated 5- to 7-membered heterocyclic group which may have a substituent, $R^{14}$ and $R^{17}$ each independently represents:
a hydrogen atom,
an alkyl group,
a hydroxyalkyl group,
a hydroxyalkylcarbonyl group,
a hydroxyalkylsulfonyl group,
an alkoxyl group,
an alkoxyalkyl group,
an alkoxyalkylcarbonyl group,
an alkoxyalkylsulfonyl group,
a formyl group,
a formylalkyl group,
a formylalkylcarbonyl group,
a formylalkylsulfonyl group,
an aklylcarbonyl group,
an alkylcarbonylalkyl group,
an alkylsulfonyl group,
an alkylsulfonylalkyl group,
a carboxyalkyl group,
a carboxyalkylcarbonyl group,
a carboxyalkylsulfonyl group,
a carboxyalkylcarbonylalkyl group,
a carboxyalkylsulfonylalkyl group,
an alkoxycarbonyl group,
an alkoxycarbonylalkyl group,
an alkoxycarbonylalkylcarbonyl group,
an alkoxycarbonylalkylsulfonyl group,
an amino group which may have one or two substituents,
an aminoalkyl group in which the amino moiety may have one or two substituents,
an aminoalkyloxy group in which the amino moiety may have one or two substituents,
an aminoalkylcarbonyl group in which the amino moiety may have one or two substituents,
an aminoalkyloxycarbonyl group in which the amino moiety may have one or two substituents,
an aminocarbonyl group in which the amino moiety may have one or two substituents,
an aminocarbonylalkyl group in which the amino moiety may have one or two substituents,
an aminocarbonyloxyalkyl group in which the amino moiety may have one or two substituents, $R^{14}$ and $R^{12}$ or $R^{13}$ may be coupled together with a carbon atom constituting the ring and a nitrogen atom to which $R^{14}$ has been bonded and represent a saturated or unsaturated 5- to 7-membered heterocyclic group which may have a substituent, $R^{17}$ and $R^{15}$ or $R^{16}$ may be coupled together with a carbon atom constituting the ring and a nitrogen atom to which $R^{17}$ has been bonded and represent a saturated or unsaturated 5- to 7-membered heterocyclic group which may have a substituent, a, b, d, e and g each independently stands for an integer of 0 or 1, c stands for an integer of 0 to 3, f, h and i each independently represents an integer of 1 to 3, with the proviso that the sum of a, b and c stands for an integer of 2 or 3, the sum of d and e stands for an integer of 0 or 1 and the sum of f, g and h stands for an integer of 3 to 5), $T^1$ represents a carbonyl group, a group —CH($R^{18}$)— (in which $R^{18}$ represents a hydrogen atom, an alkyl group, a hydroxyalkyl group, an alkoxyalkyl group, a carboxyalkyl group, an alkoxycarbonylalkyl group, an aryl group, an aralkyl group, a heteroaryl group, a heteroarylalkyl group or an aminoalkyl group in which the amino moiety may have a substituent) or a group —C(=NOR$^{19}$)— (in which $R^{19}$ represents a hydrogen atom, an alkyl group, a carboxyalkyl group, an alkoxycarbonyl group, an aryl group, an aralkyl group, a heteroaryl group, a heteroarylalkyl group or an aminoalkyl group in which the amino moiety may have a substituent, and $X^1$ and $X^2$ each independently represents a methine group or a nitrogen atom]; salt thereof; or solvate thereof.

The present invention also provides a medicament comprising as an effective ingredient a sulfonyl derivative represented by the formula (1), salt thereof or solvate thereof.

The present invention also provides a pharmaceutical composition comprising a sulfonyl derivative represented by the formula (1), salt thereof or solvate thereof; and a pharmaceutically acceptable carrier.

The present invention also provides the use of a sulfonyl derivative represented by the formula (1), salt thereof or solvate thereof as a medicament.

The present invention also provides a method for treating a disease caused by thrombosis or embolism, which comprises administering, to a patient suffering therefrom, a sulfonyl derivative represented by the formula (1), salt thereof or solvate thereof.

BEST MODE FOR CARRYING OUT THE INVENTION

A description will next be made of the substituents in the sulfonyl group derivative of the formula (I) according to the present invention.

As $R^1$, examples of the halogen atom include fluorine, chlorine, bromine and iodine.

Examples of the alkyl group include linear, branched or cyclic $C_{1-6}$ alkyl groups such as methyl, ethyl, isopropyl and cyclopropyl.

The "hydroxyalkyl group" means a group formed of a hydroxyl group and a linear, branched or cyclic $C_{1-6}$ alkylene group. Examples of the alkylene group include methylene, ethylene, trimethylene, propylene and cyclohexylene. Examples of the hydroxyalkyl group include hydroxymethyl and hydroxyethyl.

The "alkoxyl group" means a group formed of the above-described $C_{1-6}$ alkyl group and an oxygen atom. Examples include methoxyl, ethoxyl and isopropoxyl.

The "alkoxyalkyl group" means a group formed of the above-described alkoxyl group and the above-described $C_{1-6}$ alkylene group. Examples include methoxymethyl, methoxyethyl and ethoxymethyl.

The "carboxyalkyl group" means a group formed of a carboxyl group and the above-described $C_{1-6}$ alkylene group. Examples include carboxymethyl and carboxyethyl.

The "alkylcarbonyl group" means a group formed of the above-described $C_{1-6}$ alkyl group and a carbonyl group. Examples include methylcarbonyl and ethylcarbonyl.

The "alkoxycarbonyl group" means a group formed of the above-described $C_{1-6}$ alkoxyl group and a carbonyl group. Examples include methoxycarbonyl and ethoxycarbonyl.

The "alkoxycarbonylalkyl group" means a group formed of the above-described alkoxycarbonyl group and the above-described alkylene group. Examples include methoxycarbonylethyl and ethoxycarbonylmethyl.

The "alkylcarbonyloxy group" means a group formed of the above-described $C_{1-6}$ alkyl group, a carbonyl group and an oxygen atom. Examples include methylcarbonyloxy, ethylcarbonyloxy and isopropylcarbonyloxy.

In the group $A^1$-$B^1$—, $A^1$ represents an amino group which may have one or two substituents, a saturated or unsaturated 5- or 6-membered cyclic hydrocarbon group which may have a substituent or a saturated or unsaturated 5- or 6-membered heterocyclic group which may have a substituent.

When $A^1$ represents an amino group which may have one or two substituents, $B^1$ represents a single bond, a carbonyl group, an alkylene group, a carbonylalkyl group, a carbonylalkyloxy group or an alkylenecarbonyloxy group. The group $A^1$-$B^1$— therefore represents, for example, a group as shown in the following class (A).

Class (A):
  an amino group which may have one or two substituents,
  an aminocarbonyl group in which the amino moiety may have one or two substituents,
  an aminoalkyl group in which the amino moiety may have one or two substituents,
  an aminocarbonylalkyl group in which the amino moiety may have one or two substituents,
  an aminocarbonylalkyloxy group in which the amino moiety may have one or two substituents or
  an aminoalkylcarbonyl group in which the amino moiety may have one or two substituents and
  an aminoalkylcarbonyloxy group in which the amino moiety may have one or two substituents.

A description will next be made of the groups shown in Class (A).

The "aminocarbonyl group in which the amino moiety may have one or two substituents" means a group formed of an amino group which may have one or two substituents and a carbonyl group.

The "aminoalkyl group in which the amino moiety may have one or two substituents" means a group formed of an amino group which may have one or two substituents and the above-described $C_{1-6}$ alkylene group. Examples of the aminoalkyl group include aminomethyl and aminoethyl.

The "aminocarbonylalkyl group in which the amino moiety may have one or two substituents" means a group formed of the above-described aminocarbonyl group and the above-described $C_{1-6}$ alkylene group. Examples of the aminocarbonylalkyl group include aminocarbonylmethyl and aminocarbonylethyl.

The "aminocarbonylalkyloxy group in which the amino moiety may have one or two substituents" means a group formed of the above-described aminocarbonylakyl group and an oxygen atom. Examples of the aminocarbonylalkyloxy group include aminocarbonylmethoxyl and aminocarbonylethoxyl.

The "aminoalkylcarbonyl group in which the amino moiety may have one or two substituents" means a group formed of the above-described aminoalkyl group and a carbonyl group. Examples of the aminoalkylcarbonyl group include aminomethylcarbonyl and aminoethylcarbonyl.

The "aminoalkylcarbonyloxy group in which the amino moiety may have one or two substituents" means a group formed of the above-described aminoalkylcarbonyl group and an oxygen atom. Examples of the aminoalkylcarbonyloxy group include aminomethylcarbonyloxy and aminoethylcarbonyloxy.

Examples of the substituent which can be substituted for an amino group include those as shown in the following Class, (1).

Class (1):
  an alkyl group,
  an alkenyl group,
  a halogenoalkyl group,
  a halogenoalkenyl group,
  a hydroxyalkyl group,
  a hyroxyalkylcarbonyl group,
  a hydroxyalkylsulfonyl group,
  an alkoxyl group,
  an alkoxyalkyl group,
  an alkoxyalkylcarbonyl group,
  an alkoxyalkylsulfonyl group,
  a formyl group,
  a formylalkyl group,
  a formylalkylcarbonyl group,
  a formylalkylsulfonyl group,
  an alkylcarbonyl group,
  an alkylcarbonylalkyl group,
  an alkylsulfonyl group,
  an alkylsulfonylalkyl group,
  a carboxyalkyl group,
  a carboxyalkylcarbonyl group,
  a carboxyalkylsulfonyl group,
  a carboxyalkylcarbonylalkyl group,
  a carboxyalkylsulfonylalkyl group,
  an alkoxycarbonyl group,
  an alkoxycarbonylalkyl group,
  an alkoxycarbonylalkylcarbonyl group,
  an alkoxycarbonylalkylsulfonyl group,
  a trifluoromethylsulfonyloxyalkenyl group and
  a group $a^1$-$b^1$— (wherein $a^1$ represents a saturated or unsaturated 5- or 6-membered cyclic hydrocarbon group or saturated or unsaturated 5- or 6-membered heterocyclic group which may have one to three substituents selected from the group consisting of a halogen atom, a hydroxyl group, an amino group, an alkoxyl group, an alkyl group, a cyano group, a nitro group, a carboxyl group, an alkoxycarbonyl group and an aminocarbonyl group; and
  $b^1$ represents a single bond, a carbonyl group, an alkylene group, a carbonylalkyl group, a carbonylalkyloxy group, an alkylenecarbonyloxy group, an alkyleneaminocarbonyl group, an alkyleneaminocarbonylalkyl group, an alkyleneaminosulfonyl group or an alkyleneaminosulfonylalkyl group).

The substituents which can be substituted for an amino group in Class (1) will next be described.

The alkyl group has the same meaning as described above.

The "alkenyl group" means a linear, branched or cyclic $C_{2-6}$ alkenyl group. Examples include vinyl and allyl.

The "halogenoalkyl group" means a group formed of a halogen atom and the above-described alkylene group. Examples include chloromethyl and bromoethyl.

The "halogenoalkenyl group" means a group formed of a halogen atom and a linear or branched $C_{2-6}$ alkenylene group. Examples include chloroethenyl and bromopropenyl groups. There is no particular limitation on the position of a double bond.

The "hydroxyalkyl group" means a group formed of a hydroxyl group and a linear, branched or cyclic $C_{2-6}$ alkylene group. Examples include hydroxyethyl and hydroxypropyl.

The "hydroxyalkylcarbonyl group" means a group formed of the above-described hydroxyalkyl group and a carbonyl group. Examples include hydroxymethylcarbonyl and hydroxyethylcarbonyl.

The "hydroxyalkylsulfonyl group" means a group formed of the above-described hydroxyalkyl group and a sulfonyl group. Examples include hydroxymethylsulfonyl and hydroxyethylsulfonyl.

The alkoxyl group has the same meaning as described above.

The "alkoxyalkyl group" means a group formed of the above-described alkoxyl group and linear, branched or cyclic $C_{2-6}$ alkylene group. Examples include methoxyethyl, ethoxyethyl and methoxypropyl.

The "alkoxyalkylcarbonyl group" means a group formed of the above-described alkoxyalkyl group and a carbonyl group. Examples include methoxyethylcarbonyl and ethoxymethylcarbonyl.

The "alkoxyalkylsulfonyl group" means a group formed of the above-described alkoxyalkyl group and a sulfonyl group. Examples include methoxymethylsulfonyl and ethoxymethylsulfonyl.

The "formylalkyl group" means a group formed of a formyl group and the above-described $C_{1-6}$ alkylene group. Examples include formylmethyl and formylethyl.

The "formylalkylcarbonyl group" means a group formed of the above-described formylalkyl group and a carbonyl group. Examples include formylmethylcarbonyl and formylethylcarbonyl.

The "formylalkylsulfonyl group" means a group formed of the above-described formylalkyl group and a sulfonyl group. Examples include formylmethylsulfonyl and formylethylsulfonyl.

The "alkylcarbonyl group" means a group formed of the above-described alkyl group and a carbonyl group. Examples include methylcarbonyl and ethylcarbonyl.

The "alkylcarbonylalkyl group" means a group formed of the above-described alkylcarbonyl group and the above-described $C_{1-6}$ alkylene group. Examples include methylcarbonylmethyl and ethylcarbonylmethyl.

The "alkylsulfonyl group" means a group formed of the above-described alkyl group and a sulfonyl group. Examples include methylsulfonyl and ethylsulfonyl.

The "alkylsulfonylalkyl group" means a group formed of the above-described alkylsulfonyl group and the above-described $C_{1-6}$ alkylene group. Examples include methylsulfonylmethyl and ethylsulfonylmethyl.

The carboxyalkyl group has the same meaning as described above.

The "carboxyalkylcarbonyl group" means a group formed of the above-described carboxyalkyl group and a carbonyl group. Examples include carboxymethylcarbonyl and carboxyethylcarbonyl.

The "carboxyalkylsulfonyl group" means a group formed of the above-described carboxyalkyl group and a sulfonyl group. Examples include carboxymethylsulfonyl and carboxyethylsulfonyl.

The "carboxyalkylcarbonylalkyl group" means a group formed of the above-described carboxyalkylcarbonyl group and the above-described $C_{1-6}$ alkylene group. Examples include carboxymethylcarbonylmethyl and carboxyethylcarbonylmethyl.

The "carboxyalkylsulfonylalkyl group" means a group formed of the above-described carboxyalkylsulfonyl group and the above-described $C_{1-6}$ alkylene group. Examples include carboxymethylsulfonylmethyl and carboxyethylsulfonylmethyl.

The alkoxycarbonyl and alkoxycarbonylalkyl groups have the same meanings as described above.

The "alkoxycarbonylalkylcarbonyl group" means a group formed of the above-described alkoxycarbonylalkyl group and a carbonyl group. Examples include methoxycarbonylethylcarbonyl and ethoxycarbonylmethylcarbonyl.

The "alkoxycarbonylalkylsulfonyl group" means a group of the above-described alkoxycarbonylalkyl group and a sulfonyl group. Examples include methoxycarbonylethylsulfonyl and ethoxycarbonylmethylsulfonyl.

The "trifluoromethylsulfonyloxyalkenyl group" means a group formed of a trifluoromethylsulfonyloxy group and a linear or branched $C_{2-6}$ alkenylene group. Examples include trifluoromethylsulfonyloxyvinyl and trifluoromethylsulfonyloxyallyl.

In the group $a^1-b^1-$, $a^1$ represents a saturated or unsaturated 5- or 6-membered cyclic hydrocarbon group or saturated or unsaturated 5- or 6-membered heterocyclic group which may have a substituent such as a halogen atom. Examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl. Where the group has, as the cyclopentenyl, plural structural isomers, it is to be noted that they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, pyrazinyl, tetrahydropyrazinyl, imidazolyl, pyrazolinyl, oxazolyl, oxazolinyl, thiazolyl, thiazolinyl, thiazolidinyl, oxatriazolyl, thiadiazolyl, furazanyl, pyranyl, pyridyl, pyrimidinyl, tetrahydropyrimidinyl, pyridazinyl, tetrahydropyridazinyl, pyrrolidinyl, piperazinyl, piperidinyl, oxazinyl, oxadiazinyl, morpholinyl, thiazinyl, thiadiazinyl, thiomorpholinyl, tetrazolyl, tetrazinyl, triazolyl and triazinyl. Where the group has, as the pyranyl, plural structural isomers, it is to be noted that they are all embraced in it.

$b^1$ represents a single bond or a carbonyl, alkylene, carbonylalkyl, carbonylalkyloxy, alkylenecarbonyloxy, alkyleneaminocarbonyl, alkyleneaminocarbonylalkyl, alkyleneaminosulfonyl or alkyleneaminosulfonylalkyl group. The alkylene group has the same meaning as described above.

The "carbonylalkyl group" means a group formed of a carbonyl group and the above-described $C_{1-6}$ alkylene group. Examples include carbonylmethyl and carbonylethyl.

The "carbonylalkyloxy group" means a group formed of the above-described carbonylalkyl group and an oxygen atom. Examples include carbonylmethoxy and carbonylethoxy.

The "alkylenecarbonyloxy group" means a group formed of the above-described $C_{1-6}$ alkylene group, a carbonyl group and an oxygen atom. Examples include methylenecarbonyloxy and ethylenecarbonyloxy.

The "alkyleneaminocarbonyl group" means a group formed of the above-described $C_{1-6}$ alkylene group, an imino group and a carbonyl group. Examples include methyleneaminocarbonyl and ethyleneaminocarbonyl.

The "alkyleneaminocarbonylalkyl group" means a group formed of the above-described alkyleneaminocarbonyl and the above-described $C_{1-6}$ alkylene. Examples include methyleneaminocarbonylmethyl and ethyleneaminocarbonylmethyl.

The "alkyleneaminosulfonyl group" means a group formed of the above-described $C_{1-6}$ alkylene group, an imino group and a sulfonyl group. Examples include methyleneaminosulfonyl and ethyleneaminosulfonyl.

The "alkyleneaminosulfonylalkyl group" means a group formed of the above-described alkyleneaminosulfonyl and the above-described $C_{1-6}$ alkylene. Examples include methyleneaminosulfonylmethyl and ethyleneaminosulfonylmethyl.

A description will next be made of the substituents which can be introduced to, as the above-described $a^1$, a saturated or unsaturated 5- or 6-membered cyclic hydrocarbon group or saturated or unsaturated 5- or 6-membered heterocyclic group which may have a substituent. Examples of the halogen atom include fluorine, chlorine, bromine and iodine. The alkoxyl, alkyl, alkoxycarbonyl and aminocarbonyl groups have the same meanings as described above.

As the group $a^1$-$b^1$—, there exist various kinds according to the combination of $a^1$ and $b^1$. Examples include:

a saturated or unsaturated 5- or 6-membered cyclic hydrocarbon group which may have a substituent, a group formed of a saturated or unsaturated 5- or 6-membered heterocyclic group which may have a substituent and a carbonyl group, a group formed of a saturated or unsaturated 5- or 6-membered cyclic hydrocarbon group which may have a substituent and an alkylene group, a group formed of a saturated or unsaturated 5- or 6-membered heterocyclic group which may have a substituent and a carbonylalkyl group, a group formed of a saturated or unsaturated 5- or 6-membered cyclic hydrocarbon group which may have a substituent and a carbonylalkyloxy group, a group formed of a saturated or unsaturated 5- or 6-membered heterocyclic group which may have a substituent and a alkylenecarbonyloxy group, a group formed of a saturated or unsaturated 5- or 6-membered cyclic hydrocarbon group which may have a substituent and a alkyleneaminocarbonyl group, a group formed of a saturated or unsaturated 5- or 6-membered heterocyclic group which may have a substituent and an alkyleneaminocarbonylalkyl group, a group formed of a saturated or unsaturated 5- or 6-membered cyclic hydrocarbon group which may have a substituent and an alkyleneaminosulfonyl group, a group formed of a saturated or unsaturated 5- or 6-membered heterocyclic group which may have a substituent and an alkyleneaminosulfonylalkyl group and the like.

In addition to the above-described Class (1), the following Class (2) can be given as examples of the substituent which can be substituted for the amino group.

Class (2):

an amino group which may have one or two substituents selected from Class (1), an aminoalkyl group in which the amino moiety may have one or two substituents selected from Class (1), an aminocarbonyl group in which the amino moiety may have one or two substituents selected from Class (1), an aminocarbonylalkyl group in which the amino moiety may have one or two substituents selected from Class (1), an aminocarbonylalkylcarbonyl group in which the amino moiety may have one or two substituents selected from Class (1), an aminocarbonylalkylsulfonyl group in which the amino moiety may have one or two substituents selected from Class (1), an aminoalkylcarbonyl group in which the amino moiety may have one or two substituents selected from Class (1), an aminosulfonyl group in which the amino moiety may have one or two substituents selected from Class (1), an aminosulfonylalkyl group in which the amino moiety may have one or two substituents selected from Class (1), an aminoalkylsulfonyl group in which the amino moiety may have one or two substituents selected from Class (1), an aminosulfonylalkylcarbonyl group in which the amino moiety may have one or two substituents selected from Class (1) and an aminosulfonylalkylsulfonyl group in which the amino moiety may have one or two substituents selected from Class (1).

A description will next be made of the substituents of Class (2).

The aminocarbonyl, aminocarbonylalkyl and aminoalkylcarbonyl groups in Class (2) have the same meanings as described above.

The "aminoalkyl group which may have a substituent" means a group formed of an amino group which may have a substituent and a linear, branched or cyclic $C_{2-6}$ alkylene group. Examples of the aminoalkyl group include aminoethyl and aminopropyl.

The "aminocarbonylalkylcarbonyl group which may have a substituent" means a group formed of an aminocarbonylalkyl group which may have a substituent and a carbonyl group. Examples of the aminocarbonylalkylcarbonyl group include aminocarbonylmethylcarbonyl and aminocarbonylethylcarbonyl.

The "aminocarbonylalkylsulfonyl group which may have a substituent" means a group formed of an aminocarbonylalkyl group which may have a substituent and a sulfonyl group. Examples of the aminocarbonylalkylsulfonyl group include aminocarbonylmethylsulfonyl and aminocarbonylethylsulfonyl.

The "aminosulfonyl group which may have a substituent" means a group formed of an amino group which may have a substituent and a sulfonyl group.

The "aminosulfonylalkyl group which may have a substituent" means a group formed of the above-described aminosulfonyl group which may have a substituent and the above-described $C_{1-6}$ alkylene group. Examples of the aminosulfonylalkyl group include aminosulfonylmethyl and aminosulfonylethyl.

The "aminoalkylsulfonyl group which may have a substituent" means a group formed of the above-described amino group which may have a substituent, the above-described $C_{1-6}$ alkylene group and a sulfonyl group. Examples of the aminoalkylsulfonyl group include aminomethylsulfonyl and aminoethylsulfonyl.

The "aminosulfonylalkylcarbonyl group which may have a substituent" means a group formed of the above-described aminosulfonylalkyl group which may have a substituent and a carbonyl group. Examples include aminosulfonylmethylcarbonyl and aminosulfonylethylcarbonyl.

The "aminosulfonylalkylsulfonyl group which may have a substituent" means a group formed of the above-described aminosulfonylalkyl group which may have a substituent and a sulfonyl group. Examples include aminosulfonylmethylsulfonyl and aminosulfonylethylsulfonyl.

$A^1$ also represents a saturated or unsaturated 5- or 6-membered cyclic hydrocarbon group or heterocyclic group which may have a substituent. Examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl groups. Where the group has plural structural isomers as the cyclopentenyl group, it is to be noted that they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, imidazolyl, pyrazolinyl, oxazolyl, oxazolinyl, thiazolyl, thiazolinyl, oxatriazolyl, thiadiazolyl, furazanyl, pyranyl, pyridyl, pyridazinyl, pyrrolidinyl, piperazinyl, piperidinyl, oxazinyl, oxadiazinyl, morpholinyl, thiazinyl, thiadiazinyl, thiomorpholinyl, triazolyl and triazinyl. Where the group has plural structural isomers as pyranyl, it is to be noted that they are all embraced in it.

When $A^1$ represents a saturated or unsaturated 5- or 6-membered cyclic hydrocarbon group or heterocyclic group which may have a substituent, $B^1$ represents a single bond, a carbonyl group, an alkylene group, a carbonylalkyl group, a carbonylalkyloxy group or an alkylenecarbonyloxy group. Accordingly, the group $A^1$-$B^1$—, for example, represents a group as shown in the following Class (B):

Class (B):
- a saturated or unsaturated 5- or 6-membered cyclic hydrocarbon group or heterocyclic group which may have a substituent
- a group formed of a saturated or unsaturated 5- or 6-membered cyclic hydrocarbon group or heterocyclic group which may have a substituent and a carbonyl group,
- a group formed of a saturated or unsaturated 5- or 6-membered cyclic hydrocarbon group or heterocyclic group which may have a substituent and an alkylene group,
- a group formed of a saturated or unsaturated 5- or 6-membered cyclic hydrocarbon group or heterocyclic group which may have a substituent, a carbonyl group and an alkylene group,
- a group formed of a saturated or unsaturated 5- or 6-membered cyclic hydrocarbon group or heterocyclic group which may have a substituent, a carbonyl group, an alkylene group and an oxygen atom,
- a group formed of a saturated or unsaturated 5- or 6-membered cyclic hydrocarbon group or heterocyclic group which may have a substituent, an alkylene group and a carbonyl group,
- a group formed of a saturated or unsaturated 5- or 6-membered cyclic hydrocarbon group or heterocyclic group which may have a substituent, an alkylene group, a carbonyl group and an oxygen atom, and the like.

A description will next be made of the groups shown in Class (B).

In the group formed of a saturated or unsaturated 5- or 6-membered cyclic hydrocarbon group or heterocyclic group which may have a substituent and a carbonyl group, examples of the group formed of the cyclic hydrocarbon group and a carbonyl group include cyclopentylcarbonyl and phenylcarbonyl; while those of the group formed of the heterocyclic group and a carbonyl group include furylcarbonyl, thienylcarbonyl and pyridylcarbonyl groups.

In the group formed of a saturated or unsaturated 5- or 6-membered cyclic hydrocarbon group or heterocyclic group which may have a substituent and an alkylene group, the "group formed of a cyclic hydrocarbon group and an alkylene group" means a group formed of the above-described cyclic hydrocarbon group and the above-described $C_{1-6}$ alkylene group, for example, cyclohexylmethyl and benzyl, while the "group formed of a heterocyclic group and an alkylene group" means a group formed of the above-described heterocyclic group and the above-described $C_{1-6}$ alkylene group, for example, furylmethyl, thienylethyl and pyridylpropyl.

In the group formed of a saturated or unsaturated 5- or 6-membered cyclic hydrocarbon group or heterocyclic group which may have a substituent, a carbonyl group and an alkylene group, the "group formed of a cyclic hydrocarbon group, a carbonyl group and an alkylene group" means a group formed of the above-described cyclic hydrocarbon group, a carbonyl group and the above-described $C_{1-6}$ alkylene group, for example, cyclopentadienylcarbonylmethyl and phenylcarbonylethyl, while the "group formed of a heterocyclic group, a carbonyl group and an alkylene group" means a group formed of the above-described heterocyclic group, a carbonyl group and the above-described $C_{1-6}$ alkylene group, for example, furylcarbonylmethyl, thienylcarbonylethyl and pyridylcarbonylpropyl.

In the group formed of a saturated or unsaturated 5- or 6-membered cyclic hydrocarbon group or heterocyclic group which may have a substituent, a carbonyl group, an alkylene group and an oxygen atom, the "group formed of a cyclic hydrocarbon group, a carbonyl group, an alkylene group and an oxygen atom" means a group composed of the above-described group, which is formed of a cyclic hydrocarbon group, a carbonyl group and an alkylene group, and an oxygen atom, for example, cyclopentylcarbonylmethoxy and phenylcarbonylethoxy, while the "group formed of a heterocyclic group, a carbonyl group, an alkylene group and an oxygen atom" means a group composed of the above-described group, which is formed of a heterocyclic group, a carbonyl group and an alkylene group, and an oxygen atom, for example, furylcarbonylmethoxy, thienylcarbonylethoxy and pyridylcarbonylpropoxy.

In the group formed of a saturated or unsaturated 5- or 6-membered cyclic hydrocarbon group or heterocyclic group which may have a substituent, an alkylene group and a carbonyl group, "the group formed of a cyclic hydrocarbon group, an alkylene group and a carbonyl group" means a group composed of the above-described group, which is formed of a cyclic hydrocarbon group and an alkylene group, and a carbonyl group, for example, cyclohexylmethylcarbonyl and phenylethylcarbonyl, while "the group formed of a heterocyclic group, an alkylene group and a carbonyl group" means a group composed of the above-described group, which is formed of a heterocyclic group and an alkylene group, and a carbonyl group, for example, furylmethylcarbonyl, thienylethylcarbonyl and pyridylpropylcarbonyl.

In the group formed of a saturated or unsaturated 5- or 6-membered cyclic hydrocarbon group or heterocyclic group which may have a substituent, an alkylene group, a carbonyl group and an oxygen atom, "the group formed of a cyclic hydrocarbon group, an alkylene group, a carbonyl group and an oxygen atom" means a group composed of the above-described group, which is formed of a cyclic hydrocarbon group, an alkylene group and a carbonyl group, and an oxygen atom, for example, cyclohexadienylmethylcarbonyloxy and phenylethylcarbonylyoxy, while "the group formed of a heterocyclic group, an alkylene group, a carbonyl group and an oxygen atom" means a group composed of the above-described group, which is formed of a heterocyclic group, an alkylene group and a carbonyl group, and an oxygen atom such as furylmethylcarbonyloxy, thienylethylcarbonyloxy and pyridylpropylcarbonyloxy.

As examples of a substituent which can be substituted for the saturated or unsaturated 5- or 6-membered cyclic hydrocarbon group or heterocyclic group, those as shown in Class (3) can be given.

Class (3):
 a hydroxyl group,
 an alkyl group,
 an alkoxyl group,
 a hydroxyalkyl group,
 an alkoxyalkyl group,
 a halogen atom,
 a cyano group,
 a nitro group,
 a carboxyl group,
 an alkoxycarbonyl group,
 a formyl group,
 a heteroaryl group,
 a heteroarylalkyl group,
 an alkylimino group,
 an amidino group,
 a guanidino group,
 an amino(hydroxyimino)alkyl group,
 an amino(alkoxyimino)alkyl group,
 an amino(aryloxyimino)alkyl group,
 an amino group which may have one or two substituents,
 an aminocarbonyl group in which the amino moiety may have one or two substituents,
 an aminocarbonylalkyl group in which the amino moiety may have one or two substituents,
 an aminocarbonylalkyloxy group in which the amino moiety may have one or two substituents,
 an aminoalkyl group in which the amino moiety may have one or two substituents,
 an aminoalkyloxy group in which the amino moiety may have one or two substituents,
 an aminoalkylcarbonyl group in which the amino moiety may have one or two substituents,
 an aminoalkylcarbonyloxy group in which the amino moiety may have one or two substituents, and
 an oxygen atom.

The number of the replaceable substituents ranges from 1 to 3.

A description will next be made of the substituents which can be substituted for the saturated or unsaturated 5- or 6-membered heterocyclic group in Class (3).

The alkyl group, alkoxyl group, hydroxyalkyl group, alkoxyalkyl group, halogen atom, alkoxycarbonyl group have the same meanings as described above in $R^1$.

The "heteroaryl group" means a monovalent aromatic group having at least one hetero atom. Examples include pyridyl, furyl and thienyl.

The "heteroarylalkyl group" means a group formed of the above-described heteroaryl group and the above-described $C_{1-6}$ alkylene group. Examples include pyridylmethyl, furylethyl and thienylmethyl.

The "alkylimino group" means a group formed of the above-described alkyl group and a nitrogen atom. Examples include methylimino and ethylimino.

The "amino(hydroxyimino)alkyl group" means a group in which amino and hydroxyimino groups have been bonded to the same carbon atom of the above-described alkyl group. Examples include amino(hydroxyimino)methyl and amino(hydroxyimino)ethyl.

The "amino(alkoxyimino)alkyl group" means a group in which amino and alkoxyimino groups have been bonded to the same carbon atom of the above-described alkyl group. Here, the "alkoxyimino group" means a divalent group formed of the above-described alkoxyl group and an imino group. Examples of the amino(alkoxyimino)alkyl group include amino(methoxyimino)methyl and amino(ethoxyimino)methyl.

The "amino(aryloxyimino)alkyl group" means a group in which amino and aryloxyimino groups have been bonded to the same carbon atom of the above-described alkyl group. Here, the "aryloxyimino group" means a divalent group formed of aryl and imino groups. Examples of the aryl group include phenyl, naphthyl, anthryl and phenanthryl. Examples of the amino(aryloxyimino)alkyl group include amino(phenoxyimino)methyl and amino(naphthyloxyimino)methyl.

The "aminocarbonyl group in which the amino moiety may have one or two substituents" means a group formed of an amino group which may have one or two substituents and a carbonyl group.

The "aminoalkyl group in which the amino moiety may have one or two substituents" means a group formed of an amino group which may have one or two substituents and the above-described $C_{1-6}$ alkylene group. Examples of the aminoalkyl group include aminomethyl and aminoethyl.

The "aminocarbonylalkyl group in which the amino moiety may have one or two substituents" means a group formed of the above-described aminocarbonyl group in which the amino moiety may have one or two substituents and the above-described $C_{1-6}$ alkylene group. Examples of the aminocarbonylalkyl group include aminocarbonylmethyl and aminocarbonylethyl.

The "aminocarbonylalkyloxy group in which the amino moiety may have one or two substituents" means a group formed of the above-described aminocarbonylalkyl group in which the amino moiety may have one or two substituents and an oxygen atom. Examples of the aminocarbonylalkyloxy group include aminocarbonylmethoxyl and aminocarbonylethoxyl.

The "aminoalkylcarbonyl group in which the amino moiety may have one or two substituents" means a group formed of the above-described aminoalkyl group in which the amino moiety may have one or two substituents and a carbonyl group. Examples of the aminoalkylcarbonyl group include aminomethylcarbonyl and aminoethylcarbonyl.

The "aminoalkylcarbonyloxy group in which the amino moiety may have one or two substituents" means a group formed of the above-described aminoalkylcarbonyl group in which the amino moiety may have one or two substituents and an oxygen atom. Examples of the aminoalkylcarbonyloxy group include aminomethylcarbonyloxy and aminoethylcarbonyloxy.

The "aminoalkyloxy group in which the amino moiety may have one or two substituents" means a group formed of an amino group which may have a substituent, a linear, branched or cyclic $C_{2-6}$ alkylene group and an oxygen atom. Examples of the aminoalkyloxy group include aminoethyloxy and aminopropyloxy.

In the case of the cyclic hydrocarbon group, an oxygen atom can serve as a substituent when the corresponding keto compound is formed, while, in the case of the heterocyclic group or dicyclic or tricyclic fused ring group, an oxygen atom can serve as a substituent when the oxygen atom is bonded to a nitrogen or sulfur atom forming the ring and the corresponding N-oxide or S-oxide or keto compound is formed.

In the present invention, when $R^1$ is not coupled with $R^2$ or $R^3$ to form a $C_{1-3}$ alkylene or alkenylene group, preferred examples of $R^1$ include a hydrogen atom, an alkyl group, a hydroxyalkyl group and a group $A^1$-$B^1$—.

In $R^2$ and $R^3$, examples of the halogen atom include fluorine, chlorine, bromine and iodine.

The "alkyl group" means a linear, branched or cyclic $C_{1-8}$ alkyl group. Examples include methyl, ethyl, isopropyl, cyclopropyl, heptyl and octyl.

The "hydroxyalkyl group" means a group formed of a hydroxyl group and a linear, branched or cyclic $C_{1-8}$ alkylene group. Examples include hydroxymethyl and hydroxyethyl.

The "alkoxyalkyl group" means a group formed of the above-described alkyl group, an oxygen atom and a linear, branched or cyclic $C_{1-8}$ alkylene group. Examples include methoxymethyl, methoxyethyl and ethoxymethyl.

When $R^2$ or $R^3$ is coupled with $R^1$ to form a $C_{1-3}$ alkylene or alkenylene group, the following group, in the formula (I):

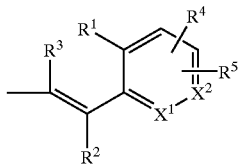

means the below-described group or the like.

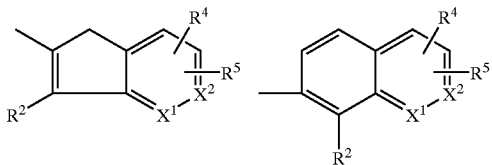

In the present invention, when $R^2$ or $R_3$ is not coupled with $R^1$ to form a $C_{1-3}$ alkylene or alkenylene group, a hydrogen atom and alkyl group are preferred as $R^2$ or $R^3$.

In the present invention, it is preferred that $R^1$ and $R^2$ or $R^3$ are coupled together to form a $C_{1-3}$ alkylene or alkenylene group.

In $R^4$ or $R^5$, examples of the halogen atom include fluorine, chlorine, bromine and iodine. The alkyl and alkoxyl groups have the same meanings as described above in $R^1$. In the present invention, as $R^4$ or $R^5$, a halogen atom is preferred, with fluorine, chlorine and bromine being particularly preferred.

$Q^1$ represents a saturated or unsaturated 5- or 6-membered cyclic hydrocarbon group which may have a substituent, a saturated or unsaturated 5- or 6-membered heterocyclic group which may have a substituent, or a saturated or unsaturated, dicyclic or tricyclic fused ring group which may have a substituent.

Here, examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl. When the group has plural structural isomers as cyclopentenyl, it is to be noted that they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, imidazolyl, pyrazolinyl, oxazolyl, oxazolinyl, thiazolyl, thiazolinyl, oxatriazolyl, thiadiazolyl, furazanyl, pyranyl, pyridyl, pyridazinyl, pyrrolidinyl, piperazinyl, piperidinyl, oxazinyl, oxadiazinyl, morpholinyl, thiazinyl, thiadiazinyl, thiomorpholinyl, triazolyl and triazinyl. Where the group has plural structural isomers as pyranyl, it is to be noted that they are all embraced in it.

The "saturated or unsaturated, dicyclic or tricyclic fused ring group which may have a substituent" means: ① a group obtained by the condensation of the above-described saturated or unsaturated 5- or 6-membered cyclic hydrocarbon groups which may have a substituent, ② a group obtained by the condensation of the above-described saturated or unsaturated 5- or 6-membered cyclic hydrocarbon group which may have a substituent and the above-described saturated or unsaturated 5- or 6-membered heterocyclic group which may have a substituent and ③ a group obtained by the condensation of the above-described saturated or unsaturated 5- or 6-membered heterocyclic groups which may have a substituent. Examples of the group ① include indenyl, indanyl, naphthyl, tetrahydronaphthyl, anthryl and phenanthryl; those of the group ② include benzofuranyl, indolyl, indolinyl, quinolyl, benzodiazinyl and tetrahydroisoquinolyl; and those of the group ③ include naphthyridinyl, tetrahydrothienopyridyl, tetrahydrothiazolopyridyl and tetrahydropyridinopyridyl.

Examples of the substituent which can be substituted for the above-described cyclic hydrocarbon, heterocyclic, dicyclic or tricyclic fused ring group include the groups shown in the following Class (4):

Class (4):

a hydroxyl group, an alkyl group, an alkenyl group, a halogenoalkyl group, a halogenoalkenyl group, an alkoxyl group, a hydroxyalkyl group, an alkoxyalkyl group, a halogen atom, a cyano group, a nitro group, a carboxyl group, an alkoxycarbonyl group, a formyl group, a heteroaryl group, a heteroarylalkyl group, an alkylimino group, an amidino group, a guanidino group, an amino(hydroxyimino)alkyl group, an amino(alkoxyimino)alkyl group, an amino(aryloxyimino)alkyl group, an amino group which may have one or two substituents, an aminocarbonyl group in which the amino moiety may have one or two substituents, an aminocarbonylalkyl group in which the amino moiety may have one or two substituents, an aminocarbonylalkyloxy group in which the amino moiety may have one or two substituents, an aminoalkyl group in which the amino moiety may have one or two substituents, an aminoalkyloxy group in which the amino moiety may have one or two substituents, an aminoalkylcarbonyl group in which the amino moiety may have one or two substituents, an aminoalkylcarbonyloxy group in which the amino moiety may have one or two substituents, an oxygen atom, a trifluoromethylsulfonyloxy group, a trifluoromethylsulfonyloxyalkenyl group, a boric acid group (—B(OH)$_2$)), a saturated or unsaturated 5- or 6-membered cyclic hydrocarbon group which may have 1 to 3 substituents selected from the group consisting of halogen, hydroxyl, amino, alkoxyl, alkyl, cyano, nitro, carboxyl, alkoxycarbonyl and aminocarbonyl, and a saturated or unsaturated 5- or 6-membered heterocyclic group which may have 1 to 3 substituents selected from the group consisting of halogen, hydroxyl, amino, alkoxyl, alkyl, cyano, nitro, carboxyl, alkoxycarbonyl and aminocarbonyl.

Incidentally, the number of the replaceable substituents ranges from 1 to 7. The substituents in Class (4) have the same meanings as described in Classes (1) to (3).

In the present invention, preferred examples of $Q^1$ include a phenyl group which may have a substituent, an imidazolyl group which may have a substituent, a pyridyl group which may have a substituent, a pyrimidinyl group which may have a substituent, a pyrrolidinyl group which may have a substituent, a tetrahydrothienopyridyl group which may have a substituent and a tetrahydrothiazolopyridyl group which may have a substituent.

In $Q^2$, examples of the linear or branched $C_{1-6}$ alkylene group include methylene, ethylene, trimethylene, propylene, tetramethylene, butylene, pentamethylene and hexamethylene.

Examples of the linear or branched $C_{2-6}$ alkenylene group include vinylene, propenylene, butenylene and pentenylene. There is no particular limitation on the position of the double bond.

Examples of the linear or branched $C_{2-6}$ alkynylene group include propynylene, butynylene, pentynylene and hexynylene.

The following group:

means a divalent, saturated or unsaturated 5- or 6-membered cyclic hydrocarbon group which may have a substituent, a divalent, saturated or unsaturated 5- or 6-membered heterocyclic group which may have a substituent, or a divalent, saturated or unsaturated dicyclic fused group which may have a substituent, and ←C means the bonding of the carbon atom of this group to $Q^1$. Examples of this group include divalent groups derived from thiophene, furan, pyran, pyrrole, pyrrolidine, pyrroline, imidazole, imidazoline, imidazolidine, pyrazole, pyrazolidine, thiazole, oxazole, oxathiolan, benzene, pyridine, piperidine, piperazine, morpholine, thiomorpholine, pyrazine, pyrimidine, pyridazine, triazine, tetrazine, thiadiazine, dithiazine, cyclopentane, cyclopentene, cyclopentadiene, cyclohexane, cyclohexene, cyclohexadiene or the like and they may have a substituent. As the substituent, those exemplified above in Class (4) can be mentioned as examples.

The alkyl group in $R^6$ or $R^7$ of the group —N($R^6$)—CO— or —N($R^7$)—(CH$_2$)$_m$— means a linear, branched or cyclic $C_{1-6}$ alkyl group. Examples include methyl, ethyl, isopropyl and cyclopropyl. As the group —N($R^6$)—CO—, a group ←N($R^6$)—CO— (wherein ← means the bonding of the nitrogen atom of this group to $Q^1$) is preferred, while as the group —N($R^7$)—(CH$_2$)$_m$—, a group ←N($R^7$)—(CH$_2$)$_m$— (wherein ← means the bonding of the nitrogen atom of this group to $Q^1$) is preferred.

In the present invention, preferred examples of $Q^2$ include a single bond, a carbonyl group and groups represented by the following formula:

Among the groups represented by the following formula:

divalent groups derived from benzene, pyrimidine, tetrahydropyrimidine, pyrazine, pyridazine, triazine, tetrazine, imidazole, imidazoline, thiazole, thiazoline, furan, thiophene, pyrrole, oxazole, oxazoline, thiadiazole, cyclopentane, cyclopentene, cyclohexane or cyclohexene are preferred.

In $R^8$, $R^9$, $R^{10}$, $R^{11}$, $R^{12}$, $R^{13}$, $R^{15}$ and $R^{16}$ as the substituents in $Q^3$, the alkyl, alkoxyl, alkoxyalkyl, hydroxyalkyl, hydroxyalkyloxy, hydroxyalkylcarbonyl, hydroxyalkylsulfonyl, formylalkyl, formylalkylcarbonyl, formylalkylsulfonyl, alkylcarbonyl, alkylsulfonyl, alkylcarbonylalkyl, alkylsulfonylalkyl, carboxyalkylcarbonyl, carboxyalkylsulfonyl, carboxyalkylcarbonylalkyl, carboxyalkylsulfonylalkyl, alkoxycarbonyl, alkoxycarbonylalkyl, alkoxycarbonylalkylcarbonyl, alkoxycarbonylalkylsulfonyl, amino which may have 1 to 2 substituents, aminoalkyl in which the amino moiety may have 1 or 2 substituents, aminoalkylcarbonyl in which the amino moiety may have 1 or 2 substituents, aminoalkylcarbonyloxy in which the amino moiety may have 1 or 2 substituents, aminocarbonyl in which the amino moiety may have 1 or 2 substituents, aminocarbonylalkyl in which the amino moiety may have 1 or 2 substituents, and aminocarbonylalkyloxy in which the amino moiety may have 1 or 2 substituents have the same meanings as described above in $R^1$.

The "alkoxyalkyloxy group" means a group formed of the above-described alkoxyalkyl group and an oxygen atom and examples include methoxymethyloxy, methoxyethyloxy and ethoxymethyloxy.

The "carboxyalkyl group" means a group formed of a carboxyl group and the above-described $C_{1-6}$ alkylene group and examples include carboxymethyl and carboxyethyl.

The "carboxyalkyloxy group" means a group formed of the above-described carboxylalkyl group and an oxygen atom and examples include carboxymethoxyl and carboxyethoxyl.

The "alkoxycarbonylalkyloxy group" means a group formed of the above-described alkoxycarbonylalkyl group and an oxygen atom and examples include methoxycarbonylethyl and ethoxycarbonylethyl.

The "aminoalkyloxy group in which the amino moiety may have 1 or 2 substituents" means a group formed of an amino group which may have a substituent, a linear, branched or cyclic $C_{2-6}$ alkylene group and an oxygen atom and examples include aminoethoxyl and aminopropoxyl.

In the group $A^2$-$B^2$—, $A^2$ represents a saturated or unsaturated 5- or 6-membered cyclic hydrocarbon group which may have a substituent or a saturated or unsaturated 5- or 6-membered heterocyclic group which may have a substituent. Here, examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl. When the group has various structural isomers as the cyclopentenyl, they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, pyrazinyl, tetrahydropyrazinyl, imidazolyl, pyrazolinyl, oxazolyl, oxazolinyl, thiazolyl, thiazolinyl, thiazolidinyl, oxatriazolyl, thiadiazolyl, furazanyl, pyranyl, pyridyl, pyrimidinyl, tetrahydropyrimidinyl, pyridazinyl, tetrahydropyridazinyl, pyrrolidinyl, piperazinyl, piperidinyl, oxazinyl, oxadiazinyl, morpholinyl, thiazinyl, thiadiazinyl, thiomorpholinyl, tetrazolyl, tetrazinyl, triazolyl and triazinyl. Where the group has plural structural isomers as the pyranyl, it is to be noted that they are all embraced in it.

$B^2$ represents a single bond, carbonyl group or alkylene group. The "alkylene group" means a linear, branched or cyclic $C_{1-6}$ alkylene group.

Examples of the group $A^2$-$B^2$— include the following groups:
  a saturated or unsaturated 5- or 6-membered cyclic hydrocarbon group which may have a substituent,
  a group formed of a saturated or unsaturated 5- or 6-membered heterocyclic group which may have a substituent and a carbonyl group, and
  a group formed of a saturated or unsaturated 5- or 6-membered cyclic hydrocarbon group which may have a substituent and an alkylene group.

Each of $R^8$ and $R^9$, $R^{10}$ and $R^{11}$, $R^{12}$ and $R^{13}$, and $R^{15}$ and $R^{16}$ is coupled together with a carbon atom which constitutes the ring and represents a saturated or unsaturated 5- to 7-membered cyclic hydrocarbon group which may have a substituent or a saturated or unsaturated 5- to 7-membered heterocyclic group which may have a substituent. Here, examples of the saturated or unsaturated 5- to 7-membered cyclic hydrocarbon group include cyclopentyl, cyclopentenyl, cyclopentadienyl, cyclohexyl, cyclohexenyl, cyclohexadienyl and phenyl. When the group has various structural isomers as the cyclopentenyl, they are all embraced in it.

The saturated or unsaturated 5- to 7-membered heterocyclic group is a cyclic group having at least one hetero atom. Examples of the hetero atom include oxygen, nitrogen and sulfur. Examples of the saturated or unsaturated 5- to 7-membered heterocyclic group include furyl, pyrrolyl, thienyl, pyrazolyl, pyrazinyl, tetrahydropyrazinyl, imidazolyl, pyrazolinyl, oxazolyl, oxazolinyl, thiazolyl, thiazolinyl, thiazolidinyl, oxatriazolyl, thiadiazolyl, furazanyl, pyranyl, pyridyl, pyrimidinyl, tetrahydropyrimidinyl, pyridazinyl, tetrahydropyridazinyl, pyrrolidinyl, piperazinyl, piperidinyl, oxazinyl, oxadiazinyl, morpholinyl, thiazinyl, thiadiazinyl, thiomorpholinyl, tetrazolyl, tetrazinyl, triazolyl and triazinyl. Where the group has plural structural isomers as the pyranyl, it is to be noted that they are all embraced in it.

a, b, d, e and g each independently stands for an integer of 0 or 1, c stands for an integer of 0 to 3 and f, h and i each independently represents an integer of 1 to 3, with the proviso that the sum of a, b and c stands for an integer of 2 or 3, the sum of d and e stands for an integer of 0 or 1 and the sum of f, g and h stands for an integer of 3 to 5.

In $R^{14}$ or $R^{17}$ as the substituent in $Q^3$, the alkyl, alkoxyl, hydroxyalkylcarbonyl, hydroxyalkylsulfonyl, alkoxyalkylcarbonyl, alkoxyalkylsulfonyl, formylalkyl, formylalkylcarbonyl, formylalkylsulfonyl, alkylcarbonyl, alkylsulfonyl, alkylcarbonylalkyl, alkylsulfonylalkyl, carboxyalkylcarbonyl, carboxyalkylsulfonyl, carboxyalkylcarbonylalkyl, carboxyalkylsulfonylalkyl, alkoxycarbonyl, alkoxycarbonylalkyl, alkoxycarbonylalkylcarbonyl, alkoxycarbonylalkylsulfonyl, amino which may have 1 to 2 substituents, aminoalkylcarbonyl in which the amino moiety may have 1 or 2 substituents, aminoalkyloxycarbonyl in which the amino moiety may have 1 or 2 substituents, aminocarbonyl in which the amino moiety may have 1 or 2 substituents, aminocarbonylalkyl in which the amino moiety may have 1 or 2 substituents, and aminocarbonyloxyalkyl in which the amino moiety may have 1 or 2 substituents have the same meanings as described above in $R^1$.

The "hydroxyalkyl group" means a group formed of a hydroxyl group and a linear, branched or cyclic $C_{2-6}$ alkylene group and examples include hydroxyethyl and hydroxypropyl.

The "alkoxyalkyl group" means a group formed of the above-described alkoxyl group and a linear, branched or cyclic $C_{2-6}$ alkylene group and examples include methoxyethyl and ethoxyethyl. The "aminoalkyl group in which the amino moiety may have one or two substituents" means a group formed of the above-described amino group which may have a substituent and a linear, branched or cyclic $C_{2-6}$ alkylene group and examples include aminoethyl and aminopropyl.

The "aminoalkyloxy group in which the amino moiety may have one or two substituents" means a group formed of the above-described amino group which may have a substituent, a linear, branched or cyclic $C_{2-6}$ alkylene group and an oxygen atom and examples include aminoethoxyl and aminopropoxyl.

In the group A³-B³—, A³ represents a saturated or unsaturated 5- or 6-membered cyclic hydrocarbon group which may have a substituent or a saturated or unsaturated 5- or 6-membered heterocyclic group which may have a substituent. Here, examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl. When the group has various structural isomers as the cyclopentenyl, they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, pyrazinyl, tetrahydropyrazinyl, imidazolyl, pyrazolinyl, oxazolyl, oxazolinyl, thiazolyl, thiazolinyl, thiazolidinyl, oxatriazolyl, thiadiazolyl, furazanyl, pyranyl, pyridyl, pyrimidinyl, tetrahydropyrimidinyl, pyridazinyl, tetrahydropyridazinyl, pyrrolidinyl, piperazinyl, piperidinyl, oxazinyl, oxadiazinyl, morpholinyl, thiazinyl, thiadiazinyl, thiomorpholinyl, tetrazolyl, tetrazinyl, triazolyl and triazinyl. Where the group has plural structural isomers as the pyranyl, it is to be noted that they are all embraced in it.

B³ represents a single bond, carbonyl group or alkylene group. The "alkylene group" means a linear, branched or cyclic $C_{1-6}$ alkylene group.

Examples of the group A³-B³— include the following groups: a saturated or unsaturated 5- or 6-membered heterocyclic group which may have a substituent, a group formed of a saturated or unsaturated 5- or 6-membered cyclic hydrocarbon group which may have a substituent and a carbonyl group, and a group formed of a saturated or unsaturated 5- or 6-membered heterocyclic group which may have a substituent and an alkylene group.

$R^{14}$ and $R^{12}$, $R^{14}$ and $R^{13}$, $R^{17}$ and $R^{15}$, and $R^{17}$ and $R^{16}$ are each coupled together with the carbon atom which constitutes the ring and the nitrogen atom to which $R^{14}$ or $R^{17}$ has been bonded and represent a saturated or unsaturated 5- to 7-membered heterocyclic group which may have a substituent. Here, examples of the saturated or unsaturated 5- to 7-membered heterocyclic group is a cyclic group which has at least one nitrogen atom and may have a hetero atom. Examples of the hetero atom include oxygen, nitrogen and sulfur. Examples of the saturated or unsaturated 5- to 7-membered heterocyclic group include furyl, pyrrolyl, thienyl, pyrazolyl, pyrazinyl, tetrahydropyrazinyl, imidazolyl, pyrazolinyl, oxazolyl, oxazolinyl, thiazolyl, thiazolinyl, thiazolidinyl, oxatriazolyl, thiadiazolyl, furazanyl, pyranyl, pyridyl, pyrimidinyl, tetrahydropyrimidinyl, pyridazinyl, tetrahydropyridazinyl, pyrrolidinyl, piperazinyl, piperidinyl, oxazinyl, oxadiazinyl, morpholinyl, thiazinyl, thiadiazinyl, thiomorpholinyl, tetrazolyl, tetrazinyl, triazolyl and triazinyl. Where the group has plural structural isomers as the pyranyl, it is to be noted that they are all embraced in it.

In the present invention, $Q^3$ represents a group of the following formula:

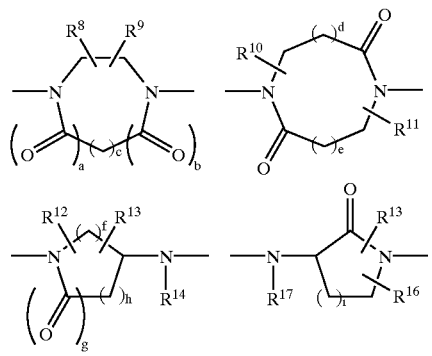

(wherein $R^8$, $R^9$, $R^{10}$, $R^{12}$, $R^{13}$, $R^{14}$, $R^{15}$, $R^{16}$, $R^{17}$, a, b, c, d, e, f, g, h and i have the same meanings as described above), with the group of the following formula:

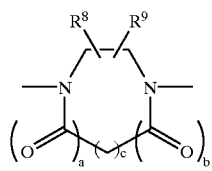

(wherein $R^8$, $R^9$, a, b and c have the same meanings as described above) being preferred.

$T^1$ represents a carbonyl group, a group —CH($R^{18}$)—

(in which $R^{18}$ represents a hydrogen atom, an alkyl group, a hydroxyalkyl group, an alkoxyalkyl group, a carboxyalkyl group, an alkoxycarbonylalkyl group, an aryl group, an aralkyl group, a heteroaryl group, a heteroarylalkyl group or an aminoalkyl group in which the amino moiety may have a substituent) or a group —C(=NOR¹⁹)—

(in which $R^{19}$ represents a hydrogen atom, an alkyl group, a carboxyalkyl group, an alkoxycarbonyl group, an aryl group, an aralkyl group, a heteroaryl group, a heteroarylalkyl group or an aminoalkyl group in which the amino moiety may have a substituent).

Here, the alkyl, carboxyalkyl, alkoxycarbonyl, aryl, aralkyl, heteroaryl, heteroarylalkyl and aminoalkyl in which the amino moiety may have a substituent in $R^{18}$ or $R^{19}$ have the same meanings as described in $R^1$. In the present invention, a carbonyl group is preferred as $T^1$.

In the present invention, the group:

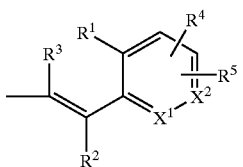

in the formula (1) means a group:

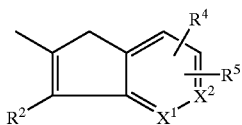

or another group:

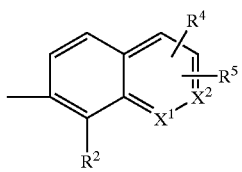

and, $R^4$ represents a halogen atom.

In the present invention, preferred as $Q^1$ are a cyclopentyl group which may have a substituent, a cyclohexyl group which may have a substituent, a cyclopentenyl group which may have a substituent, a cyclohexenyl group which may have a substituent, a phenyl group which may have a substituent, a pyrrolidinyl group which may have a substituent, a piperidinyl group which may have a substituent, an imidazolyl group which may have a substituent, a thiazolyl group which may have a substituent, a thiadiazolyl group which may have a substituent, a pyridyl group which may have a substituent, a pyrimidinyl group which may have a substituent, a pyridazinyl group which may have a substituent, a thiazolidinyl group which may have a substituent, a morpholinyl group which may have a substituent, a piperazinyl group which may have a substituent, a thiomorpholinyl group which may have a substituent, a pyrrolyl group which may have a substituent, a thienyl group which may have a substituent, a furanyl group which may have a substituent, a tetrahydropyrimidinyl group which may have a substituent, a tetrahydrofuranyl group which may have a substituent, a tetrahydrothienyl group which may have a substituent, a sulfolanyl group which may have a substituent, an imidazolinyl group which may have a substituent, a thiazolinyl group which may have a substituent, an oxazolyl group which may have a substituent, an oxadiazinyl group which may have a substituent, a triazinyl group which may have a substituent, a tetrazinyl group which may have a substituent, a pyrazinyl group which may have a substituent, a pyrazolyl group which may have a substituent, a pyrazolinyl group which may have a substituent, a pyrazolidinyl group which may have a substituent, a thienopyridyl group which may have a substituent, a tetrahydrothienopyridyl group which may have a substituent, a thiazolopyridyl group which may have a substituent, and a tetrahydrothiazolopyridyl group which may have a substituent.

Preferred as the substituent are saturated or unsaturated, 5- or 6-membered cyclic hydrocarbon groups each of which may have 1 to 3 substituents selected from the group consisting of a hydroxyl group, alkyl groups, hydroxyalkyl groups, halogen atoms, a cyano group, a nitro group, a carboxyl group, alkoxycarbonyl groups, a formyl group, alkylsulfonyl groups, amino groups which may have 1 or 2 substituents, aminosulfonyl groups which may have, at the amino moiety thereof, 1 or 2 substituents, aminoalkyl groups which may have, at the amino moiety thereof, 1 or 2 substituents, an oxygen atom, a trifluoromethyl group, halogen atoms, a hydroxyl group, amino groups, alkoxyl groups, alkyl groups, a cyano group, a nitro group, a carboxyl group, alkoxycarbonyl groups, aminocarbonyl groups which may have, at the amino moiety thereof, 1 or 2 substituents, aminosulfonyl groups which may have, at the amino moiety thereof, 1 or 2 substituents, aminoalkyl groups which may have, at the amino moiety thereof, 1 or 2 substituents and a trifluoromethyl group; and saturated or unsaturated 5- or 6-membered heterocyclic groups each of which may have 1 to 3 substituents selected from the group consisting of halogen atoms, a hydroxyl group, amino groups, alkoxyl groups, alkyl groups, a cyano group, a nitro group, a carboxyl group, alkoxycarbonyl groups, aminocarbonyl groups which may have, at the amino moiety thereof, 1 or 2 substituents, aminosulfonyl groups which may have, at the amino moiety thereof, 1 or 2 substituents, aminoalkyl groups which may have, at the amino moiety thereof, 1 or 2 substituents and a trifluoromethyl group.

In the present invention, preferred examples of $Q^2$ include a single bond, a carbonyl group and groups represented by the following formula:

Among the groups represented by the following formula:

divalent groups derived from benzene, pyrimidine, tetrahydropyrimidine, pyrazine, pyridazine, triazine, tetrazine, imidazole, imidazoline, thiazole, thiazoline, furan, thiophene, pyrrole, oxazole, oxazoline, thiadiazole, cyclopentane, cyclopentene, cyclohexane or cyclohexene are preferred.

Particularly preferred is the case where: $Q^3$ means the following group:

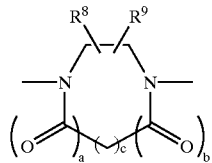

[wherein, $R^8$, $R^9$, a, b and c have the same meanings as described above]; and $T^1$ represents a carbonyl group.

The sulfonyl derivative of the present invention has optical isomers or stereoisomers based on an asymmetric carbon atom. These optical isomers and stereoisomers and mixtures thereof are all embraced in the present invention.

There is no particular limitation imposed on the salt of the sulfonyl derivative according to the present invention insofar as it is pharmaceutically acceptable. Specific examples include salts of a mineral acid such as hydrochloride, hydrobromide, hydroiodide, phosphate, nitrate and sulfate, benzoate, salts of an organic sulfonic acid such as methanesulfonate, 2-hydroxyethanesulfonate and p-toluenesulfonate and salts of an organic carboxylic acid such as acetate, propanoate, oxalate, malonate, succinate, glutarate, adipate, tartrate, maleate, malate and mandelate. There is no particular limitation imposed on the solvate insofar as it is pharmaceutically acceptable. Specific examples include hydrates and ethanolates.

The following are the preferred compounds as the sulfonyl derivative of the present invention.

1-[(6-Chloronaphthalen-2-yl)sulfonyl]-4-[4-(pyridin-4-yl)benzoyl]piperazine hydrochloride
4-[(6-Chloronaphthalen-2-yl)sulfonyl]-1-[4-(pyridin-4-yl)benzoyl]piperazine-2-carboxylic acid hydrochloride
1-[(6-Chloronaphthalen-2-yl)sulfonyl]-4-[4-(pyridin-4-yl)nicotinyl]piperazine hydrochloride
4-[4-[[4-[(6-Chloronaphthalen-2-yl)sulfonyl]piperazin-1-yl]carbonyl]phenyl]pyridine N-oxide
1-[4-(2-Aminopyridin-5-yl)benzoyl]-4-[(6-chloronaphthalen-2-yl)sulfonyl]piperazine hydrochloride
1-[(6-Chloronaphthalen-2-yl)sulfonyl]-4-[4-[imidazol-4(5)-yl]benzoyl]piperazine hydrochloride
1-[4-[2-Aminoimidazol-4-yl]benzoyl]-4-[(6-chloronaphthalen-2-yl)sulfonyl]piperazine hydrochloride
1-[(6-Chloronaphthalen-2-yl)sulfonyl]-4-[4-(pyridin-2-yl)benzoyl]piperazine hydrochloride
2-[4-[[4-[(6-Chloronaphthalen-2-yl)sulfonyl]piperazin-1-yl]carbonyl]phenyl]pyridine N-oxide
2-[4-[[4-[(6-Chloronaphthalen-2-yl)sulfonyl]piperazin-1-yl]carbonyl]phenyl]-1-methylpyridinium iodide
1-[(6-Chloronaphthalen-2-yl)sulfonyl]-4-[4-(2,4-diaminopyrimidin-6-yl)benzoyl]piperazine hydrochloride
1-[(E)-4-Chlorostyrylsulfonyl]-4-[4-(2,4-diaminopyrimidin-6-yl)benzoyl]piperazine hydrochloride
2-[4-[[4-[(E)-4-Chlorostyrylsulfonyl]piperazin-1-yl]carbonyl]phenyl]pyridine N-oxide
1-[(E)-4-Chlorostyrylsulfonyl]-4-[4-(pyridin-4-yl)benzoyl]piperazine hydrochloride
3-[4-[[4-[(6-Chloronaphthalen-2-yl)sulfonyl]piperazin-1-yl]carbonyl]phenyl]-1-methylpyridinium iodide
1-[(6-Chloronaphthalen-2-yl)sulfonyl]-4-[2-hydroxy-4-(pyridin-4-yl)benzoyl]piperazine hydrochloride
1-[(6-Chloronaphthalen-2-yl)sulfonyl]-2-ethoxycarbonyl-4-[4-(pyridin-4-yl)benzoyl]piperazine
1-[(6-Chloronaphthalen-2-yl)sulfonyl]-4-[4-(pyridin-4-yl)benzoyl]piperazine-2-carboxylic acid
2-Carbamoyl-4-[(6-chloronaphthalen-2-yl)sulfonyl]-1-[4-(pyridin-3-yl)benzoyl]piperazine hydrochloride
2-Carbamoyl-4-[(6-chloronaphthalen-2-yl)sulfonyl]-1-[4-(pyridin-4-yl)benzoyl]piperazine hydrochloride
4-[4-[[2-Carbamoyl-4-[(6-chloronaphthalen-2-yl)sulfonyl]piperazin-1-yl]carbonyl]phenyl]pyridine N-oxide
4-[4-[[4-[(6-Chloronaphthalen-2-yl)sulfonyl]-2-ethoxycarbonylpiperazin-1-yl]carbonyl]phenyl]pyridine N-oxide
4-[4-[[2-Carboxy-4-[(6-Chloronaphthalen-2-yl)sulfonyl]piperazin-1-yl]carbonyl]phenyl]pyridine N-oxide
2-Carbamoyl-4-[(E)-4-chlorostyrylsulfonyl]-[1-[4-(pyridin-4-yl)benzoyl]piperazine hydrochloride
1-[trans-4-(Aminomethyl)cyclohexylcarbonyl]-4-[(6-chloronaphthalen-2-yl)sulfonyl]piperazine hydrochloride
1-[[(6RS)-6-Aminomethyl-5,6,7,8-tetrahydronaphthalen-2-yl]carbonyl]-4-[(6-chloronaphthalen-2-yl)sulfonyl]piperazine hydrochloride
1-[(7-Aminomethylnaphthalen-2-yl]carbonyl]-4-[(6-chloronaphthalen-2-yl)sulfonyl]piperazine hydrochloride
1-[(6-Chloronaphthalen-2-yl]sulfonyl]-4-[4-[[(3S)-pyrrolidin-3-yl]oxy]benzoyl]piperazine hydrochloride
1-[(6-Chloronaphthalen-2-yl)sulfonyl]-4-[4-[(3RS)-pyrrolidin-3-yl]benzoyl]piperazine hydrochloride
1-[(6-Chloronaphthalen-2-yl)sulfonyl]-4-[(4,5,6,7-tetrahydrothieno[3,2-c]pyridin-2-yl)carbonyl]piperazine hydrochloride
4-[(6-Chloronaphthalen-2-yl)sulfonyl]-2-ethoxycarbonyl-1-[(4,5,6,7-tetrahydrothieno[3,2-c]pyridin-2-yl)carbonyl]piperazine hydrochloride
2-Carboxy-4-[(6-Chloronaphthalen-2-yl)sulfonyl]-1-[(4,5,6,7-tetrahydrothieno[3,2-c]pyridin-2-yl)carbonyl]piperazine hydrochloride
1-[(6-Chloronaphthalen-2-yl)sulfonyl]-4-[(5-aminohydroxyiminomethyl-4,5,6,7-tetrahydrothieno[3,2-c]pyridin-2-yl)carbonyl]piperazine
1-[(6-Chloronaphthalen-2-yl)sulfonyl]-4-[[5-(1-pyrrolin-2-yl)-4,5,6,7-tetrahydrothieno[3,2-c]pyridin-2-yl]carbonyl]piperazine hydrochloride
1-[(6-Chloronaphthalen-2-yl)sulfonyl]-4-[(4,5,6,7-tetrahydrothiazolo[5,4-c]pyridin-2-yl)carbonyl]piperazine hydrochloride
1-[(6-Chloronaphthalen-2-yl)sulfonyl]-4-[(6-aminohydroxyiminomethyl-4,5,6,7-tetrahydrothiazolo[5,4-c]pyridin-2-yl)carbonyl]piperazine hydrochloride
1-[(6-Chloronaphthalen-2-yl)sulfonyl]-4-[(6-formyl-4,5,6,7-tetrahydrothiazolo[5,4-c]pyridin-2-yl)carbonyl]piperazine
1-[(6-Chloronaphthalen-2-yl)sulfonyl]-4-[[6-methyl-4,5,6,7-tetrahydrothiazolo[5,4-c]pyridin-2-yl)carbonyl]piperazine hydrochloride
2-[[4-[(6-Chloronaphthalen-2-yl)sulfonyl]piperazin-1-yl]carbonyl]-6,6-dimethyl-4,5,6,7-tetrahydrothiazolo[5,4-c]pyridinium iodide
2-[[4-[(6-Chloronaphthalen-2-yl)sulfonyl]piperazin-1-yl]carbonyl]-6-methyl-4,5,6,7-tetrahydrothiazolo[5,4-c]pyridine N-oxide
2-Carbamoyl-4-[(6-Chloronaphthalen-2-yl)sulfonyl]-1-[(4,5,6,7-tetrahydrothiazolo[5,4-c]pyridin-2-yl)carbonyl]piperazine trifluoroacetate
2-Carbamoyl-4-[(6-chloronaphthalen-2-yl)sulfonyl]-1-[(6-methyl-4,5,6,7-tetrahydrothiazolo[5,4-c]pyridin-2-yl)carbonyl]piperazine hydrochloride
1-[(6-Chloronaphthalen-2-yl)sulfonyl]-4-[[6-(2-hydroxyethyl)-4,5,6,7-tetrahydrothiazolo[5,4-c]pyridin-2-yl]carbonyl]piperazine hydrochloride
1-[(6-Chloronaphthalen-2-yl)sulfonyl]-4-[[6-(pyridin-3-yl)methyl-4,5,6,7-tetrahydrothiazolo[5,4-c]pyridin-2-yl]carbonyl]piperazine hydrochloride
1-[(E)-4-Chlorostyrylsulfonyl]-4-[(4,5,6,7-tetrahydrothiazolo[5,4-c]pyridin-2-yl)carbonyl]piperazine hydrochloride
1-[(6-Chloronaphthalen-2-yl)sulfonyl]-4-[[(1RS)-4-(pyridin-4-yl)-3-cyclohexenyl]carbonyl]piperazine hydrochloride
cis-, trans-1-[(6-Chloronaphthalen-2-yl)sulfonyl]-4-[[4-(pyridin-4-yl)cyclohexanyl]carbonyl]piperazine hydrochloride
6-[[4-[(6-Chloronaphthalen-2-yl)sulfonyl]piperazin-1-yl]carbonyl]-2,2-dimethyl-1,2,3,4-tetrahydroisoquinolinium iodide
1-[(6-Chloronaphthalen-2-yl)sulfonyl]-4-[4-(1,2,3,6-tetrahydropyridin-4-yl)benzoyl]piperazine hydrochloride
1-[[(E)-2-(6-Chloropyridin-3-yl)vinyl]sulfonyl]-4-[4-(pyridin-4-yl)benzoyl]piperazine
1-[(6-Chloronaphthalen-2-yl)sulfonyl]-4-[2-methyl-4-(pyridin-4-yl)benzoyl]piperazine hydrochloride
4-[4-[[4-[(6-Chloronaphthalen-2-yl)sulfonyl]piperazin-1-yl]carbonyl]-2-methylphenyl]pyridine N-oxide
1-[(6-Chloronaphthalen-2-yl)sulfonyl]-4-[4-(2-methylpyridin-4-yl)benzoyl]piperazine hydrochloride
4-[4-[[4-[(6-Chloronaphthalen-2-yl)sulfonyl]-piperazin-1-yl]carbonyl]phenyl]-2-methylpyridine N-oxide
4-[4-[[4-(6-Chloronaphthalen-2-yl)sulfonyl]-2-[[2-(morpholin-4-yl)ethylamino]carbonyl]piperazin-1-yl]carbonyl]phenyl]pyridine N-oxide
4-[4-[[4-[(6-Chloronaphthalen-2-yl)sulfonyl]-2-[[2-(dimethylamino)ethylamino]carbonyl]piperazin-1-yl]carbonyl]phenyl]pyridine N-oxide 4-[(6-Chloronaphthalen-2-yl)sulfonyl]-2-methoxycarbonylmethyl-1-[4-(pyridin-2-yl)benzoyl]piperazine 4-[(6-Chloronaphthalen-2-yl)sulfonyl]-2-carboxymethyl-1-[4-(pyridin-2-yl)benzoyl]piperazine hydrochloride 2-Carbamoylmethyl-4-[(6-chloronaphthalen-2-yl)sulfonyl]-1-[4-(pyridin-2-yl)benzoyl]piperazine hydrochloride 1-[4-[(3RS)-1-Acetimidoylpyrrolidin-3-yl]benzoyl]-4-[(6-chloronaphthalen-2-yl)sulfonyl]piperazine hydrochloride 1-[(6-Chloronaphthalen-2-yl)sulfonyl]-4-[4-(2-acetoxymethylpyrrolidin-4-yl)benzoyl]piperazine 1-[(6-Chloronaphthalen-2-yl)sulfonyl]-4-[4-(2-hydroxymethylpyridin-4-yl)benzoyl]piperazine hydrochloride 2-Hydroxymethyl-4-[4-[[4-[(6-chloronaphthalen-2-yl)sulfonyl]piperazin-1-yl]carbonyl]phenyl]pyridine N-oxide 2-Carbamoyl-4-[(6-chloronaphthalen-2-yl)sulfonyl]-1-[4-(2-aminoimidazol-4-yl)benzoyl]piperazine 2-[[1-[(6-Chloronaphthalen-2-yl)sulfonyl]piperazin-4-yl]carbonyl-4-phenyl]-6-methylpyridine N-oxide 1-[(6-Chloronaphthalen-2-yl)sulfonyl]-4-[4-(6-methylpyridin-2-yl)benzoyl]piperazine hydrochloride 1-[(6-Chloronaphthalen-2-yl)sulfonyl]-4-[4-(3-aminopyridin-2-yl)benzoyl]piperazine hydrochloride 4-[4-[[1-[(6-Chloronaphthalen-2-yl)sulfonyl]piperazin-4-yl]carbonyl]-3-methylphenyl]pyridine N-oxide 1-[2-tert-Butoxycarbonyl-4-(pyridin-4-yl)benzoyl]-4-[(6-chloronaphthalen-2-yl)sulfonyl]piperazine 1-[2-Carboxy-4-(pyridin-4-yl)benzoyl]-4-[(6-chloronaphthalen-2-yl)sulfonyl]piperazine 1-(4-Amidinobenzoyl)-4-[(6-chloronaphthalen-2-yl)sulfonyl]piperazine hydrochloride 2-Carbamoyl-4-[(6-chloronaphthalen-2-yl)sulfonyl]-1-[4-[imidazol-4(5)-yl]benzoyl]piperazine hydrochloride 1-[4-(2-Aminopyridin-4-yl)benzoyl]-4-[(6-chloronaphthalen-2-yl)sulfonyl]piperazine hydrochloride 1-[4-(2-Aminothiazol-4-yl)benzoyl]-4-[(6-chloronaphthalen-2-yl)sulfonyl]piperazine 2-Carbamoyl-4-[(E)-4-chlorostyrylsulfonyl]-1-[4-(pyridin-4-yl)benzoyl]piperazine hydrochloride 4-[5-[[4-[(6-Chloronaphthalen-2-yl)sulfonyl]piperazin-1-yl]carbonyl]pyridin-2-yl]pyridine N-oxide 2-Amino-4-[4-[[4-[(6-chloronaphthalen-2-yl)sulfonyl]piperazin-1-yl]carbonyl]phenyl]pyridine N-oxide 4-[4-[[4-[(E)-4-Chlorostyrylsulfonyl]piperazin-1-yl]carbonyl]phenyl]pyridine N-oxide 4-[4-[[4-[(6-Chloronaphthalen-2-yl)sulfonyl]-2-ethoxycarbonylpiperazin-1-yl]carbonyl]phenyl]pyridine N-oxide 4-[(6-Chloronaphthalen-2-yl)sulfonyl]-2-methoxycarbonylmethyl-1-[4-(pyridin-2-yl)benzoyl]piperazine hydrochloride 2-Carboxymethyl-4-[(6-chloronaphthalen-2-yl)sulfonyl]-1-[4-(pyridin-2-yl)benzoyl]piperazine hydrochloride 2-Carbamoylmethyl-4-[(6-chloronaphthalen-2-yl)sulfonyl]-1-[4-(pyridin-2-yl)benzoyl]piperazine hydrochloride 2-[4-[[2-carbamoylmethyl-4-[(6-chloronaphthalen-2-yl)sulfonyl]piperazin-1-yl]carbonyl]phenyl]pyridine N-oxide 2-Methyl-4-[4-[[4-[(6-chloronaphthalen-2-yl)sulfonyl]piperazin-1-yl]carbonyl]phenyl]pyridine N-oxide 1-[(6-Chloronaphthalen-2-yl)sulfonyl]-2,3-dimethyl-4-[4-(pyridin-4-yl)benzoyl]piperazine hydrochloride 2-[4-[[4-[(6-Chloronaphthalen-2-yl)sulfonyl]-2-hydroxymethyl-3-methylpiperazin-1-yl]carbonyl]phenyl]pyridine N-oxide 4-[4-[[4-[(6-Chloronaphthalen-2-yl)sulfonyl]-2,3-dimethylpiperazin-1-yl]carbonyl]phenyl]pyridine N-oxide 4-[(6-Chloronaphthalen-2-yl)sulfonyl]-2,6-dimethyl-1-[4-(pyridin-4-yl)benzoyl]piperazine hydrochloride 4-[(6-Chloronaphthalen-2-yl)sulfonyl]-2,2-dimethyl-1-[4-(pyridin-4-yl)benzoyl]piperazine hydrochloride 2-[4-[[4-[(6-Chloronaphthalen-2-yl)sulfonyl]-2,2-dimethylpiperazin-1-yl]carbonyl]phenyl]pyridine N-oxide 4-[(6-Chloronaphthalen-2-yl)sulfonyl]-2-oxo-1-[4-(pyridin-4-yl)benzoyl]piperazine N-oxide 1-[(6-Chloronaphthalen-2-yl)sulfonyl]-2,3-dicarbamoyl-4-[4-(pyridin-2-yl)benzoyl]piperazine hydrochloride 1-[(6-Chloronaphthalen-2-yl)sulfonyl]-2-methyl-3-[2-(morpholin-4-yl)ethylamino]carbonyl]-4-[4-(pyridin-4-yl)benzoyl]piperazine hydrochloride 4-[4-[[4-(6-Chloronaphthalen-2-yl)sulfonyl-3-methyl-2-[[2-(morpholin-4-yl)ethylamino]carbonyl]piperazin-1-yl]carbonyl]phenyl]pyridine N-oxide 2-Carbamoylmethyl-4-[(6-chloronaphthalen-2-yl)sulfonyl]-3-methyl-1-[4-(pyridin-4-yl)benzoyl]piperazine hydrochloride 4-[4-[[2-Carbamoylmethyl-4-[(6-chloronaphthalen-2-yl)sulfonyl]-6-methylpiperazin-1-yl]carbonyl]phenyl]pyridine N-oxide 2-[4-[[2-Carbamoylmethyl-4-[(6-chloronaphthalen-2-yl)sulfonyl]-6-oxopiperazin-1-yl]carbonyl]phenyl]pyridine N-oxide 1-[(6-Chloronaphthalen-2-yl)sulfonyl]-4-[4-(pyridin-2-yl)benzoyl]-1,2,3,4-tetrahydroquinoxaline hydrochloride 1-[(6-Chloronaphthalen-2-yl)sulfonyl]-4-[4-(pyridin-4-yl)benzoyl]decahydroquinoxaline hydrochloride 1-[(6-Chloronaphthalen-2-yl)sulfonyl]-3-[(ethoxycarbonylmethylsulfonylamino)methyl]-2-methyl-4-[4-(pyridin-2-yl)benzoyl]piperazine hydrochloride 2-Carbamoylmethyl-4-[(6-chloronaphthalen-2-yl)sulfonyl]-3-oxo-1-[4-(pyridin-2-yl)benzoyl]piperazine hydrochloride 1-[(6-Chloronaphthalen-2-yl)sulfonyl]-3-(imidazol-4-yl)methyl-2-oxo-4-[4-(pyridin-2-yl)benzoyl]piperazine hydrochloride 4-[(6-Chloronaphthalen-2-yl)sulfonyl]-1-[4-(pyridin-4-yl)benzoyl]-7-oxodecahydropyrido[3,4-b]pyrazine hydrochloride.

2-Carbamoyl-4-[(6-chloronaphthalen-2-yl)sulfonyl]-3-methyl-1-[(6-methyl-4,5,6,7-tetrahydrothiazolo[5,4-c]pyridin-2-yl)carbonyl]piperazine hydrochloride 2-Carbamoyl-4-[(6-chloronaphthalen-2-yl)sulfonyl]-6-methyl-1-[(6-methyl-4,5,6,7-tetrahydrothiazolo[5,4-c]pyridin-2-yl)carbonyl]piperazine hydrochloride 4-[(6-Chloronaphthalen-2-yl)sulfonyl]-1-[(6-methyl-4,5,6,7-tetrahydrothiazolo[5,4-c]pyridin-2-yl)carbonyl]-2-[[2-(morpholin-4-yl)ethylamino]carbonyl]piperazine hydrochloride 1-[(6-Chloronaphthalen-2-yl)sulfonyl]-4-[(6-methyl-5,6,7,8-tetrahydro-1,6-naphthyridin-2-yl)carbonyl]piperazine hydrochloride 2-Carbamoyl-4-[(6-chloronaphthalen-2-yl)sulfonyl]-3-methyl-1-[(6-methyl-5,6,7,8-tetrahydropyrido-1,6-naphthyridin-2-yl)carbonyl]piperazine hydrochloride The process for the preparation of the sulfonyl derivative of the present invention will next be described.

The sulfonyl derivative, salt thereof and solvate thereof according to the present invention can be prepared by using general, conventionally-known chemical processes in combination. Typical synthesis processes will be described subsequently.

Upon synthesis of the sulfonyl derivative of the present invention, when it is necessary to protect a substituent such as nitrogen atom, hydroxyl group or carboxyl group, it may be protected with a ordinary, conventionally-known protecting group which can be removed as needed. Such a protecting group can be removed at need by the synthesis process ordinarily employed in the organic chemistry which will be described below. The starting materials necessary for the synthesis can be obtained by the synthesis process ordinarily employed in the organic chemistry and such a process will be described in Referential Examples. The starting materials can also be synthesized by the application of the process described in Referential Examples.

A description will next be made of a protecting group for the substituent such as nitrogen atom, hydroxyl group or carboxyl group and deprotection process thereof.

As a protecting group for the nitrogen atom in an amino or alkylamino group, ordinary acyl-type protecting groups are suited. Examples include alkanoyl groups such as acetyl, alkoxycarbonyl groups such as methoxycarbonyl, ethoxycarbonyl and tertiary butoxy carbonyl, arylmethoxycarbonyl groups such as benzyloxycarbonyl, paramethoxybenzyloxycarbonyl and para-(ortho-)nitrobenzyloxycarbonyl groups, aryolmethyl groups such as benzyl and triphenylmethyl and aroyl groups such as benzoyl. The removing process of such a protecting group differs with the chemical properties of the protecting group adopted. For example, the acyl-type protecting group such as alkanoyl, alkoxycarbonyl or aroyl can be removed by hydrolysis using an appropriate base such as alkali metal hydroxide, for example, lithium hydroxide, sodium hydroxide or potassium hydroxide.

The substituted methoxycarbonyl type protecting group such as tertiary butoxycarbonyl or paramethoxybenzyloxycarbonyl can be removed by using an appropriate acid, for example, acetic acid, hydrochloric acid, hydrobromic acid, sulfuric acid, phosphoric acid, trifluoroacetic acid or trifluoromethanesulfonic acid or combination thereof. The arylmethoxycarbonyl group such as benzyloxycarbonyl, paramethoxybenzyloxycarbonyl or para-(ortho-)nitrobenzyloxycarbonyl, or the arylmethyl group such as benzyl can be removed by hydrogenolysis in the presence of a palladium-carbon catalyst. The benzyl group can also be removed by Birch reduction, in liquid ammonia, in the presence of a metal sodium, whereby conversion into a nitrogen-hydrogen bond can be effected. The triphenylmethyl group can be removed by using an appropriate acid such as acetic acid, hydrochloric acid, hydrobromic acid, sulfuric acid, phosphoric acid, trifluoroacetic acid or trifluoromethanesulfonic acid or combination thereof. It can also be removed by Birch reduction, in liquid ammonia, in the presence of a metal sodium or by hydrogenolysis in the presence of a palladium-carbon catalyst.

In addition to the above-described amino-protecting group, a phthaloyl type protecting group can be adopted for a primary amino group and it can be removed using hydrazine, dimethylaminopropylamine or the like.

As the protecting group suited for a hydroxyl group, there are acyl type and ether type ones. Examples of the acyl type protecting group include alkanoyl groups such as acetyl and aroyl groups such as benzoyl, while those of the ether type protecting group include arylmethyl groups such as benzyl, silyl ether groups such as tertiary butyl dimethylsilyl, methoxymethyl and tetrahydropyranyl. The removal of such a protecting group differs with the chemical properties of the protecting group adopted. For example, the acyl group such as alkanoyl or aroyl can be removed by the hydrolysis using an appropriate base such as an alkali metal hydroxide, for example, lithium hydroxide, sodium hydroxide or potassium hydroxide. The arylmethyl type protecting group can be removed by the hydrogenolysis using a palladium-carbon catalyst. The silyl group such as tertiary butyl dimethylsilyl can be removed using a hydrofluoride salt such as tetrabutyl ammonium fluoride. The methoxymethyl or tetrahydropyranyl group can be removed using acetic acid, hydrochloric acid or the like. The hydroxyl group substituted for an aryl group can be protected with a methyl group and deprotection can be carried out using a Lewis acid such as aluminum chloride or phosphorus tribromide, trimethylsilyl iodide or hydrogen bromide.

A carboxyl group can be protected by the esterification of it. A methyl or ethyl ester can be deprotected by the hydrolysis using an appropriate base such as alkali metal hydroxide, e.g., lithium hydroxide, sodium hydroxide or potassium hydroxide, while from a tertiary butyl ester, the tertiary butyl group can be removed by treating with trifluoroacetic acid or hydrochloric acid. From an arylmethyl type ester such as benzyl, the arylmethyl group can be removed by the hydrogenolysis in the presence of a palladium-carbon catalyst.

[Preparation Process-1]

A process for preparing a sulfonyl derivative represented by the following formula (I):

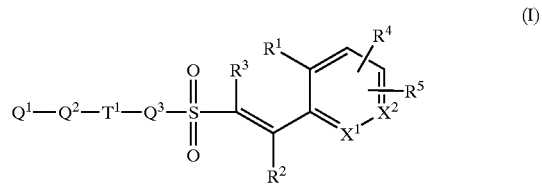

[wherein $R^1$, $R^2$, $R^3$, $R^4$, $R^5$, $Q^1$, $Q^2$, $Q^3$, $T^1$, $X^1$ and $X^2$ have the same meanings as described above], which comprises sulfonylating the nitrogen atom of $Q^{3a}$ of the compound represented by the following formula (Ia):

[wherein $Q^1$, $Q^2$ and $T^1$ have the same meanings as described above and $Q^{3a}$ represents any one of the groups represented by the following formulas:

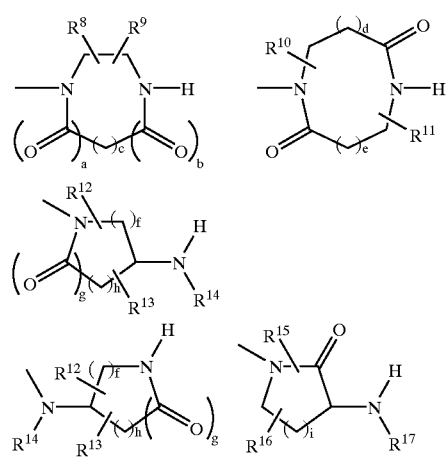

-continued

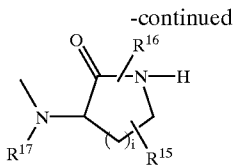

(in which $R^8$, $R^9$, $R^{10}$, $R^{11}$, $R^{12}$, $R^{13}$, $R^{14}$, $R^{15}$, $R^{16}$, $R^{17}$, a, b, c, d, e, f, g, h and i have the same meanings as described above)] with a sulfonic acid halide represented by the following formula (IIa):

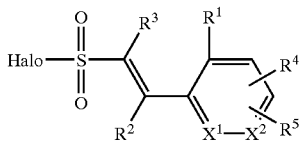

[wherein $R^1$, $R^2$, $R^3$, $R^4$, $R^5$, $X^1$ and $X^2$ have the same meanings as described above and Halo represents a halogen atom such as chlorine, bromine or iodine].

<Synthesis of the Compound of the Formula (Ia)>

The compound of the formula (Ia) can be synthesized by a series of operations in accordance with the known technique.

For example, a compound of the following formula (Ib):

$$Q^1\text{—}Q^2\text{—}T^1\text{—}Q^{3b} \quad (Ib)$$

[wherein $Q^1$, $Q^2$ and $T^1$ have the same meanings as described above and $Q^{3b}$ represents any one of the following groups:

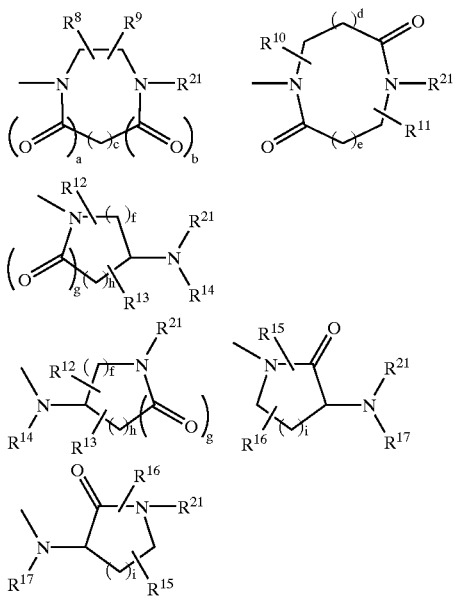

(in which $R^8$, $R^9$, $R^{10}$, $R^{11}$, $R^{12}$, $R^{13}$, $R^{14}$, $R^{15}$, $R^{16}$, $R^{17}$, a, b, c, d, e, f, g, h and i have the same meanings as described above and $R^{21}$ represents an ordinary nitrogen protecting group such as tertiary butoxycarbonyl, benzyloxycarbonyl, paramethoxybenzyloxycarbonyl, paranitrobenzyloxycarbonyl or benzyl)] can be synthesized by acylating the nitrogen atom of the compound represented by the following formula (IIIa):

$$Q^{3b}\text{—}H \quad (IIIa)$$

(wherein $Q^3$ has the same meaning as described above), to which nitrogen atom, the hydrogen atom of $Q^{3b}$ has been bonded, with a carboxylic acid in an activated form represented by any one of the following formulas (IVa) to (IVd):

$$Q^1\text{—}Q^{2b}\text{—}COOH \quad (IVa)$$

$$Q^1\text{—}N(R^{20})\text{—}(CH_2)_{m1}\text{—}COOH \quad (IVb)$$

$$Q^1\text{—}O\text{—}(CH_2)_{m1}\text{—}COOH \quad (IVc)$$

$$Q^1\text{—}S\text{—}(CH_2)_{m1}\text{—}COOH \quad (IVd)$$

[wherein $Q^1$ has the same meaning as described above, $R^{20}$ represents a linear or branched alkylene or an ordinary nitrogen protecting group such as tertiary butoxycarbonyl, benzyloxycarbonyl, paramethoxybenzyloxycarbonyl, paranitrobenzyloxycarbonyl or benzyl, $Q^{2b}$ represents single bond, a linear or branched $C_{1-6}$ alkylene, linear or branched $C_{2-6}$ alkenylene, linear or branched $C_{2-6}$ alkynylene or a group of the following formula:

(which has the same meaning as described above) and m1 stands for an integer of 1 to 6].

When the nitrogen atom of $Q^{3b}$ of the compound represented by the formula (IIIa) forms an amide bond, the compound of the formula (Ib) can be synthesized by alkylating the nitrogen atom of $Q^{3b}$ of the compound represented by the formula (IIIa) with any one of the compounds represented by the following formulas (Va) to (Vd):

$$Q^1\text{—}Q^{2b}\text{—}CHL^1R^{18} \quad (Va)$$

$$Q^1\text{—}N(R^{20})\text{—}(CH_2)_{m1}\text{—}CHL^1R^{18} \quad (Vb)$$

$$Q^1\text{—}O\text{—}(CH_2)_{m1}\text{—}CHL^1R^{18} \quad (Vc)$$

$$Q^1S\text{—}(CH_2)_{m1}\text{—}CHL^1R^{18} \quad (Vd)$$

[wherein $Q^1$, $Q^{2b}$, $R^{18}$, $R^{20}$ and m1 have the same meanings as described above, and $L^1$ represents an eliminating group frequently used in the organic chemistry, such as chlorine, bromine, iodine, methylsulfonyloxy or paratoluenesulfonyloxy].

When the nitrogen atom of $Q^{3b}$ of the compound represented by the formula (IIIa) exists as a primary or secondary amine, the compound of the formula (Ib) can be prepared by reductive alkylation, that is, by forming the corresponding imine with a carbonyl compound represented by any one of the following formulas (VIa) to (VId):

$$Q^1\text{—}Q^{2b}\text{—}C(\!=\!O)R^{18} \quad (VIa)$$

$$Q^1\text{—}N(R^{20})\text{—}(CH_2)_{m1}\text{—}C(\!=\!O)R^{18} \quad (VIb)$$

$$Q^1\text{—}O\text{—}(CH_2)_{m1}\text{—}C(\!=\!O)R^{18} \quad (VIc)$$

$$Q^1S\text{—}(CH_2)_{m1}\text{—}C(\!=\!O)R^{18} \quad (VId)$$

[wherein $Q^1$, $Q^{2b}$, $R^{18}$, $R^{20}$ and m1 have the same meanings as described above], followed by reduction; by reacting the compound of the formula (IIIa) with a reagent such as 1,1'-carbonyldiimidazole and a compound containing a primary amine represented by any one of the following formulas (VIIa) to (VIId):

$$Q^1\text{—}Q^2\text{—}NH_2 \quad (VIIa)$$

$$Q^1\text{—}N(R^{20})\text{—}(CH_2)_{m2}\text{—}NH_2 \quad (VIIb)$$

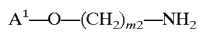 (VIIc)

 (VIId)

 (VIIe)

[wherein $Q^1$, $Q^2$ and $R^{20}$ have the same meanings as described above and m2 stands for an integer of 2 to 6 and a group of the following formula:

represents a 5- or 6-membered heterocyclic group which may have a substituent], thereby forming an urea derivative; or by reacting the amine of the formula (IIIa) with an isocyanate derivative or an isocyanate prepared from a carboxylic acid represented by any one of the formulas (IVa) to (IVd).

When in the structure of $Q^1$ of the compound represented by the formula (Ib), a halogen- or trifluoromethanesulfonyloxy-substituted aryl group or a halogen- or trifluoromethanesulfonyloxy-substituted alkenyl group is contained, coupling reaction can be effected with a boric-acid-substituted aryl compound in the presence of a transition metal catalyst.

When in the structure of $Q^1$ of the compound represented by the formula (Ib), an alkenyl group is contained, it can be subjected to coupling reaction with a halogen-substituted or trifluoromethanesulfonyloxy-substituted aryl group in the presence of a transition metal catalyst.

When in the structure of $Q^1$ of the compound represented by the formula (Ib), a boric-acid-substituted aryl group is contained, it can be subjected to coupling reaction with a halogen- or trifluoromethanesulfonyloxy-substituted aryl compound or a halogen- or trifluoromethanesulfonyloxy-substituted alkenyl compound. When in the structure of $Q^1$ of the compound represented by the formula (Ib), a halogen- or trifluoromethanesulfonyloxy-substituted aryl group is contained, it can be subjected to coupling reaction with an alkenyl compound in the presence of a transition metal catalyst. If the nitrogen atom of $Q^{3b}$ of the compound (Ib) so obtained has been protected, the compound of the formula (Ia) can be obtained by deprotection as needed.

Examples of the carboxylic acids of the following formulas (IVa) to (IVd) in an activated form include mixed acid anhydrides available by reacting any one of the carboxylic acids of the formulas (IVa) to (IVd) with a chloroformate ester such as isobutyl chloroformate, acid halides such as acyl chloride prepared using an acid halide such thionyl chloride, active esters obtained by reacting with a phenol such as paranitrophenol or pentafluorophenyl-trifluoroacetate, active esters obtained by reacting with N-hydroxybenztriazole or N-hydroxysuccinimide, reaction products with N,N'-dicyclohexylcarbodiimide or N-(3-dimethylaminopropyl)-N'-ethylcarbodiimide hydrochloride which is usually employed for the synthesis of amino acid peptide, reaction products with diethyl cyanophosphonate (Shioiri's method) and reaction products with triphenylphosphine and 2,2'-dipyridylsulfide (Mukaiyama's method).

The resulting carboxylic acid in an activated form is then reacted with the compound of the formula (IIIa) or salt thereof generally in the presence of an appropriate base in an inert solvent at −78° C. to 150° C., whereby the compound of the formula (Ib) can be obtained. Specific examples of the base include carbonates, alkoxides, hydroxides and hydrides of an alkali metal or alkaline earth metal, such as sodium carbonate, potassium carbonate, sodium ethoxide, potassium botoxide, sodium hydroxide, potassium hydroxide, sodium hydride and potassium hydride; organic metal bases typified by an alkyl lithium such as n-butyl lithium and a dialkylamino lithium such as lithium diisopropylamide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent include alkyl halide solvents such as dichloromethane, chloroform and carbon tetrachloride; ether solvents such as tetrahydrofuran, 1,2-dimethoxyethane and dioxane; aromatic solvents such as benzene and toluene; and amide solvents such as N,N-dimethylformamide, N,N-dimethylacetamide and N-methylpyrrolidin-2-one. In addition to them, sulfoxide solvents such as dimethylsulfoxide and sulfolane and ketone solvents such as acetone and methyl ethyl ketone can be used if they are suited.

When the nitrogen atom of $Q^{3b}$ of the compound represented by the formula (IIIa) forms an amide bond, the alkylation of the nitrogen atom is carried out by reacting the compound (IIIa) with the compound represented by any one of the formulas (Va) to (Vd) in the presence of an appropriate base in an inert solvent at −78 to 150° C., whereby the compound of the formula (Ib) can be obtained. Specific examples of the base include alkoxides and hydrides of an alkali metal or alkaline earth metal such as sodium ethoxide, potassium butoxide, sodium hydride and potassium hydride; organic metal bases typified by an alkyl lithium such as n-butyl lithium and a dialkylamino lithium such as lithium diisopropylamide; and organic bases such as diazabicyclo[5.4.0]undec-7-ene (DBU).

Examples of the inert solvent include ether solvents such as tetrahydrofuran, 1,2-dimethoxyethane and dioxane and amide solvents such as N,N-dimethylformamide.

When the nitrogen atom of $Q^{3b}$ of the compound represented by the formula (IIIa) exists as a primary or secondary amine, the compound of the formula (Ib) can be obtained by reacting the compound of the formula (IIIa) with the carbonyl compound of any one of the formulas (VIa) to (VId), to form the corresponding imine, generally in an inert solvent, in the presence of an organic acid such as acetic acid, a mineral acid such as hydrochloric acid or a Lewis acid such as aluminum chloride at −20 to 150° C.; and then hydrogenating the resulting imine in an inert solvent in the presence of a boron hydride reducing agent such as sodium borohydride, sodium cyanoborohydride or sodium triacetoxyborohydride or a catalytic reduction catalyst such as palladium-carbon catalyst at 10 to 110° C.

Preferred examples of the inert solvent include carbon halides such as dichloromethane, chloroform and carbon tetrachloride, ether solvents such as tetrahydrofuran, 1,2-dimethoxyethane and dioxane, benzene solvents such as toluene and amide solvents such as N,N-dimethylformamide, N,N-dimethylacetamide and N-methylpyrrolidin-2-one.

When the nitrogen atom of $Q^3$ of the compound represented by the formula (IIIa) exists as a primary or secondary amine, the reaction product between the compound of any one of the formulas (VIIa) to (VIIb) containing a primary amine or the compound of the formula (VIIe) containing a secondary amine and a reagent such as 1,1'- carbonyldiimidazole can be reacted with the compound of the formula (IIIa) to introduce it to the corresponding urea derivative. The derivative can be synthesized by reacting the primary amine compound of any one of the formulas (VIIa) to (VIId) or the secondary amine compound of the formula (VIIe), a reagent such as carbonyldiimidazole and the compound of the formula (IIIa) successively in this order, if necessary in the presence of a base, in an inert solvent.

Examples of the inert solvent include halogen solvents such as dichloromethane, chloroform and carbon tetrachloride; ether solvents such as tetrahydrofuran, 1,2-dimethoxyethane and dioxane; benzene solvents such as toluene; and amide solvents such as N,N-dimethylformamide, N,N-dimethylacetamide and N-methylpyrrolidin-2-one. Among them, dichloromethane, tetrahydrofuran and toluene are preferred.

Examples of the base include carbonates and hydroxides of an alkali metal or alkaline earth metal, such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU). The reaction is effected within a temperature range of from --70° C. to 110° C.

When the nitrogen atom of $Q^{3b}$ of the compound represented by the formula (IIIa) exists as a primary or secondary amine, the compound of the formula (Ib) can also be obtained by reacting the compound of the formula (IIIa) with an isocyanate derivative in an inert solvent at –20 to 100° C.

The isocyanate derivative can be synthesized by converting the carboxylic acid of the formula (IVa) into the corresponding acid halide by using an acid halide such as thionyl chloride or oxalyl chloride in an inert solvent such as tetrahydrofuran, chloroform or toluene at –20 to 110° C., reacting the resulting acid halide with sodium azide in an inert solvent such as tetrahydrofuran, chloroform or toluene at a temperature range of from 0 to 80° C., and then heating the reaction mixture at 20 to 100° C.; reacting the carboxylic acid of the formula (IVa) with a chloroformate such as isobutyl chloroformate in an inert solvent such as tetrahydrofuran, chloroform or toluene at –20 to 110° C. to obtain the corresponding mixed acid anhydride, reacting the mixed acid anhydride with sodium azide within a temperature range of from 0 to 80° C. and then heating the reaction mixture at 20 to 100° C.; or by introducing the carboxylic acid of the formula (IVa) into the corresponding hydrazide through an ester in an inert solvent such as tetrahydrofuran, chloroform or toluene at –20 to 110° C., reacting the hydrazide with nitric acid or alkyl ester thereof to convert it into the corresponding acyl azide and then heating the resulting acyl azide in a solvent such as chloroform, dichloroethane, toluene, xylene or N,N-dimethylformamide at 20 to 150° C.

The compound of the formula (Ib) can also be prepared by reacting the carboxylic acid of the formula (IVa) with diphenylphosphoryl azide in the presence of a base such as triethylamine, in an inert solvent such as chloroform, tetrahydrofuran, toluene or N,N-dimethylformamide at a temperature range of 10 to 140° C. and then reacting the reaction mixture with the amine of the formula (IIIa).

When in the structure of $Q^1$ of the compound represented by the formula (Ib), a halogen- or trifluoromethanesulfonyloxy-substituted aryl group or a halogen- or tri-fluoromethanesulfonyoxy-substituted alkenyl group is contained, the compound can be subjected to coupling reaction with a boric-acid-substituted aryl derivative by using a transition metal catalyst such as tetrakis (triphenylphosphine)palladium (O), in a two-phase solvent such as benzene-water or toluene-water, amide solvent such as N,N-dimethylformamide or ether solvent such as tetrahydrofuran or dimethoxyethane, in the presence of a base such as sodium carbonate, sodium hydroxide, barium hydroxide, potassium phosphate or cesium carbonate at a temperature range of 20 to 150° C. for 0.5 to 120 hours.

When an alkenyl group is contained in the structure of $Q^1$ of the compound represented by the formula (Ib), coupling reaction of the compound with a halogen- or trifluoromethanesulfonyloxy-substituted aryl group can be effected using a transition metal catalyst such as palladium acetate, in the presence of an appropriate base, in an amide solvent such as N,N-dimethylformamide, at a temperature range of 20 to 150° C. for 0.5 to 120 hours. When a boric-acid-substituted aryl group is contained in the structure of $Q^1$ of the compound represented by the formula (Ib), coupling reaction of the compound with a halogen- or trifluoromethanesulfonyloxy-substituted aryl derivative or a halogen- or trifluoromethanesulfonyloxy-substituted alkenyl derivative can be effected. When a halogen- or trifluoromethanesulfonyloxy-substituted aryl group is contained in the structure of $Q^1$ of the compound represented by the formula (Ib), coupling reaction of the compound with an alkenyl compound can be effected using a transition metal catalyst.

If the nitrogen atom of $Q^{3b}$ of the compound represented by the formula (Ib) has been protected as described above, the compound of the formula (Ia) can be obtained by deprotection as needed.

<Synthesis of the Compound Represented by the Formula (IIa)>

The sulfonic acid halide of the formula (IIa) can be synthesized by any one of the various conventionally-reported processes (The Chemistry of Sulfonic Acids Esters and their Derivatives, Edited by S. Patai and Z. Rappoport, 1991, John Wiley & Sons Ltd.), for example, halogenation of the corresponding sulfonic acid of the following formula (IIb):

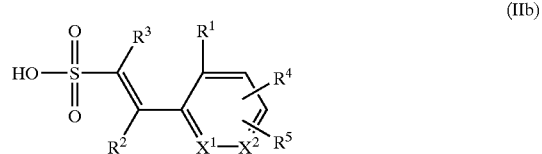

(IIb)

or halogenosulfonylation of an unsaturated-bond-containing compound represented by the following formula (IIc):

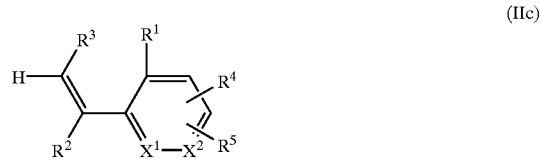

(IIc)

[wherein in the above formulas (IIb) and (IIc), $R^1$, $R^2$, $R^3$, $R^4$, $R^5$, $X^1$ and $X^2$ have the same meanings as described above].

For example, the sulfonic acid halide of the formula (IIa) can be obtained by reacting the sulfonic acid of the formula (IIb) with a thionyl halide in the presence of N,N-dimethylformamide at 0 to 150° C. for 0.5 to 24 hours. At this time, the reaction system can be diluted with a solvent such as dichloromethane, chloroform, carbon tetrachloride, N-methylpyrrolidin-2-one, dimethylsulfoxide or sulfolane.

The sulfonic acid halide of the formula (IIa) can also be obtained by reacting the unsaturated-bond-containing compound of the formula (IIc) with a thionyl halide or chlorosulfonic acid in a solvent such as N,N-dimethylformamide at 0 to 150° C. for 0.5 to 24 hours.

The compound of the formula (I) can be obtained generally by reacting the compound of the formula (Ia), which has been synthesized by the above-described process or the like, with the sulfonic acid halide of the formula (IIa) which has been synthesized by the above-described process or the like, in the presence of an appropriate base, in an inert solvent at −78 to 150° C.

Specific examples of the base include carbonates, alkoxides, hydroxides and hydrides of an alkali metal or alkaline earth metal, such as sodium carbonate, potassium carbonate, sodium ethoxide, potassium botoxide, sodium hydroxide, potassium hydroxide, sodium hydride and potassium hydride; organic metal bases typified by an alkyl lithium such as n-butyl lithium and a dialkylamino lithium such as lithium diisopropylamide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide, sulfolane and acetone.

[Preparation Process-1-(1)]

When the nitrogen atom of $Q^{3a}$ of the compound represented by the formula (Ia), which is to be sulfonylated, exists as a primary or secondary amine, preferred examples of the base include carbonates and hydroxides of an alkali metal or an alkaline earth metal such as sodium carbonate, potassium carbonate, sodium hydroxide and potassium hydroxide and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU) and usable examples of the solvent include, in addition to inert solvents, alcohol solvents such as ethanol and butanol and ester solvents such as ethyl acetate.

[Preparation Process-1-(2)]

When the nitrogen atom of $Q^3$ of the compound represented by the formula (Ia), which is to be sulfonylated, forms an amide group, preferred examples of the base include alkoxides and hydrides of an alkali metal or an alkaline earth metal such as sodium ethoxide, potassium botoxide, sodium hydride and potassium hydride, organic metal bases typified an alkyl lithium such as n-butyl lithium and a dialkylamino lithium such as lithium diisopropylamide and organic bases such as diazabicyclo[5.4.0]undec-7-ene (DBU). Examples of the inert solvent include tetrahydrofuran, 1,2-dimethoxyethane, dioxane and N,N-dimethylformamide.

[Preparation Process-2]

A process for preparing the sulfonyl derivative (I) by acylating the nitrogen atom of $Q^{3a}$ of the compound represented by the formula (VIIIa):

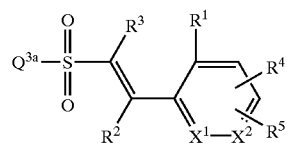

(VIIIa)

[wherein $R^1$, $R^2$, $R^3$, $R^4$, $R^5$, $X^1$, $X^2$, and $Q^{3a}$ have the same meanings as described above] with a carboxylic acid of the following formula (IVa):

$$Q^1-Q^2-COOH \quad (IVa)$$

[wherein $Q^1$ and $Q^2$ have the same meanings as described above] or the carboxylic acid in an activated form.

The compound of the following formula (VIIIb):

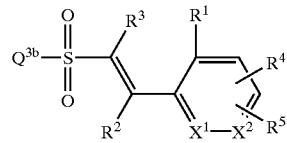

(VIIIb)

[wherein $R^1$, $R^2$, $R^3$, $R^4$, $R^5$, $X^1$, $X^2$, and $Q^{3b}$ have the same meanings as described above] can be obtained by sulfonylating the nitrogen atom of the primary amine, secondary amine or amide compound of the formula (IIIa) with a sulfonic acid halide represented by the following formula (IIa):

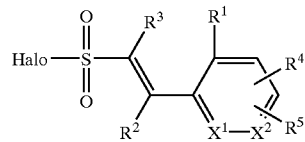

(IIa)

[wherein $R^1$, $R^2$, $R^3$, $R^4$, $R^5$, $X^1$, $X^2$, and Halo have the same meanings as described above] in the presence of an appropriate base in an inert solvent at −78 to 150° C.

Specific examples of the base include carbonates, alkoxides, hydroxides and hydrides of an alkali metal or alkaline earth metal, such as sodium carbonate, potassium carbonate, sodium ethoxide, potassium butoxide, sodium hydroxide, potassium hydroxide, sodium hydride and potassium hydride; organic metal bases typified by an alkyl lithium such as n-butyl lithium and a dialkylamino lithium such as lithium diisopropylamide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide, sulfolane and acetone.

If the nitrogen atom of $Q^{3b}$ of the resulting compound represented by the formula (VIIIb) has been protected, the compound of the formula (VIIIa) can be obtained by deprotection as needed.

The compound of the formula (VIIIa) can be obtained by removing the protecting group of the nitrogen atom from the compound represented by the following formula (VIIIc):

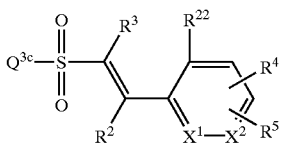

(VIIIc)

[wherein $R^2$, $R^3$, $R^4$, $R^5$, $X^1$ and $X^2$ have the same meanings as described above and $Q^{3c}$ represents any one of the following groups:

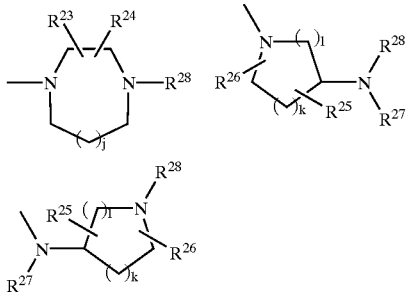

(wherein $R^{22}$ represents a hydrogen atom,
an alkyl group,
a hydroxyl group protected with methoxymethyl, tetrahydropyranyl or the like,
a hydroxyalkyl group protected with methoxymethyl, tetrahydropyranyl or the like,
an alkoxyl group,
an alkoxyalkyl group ,
a dialkoxyalkyl group,
a dialkylamino group,
a monoalkylamino group in which the amino moiety has been protected with tertiary butoxycarbonyl,
a dialkylaminoalkyl group,
a monoalkylaminoalkyl group in which the amino moiety has been protected with tertiary butoxycarbonyl,
a dialkylaminocarbonyl group,
a dialkylaminocarbonylalkyl group,
a dialkylaminoalkyloxy group,
a monoalkylaminoalkyloxy group in which the amino moiety has been protected with tertiary butoxycarbonyl,
a dialkylaminoalkylalkyloxy group,
a monoalkylaminoalkyloxy group in which the amino moiety has been protected with tertiary butoxycarbonyl,
a dialkylaminocarbonylalkyloxy group or the like.

When the carbon atom to which $R^{23}$, $R^{24}$, $R^{25}$ or $R^{26}$ has been bonded is not adjacent to the nitrogen atom, $R^{23}$, $R^{24}$, $R^{25}$ and $R^{26}$ each independently represents:

a hydrogen atom,
an alkyl group,
a hydroxyl group protected with methoxymethyl, tetrahydropyranyl or the like,
a hydroxyalkyl group protected with methoxymethyl, tetrahydropyranyl or the like,
an alkoxyl group,
an alkoxyalkyl group,
a dialkoxyalkyl group,
a dialkylamino group,
a monoalkylamino group in which the amino moiety has been protected with tertiary butoxycarbonyl,
a dialkylaminoalkyl group,
a monoalkylaminoalkyl group in which the amino moiety has been protected with tertiary butoxycarbonyl,
a dialkylaminocarbonyl group,
a dialkylaminocarbonylalkyl group,
a dialkylaminoalkyloxy group,
a monoalkylaminoalkyloxy group in which the amino moiety has been protected with tertiary butoxycarbonyl,
a dialkylaminocarbonylalkyloxy group or the like.

When the carbon atom to which $R^{23}$, $R^{24}$, $R^{25}$or $R^{26}$ has been bonded is adjacent to the nitrogen atom, $R^{23}$, $R^{24}$, $R^{25}$ and $R^{26}$ each independently represents:

a hydrogen atom,
an alkyl group,
a hydroxyalkyl group in which the hydroxyl moiety has been protected with methoxymethyl, tetrahydropyranyl or the like,
an alkoxyalkyl group,
a dialkoxyalkyl group,
a dialkylaminoalkyl group,
a monoalkylaminoalkyl group in which the amino moiety has been protected with tertiary butoxycarbonyl,
a dialkylaminocarbonyl group,
a dialkylaminocarbonylalkyl group,
a dialkylaminoalkyloxy group or the like.

$R^{23}$ and $R^{24}$, as well as $R^{25}$ and $R^{26}$, may be coupled together to form a saturated or unsaturated 5- to 7-membered cyclic hydrocarbon group which may have a substituent or a saturated or unsaturated 5- to 7-membered heterocyclic group which may have a substituent.

$R^{27}$ represents:

an alkyl group,
a hydroxyalkyl group in which the hydroxyl moiety has been protected,
a hydroxyalkylcarbonyl group in which the hydroxyl moiety has been protected,
a hydroxyalkylsulfonyl group in which the hydroxyl moiety has been protected,
an alkoxyalkyl group,
an alkoxyalkylcarbonyl group,
an alkoxyalkylsulfonyl group,
an alkylcarbonyl group,
an alkylcarbonylalkyl group,
an alkylsulfonyl group,
an alkylsulfonylalkyl group,
an alkoxycarbonyl group,
an alkoxycarboylalkyl group,
an alkoxycarbonylalkylcarbonyl group,
an alkoxycarbonylalkylsulfonyl group,
a dialkylaminoalkyl group,
a monoalkylaminoalkyl group in which the amino moiety has been protected with tertiary butoxycarbonyl,
a dialkylaminocarbonyl group,
a dialkylaminocarbonylalkyl group, or the like.

$R^{25}$ and $R^{27}$, or $R^{26}$ and $R^{27}$ may be coupled together to form a saturated or unsaturated 5- to 7-membered heterocyclic group which may have a substituent.

$R^{28}$ represents a tertiary butoxycarbonyl, benzyl or triphenylmethyl group, j and k each independently represents an integer of 0 or 1 and l stands for an integer of 1 to 3 with the proviso that the sum of k and l stands for an integer of 1 to 4.)]

The compound represented by the formula (VIIIc) can be obtained by reacting an amino compound which is available by the known process or application thereof and is represented by the following formula (IIIb):

(IIIb)

[wherein $Q^{3c}$ has the same meaning as described above] with an alkylsulfonic acid halide in the presence of an appropriate base; reacting the resulting sulfonamide represented by the following formula (IXa):

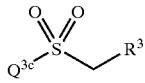
(IXa)

[wherein $R^3$ and $Q^{3c}$ have the same meanings as described above] with a carbonyl compound represented by the following formula (XIa):

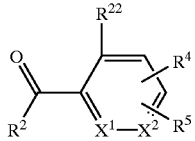
(XIa)

[wherein $R^2$, $R^4$, $R^5$, $R^{22}$, $X^1$ and $X^2$ have the same meanings as described above ] in an inert solvent in the presence of an appropriate base to obtain the alcohol product represented by the following formula (XIIa):

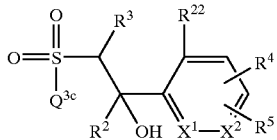
(XIIa)

[wherein $R^2$, $R^3$, $R^4$, $R^5$, $R^{22}$, $Q^{3c}$, $X^1$ and $X^2$ have the same meanings as described above]; converting the alcohol moiety of the alcohol product (XIIa) into a methanesulfonyloxy group or the like in the presence of an appropriate base, or converting the alcohol moiety into a halogen atom by a phosphorus halide or triphenylphosphine/carbon tetrahalide, thereby forming an eliminating group; and then eliminating methanesulfonic acid or hydrogen halide in the presence of an appropriate base.

The sulfonamide compound of the formula (IXa) can be obtained by reacting the amino compound of the formula (IIIb) available by the known method or application thereof with an alkylsulfonic halide which may have a substituent, in the presence of an appropriate base, in an inert solvent at −78 to 150° C.

Examples of the base include carbonates of an alkali metal or alkaline earth metal, such as sodium carbonate and potassium carbonate and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU). Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide and N-methylpyrrolidin-2-one. Dimethylsulfoxide, sulfolane, acetone or the like can be used, though depending on the kind of the bases employed.

The alcohol compound of the formula (XIIa) can be obtained by reacting the sulfonamide of the formula (IXa) with a carbonyl compound of the formula (XIa) in the presence of an appropriate base in an inert solvent at −78 to 110° C.

Examples of the base include hydrides of an alkali metal or alkaline earth metal such as sodium ethoxide, potassium botoxide, sodium hydride and potassium hydride and organic metal bases typified by an alkyl lithium such as n-butyl lithium and a dialkylamino lithium such as lithium diisopropylamide. Examples of the inert solvent include tetrahydrofuran, 1,2-dimethoxyethane and dioxane.

The compound of the formula (VIIIc) can be obtained by treating the hydroxyl group of the alcohol product of the formula (XIIa) with a phosphorus halide such as phosphorus pentachloride or a triphenylphosphine-halogen complex such as triphenylphosphine dibromide in the presence of an appropriate base, for example, the carbonate of an alkali metal or alkaline earth metal, such as sodium carbonate or potassium carbonate, or an organic base such as pyridine, 2,6-lutidine, collidine, 4-dimethylaminopyridine, triethylamine, N-methylmorpholine, diisopropylethylamine or diazabicyclo[5.4.0]undec-7-ene (DBU), in a solvent such as dichloromethane, chloroform, carbon tetrachloride, tetrahydrofuran, 1,2-dimethoxyethane, dioxane, toluene or N,N-dimethylformamide at −20 to 110° C., thereby obtaining the corresponding halide, and then eliminating the hydrogen halide from the resulting halide under basic conditions, for example, by treating at −78 to 150° C. with a carbonate, alkoxide, hydroxide or hydride of an alkali metal or alkaline earth metal, such as sodium carbonate, potassium carbonate, sodium ethoxide, potassium butoxide, sodium hydroxide, potassium hydroxide, sodium hydride or potassium hydride, an organic metal base typified by alkyl lithium such as n-butyl lithium and a dialkylamino lithium such as lithium diisopropylamide, or an organic base such as pyridine, 2,6-lutidine, collidine, 4-dimethylaminopyridine, triethylamine, N-methylmorpholine, diisopropylethylamine and diazabicyclo[5.4.0]undec-7-ene (DBU) in dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one or dimethylsulfoxide.

The compound of the formula (VIIIc) can also be obtained by treating the hydroxyl group of the alcohol product represented by the formula (XIIa) with an alkyl- or arylsulfonic acid chloride such as methanesulfonic acid chloride in the presence of an appropriate base, for example, a carbonate of an alkali metal or alkaline earth metal such as sodium carbonate or potassium carbonate or an organic base such as pyridine, 2,6-lutidine, collidine, 4-dimethylaminopyridine, triethylamine, N-methylmorpholine, diisopropylethylamine or diazabicyclo[5.4.0]undec-7-ene (DBU), in a solvent such as dichloromethane, chloroform, carbon tetrachloride, tetrahydrofuran, 1,2-dimethoxyethane, dioxane, toluene or N,N-dimethylformamide at −20 to 110° C. to obtain the corresponding alkyl- or arylsulfonate derivative; and then eliminating the alkyl- or arylsulfonic acid from the resulting alkyl- or arylsulfonate derivative under basic conditions, described specifically, by treating the resulting alkyl- or arylsulfonate derivative at −78 to 150° C. in the presence of a carbonate, alkoxide, hydroxide or hydride of an alkali metal or alkaline earth metal such as sodium carbonate, potassium carbonate, sodium ethoxide, potassium butoxide, sodium hydroxide, potassium hydroxide, sodium hydride or potassium hydride, an organic metal base typified by an alkyl lithium such as n-butyl lithium and a dialkylamino lithium such as lithium diisopropylamide, or an organic base such as pyridine, 2,6-lutidine, collidine, 4-dimethylaminopyridine, triethylamine, N-methylmorpholine, diisopropylethylamine or diazabicyclo[5.4.0]undec-7-ene (DBU) in an inert solvent such as dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one or dimethylsulfoxide.

The compound of the formula (VIIIc) can also be obtained by treating the sulfonamide of the formula (IXa) with a silyl halide such as trimethylsilyl chloride in the presence of an appropriate base in an inert solvent to convert it to the corresponding silyl compound, reacting the resulting silyl compound with a carbonyl compound of the formula (XIa) in the presence of a base in an inert solvent and then treating the reaction product under acidic to basic aqueous conditions (Peterson's reaction). Described specifically, the compound of the formula (VIIIc) can be obtained by treating the sulfonamide of the formula (IXa) with an alkylsilyl chloride such as trimethylsilyl chloride at −78 to 110° C. in the presence of a hydroxide of an alkali metal or alkaline earth metal such as sodium ethoxide, potassium butoxide, sodium hydride or potassium hydride or an organic metal base typified by an alkyl lithium such as n-butyl lithium or a dialkylamino lithium such as lithium diisopropylamide in a solvent such as tetrahydrofuran, 1,2-dimethoxyethane or dioxane, to convert it to the corresponding silyl compound, condensing with the carbonyl compound of the formula (XIa) under the same conditions and then treating the condensate under acidic to basic aqueous conditions.

The protecting group for the nitrogen atom of the compound represented by the formula (VIIIc) can be removed by the ordinarily employed method. Described specifically, when the protecting group is a tertiary butoxycarbonyl group, it can be removed by using an appropriate acid such as acetic acid, hydrochloric acid, hydrobromic acid, sulfuric acid, phosphoric acid, trifluoroacetic acid or trifluoromethanesulfonic acid or combination thereof. The arylmethyl group such as benzyl can be removed by the hydrogenolysis in the presence of a palladium-carbon catalyst. The triphenylmethyl group can be removed by using an appropriate acid such as acetic acid, hydrochloric acid, hydrobromic acid, sulfuric acid, phosphoric acid, trifluoroacetic acid or trifluoromethanesulfonic acid or combination thereof. It can also be removed by Birch reduction with a metal sodium in liquid ammonia or by hydrogenolysis in the presence of a palladium-carbon catalyst.

Thus, by the removal of the protecting group from the compound of the formula (VIIIc), the compound of the formula (VIIIa) can be obtained. Examples of the carboxylic acid of the formula (IVa) in an appropriate activated form include mixed acid anhydrides available by reacting the carboxylic acid of the formula (IVa) with a chloroformate ester such as isobutyl chloroformate, thereby converting it into the corresponding acid anhydride, acid halides such as acyl chloride prepared by treating with an inorganic acid halide such thionyl chloride, active esters obtained by reacting with a phenol such as paranitrophenol or pentafluorophenyl-trifluoroacetate, active esters obtained by reacting it with N-hydroxybenztriazole or N-hydroxysuccinimide, reaction products with N,N'-dicyclohexylcarbodiimide or N-(3-dimethylaminopropyl)-N'-ethylcarbodiimide hydrochloride which is ordinarily employed in the synthesis of an amino acid, reaction products with diethyl cyanophosphonate (Shioiri's method) and reaction products with triphenylphosphine and 2,2'-dipyridylsulfide (Mukaiyama's method).

The resulting carboxylic acid in an activated form is then reacted with the compound of the formula (VIIIa) at −78° C. to 150° C., generally in the presence of an appropriate base in an inert solvent, whereby the sulfonyl derivative of the formula (I) can be obtained.

Specific examples of the base include carbonates, alkoxides, hydroxides and hydrides of an alkali metal or alkaline earth metal, such as sodium carbonate, potassium carbonate, sodium ethoxide, potassium butoxide, sodium hydroxide, potassium hydroxide, sodium hydride and potassium hydride; organic metal bases typified by an alkyl lithium such as n-butyl lithium and a dialkylamino lithium such as lithium diisopropylamide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide, sulfolane and acetone.

[Preparation Process-2-(1)]

When the nitrogen atom of $Q^3$ of the compound of the formula (VIIIa):

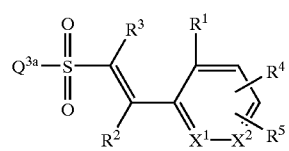

(VIIIa)

[wherein $R^1$, $R^2$, $R^3$, $R^4$, $R^5$, $X^1$, $X^2$ and $Q^{31}$ have the same meanings as described above] which is to be acylated exists as a primary or secondary amine, preferred examples of the base include carbonates and hydroxides of an alkali metal or alkaline earth metal, such as sodium carbonate, potassium carbonate, sodium hydroxide and potassium hydroxide and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU); and examples of the solvent include, in addition to inert solvents, alcohol solvents such as ethanol and butanol and ester solvents such as ethyl acetate.

[Preparation Process-2-(2)]

When the nitrogen atom of $Q^3$ of the compound of the formula (VIIIa):

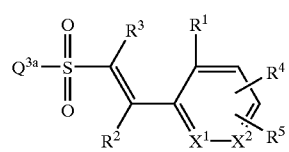

(VIIIa)

[wherein $R^1$, $R^2$, $R^3$, $R^4$, $R^5$, $X^1$, $X^2$ and $Q^{3a}$ have the same meanings as described above] which is to be acylated forms an amide bond, examples of the base include alkoxides and hydrides of an alkali metal or alkaline earth metal such as sodium ethoxide, potassium butoxide, sodium hydride and potassium hydride, organic metal bases typified by an alkyl lithium such as n-butyl lithium and a dialkylamino lithium such as lithium diisopropylamide and organic bases such as diazabicyclo[5.4.0]undec-7-ene (DBU) and preferred examples of the inert solvent include tetrahydrofuran, 1,2-dimethoxyethane, dioxane and N,N-dimethylformamide.

[Preparation Process-3]

A process for preparing the sulfonyl derivative of the present invention, in the case where the nitrogen atom of $Q^3a$ of the compound represented by the following formula (VIIIa):

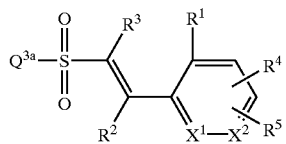

(VIIIa)

[wherein $R^1$, $R^2$, $R^3$, $R^4$, $R^5$, $X^1$, $X^2$ and $Q^{3a}$ have the same meanings as described above] forms an amide, by alkylating the nitrogen atom of the compound represented by the formula (VIIIa) with the compound represented by any one of the following formulas (Va) to (Vd).

$Q^1$—$Q^{2b}$—$CHL^1R^{18}$ (Va)

$Q^1$—$N(R^{20})$—$(CH_2)_{m1}$—$CHL^1R^{18}$ (Vb)

$Q^1$—O—$(CH_2)_{m1}$—$CHL^1R^{18}$ (Vc)

$Q^1$—S—$(CH_2)_{m1}$—$CHL^1R^{18}$ (Vd)

[wherein $Q^1$, $Q^{2b}$, $R^{18}$, $R^{20}$, ml and $L^1$ have the same meanings as described above].

When the nitrogen atom of $Q^{3a}$ of the compound represented by the formula (VIIIa) forms an amide bond, the sulfonyl derivative of the formula (I) can be synthesized by alkylating the nitrogen atom with the compound of any one of the formulas (Va) to (Vd), described specifically, by reacting the compound of the formula (VIIIa) with the compound of any one of the formulas (Va) to (Vd) at −78 to 150° C. in the presence of an appropriate base in an inert solvent for 0.5 to 120 hours, thereby alkylating the nitrogen atom.

Examples of the base include alkoxides and hydrides of an alkali metal or alkaline earth metal such as sodium ethoxide, potassium butoxide, sodium hydride and potassium hydride, organic metal bases typified by an alkyl lithium such as n-butyl lithium and a dialkylamino lithium such as lithium diisopropylamide and organic bases such as diazabicyclo[5.4.0]undec-7-ene (DBU). Preferred examples of the inert solvent include tetrahydrofuran, 1,2-dimethoxyethane, toluene, dioxane and N,N-dimethylformamide.

[Preparation Process-4]

A process of preparing the sulfonyl derivative (I), in the case where the nitrogen atom of $Q^3$ of the compound represented by the following formula (VIIIa):

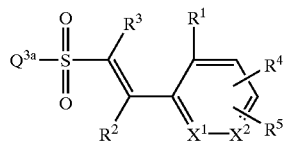

(VIIIa)

[wherein $R^1$, $R^2$, $R^3$, $R^4$, $R^5$, $X^1$, $X^2$ and $Q^{3a}$ have the same meanings as described above] exists as a primary or secondary amine, by forming the corresponding imine with the carbonyl compound of any one of the following formulas (VIa) to (VId):

$Q^1$—$Q^{2b}$—$C(=O)R^{18}$ (VIa)

$Q^1$—$N(R^{20})$—$(CH_2)_{m1}$—$C(=O)R^{18}$ (VIb)

$Q^1$—O—$(CH_2)_{m1}$—$C(=O)R^{18}$ (VIc)

$Q^1$—S—$(CH_2)_{m1}$—$C(=O)R^{18}$ (VId)

[wherein $Q^1$, $Q^{2b}$, $R^{18}$, $R^{20}$ and m1 have the same meanings as described above], followed by reduction.

When the nitrogen atom of $Q^{3a}$ of the compound of the formula (VIIIa) exists as an amine, the sulfonyl derivative of the formula (I) can be obtained by reacting the compound of the formula (VIIIa) with the carbonyl compound of any one of the formulas (VIa) to (VId) at −20 to 150° C. for 0.5 to 120 hours generally in an inert solvent and if necessary in the presence of an organic acid such as acetic acid, mineral acid such as hydrochloric acid or Lewis acid such as aluminum chloride, thereby forming the corresponding imine; and hydrogenating the resulting imine at 10 to 110° C. for 0.5 to 120 hours in an inert solvent in the presence of a boron hydride reducing agent such as sodium borohydride, sodium cyanoborohydride or sodium triacetoxyborohydride or a catalytic reduction catalyst such as palladium-carbon.

Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide and sulfolane.

[Preparation Process-5]

A process of making use of the reaction wherein a urea derivative is formed by reacting, when $Q^{3a}$ of the compound of the following formula (VIIIa):

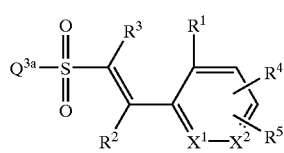

(VIIIa)

[wherein $R^1$, $R^2$, $R^3$, $R^4$, $R^5$, $X^1$, $X^2$ and $Q^{3a}$ have the same meanings as described above] exists as a primary or secondary amine, the compound of the formula (VIIIa) with the primary-amine-containing compound of any one of the formulas (VIIa) to (VIId):

$Q^1$—$Q^2$—$NH_2$ (VIIa)

$Q^1$—$N(R^{20})$—$(CH_2)_{m2}$—$NH_2$ (VIIb)

$Q^1$—O—$(CH_2)_{m2}$—$NH_2$ (VIIc)

$Q^1$—S—$(CH_2)_{m2}$—$NH_2$ (VIId)

or the secondary-amine-containing compound of the formula (VIIe):

(VIIe)

[wherein in the above formulas, $Q^1$, $Q^{2b}$ and $R^{20}$ and m2 have the same meanings as described above and a group of the following formula:

has the same meaning as described above] by using a reagent such as carbonyldiimidazole.

When $Q^{3a}$ of the compound represented by the formula (VIIIa) is an amine, the primary-amine-containing compound of any one of the formulas (VIIa) to (VIId) or the secondary-amine-containing compound of the formula (VIIe) and a reagent such as 1,1'-carbonyldiimidazole are reacted with the compound of the formula (VIIIa) to introduce it into the sulfonyl derivative of the formula (I) of the present invention which is an urea derivative.

The derivative can be synthesized by reacting the primary-amine-containing compound of any one of the formulas (VIIa) to (VIId) or the secondary-amine-containing compound of the formula (VIIe) and then the compound of the formula (VIIIa) successively with a reagent such as carbonyldiimidazole, if necessary, in the presence of a base in an inert solvent. Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide and sulfolane. Among them, dichloromethane, tetrahydrofuran and toluene are preferred.

Examples of the base include carbonates and hydroxides of an alkali metal or alkaline earth metal, such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU). It is only necessary to effect the reaction within a temperature range of from −70° C. to 110° C.

[Preparation Process-6]

A process of preparing the urea-containing sulfonyl derivative of the formula (I), in the case where the nitrogen atom of $Q^{3a}$ of the compound represented by the following formula (VIIIa):

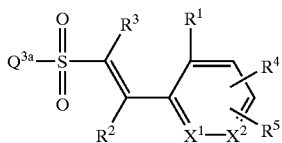
(VIIIa)

[wherein $R^1$, $R^2$, $R^3$, $R^4$, $R^5$, $X^1$, $X^2$ and $Q^{3a}$ have the same meanings as described above] exists as a primary or secondary amine, by reacting the amine of the formula (VIIIa) with a known isocyanate derivative ($Q^1$—$Q^{2b}$—N=C=O) [wherein $Q^1$ and $Q^{2b}$ have the same meanings as described above] or an isocyanate prepared from the carboxylic acid of any one of the following formulas (Iva)–(Ivd):

(IVa)

(IVb)

(IVc)

(IVd)

[wherein $Q^1$, $Q^{2b}$, $R^{20}$ and m1 have the same meanings as described above].

When $Q^{3a}$ of the compound represented by the formula (VIIIa) is an amine, the sulfonyl derivative of the formula (I) can be obtained by reacting the compound of the formula (VIIIa) with a known isocyanate derivative in an inert solvent at −20 to 100° C. for 0.5 to 120 hours.

The isocyanate derivative can also be synthesized from the carboxylic acid of any one of the formulas (IVa) to (IVd), described specifically, by converting the carboxylic acid of any one of the formulas (IVa) to (IVd) into the corresponding acid halide by using thionyl chloride or oxalyl chloride, reacting the resulting acid halide with sodium azide in an inert solvent at a temperature range of from 0 to 60° C. and then heating the reaction mixture; by reacting the carboxylic acid of the formula (IVa) with a chloroformate such as isobutyl chloroformate to obtain the corresponding mixed acid anhydride, reacting the resulting anhydride with sodium azide and then heating; or by introducing the carboxylic acid of any one of the formulas (IVa) to (IVd) into the corresponding hydrazide through an ester in an inert solvent such as tetrahydrofuran, chloroform or toluene at −20 to 110° C., reacting the hydrazide with nitric acid or alkyl ester thereof, thereby introducing into the corresponding acylazide and then heating the acylazide at 20 to 150° C. in a solvent such as chloroform, dichloroethane, toluene, xylene or N,N-dimethylformamide.

The sulfonyl derivative of the formula (I) can also be prepared by reacting the carboxylic acid of any one of the formulas (IVa) to (IVd) with diphenylphosphoryl azide in the presence of a base such as triethylamine, in an inert solvent at a temperature range of 10 to 100° C. and then reacting the resulting compound with the amine of the formula (VIIIa).

[Preparation Example-7]

A process for synthesizing the sulfonyl derivative represented by the following formula (I):

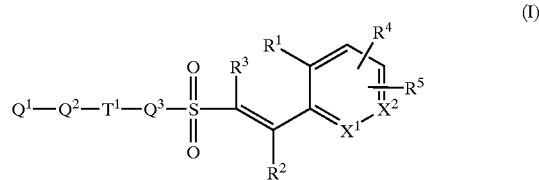
(I)

[wherein $R^1$, $R^2$, $R^3$, $R^4$, $R^5$, $Q^1$, $Q^2$, $Q^3$, $T^1$, $X^1$ and $X^2$ have the same meanings as described above] by coupling reaction using a transition metal catalyst.

When the structure of $Q^1$ of the sulfonyl derivative represented by the formula (I) contains a halogen- or trifluoromethanesulfonyloxy-substituted aryl group, or a halogen or trifluoromethanesulfonyl-substituted alkenyl group, coupling reaction with a boric-acid-substituted aryl compound can be effected in the presence of a transition metal catalyst.

When an alkenyl group is contained in the structure of $Q^1$ of the sulfonyl derivative of the formula (I), coupling reaction can be effected with a halogen- or trifluoromethanesulfonyloxy-substituted aryl group in the presence of a transition metal catalyst.

When a boric-acid-substituted aryl group is contained in the structure of $Q^1$ of the sulfonyl derivative of the formula (I), coupling reaction can be effected with a halogen- or trifluoromethanesulfonyloxy-substituted aryl compound or a halogen- or trifluoromethanesulfonyloxy-substituted alkenyl compound.

When in the structure of $Q^1$ of the sulfonyl derivative represented by the formula (I), a halogen- or trifluoromethanesulfonyloxy-substituted aryl group is contained, coupling reaction can be effected with an alkenyl compound in the presence of a transition metal catalyst, whereby the sulfonyl derivative of the formula (I) can be obtained. The sulfonyl derivative of the formula (I) so obtained is subjected to deprotection as needed, whereby the compound of the formula (Ia) can be obtained.

When in the structure of $Q^1$ of the sulfonyl derivative represented by the formula (I), a halogen- or trifluoromethanesulfonyloxy-substituted aryl group or a halogen- or trifluoromethanesulfonyloxy-substituted alkenyl group is contained, coupling reaction with a boric-acid-substituted aryl derivative can be effected using a transition metal catalyst such as tetrakis(triphenylphosphine) palladium (O), in a two-phase solvent such as benzene-water or toluene-water, an amide solvent such as N,N-dimethylformamide or an ether solvent such as tetrahydrofuran or dimethoxyethane, in the presence of a base such as sodium carbonate, sodium hydroxide, barium hydroxide, potassium phosphate or cesium carbonate at a temperature range of 20 to 150° C. for 0.5 to 120 hours.

When in the structure of $Q^1$ of the sulfonyl derivative represented by the formula (I), a boric-acid-substituted aryl group is contained, coupling reaction can be effected with a halogen- or trifluoromethanesulfonyloxy-substituted aryl compound or a halogen- or trifluoromethanesulfonyloxy-substituted alkenyl derivative.

When in the structure of $Q^1$ of the sulfonyl derivative represented by the formula (I), an alkenyl group is contained, coupling reaction can be effected with a halogen- or trifluoromethanesulfonyloxy-substituted aryl group by using a transition metal catalyst such as palladium acetate, in the presence of an appropriate base, in an amide solvent such as N,N-dimethylformamide at a temperature range of from 20 to 150° C. for 0.5 to 120 hours.

When in the structure of $Q^1$ of the sulfonyl derivative represented by the formula (I), a boric-acid-substituted aryl group is contained, coupling reaction can be effected with a halogen- or trifluoromethanesulfonyloxy-substituted aryl derivative or a halogen- or trifluoromethanesulfonyloxy-substituted alkenyl derivative.

When in the structure of $Q^1$ of the sulfonyl derivative represented by the formula (I), a halogen- or trifluoromethanesulfonyloxy-substituted aryl group, coupling reaction can be effected with an alkenyl compound by using a transition metal catalyst, whereby the sulfonyl derivative of the formula (I) can be obtained. From the sulfonyl derivative of the formula (I) so obtained, the sulfonyl derivative of the formula (I) with a changed substituent can be obtained by deprotection as needed.

[Preparation Process-8]

A process for preparing an amidoxime type sulfonamide product:

When $T^1$—$Q^3$ of the sulfonyl derivative represented by the following formula (I):

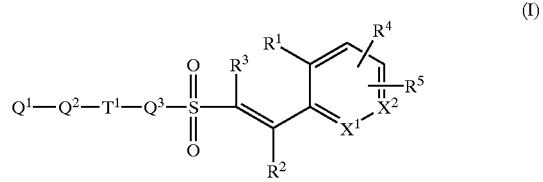

[wherein $R^1$, $R^2$, $R^3$, $R^4$, $R^5$, $Q^1$, $Q^2$, $Q^3$, $T^1$, $X^1$ and $X^2$ have the same meanings as described above] represents any one of the following formulas:

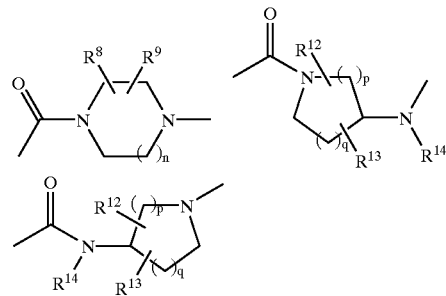

[wherein $R^8$, $R^9$, $R^{12}$, $R^{13}$ and $R^{14}$ have the same meanings as described above, n stands for an integer of 1 or 2, p stands for an integer of 1 to 3 and q stands for an integer of 0 to 3 with the proviso that the sum of p and 1 stands for an integer of 3 or 4] and none of amine-, alkylamine-, amido-, hydroxyl- and carboxylic-acid-containing substituents exist on $R^1$, $Q^1$ or $Q^2$, or $R^8$, $R^9$, $R^{12}$, $R^{13}$ or $R^{14}$ of $Q^3$, or a substituent replaceable therewith, the sulfonyl derivative of the formula (I) is reacted with a halogenating agent such as phosphorus pentachloride or an alkylating agent such as Meerwein reagent in an inert solvent at −30 to 140° C., preferably, in a halogen solvent such as chloroform at 0 to 80° C. to obtain the corresponding imino chloride or imino ether and then the resulting imino chloride or imino ether is reacted with hydroxylamine, alkoxyamine which may have a substituent or salt thereof at 0 to 80° C., preferably at 20 to 60° C., if necessary in the presence of a base catalyst, whereby the target sulfonyl derivative of the formula (I) can be obtained.

Examples of the inert solvent include alkyl halide solvents such as dichloromethane, chloroform and carbon tetrachloride, ether solvents such as tetrahydrofuran, 1,2-dimethoxyethane and dioxane and aromatic solvents such as benzene and toluene. Among them, the alkyl halide solvents are particularly preferred. Examples of the base include carbonates, alkoxides, hydroxides and hydrides of an alkali metal or alkaline earth metal, such as sodium carbonate, potassium carbonate, sodium ethoxide, potassium butoxide, sodium hydroxide, potassium hydroxide, sodium hydride and potassium hydride; organic metal bases typified by an alkyl lithium such as n-butyl lithium and a dialkylamino lithium such as lithium diisopropylamide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

[Preparation Process-9]

N-oxide Formation

When in the sulfonyl derivative of the formula (I), there exists a nitrogen-containing heterocyclic aromatic ring or aliphatic tertiary amine on $R^1$, $Q^1$, $Q^2$, $Q^3$ or $T^1$ or a substituent replaceable therewith, the sulfonyl derivative of the formula (I) is reacted with a peroxide such as hydrogen peroxide, metachloroperbenzoic acid or tertiary butyl hydroperoxide at −40 to 60° C. for 0.5 to 120 hours preferably −20 to 20° C. in water, acetic acid, a ketone solvent such as acetone, benzene solvent such as benzene, toluene or xylene, ether solvent such as tetrahydrofuran or dimethoxyethane or an alkyl halide solvent such as dichloromethane, chloroform or carbon tetrachloride, whereby the sulfonyl derivative of the formula (I) can be obtained as an N-oxide derivative.

[Preparation Process-10]
Quaternization of a Nitrogen Atom

When in the sulfonyl derivative of the formula (I), there exists a nitrogen-containing heterocyclic aromatic group or aliphatic tertiary amine on $R^1$, $Q^1$, $Q^2$, $Q^3$ or $T^1$ or a substituent replaceable therewith, the sulfonyl derivative of the formula (I) is reacted with an alkyl halide such as methyl iodide or ethyl iodide in an ether solvent such as 1,2-dimethoxyethane or dioxane, an aromatic solvent such as benzene or toluene, an amide solvent such as N,N-dimethylformamide, N,N-dimethylacetamide or N-methylpyrrolidin-2-one or a sulfoxide solvent such as dimethyl sulfoxide or sulfolane at −10 to 150° C., preferably 0 to 80° C., whereby the sulfonyl derivative of the formula (I) can be obtained as a quaternary amine product.

[Preparation Process-11]
Sulfoxide or Sulfone Formation

When in the sulfonyl derivative of the formula (I), a sulfur-containing hetero ring or aliphatic thioether exists on $R^1$, $Q^1$, $Q^2$, $Q^3$ or $T^1$ or a substituent replaceable therewith, the sulfonyl derivative of the formula (I) is reacted with a peroxide such as hydrogen peroxide, metachloroperbenzoic acid or tertiary butyl hydroperoxide at −40 to 60° C. for 0.5 to 120 hours, preferably −20 to 20° C. in water, acetic acid, a ketone solvent such as acetone, a benzene solvent such as benzene, toluene or xylene, an ether solvent such as tetrahydrofuran or dimethoxyethane or an alkyl halide solvent such as dichloromethane, chloroform or carbon tetrachloride, whereby the sulfonyl derivative (I) can be obtained in the form of sulfoxide or sulfone.

[Preparation Process-12]
Amidino Formation-1

When in the sulfonyl derivative of the formula (I), a nitrile group exists on $R^1$, $Q^1$, $Q^2$, $Q^3$ or $T^1$ or a substituent replaceable therewith, it can be converted into an amidino group by the ordinarily employed method. The amidino-containing sulfonyl derivative of the formula (I) can be obtained, for example, by allowing an equal amount to large excess of a $C_{1-4}$ alcohol such as methanol, ethanol or propanol to act on the sulfonyl derivative of the formula (I) at −10 to 60° C. for 3 to 120 hours in an aliphatic ether solvent such as diethyl ether, an alkyl halide solvent such as chloroform or dichloromethane or an aprotic solvent such as benzene or a mixed solvent thereof in the presence of a hydrogen halide such as hydrogen chloride or hydrogen bromide, thereby converting it to the corresponding imino ether; then reacting the resulting imino ether product with ammonium, a monoalkylamine which may have a substituent or a dialkylamine which may have a substituent or a carbonate or acetate thereof at −10 to 140° C. for 0.5 to 200 hours in a $C_{1-4}$ alcohol such as ethanol or propanol, an aliphatic ether solvent such as diethyl ether, an alkyl halide solvent such as chloroform, an aprotic solvent such as benzene, a solvent such as dimethylformamide or dimethylsulfoxide or a mixed solvent thereof, preferably at −8 to 30° C. for 10 to 96 hours in ethanol.

[Preparation Process-13]
Amidino Formation-2

When in the sulfonyl derivative of the formula (I), a primary or secondary amino group exists on $R^1$, $Q^1$, $Q^2$, $Q^3$ or $T^1$ or a substituent replaceable therewith, it can be converted into a substituted amidino group by the ordinarily employed process.

Described specifically, the amidino-containing sulfonyl derivative of the formula (I) can be obtained by reacting the sulfonyl derivative of the formula (I) with an imino ether, imino chloride or salt thereof, which has been synthesized from an amide compound or nitrile compound, in an aliphatic ether solvent such as diethyl ether, an alkyl halide solvent such as chloroform or dichloromethane or an aprotic solvent such as benzene or a mixed solvent thereof, if necessary in the presence of a base catalyst, at −10 to 140° C. for 0.5 to 200 hours, preferably 0 to 80° C. for 10 to 96 hours. Examples of the base include carbonates and hydroxides of an alkali metal or alkaline earth metal, such as sodium carbonate, potassium carbonate, sodium hydroxide and potassium hydroxide and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

[Preparation Process-14]
N-nitrile Formation

When in the sulfonyl derivative of the formula (I), a primary or secondary amine group exists on $R^1$, $Q^1$, $Q^2$, $Q^3$ or $T^1$ or a substituent replaceable therewith, it can be cyanated by the ordinarily employed process.

Described specifically, the sulfonyl derivative of the formula (I) is reacted with cyanogen bromide in an alcohol solvent such as methanol, ethanol or propanol in the presence. of a salt such as sodium acetate or a base at −10 to 110° C., preferably 0 to 60° C., whereby the sulfonyl derivative (I) having a nitrile group on its nitrogen atom can be obtained. Examples of the base include carbonates and hydroxides of an alkali metal or alkaline earth metal, such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

[Preparation Process-15]
Amidoxime or Carboxamido-O-alkyloxime Introduction

When in the sulfonyl derivative of the formula (I), a nitrile group exists on $R^1$, $Q^1$, $Q^2$, $Q^3$ or $T^1$ or a substituent replaceable therewith, it can be converted into an amidoxime or carboxamido-O-alkyloxime group by the ordinarily employed process.

Described specifically, the sulfonyl derivative of the formula (I) is reacted with hydroxylamine or an alkoxyamine which may have a substituent or salt thereof in an alcohol solvent such as methanol, ethanol or propanol, an ether solvent such as diethyl ether or tetrahydrofuran, a halogenated hydrocarbon such as chloroform or dichloromethane, an aprotic solvent such as toluene, an amide solvent such as N,N-dimethylformamide or a solvent such as dimethylsulfoxide or a mixed solvent thereof at −10 to 110° C., preferably 0 to 60° C., if necessary in the presence of a base catalyst, whereby the sulfonyl derivative of the formula (I) having an amidoxime or carboxamido-O-alkyloxime group can be obtained. Examples of the base include carbonates and hydroxides of an alkali metal or alkaline earth metal, such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

[Preparation Process-16]

Guanidino Introduction

When in the sulfonyl derivative of the formula (I), a primary or secondary amino group exists on $R^1$, $Q^1$, $Q^2$, $Q^3$ or $T^1$ or a substituent replaceable therewith, it can be converted into a substituted or unsubstituted guanidino group by the ordinarily employed process.

Described specifically, the sulfonyl derivative of the formula (I) having a primary or secondary amino group is reacted with N,N'-di(tert-butoxy)carbonylthiourea by using as a condensing agent N,N'-dicyclohexylcarbodiimide in an aliphatic ether solvent such as diethyl ether, a halogenated hydrocarbon such as chloroform or dichloromethane or an aprotic solvent such as benzene, or a mixed solvent thereof at −10 to 140° C. for 0.5 to 200 hours, preferably 0 to 80° C. for 10 to 96 hours, if necessary in the presence of a base catalyst, and then, as usual, the tertiary butoxycarbonyl group is removed, whereby the sulfonyl derivative of the formula (I) as a guanidino compound can be synthesized. Examples of the base include carbonates and hydroxides of an alkali metal or alkaline earth metal, such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

[Preparation Process-17]

Deprotection from the Protected Nitrogen Atom

When in the sulfonyl derivative of the formula (I), an acylamino or alkoxycarbonylamino group exists on $R^1$, $Q^1$, $Q^2$, $Q^3$ or $T^1$ or a substituent replaceable therewith, the derivative can be hydrolyzed at 0 to 80° C. in a solvent such as water, a lower alcohol or tetrahydrofuran or a mixed solvent thereof in the presence of a base such as an alkali metal hydroxide e.g. lithium hydroxide, sodium hydroxide or potassium hydroxide, whereby an amino-containing derivative can be obtained. The nitrogen atom to which an acyl type protecting group such as tertiary butoxycarbonyl or paramethoxybenzyloxycarbonyl has been bonded can be converted into a nitrogen-hydrogen bond by using an appropriate acid such as acetic acid, hydrochloric acid, hydrobromic acid, sulfuric acid, phosphoric acid, trifluoroacetic acid or trifluoromethanesulfonic acid or combination thereof and removing the acyl type protecting group from the nitrogen atom at 0 to 80° C. in an alkyl halide solvent such as dichloromethane, chloroform or carbon tetrachloride, an ether solvent such as tetrahydrofuran, 1,2-dimethoxyethane or dioxane or an aromatic solvent such as benzene or toluene.

The nitrogen atom to which an arylmethoxycarbonyl group such as benzyloxycarbonyl, paramethoxybenzyloxycarbonyl or para(ortho)-nitrobenzyloxycarbonyl has been bonded can be converted into a nitrogen-hydrogen bond by removing the arylmethoxycarbonyl group from the protected nitrogen through hydrogenolysis in the presence of a palladium-carbon catalyst in a solvent such as ethanol, tetrahydrofuran, acetic acid or N,N-dimethylformamide. The nitrogen atom to which a silyl type protecting group such as trimethylsilyl or tertiary butyl dimethylsilyl has been bonded can be converted into a nitrogen-hydrogen bond by reacting with hydrochloric acid or a hydrofluoride such as tetrabutylammonium fluoride at 0 to 80° C. in an alkyl halide solvent such as dichloromethane, chloroform or carbon tetrachloride, an ether solvent such as tetrahydrofuran, 1,2-dimethoxyethane or dioxane or an aromatic solvent such as benzene or toluene, thereby removing the silyl group from the protected nitrogen atom. The nitrogen atom to which a benzyl group has been bonded can be converted into a nitrogen-hydrogen bond by removing the benzyl group through the catalytic reduction with a palladium-carbon catalyst or the like at 0 to 80° C. in a solvent such as ethanol, tetrahydrofuran or acetic acid or through the Birch's reduction with a metal sodium in a liquid ammonia. The nitrogen atom to which a triphenyl group has been bonded can be converted into a nitrogen-hydrogen bond by removing the triphenyl group through the catalytic reduction with a palladium-carbon catalyst or the like at 0 to 80° C. in a solvent such as ethanol, tetrahydrofuran or acetic acid or through the Birch's reduction with a metal sodium in a liquid ammonia. The removal of the triphenylmethyl group and conversion into a nitrogen-hydrogen bond can be carried out by using an appropriate acid, such as acetic acid, hydrochloric acid, hydrobromic acid, sulfuric acid, phosphoric acid, trifluoroacetic acid or trifluoromethanesulfonic acid or a combination thereof at 0 to 80° C.

[Preparation Process-18]

Ester Hydrolysis

When in the sulfonyl derivative of the formula (I), an alkoxycarbonyl group exists on $R^1$, $Q^1$, $Q^2$, $Q^3$ or $T^1$ or a substituent replaceable therewith, the alkoxycarbonyl group protected in the methyl or ethyl ester form can be converted into the corresponding carboxylic acid by the hydrolysis with an appropriate base, for example, an alkali metal hydroxide such as lithium hydroxide, sodium hydroxide or potassium hydroxide. In the case of the protection in the form of a tertiary butyl ester, the tertiary butyl group can be removed by treating with trifluoroacetic acid or hydrochloric acid, while in the case of the protection in the form of an arylmethyl type ester such as benzyl, the carboxylic acid can be obtained by removing the arylmethyl group by hydrogenolysis in the presence of a palladium-carbon catalyst.

[Preparation Process-19]

When in the sulfonyl derivative of the formula (I), an acyloxy, arylmethyloxy, silylether, methoxymethyl or tetrahydropyranyl group exists on $R^1$, $Q^1$, $Q^2$, $Q^3$ or $T^1$ or a substituent replaceable therewith, the acyl group such as alkanoyl or aroyl can be removed by the hydrolysis with an appropriate base, for example, an alkali metal hydroxide such as lithium hydroxide, sodium hydroxide or potassium hydroxide. The arylmethyl type protecting group can be removed by the hydrogenolysis with a palladium-carbon catalyst. The silylether group such as tertiary butyl dimethylsilyl can be removed by a salt of hydrofluoride such as tetrabutylammonium fluoride. The methoxymethyl or tetrahydropyranyl group can be removed by acetic acid or hydrochloric acid.

[Preparation Process-20]

When in the sulfonyl derivative of the formula (I), an amino group exists on $R^1$, $Q^1$, $Q^2$, $Q^3$ or $T^1$ or a substituent replaceable therewith, it can be acylated by the ordinarily employed process which uses an acyl halide or carboxylic acid in an activated form. Alternatively, it can be alkylated by reductive alkylation or the like method. The sulfonyl derivative of the formula (I) which is an urea derivative can be prepared by sulfonylation through sulfonic acid chloride or by reacting with an isocyanate or an isocyanate derived from a carboxylic acid.

[Preparation Process-21]

When in the sulfonyl derivative of the formula (I), an carboxyl group exists on $R^1$, $Q^1$, $Q^2$, $Q^3$ or $T^1$ or a substituent replaceable therewith, it can be converted into a carbamoyl, alkylcarbamoyl or dialkylcarbamoyl group by the ordinarily employed active ester method or mixed acid anhydride method and then converted into a hydroxyl or aldehyde group by reduction. The resulting hydroxyl or aldehyde group can be subjected to conversion of a functional group, such as ether bond formation, conversion into an amino group or conversion into an alkylamino group by the process ordinarily employed in organic chemistry. The carboxyl group, after conversion into its ester or mixed acid anhydride directly or by the usual process, is reduced, whereby the corresponding alcohol can be obtained.

[Preparation-22]
Formation of Phenol

When in the sulfonyl derivative of the formula (I), an aryl-substituted methoxy group exists on $R^1$, $Q^1$, $Q^2$, $Q^3$ or $T^1$ or a substituent replaceable therewith, it can be converted into a hydroxyl group by removing the methyl group using trimethylsilyl iodide in an alkyl halide solvent such as dichloromethane, chloroform or carbon tetrachloride or a benzene solvent such as toluene, a Lewis acid such as aluminum chloride or phosphorus tribromide, an alkyl halide solvent or an ether solvent at −78 to 110° C.

The sulfonyl derivative of the formula (I) according to the present invention, salt thereof or solvate thereof has peculiar and excellent FXa inhibitory activity and is therefore useful as a coagulation suppressor or a preventive and/or remedy for thrombosis or embolism.

The sulfonyl derivative of the present invention exhibits effects even by the oral administration so that it can be administered either orally or parenterally. The dose of the sulfonyl derivative may be changed as needed depending on the symptom, age, weight and/or the like of a patient. It is necessary to administer the derivative in an amount of 1 to 1000 mg/day, preferably 5 to 300 mg/day per adult. Although no particular limitation is imposed on the dosage form, examples include tablets, capsules, powders, granules, suspensions, syrups and dry syrups. The derivative together with ordinarily employed additives such as excipient, lubricant or binder can be formulated into the above-described dosage forms in accordance with the known formulation technique.

No particular limitation is imposed on the dosage form in the case of parenteral administration but examples include ointments, plasters, injections and suppositories. As an injection, the derivative may be administered subcutaneously or intravenously or by intravenous drip in an amount of 0.1 to 100 mg/day, preferably 0.5 to 30 mg/day per adult.

The present invention will hereinafter be described more specifically by Referential Examples, Examples and Tests, but it should however be borne in mind that the present invention is not limited to or by them.

EXAMPLES

A detailed description will next be made of the sulfonyl derivative of the present invention and preparing process therefor. Some of the raw material compounds used for preparing the sulfonyl derivative of the present invention are novel compounds. These compounds and preparation process therefor will be described in Referential Examples.

Upon preparation of the compound, Merck Silica Gel 60 or Yamazen Silica Gel for moderate pressure liquid chromatography were employed for silica gel column chromatography.

In the nuclear magnetic resonance spectrum (NMR), tetramethylsilane was used an internal standard.

Referential Example 1

1-[(6-Chloronaphthalen-2-yl)sulfonyl]piperazine hydrochloride and trifluoroacetate In dichloromethane (20 ml), tert-butyl 1-piperazine carboxylate (856 mg) was dissolved. To the resulting solution, triethylamine (0.77 ml) and 6-chloro-2-naphthylsulfonylchloride (1.20 g) were added, followed by stirring at room temperature for 5 hours. The reaction mixture was concentrated under reduced pressure. Ethyl acetate was added to the residue and the resulting mixture was washed with 1N hydrochloric acid. The organic layer extracted was dried over anhydrous sodium sulfate. The solvent was then distilled off under reduced pressure. The residue was dissolved in saturated ethanol hydrochloride (10 ml), followed by concentration under reduced pressure and washing with ethyl acetate, whereby the hydrochloride (1.62 g, quant.) of the title compound was obtained as a colorless solid.

$^1$H-NMR (DMSO-$d_6$) δ: 3.1–3.4(8H,m), 7.75(1H,dd,J=8.8,2.0 Hz), 7.86(1H,dd,J=8.8,1.5 Hz), 8.22(1H,d,J=8.8 Hz), 8.26–8.32(2H,m), 8.56(1H,s), 8.63(2H,br s).

MS (FAB) m/z: 311 [(M+H)$^+$, Cl$^{35}$], 313 [(M+H)$^+$, Cl$^{37}$].

Elementary analysis for $C_{14}H_{15}ClN_2O_2S.HCl.0.1H_2O$

Calculated: C, 48.17; H, 4.68, Cl, 20.31; N, 8.03; S, 9.19.

Found: C, 47.91; H, 4.68; Cl, 20.41; N, 7.80; S, 9.21.

Instead of the saturated ethanol hydrochloride, treatment was carried out using trifluoroacetic acid, whereby the trifluoroacetate was obtained. Elementary analysis for $C_{14}H_{15}ClN_2O_2S.CF_3CO_2H$ Calculated: C, 45.24; H, 3.80, Cl, 8.35; F, 13.42; N, 6.59; S, 7.55.

Found: C, 44.84; H, 3.80; Cl, 8.27; F, 13.72; N, 6.29; S, 7.50.

Referential Example 2

4-(4-Pridyl)benzoic acid hydrochloride

At room temperature, 4-bromopyridine hydrochloride (11.7 g) and 4-carboxybenzeneboronic acid (10.0 g) were dissolved in toluene (250 ml) and water (250 ml). To the resulting solution, tetrakis(triphenylphosphine)palladium (O) (5.00 g) and anhydrous sodium carbonate (25.4 g) were added successively, followed by refluxing under heat at 120° C. for 19 hours. After allowed to cool down, the reaction mixture was added with ethyl acetate and water, whereby the water layer was separated. The organic layer was extracted twice with water. All the water layers so obtained were combined and to the resulting solution, concentrated hydrochloric acid was added to make it acidic, followed by washing with ethyl acetate again. The solvent was distilled off from the water layer until it decreased to 100 ml. The colorless solid so precipitated was collected by filtration and dried under reduced pressure, whereby the title compound (8.37 g, 59%) was obtained.

$^1$H-NMR (DMSO-$d_6$) δ: 8.11 (2H,d,J=8.8 Hz), 8.14(2H, d,J=8.8 Hz), 8.35(2H,d,J=6.6 Hz), 8.97(2H,d,J=6.6 Hz).

Elementary analysis for $C_{12}H_9NO_2.HCl.0.3H_2O$

Calculated: C, 59.79; H, 4.43, N, 5.81;

Found: C, 59.87; H, 4.35; N, 5.53.

MS (FAB) m/z: 200 (M+H)$^+$.

Referential Example 3

1-tert-Butoxycarbonyl-4-[4-(4-pyridyl)benzoyl] piperazine

In N,N-dimethylformamide (40 ml), 4-(4-pyridyl)benzoic acid hydrochloride (654 mg) and tert-butyl 1-piperazinecarboxylate (569 mg) were suspended. To the resulting suspension, 1-hydroxybenzotriazole (374 mg) and N-methylmorpholine (336 pl) were added. The resulting mixture was ice cooled, followed by the addition of 1-(3-dimethylaminopropyl-3-ethylcarbodiimide hydrochloride (796 mg). After stirring at room temperature for 7 hours, the solvent was distilled off. The residue was purified by chromatography on a silica gel column (2% methanol-dichloromethane), followed by washing with hexane, whereby the title compound (905 mg, 89%) was obtained.

$^1$H-NMR (CDCl$_3$) δ: 1.48 (9H,s) , 3.40–3.91 (8H,m), 7.51(2H,d,J=5.9 Hz), 7.53(2H,d,J=8.1 Hz), 7.69(2H,d,J=8.1 Hz), 8.69(2H,d,J=5.9 Hz).

Elementary analysis for $C_{21}H_{25}N_3O_3$

Calculated: C, 68.64; H, 6.86, N, 11.44.

Found: C, 68.48; H, 6.84; N, 11.17.

Referential Example 4

1-[4-(4-Pyridyl)benzoyl]piperazine Ditrifluoroacetate

In dichloromethane (30 ml), 1-tert-butoxycarbonyl-4-[4-(4-pyridyl)benzoyl]piperazine (944 mg) was dissolved. Under ice cooling, trifluoroacetic acid (30 ml) was added to the resulting solution, followed by stirring at room temperature for one hour. The solvent was distilled off. Tetrahydrofuran was added to the residue to solidify the same, whereby the title compound (1.28 g, 100%) was obtained as a colorless amorphous solid.

$^1$H-NMR (DMSO-d$_6$) δ: 3.1–3.3(4H,br s), 3.5–4.0(4H, m), 7.65(2H,d,J=7.8 Hz), 7.95–8.05(4H,m), 8.79(2H,d,J= 5.4 Hz), 8.95–9.10(1H,br s)

Referential Example 5

4-tert-Butoxycarbonyl-2-ethoxycarbonyl-1-[4-(4-pyridyl)benzoyl]piperazine

In toluene (150 ml), 1,2-dibromopropionic acid (58.0 g) was dissolved. To the resulting solution, a solution of N,N'-dibenzylethylenediamine (53.5 g) and triethylamine (53 ml) in toluene (toluene: 50 ml) was added dropwise under ice cooling. Toluene (100 ml) was added again to the reaction mixture, followed by stirring at room temperature for 14 hours, addition of toluene (100 ml) again and stirring at 60 to 80° C. for 4 hours. The insoluble matter was filtered off. The filtrate was washed with water and dried over anhydrous potassium carbonate. The solvent was then distilled off under reduced pressure. The residue was dissolved in acetic acid (200 ml). To the resulting solution, 10% palladium carbon (water content: about 50%, 40 g) was added, followed by catalytic reduction under 4 atmospheric pressure for 4 hours. The catalyst was filtered off and the filtrate was distilled off under reduced pressure. To the residue, dichloromethane and a saturated aqueous solution of potassium carbonate were added to separate the organic layer, followed by drying over anhydrous potassium carbonate. The solvent was distilled off under reduced pressure. The residue was dissolved in dichloromethane (350 ml), followed by the addition of 2-(tert-butoxycarbonyloxyimino)-2-phenylacetonitrile (46.5 g) under ice cooling. The reaction mixture was heated gradually to room temperature, at which stirring was conducted for 14 hours. The solvent was distilled off under reduced pressure. The residue was purified by chromatography on a silica gel column (dichloromethane ~2% methanol-dichloromethane), whereby 1-tert-butoxycarbonyl-3-ethoxycarbonylpiperazine (5.82 g, 10%) was obtained.

In a similar manner to Referential Example 3 except for the use of the resulting product and 4-(4-pyridyl)benzoic acid hydrochloride as the raw materials instead, the reaction was conducted, whereby the title compound was obtained.

$^1$H-NMR (CDCl$_3$) δ: 1.2–1.4(3H,m), 1.46(9H,s), 2.7–5.4 (7H,m), 7.51(2H,d,J=5.2 Hz), 7.59(2H,d,J=7.6 Hz), 7.69 (2H,d,J=7.6 Hz), 8.69(2H,d,J=5.2 Hz).

MS (FAB) m/z: 440 (M+H)$^+$.

Referential Example 6

6-(4-Pyridyl)nicotinic acid hydrochloride

In tetrahydrofuran (20 ml), 6-chloronicotinic acid (535 mg) and diethyl (4-pyridyl)borane (500 mg) were dissolved. To the resulting solution, tetrabutylammonium bromide (546 mg), potassium hydrochloride (570 mg), tetrakis (triphenylphosphine)palladium (0) (392 mg) and water (0.5 ml) were added, followed by heating under reflux for 6 hours. Dilute hydrochloric acid was added to the reaction mixture to make it acidic. Water and ethyl acetate were poured into the resulting mixture for extraction. The water layer so extracted was distilled off under reduced pressure. The residue was purified by chromatography through a synthetic adsorbent ("Diaion HP-20", water ~50% acetonitrile-water). To the resulting fraction, dilute hydrochloric acid was added to make it acidic. The solvent was then distilled off. Tetrahydrofuran was added to the residue and the precipitate was collected by filtration, whereby the title compound (269 mg, 32%) was obtained.

$^1$H-NMR (DMSO-d$_6$) δ: 8.45–8.55(2H,m), 8.65(2H,d,J= 6.8 Hz), 9.03(2H,d,J=6.8 Hz), 9.27(1H,s).

MS (FAB) m/z: 201 (M+H)$^+$

Referential Example 7

Methyl 4-(3-pyridyl)benzoate

In tetrahydrofuran (100 ml), methyl 4-bromobenzoate (5.04 g) and diethyl-3-pyridylborane (2.30 g) were dissolved, followed by the addition of tetrabutylammonium bromide (2.51 g), potassium hydroxide (2.63 g), tetrakis (triphenylphosphine)palladium (O) (1.8 g) and water (1 ml) under an argon atmosphere. The resulting mixture was heated under reflux for 2 hours. After ice cooling, an aqueous ammonium chloride solution and ethyl acetate were added to the reaction mixture. The organic layer so separated was dried over anhydrous magnesium sulfate. The residue obtained by distilling off the solvent was purified by chromatography on a silica gel column (hexane:ethyl acetate= 1:1). The solvent was then distilled off. To the residue, methanol and ethanolic 1N hydrochloric acid were added. The solvent was distilled off again. Tetrahydrofuran was added to the residue and the solid so precipitated was collected by filtration. After drying, the title compound (1.76 g, 45%) was obtained as a colorless solid.

$^1$H-NMR (DMSO-d$_6$) δ: 3.91(3H,s), 8.0–8.1(3H,m), 8.1–8.15(2H,m), 8.75–8.85(1H,m), 8.85–8.95(1H,m), 9.25–9.3(1H,m).

Referential Example 8

4-(3-Pyridyl)benzoic acid hydrochloride

At room temperature, methyl 4-(3-pyridyl)benzoate (1.76 g) was dissolved in a mixed solvent of 1N hydrochloric acid (50 ml) and dioxane (50 ml), followed by heating under reflux for 4 hours. The solvent was then distilled off under reduced pressure. Tetrahydrofuran was added to the residue, followed by washing, whereby the title compound (1.55 g, 93%) was obtained as a colorless solid.

$^1$H-NMR (DMSO-d$_6$) δ: 7.95–8.0(3H,m), 8.10(2H,d,J=8.3 Hz), 8.65–8.75(1H,m), 8.8–8.9(1H,m), 9.22(1H,d,J=2.0 Hz)

Referential Example 9

Methyl 4-(2-aminopyridin-5-yl)benzoate

In a similar manner to Example 2 except for the use of 5-bromo-2-aminopyridine and 4-carboxyphenyboronic acid as the raw materials instead, the reaction was conducted, whereby 4-(2-aminopyridin-5-yl)benzoic acid was obtained.

The resulting 4-(2-aminopyridin-5-yl)benzoic acid (684 mg) was dissolved in methanol (50 ml) at room temperature, followed by the addition of concentrated sulfuric acid (1 ml). After heating under reflux for 2 hours, the reaction mixture was made weakly alkaline with an aqueous solution of sodium bicarbonate. Water and ethyl acetate were added to the resulting mixture to separate the organic layer. The organic layer was then dried over anhydrous magnesium sulfate. The solvent was distilled off. Hexane was added to the residue for crystallization, whereby the title compound (243 mg, 23%) was obtained.

$^1$H-NMR (CDCl$_3$) δ: 3.94(3H,s), 4.57(2H,br s), 6.60(1H,d,J=8.8 Hz), 7.58(2H,d,J=8.8 Hz), 7.72(1H,dd,J=8.8,2.4 Hz), 8.09(2H,d,J=8.8 Hz), 8.38(1H,d,J=2.4 Hz).

MS (FAB) m/z: 229 (M+H)$^+$.

Elementary analysis for $C_{13}H_{12}N_2O_2$

Calculated: C, 68.41; H, 5.30, N, 12.27.

Found: C, 68.78; H, 5.45; N, 12.09.

Referential Example 10

Methyl 4-[2-(tert-Butoxycarbonylamino)pyridin-5-yl]benzoate

At room temperature, methyl 4-(2-aminopyridin-5-yl)benzoate (200 mg) was suspended in tert-butanol (20 ml). To the resulting suspension, di-tert-butyl dicarbonate (286 mg) was added and the resulting mixture was stirred for 24 hours. After the solvent was distilled off, the residue was purified by chromatography on a silica gel column (1% methanol-dichloromethane), whereby the title compound (155 mg, 54%) was obtained as a colorless solid.

$^1$H-NMR (CDCl$_3$) δ: 1.55(9H,s), 3.95(3H,s), 7.63(2H,d,J=8.3 Hz), 7.92(1H,dd,J=8.8,2.4 Hz), 8.07(1H,d,J=8.8 Hz), 8.09(1H,br s), 8.12(2H,d,J=8.3 Hz), 8.55(1H,d,J=2.4 Hz).

MS(FAB) m/z: 329 (M+H)$^+$.

Elementary analysis for $C_{18}H_{20}N_2O_4$

Calculated: C, 65.84; H, 6.14, N, 8.53;

Found: C, 65.67; H, 6.02; N, 8.40.

Referential Example 11

4-[2-(tert-Butoxycarbonylamino)pyridin-5-yl]benzoic acid

At room temperature, methyl 4-[2-(tert-butoxycarbonylamino)pyridin-5-yl]benzoate (250 mg) was suspended in a mixed solvent of tetrahydrofuran (10 ml) and methanol (10 ml), followed by the addition of a 1N aqueous sodium hydroxide solution (8 ml). The resulting mixture was stirred for 5 hours. The reaction mixture was made weakly acidic with an aqueous citric acid solution, followed by the addition of saturated saline and n-butanol to separate the organic layer. The organic layer was then dried over anhydrous magnesium sulfate. The solvent was distilled off, whereby the title compound (120 mg, 49%) was obtained as a crude purified product.

$^1$H-NMR (DMSO-d$_6$) δ: 1.49(9H,s), 7.83(2H,d,J=8.3 Hz), 7.91(1H,d,J=8.8 Hz), 8.02(2H,d,J=8.3 Hz), 8.13(1H,dd,J=8.8,2.4 Hz), 8.65(1H,d,J=2.4 Hz), 9.95(1H,s), 12.99 (1H,br s)

Referential Example 12

1-[4-[2-(tert-Butoxycarbonylamino)pyridin-5-yl]benzoyl]-4-[(6-chloronaphthalen-2-yl)sulfonyl]piperazine In a mixed solvent of dichloromethane (20 ml) and N,N-dimethylformamide (1 ml), 4-[2-(tert-butoxycarbonyl)amino]pyridin-5-yl]benzoic acid (74 mg) and 1-[(6-chloronaphthalen-2-yl)sulfonyl]piperazine trifluoroacetate (110 mg) were suspended. To the resulting suspension, 1-hydroxybenzotriazole (35 mg) and N-methylmorpholine (34 μl) were added, followed by the addition of 1-(3-dimethylaminopropyl)-3-ethylcarbodiimide hydrochloride (68 mg) under ice cooling. After stirring at room temperature for 6 hours, the solvent was distilled off. The residue was purified by chromatography on a silica gel column (1% methanol-dichloromethane). The solvent was then distilled off, whereby the title compound (128 mg, 90%) was obtained.

$^1$H-NMR (CDCl$_3$) δ: 1.54(9H,s), 3,00–3,30(4H,m), 3.50–4.10(4H,m), 7.39(2H,d,J=7.8 Hz), 7.54(2H,d,J=7.8 Hz), 7.60(1H,dd,J=8,8,2.0 Hz), 7.71(1H,dd,J=8.8,1.5 Hz), 7.84(1H,dd,J=8.8,2.4 Hz), 7.88(1H,br s), 7.9–8.0(3H,m), 8.03(1H,d,J=8.8 Hz), 8.31(1H,s), 8.46(1H,d,J=2.4 Hz).

Referential Example 13

4-(4-Aminophenyl)benzoic acid hydrochloride

In a similar manner to Referential Example 2 except for the use of 4-bromoaniline and 4-carboxyphenylboronic acid as raw materials, the reaction was conducted, whereby the title compound was obtained.

$^1$H-NMR (DMSO-d$_6$) δ: 7.31(2H,d,J=7.3 Hz), 7.75–7.85 (4H,m), 8.09(2H,d,J=8.3 Hz).

MS (FAB) m/z: 213 (M$^+$).

Elementary analysis for $C_{13}H_{11}NO_2 \cdot HCl$

Calculated: C, 62.53; H, 4.84, N, 5.61; Cl, 14.20.

Found: C, 62.33; H, 4.83; N, 5.50; Cl, 14.14.

Referential Example 14

Methyl 4-[4-(tert-butoxycarbonylamino)phenyl]benzoate

In a similar manner to Referential Examples 9 and 10 except for the use of 4-(4-aminophenyl)benzoic acid hydrochloride as the raw material, the reaction was conducted, whereby the title compound was obtained.

$^1$H-NMR (CDCl$_3$) δ: 1.54(9H,s), 3,94(3H,s), 6.56(1H,br s), 7.46(2H,d,J=8.8 Hz), 7.57(2H,d,J=8.8 Hz), 7.63(2H,d,J=8.3 Hz), 8.08(2H,d,J=8.3 Hz).

MS (FAB)m/z: 328 (M+H)$^+$.

Elementary analysis for $C_{19}H_{21}NO_4$

Calculated: C, 69.71; H, 6.47, N, 4.28.

Found: C, 69.49; H, 6.44; N, 4.42.

Referential Example 15

4-[4-(tert-Butoxycarbonylamino)phenyl]benzoic acid

In a similar manner to Referential Example 11 except for the use of methyl 4-[4-(tert-butoxycarbonylamino)

phenylbenzoate (501 mg), the reaction was conducted, whereby the title compound (426 mg, 89%) was obtained.

$^1$H-NMR (CDCl$_3$) δ: 1.54(9H,s), 6.57(1H,br s), 7.47(2H, d,J=8.3 Hz), 7.59(2H,d,J=8.3 Hz), 7.66(2H,d,J=8.3 Hz), 8.13(2H,d,J=8.3 Hz).

MS (FAB) m/z: 314 (M+H)$^+$.

Elementary analysis for C$_{18}$H$_{19}$NO$_4$

Calculated: C, 68.99; H, 6.11, N, 4.47.

Found: C, 68.91; H, 6.27; N, 4.24.

Referential Example 16

1-[4-[4-(tert-Butoxycarbonylamino)phenyl]benzoyl]-4-[(6-chloronaphthalen-2-yl)sulfonyl]piperazine In a similar manner to Referential Example 12 except for the use of 4-[4-(tert-butoxycarbonylamino)phenylbenzoic acid (150 mg) and 1-[(6-chloronaphthalen-2-yl)sulfonyl] piperazine trifluoroacetate (203 mg) as the raw materials, the reaction was conducted, whereby the title compound (303 mg, 100%) was obtained.

$^1$H-NMR (CDCl$_3$) δ: 1.53(9H,s), 2.90–3.30(4H,m), 3.50–4.10(4H,m), 6.56(1H,s), 7.35(2H,d,J=8.3 Hz), 7.44 (2H,d,J=8.3 Hz), 7.49(2H,d,J=8.3 Hz), 7.54(2H,d,J=8.3 Hz), 7.59(1H,dd,J=8.8,2.0 Hz), 7.76(1H,dd,J=8.8,2.0 Hz), 7.90–7.95(3H,m), 8.30(1H,br s).

Referential Example 17

Methyl 4-acetylbenzoate

In a mixed solvent of tetrahydrofuran (100 ml) and methanol (7 ml), methyl 4-acetylbenzoate (3.28 g) was dissolved at room temperature, followed by the addition of trimethylsilyldiazomethane (a 2.0M hexane solution, 12 ml) in portions under ice cooling. After heating to room temperature and stirring for 30 minutes, the solvent was distilled off. To the residue, an aqueous solution of sodium bicarbonate and ether were added. The organic layer so separated was dried over anhydrous magnesium sulfate. After the solvent was distilled off, the residue was crystallized from hexane, whereby the title compound (2.90 g, 82%) was obtained.

$^1$H-NMR (CDCl$_3$) δ: 2.65(3H,s), 3.96(3H,s), 8.01(2H,d, J=8.3 Hz), 8.13(2H,d,J=8.3 Hz).

MS (EI) m/z: 178M$^+$.

Elementary analysis for C$_{10}$H$_{10}$O$_3$

Calculated: C, 67.41; H, 5.66.

Found: C, 67.28; H, 5.53.

Referential Example 18

Methyl 4-bromoacetylbenzoate

At 15° C., methyl 4-acetylbenzoate (2.23 g) was dissolved in a hydrobromic acid acetic acid solution (30%, 10 ml). Bromine was gradually added dropwise to the reaction mixture to maintain its temperature at 15° C. After stirring for 10 minutes, the reaction mixture was cooled to 4° C. A mixed solvent of methanol (50 ml) and water (50 ml) was added to the reaction mixture for crystallization, followed by washing with hexane. By the collection through filtration, the title compound (2.29 g, 71%) was obtained as a colorless solid.

$^1$H-NMR (CDCl$_3$) δ: 3.96(3H,s), 4,47(2H,s), 8.05(2H,d, J=8.8 Hz), 8.16(2H,d,J=8.8 Hz).

MS (FAB) m/z: 257 [(M+H)$^+$, $^{79}$Br], 259 [(M+H)$^+$, $^{81}$Br].

Elementary analysis for C$_{10}$H$_9$BrO$_3$

Calculated: C, 46.72; H, 3.53.

Found: C, 46.36; H, 3.63.

Referential Example 19

Methyl 4-(2-aminothiazol-4-yl)benzoate

At room temperature, methyl 4-bromoacetylbenzoate (1.00 g) and thiourea (296 mg) were dissolved in isopropanol (100 ml), followed by heating under reflux for 15 minutes. Under stirring at the same temperature, anhydrous sodium carbonate (206 mg) was added to the reaction mixture. The resulting mixture was heated under reflux for 20 minutes. After completion of the reaction, water (50 ml) was added under ice cooling and the solid so precipitated was collected by filtration. The solid was dissolved in water and dichloromethane. The organic layer so separated was dried over anhydrous sodium sulfate. The solvent was then distilled off. The pale yellow solid so precipitated was washed with ether, whereby the title compound (634 mg, 70%) was obtained.

$^1$H-NMR (CDCl$_3$) δ: 3.93(3H,s), 4.96(2H,br s), 6.88(1H, s), 7.85(2H,d,J=8.8 Hz), 8.05(2H,d,J=8.8 Hz).

MS (FAB) m/z: 235 (M+H)$^+$.

Referential Example 20

4-(2-Aminothiazol-4-yl)benzoic acid

At room temperature, methyl 4-(2-aminothiazol-4-yl) benzoate (300 mg) was suspended in a mixed solvent of tetrahydrofuran (5 ml) and methanol (5 ml), followed by the addition of a 1N aqueous sodium hydroxide solution (10 ml). The resulting mixture was stirred for one hour. To the reaction mixture, N,N-dimethylformamide (5 ml) was added, followed by heating under reflux for 6 hours. After completion of the reaction, the solvent was distilled off. To the residue, water and 1N hydrochloric acid were added successively and the pale yellow solid so precipitated was collected by filtration, whereby the title compound (229 mg, 69%) was obtained as a pale yellow solid.

$^1$H-NMR (DMSO-d$_6$) δ: 7.30(1H,br s), 7.87(2H,d,J=8.3 Hz), 7.95–8.00(2H,m).

MS (FAB) m/z: 221 (M+H)$^+$.

Elementary analysis for C$_{10}$H$_8$N$_2$O$_2$S.0.75HCl.0.6H$_2$O

Calculated: C, 46.48; H, 3.88, N, 10.84; Cl, 10.29; S, 12.41.

Found: C, 46.36; H, 4.12, N, 10.64; Cl, 10.05; S, 12.33.

Referential Example 21

Methyl 4-(imidazol-4-yl)benzoate

At room temperature, methyl 4-bromoacetylbenzoate (2 g) was dissolved in formamide (100 ml), followed by stirring at 180° C. for 90 minutes. After completion of the reaction, the reaction mixture was ice cooled and dissolved in water and 1N hydrochloric acid. The resulting solution was purified by chromatography through a synthetic adsorbent ("Diaion HP-20", water ~50% acetonitrile-water). The crude product so obtained was purified further by chromatography on a silica gel column (5% methanol-dichloromethane), whereby the title compound (844 mg, 54%) was obtained as a pale yellow solid.

$^1$H-NMR (CDCl$_3$) δ: 3.93(3H,s), 7.46(1H,s), 7.75(1H,s), 7.86(2H,m), 8.07(2H,d,J=8.3 Hz).

MS (FAB) m/z: 203 (M+H)$^+$.

Referential Example 22

Methyl 4-[1-triphenylmethylimidazol-4(5)-yl]benzoate

Methyl 4-(imidazol-4-yl)benzoate (828 mg) was dissolved in dichloromethane (50 ml), followed by the addition of diisopropylethylamine (856 µl) and triphenylmethyl chloride (1.37 g) under ice cooling. The resulting mixture was stirred at room temperature for 16 hours. The solvent was distilled off. The residue was purified by chromatography on a silica gel column (dichloromethane), whereby the title compound (1.08 g, 59%) was obtained as a colorless glassy solid.

$^1$H-NMR (CDCl$_3$) δ: 3.90(3H,s), 7.15–7.22(6H,m), 7.23 (1H,d,J=1.5 Hz), 7.30–7.40(15H,m), 7.52(1H,d,J=1.5 Hz), 7.79(2H,d,J=8.3 Hz), 8.01(2H,d,J=8.3 Hz).

MS (FAB) m/z: 445 (M+H)$^+$.

Referential Example 23

4-[1-Triphenylmethylimidazol-4(5)-yl]benzoic acid

At room temperature, methyl 4-[1-triphenylmethylimidazol-4(5)-yl]benzoate (1.04 g) was dissolved in a mixed solvent of tetrahydrofuran (10 ml) and methanol (10 ml). To the resulting solution, a 3N aqueous sodium hydroxide solution (6 ml) was added, followed by stirring for 5 hours. Tetrahydrofuran and methanol were subjected to solvent removal by distillation under reduced pressure. An aqueous citric acid solution was added to the residue to make it weakly acidic, followed by the addition of water and dichloromethane. The organic layer so separated was washed with saturated saline and dried over anhydrous sodium sulfate. The solvent was distilled off, whereby the title compound (1.13 g, quant.) was obtained as a crude purified product in the form of a colorless glassy solid.

$^1$H-NMR (CDCl$_3$) δ: 7.15–7.22(6H,m), 7.23(1H,d,J=1.5 Hz), 7.30–7.40(9H,m), 7.69(1H,d,J=1.5 Hz), 7.81(2H,d,J=8.3 Hz), 8.10(2H,d,J=8.3 Hz).

Referential Example 24

1-[(6-Chloronaphthalen-2-yl)sulfonyl]-4-[4-[1-triphenylmethylimidazol-4(5)-yl)]benzoyl]piperazine In a similar manner to Referential Example 12 except for the use of 4-[1-triphenylmethylimidazol-4(5)-yl]benzoic acid (371 mg) and 1-[(6-chloronaphthalen-2-yl)sulfonyl]piperazine hydrochloride (300 mg) as raw materials, the reaction was conducted, whereby the title compound (560 mg, 90%) was obtained in the form of a colorless glassy solid.

$^1$H-NMR (CDCl$_3$) δ: 2.90–3.30(4H,m), 3.50–4.10(4H,m), 7.15–7.20(6H,m), 7.28(2H,d,J=8.3 Hz), 7.30–7.40(9H,m), 7.49(1H,d,J=1.0 Hz), 7.59(1H,dd,J=8.8,2.0 Hz), 7.71 (2H,d,J=8.3 Hz), 7.75(1H,dd,J=8.8,1.5 Hz), 7.90–7.95(3H,m), 8.29(1H,br s).

MS (FAB) m/z: 723 (M+H)$^+$.

Referential Example 25

4-[2-Aminoimidazol-4-yl]benzoic acid hydrochloride

At room temperature, methyl 4-bromoacetylbenzoate (1.37 g) and acetylguanidine (1.62 g) were suspended in acetonitrile, followed by heating under reflux for 16 hours. The solvent was then distilled off under reduced pressure. Water was added to the residue. The insoluble matter so precipitated was collected by filtration, followed by washing with ethanol, whereby methyl 4-[2-aminoimidazol-4-yl]benzoate was obtained. The resulting product was dissolved in a mixed solvent of dioxane (10 ml) and 1N hydrochloric acid (10 ml), followed by heating under reflux for 8 hours. The residue obtained by distilling off the solvent was solidified by tetrahydrofuran and then collected by filtration, whereby the title compound (500 mg, 39%) was obtained.

$^1$H-NMR (DMSO-d$_6$) δ: 7.55–7.65(3H,m), 7.80(2H,d,J= 8.3 Hz), 7.98(2H,d,J=8.3 Hz), 12.2–13.3(3H,m).

MS (FAB) m/z: 204 (M+H)$^+$.

Elementary analysis for $C_{10}H_9N_3O_2 \cdot HCl \cdot 0.5H_2O$

Calculated: C, 48.30; H, 4.46; N, 16.90; Cl, 14.26.

Found: C, 48.03; H, 4.10; N, 16.49; Cl, 14.12.

Referential Example 26

1-[4-Bromo-2-(tert-butoxycarbonyl)benzoyl]-4-[(6-chloronaphthalen-2-yl)sulfonyl]piperazine In dichloromethane (200 ml), 4-bromophthalic anhydride (1.96 g) and 1-[(6-chloronaphthalen-2-yl)sulfonyl] piperazine hydrochloride (3.00 g) were suspended under ice cooling. To the resulting suspension, diisopropylethylamine (3.76 ml) was added, followed by stirring for 20 minutes. To the reaction mixture, dilute hydrochloric acid and dichloromethane were added. The organic layer so separated was dried over anhydrous sodium sulfate. The solvent was concentrated so that the volume was reduced to 200 ml. To the concentrate, N,N'-diisopropyl-O-tert-butylisourea (2.6 g) was added under ice cooling and the resulting mixture was stirred at room temperature for 3 days. Dilute hydrochloric acid and dichloromethane were added to the reaction mixture. The organic layer so separated was dried over anhydrous sodium sulfate. The residue was purified by chromatography on a silica gel column (hexane:ethyl acetate=3:1~1:1), whereby the title compound (1.78 g, 35%) was obtained as a colorless solid.

$^1$H-NMR (CDCl$_3$) δ: 1.30(9H,s), 2.90–3.40(6H,m), 3.80–4.00(2H,m), 7.01(1H,d,J=8.3 Hz), 7.59(1H,dd,J=8.3, 2.0 Hz), 7.61(1H,dd,J=8.3,2.0 Hz), 7.76(1H,dd,J=8.8,2.0 Hz), 7.85–7.95(3H,m), 8.00(1H,d,J=2.0 Hz), 8.29(1H,br s).

Referential Example 27

1-[2-tert-Butoxycarbonyl-4-(pyridin-4-yl)benzoyl]-4-[(6-chloronaphthalen-2-yl)sulfonyl]piperazine hydrochloride In a similar manner to Referential Example 7 except for the use of 1-[4-bromo-2-(tert-butoxycarbonyl)benzoyl]-4-[(6-chloronaphthalen-2-yl)sulfonyl]piperazine and diethyl (4-pyridyl)borane as the raw materials, the reaction was conducted, whereby the title compound was obtained.

$^1$H-NMR (CDCl$_3$) δ: 1.37(9H,s), 2.80–3.50(6H,m), 3.80–4.00(2H,m), 7.40(1H,d,J=7.8 Hz), 7.60(1H,dd,J=8.8, 2.0 Hz), 7.77(1H,dd,J=8.3,1.5 Hz), 7.87(1H,dd,J=7.8,2.0 Hz), 7.90–7.95(3H,m), 8.10(2H,d,J=6.8 Hz), 8.25(1H,d,J= 2.0 Hz), 8.31(1H,br s), 8.90(2H,d,J=6.8 Hz).

MS (FAB) m/z: 592 (M+H)$^+$.

Elementary analysis for $C_{31}H_{30}ClN_3O_5S \cdot HCl \cdot 0.2H_2O \cdot THF$ Calculated: C, 59.69; H, 5.64; N, 5.97; Cl, 10.07; S, 4.55.

Found: C, 59.55; H, 5.45; N, 5.87; Cl, 9.97; S, 4.68.

Referential Example 28

5-(4-Pyridyl)thiophene-2-carboxylic acid hydrochloride

In a similar manner to Referential Example 6 except for the use of 5-bromothiophene-2-carboxylic acid and diethyl (4-pyridyl)borane as the raw materials, the reaction was conducted, whereby the title compound was obtained.

$^1$H-NMR (DMSO-$d_6$) δ: 7.87(1H,d,J=3.9 Hz), 8.17(1H, d,J=3.9 Hz), 8.29(2H,d,J=6.8 Hz), 8.88(2H,d,J=6.8 Hz).

MS (FAB) m/z: 206 (M+H)$^+$.

Elementary analysis for $C_{10}H_7NO_2S.HCl.0.8H_2O$

Calculated: C, 46.90; H, 3.78; N, 5.47; Cl, 13.84; S, 12.52.

Found: C, 46.77; H, 3.76; N, 5.27; Cl, 13.83; S, 12.56.

Referential Example 29

5-(4-Pyridyl)furan-2-carboxylic acid hydrochloride

In a similar manner to Referential Example 6 except for the use of 5-bromofuran-2-carboxylic acid and diethyl (4-pyridyl)borane as the raw materials, the reaction was conducted, whereby the title compound was obtained.

$^1$H-NMR (DMSO-$d_6$) δ: 7.49(1H,d,J=3.4 Hz), 7.80–7.90 (1H,m), 8.20–8.30(2H,m), 8.85–8.95(2H,m).

Referential Example 30

4-(2-Pyridyl)benzoic acid hydrochloride

To water (200 ml), 2-(p-tolyl)pyridine (17.2 g) was added. To the resulting mixture, potassium permanganate (21.0 g) was added, followed by heating under reflux for 18 hours. After the precipitate was filtered off, dichloromethane was added to the filtrate to separate the water layer. The water layer was then made acidic with 2N hydrochloric acid. The acidic aqueous solution was concentrated. The precipitate was collected by filtration, followed by washing with water and ethyl acetate, whereby the title compound (7.07 g, 35%) was obtained as a white solid.

$^1$H-NMR (DMSO-$d_6$) δ: 7.60(1H,t,J=5.9 Hz), 8.08(2H,d, J=7.8 Hz), 8.17(2H,m), 8.21(2H,d,J=7.8 Hz), 8.78(1H,d,J= 4.9 Hz).

MS (EI) m/z: 199M$^+$.

Referential Example 31

1-[(E)-4-Chlorostyrylsulfonyl)piperazine hydrochloride

In a similar manner to Referential Example 1 except for the use of tert-butyl 1-piperazinecarboxylate and (E)-4-chlorostyrylsulfonyl chloride as the raw materials, the reaction was conducted, whereby the title compound was obtained.

$^1$H-NMR (DMSO-$d_6$) δ: 3.20(4H,br s), 3.33–3.38(4H,m), 7.47(2H,s), 7.53(1H,d,J=8.8 Hz), 7.82(1H,d,J=8.8 Hz).

Elementary analysis for $C_{12}H_{15}ClN_2O_2S.HCl$

Calculated: C, 44.59; H, 4.99, Cl, 21.94; N, 8.67; S, 9.92.

Found: C, 44.42; H, 4.78, Cl, 21.83; N, 8.68; S, 9.87.

Referential Example 32

4-(2,4-Diamino-6-pyrimidinyl)benzoic acid hydrochloride

In toluene (9 ml), 6-chloro-2,4-diaminopyrimidine (434 mg) was dissolved, followed by the addition of 4-carboxyphenylboronic acid (667 mg), ethanol (2.5 ml), sodium carbonate (635 mg), water (3.0 ml) and bis (triphenylphosphine)palladium (II) dichloride (65 mg). The resulting mixture was heated under reflux for 24 hours under an argon gas atmosphere. Ethyl acetate and water were added to the reaction mixture. The water layer so separated was made acidic with 2N hydrochloric acid. The insoluble matter was collected by filtration, washed with water and tetrahydrofuran and then dried, whereby the title compound (371 mg, 54%) was obtained.

$^1$H-NMR (DMSO-$d_6$) δ: 6.43(1H,s), 7.30–7.80(2H,br), 7.96(2H,d,J=7.8 Hz), 8.12(2H,d,J=7.8 Hz), 8.27(2H,br s), 12.77(1H,br), 13.33(1H,br).

MS (EI) m/z: 230M$^+$.

Elementary analysis for $C_{11}H_{10}N_4O_2S.0.95HCl.1.9H_2O$

Calculated: C, 44.17; H, 4.97; Cl, 11.26; N, 18.73.

Found: C, 44.33; H, 4.97; Cl, 11.32; N, 18.65.

Referential Example 33

1-tert-Butoxycarbonyl-4-[4-(2-pyridyl)benzoyl] piperazine

In a similar manner to Referential Example 3 except for the use of 4-(2-pyridyl)benzoic acid hydrochloride obtained in Referential Example 30 and tert-butyl 1-piperazinecarboxylate as the raw materials, the reaction was conducted, whereby the title compound was obtained.

$^1$H-NMR (CDCl$_3$) δ: 1.47(9H,s), 3.43(4H,br), 3.51(2H, br), 3.76(2H,br), 7.28(1H,d,J=5.9 Hz), 7.52(2H,d,J=7.8 Hz), 7.76(1H,m), 7.79(1H,m), 8.05(2H,d,J=7.8 Hz), 8.71(1H,d, J=4.9).

MS (FAB) m/z: 368 (M+H)$^+$.

Elementary analysis for $C_{21}H_{25}N_3O_3.0.1H_2O$

Calculated: C, 68.31; H, 6.88; N, 11.38;

Found: C, 68.26; H, 6.86; N, 11.42.

Referential Example 34

2-[4-[[4-(tert-Butoxycarbonyl)piperazin-1-yl] carbonyl]phenyl]pyridine N-oxide

At −10° C., metachloroperbenzoic acid (789 mg) was added to a solution of 1-tert-butoxycarbonyl-4-[4-(2-pyridyl)benzoyl]piperazine (517 mg) in dichloromethane (dichloromethane: 8 ml). The resulting mixture was stirred for 24 hours, followed by dilution with dichloromethane. A small amount of an aqueous sodium thiosulfate solution and saturated saline were added to the dilute solution. The organic layer so separated was washed with a saturated aqueous solution of sodium bicarbonate and saturated saline and then dried over anhydrous sodium sulfate. The residue obtained by distilling off the solvent under reduced pressure was purified by chromatography on a silica gel column (dichloromethane:methanol=20:1), whereby the title compound (415 mg, 77%) was obtained.

$^1$H-NMR (CDCl$_3$) δ: 1.48(9H,s), 3.47(6H,br), 3.76(2H, br), 7.29(1H,m), 7.34(1H,t,J=7.8 Hz), 7.44(1H,dd,J=7.8,2.0 Hz), 7.52(2H,d,J=7.8 Hz), 7.90(2H,d,J=7.8 Hz), 8.35(1H,d, J=5.9 Hz).

MS (FAB) m/z: 384 (M+H)$^+$.

Referential Example 35

2-[4-[(1-Piperazinyl)carbonyl]phenyl]pyridine N-oxide

In dichloromethane (2.5 ml), 2-[4-[[4-(tert-butoxycarbonyl)piperazin-1-yl]carbonyl]phenyl]pyridine N-oxide was dissolved. To the resulting solution, a saturated solution of ethanol hydrochloride (2.5 ml) was added, followed by stirring at room temperature for 1 hour. After the solvent was distilled off under reduced pressure, water was added to the residue, whereby an aqueous solution was obtained. Acetone was added to the aqueous solution until the solution became turbid. The precipitate was collected by filtration and washed with acetone, whereby the title compound (274 mg, 81%) was obtained.

$^1$H-NMR (DMSO-$d_6$) δ: 3.17(4H,br s), 3.50–3.95(4H,br), 7.43(1H,d,J=3.9 Hz), 7.44(1H,d,J=3.9 Hz), 7.57(2H,d,J=8.8 Hz), 7.66(1H,t,J=3.9 Hz), 7.92(2H,d,J=8.8 Hz), 8.36(1H,t, J=3.9 Hz), 9.21 (2H,br)

MS (FAB) m/z: 284 (M+H)$^+$.

Referential Example 36

1-(tert-Butoxycarbonyl)-4-[4-(3-pyridyl)benzoyl] piperazine

In a similar manner to Referential Example 3 except for the use of 4-(3-pyridyl)benzoic acid hydrochloride obtained in Referential Example 8 and tert-butyl 1-piperazinecarboxylate as the raw materials, the reaction was conducted, whereby the title compound was obtained.

$^1$H-NMR (CDCl$_3$) δ: 1.47(9H,s), 3.35–3.85(8H,br), 7.38 (1H,dd,J=7.8,4.9 Hz), 7.52(2H,d,J=8.3 Hz), 7.63(2H,d,J= 8.3Hz), 7.88(1H,m), 8.62(1H,dd,J=1.5,4.9 Hz), 8.84 (1H,d, J=2.0 Hz).

Referential Example 37

3-[4-[[4-(tert-Butoxycarbonyl)piperazin-1-yl] carbonyl]phenyl]pyridine N-oxide

In a similar manner to Referential Example 34 except for the use of 1-(tert-butoxycarbonyl)-4-[4-(3-pyridyl)benzoyl] piperazine as the raw material, the title compound was obtained as a colorless solid.

$^1$H-NMR (CDCl$_3$) δ: 1.48(9H,s), 3.35–4.83(8H,br), 7.38 (1H,m), 7.47(1H,m), 7.49–7.65(4H,m), 8.23(1H,dd,J=6.4, 1.5 Hz), 8.47(1H,t,J=1.5 Hz).

MS (FAB) m/z: 384 (M+H)$^+$.

Elementary analysis for $C_{21}H_{25}N_3O_4 \cdot 0.25H_2O$

Calculated: C, 65.02; H, 6.63; N, 10.83.

Found: C, 65.30; H, 6.65; N, 10.43.

Referential Example 38

2-Hydroxy-4-(4-pyridyl)benzoic acid

In water (22.5 ml) and a 47% aqueous solution of hydrobromic acid (22.5 ml), 4-amino-2-hydroxybenzoic acid (5.04 g) was dissolved. While the resulting solution mixture was maintained at 5° C. or lower, an aqueous solution (water: 15.0 ml) of sodium nitrite (2.26 g) was added dropwise thereto, followed by stirring for 30 minutes under ice cooling. The reaction mixture was added, in portions, to a solution of cuprous bromide (5.63 g) dissolved in a 47% aqueous solution of hydrobromic acid (15 ml) under ice cooling. The resulting mixture was stirred at room temperature for 150 minutes. Ethyl acetate was added to the reaction mixture for extraction. The organic layer so obtained was washed with water and then dried over anhydrous sodium sulfate. The residue obtained by distilling off the solvent under reduced pressure was purified by chromatography on a silica gel column (dichloromethane~10% methanol-dichloromethane), whereby 4-bromo-2-hydroxybenzoic acid (5.51 g) was obtained as a crudely purified product.

The crudely purified product (298 mg) was reacted as in Referential Example 6, whereby the title compound (70 mg, 21%) was obtained.

$^1$H-NMR (DMSO-$d_6$) δ: 7.30–7.40(2H,m), 7.78(2H,d,J= 4.4 Hz), 7.92(1H,d,J=6.3 Hz), 8.69(2H,d,J=5.9 Hz).

MS (FAB) m/z: 216 (M+H)$^+$.

Referential Example 39

4-Bromo-3-hydroxybenzoic acid

In acetic acid (24.5 ml), 3-hydroxybenzoic acid (5.00 g) was suspended. To the resulting suspension, a solution of bromine (1.9 ml) in acetic acid (acetic acid: 5 ml) was added dropwise under ice cooling, followed by stirring at room temperature for 33 hours. The reaction mixture was ice cooled. The crystals so precipitated were collected by filtration and then washed with acetic acid, whereby the title compound (1.68 g, 21%) was obtained.

$^1$H-NMR (DMSO-$d_6$) δ: 7.28(1H,dd,J=7.8,2.0 Hz), 7.51 (1H,d,J=2.0 Hz), 7.59(1H,d,J=8.3 Hz), 10.54(1H,br s), 12.84.(1H,br).

Referential Example 40

Methyl 4-bromo-3-methoxybenzoate

In a similar manner to Referential Example 17 except for the use of 4-bromo-3-hydroxybenzoic acid as the raw material, the reaction was conducted, whereby the title compound was obtained.

$^1$H-NMR (CDCl$_3$) δ: 3.92(3H,s), 3.96(3H,s), 7.51(1H,dd, J=8.3,2.0 Hz), 7.55(1H,d,J=2.0 Hz), 7.61(1H,d,J=8.8 Hz).

Referential Example 41

3-Methoxy-4-(4-pyridyl)benzoic acid

In a similar manner to Referential Example 7 except for the use of methyl 4-bromo-3-methoxybenzoate and diethyl (4-pyridyl)borane, the reaction was conducted. The crude product so obtained was reacted as in Referential Example 8, whereby the title compound was obtained.

$^1$H-NMR (CDCl$_3$) δ: 3.93(3H,s), 7.65–7.75(3H,m), 8.20 (2H,d,J=5.4 Hz), 8.94(2H,d,J=6.3 Hz).

MS (FAB) m/z: 230 (M+H)$^+$.

Referential Example 42

4-tert-Butoxycarbonyl-1-[(6-chloronaphthalen-2-yl) sulfonyl]-2-ethoxycarbonylpiperazine In dichloromethane (18 ml), 1-tert-butoxycarbonyl-3-ethoxycarbonylpiperazine (517 mg) and 6-chloro-2-naphthylsulfonyl chloride (588 mg) were dissolved under ice cooling. To the resulting solution, diisopropylethylamine (0.59 ml) was added, followed by stirring at room temperature for 63 hours. The residue obtained by distilling off the solvent under reduced pressure was purified by chromatography on a silica gel column (hexane:ethyl acetate=3:1), whereby the title compound (688 mg, 71%) was obtained.

$^1$H-NMR (CDCl$_3$) δ: 1.05(3H,t,J=7.1 Hz), 1.38(9H,s), 2.80–4.70(9H,m), 7.55(1H,dd,J=8.6,2.2 Hz), 7.77(1H,dd,J= 8.6,1.7 Hz), 7.85–7.90(3H,m), 8.33(1H,s).

MS (FAB) m/z: 483 [(M+H)$^+$, Cl$^{35}$], 485[(M+H)$^+$, Cl$^{37}$].

Referential Example 43

4-tert-Butoxycarbonyl-2-ethoxycarbonyl-1-[4-(3-pyridyl)benzoyl]piperazine

In a similar manner to Referential Example 12 except for the use of 4-(3-pyridyl)benzoic acid and 1-tertbutoxycarbonyl-3-ethoxycarbonylpiperazine as the raw materials, the reaction was conducted, whereby the title compound was obtained.

$^1$H-NMR (CDCl$_3$) δ: 1.20–1.40(3H,m), 1.46(9H,s), 2.70–4.80(8H,m), 5.35(1H,br), 7.35–7.70(5H,m), 7.85–7.95 (1H,m), 8.64(2H,dd,J=4.6,1.7 Hz), 8.86(1H,s).

MS (FAB) m/z: 440 (M+H)$^+$.

Referential Example 44

Methyl N-tert-butoxycarbonyltranexamate

To methanol (20 ml), thionyl chloride (1 ml) was added dropwise under ice cooling, followed by the addition of tranexamic acid (2.04 g). The resulting mixture was heated under reflux for 3 hours. The residue obtained by distilling off the reaction mixture under reduced pressure was pulverized in ether and then collected by filtration, whereby colorless crystals (2.31 g) were obtained.

The resulting crystals (2.10 g) were dissolved in dichloromethane (40 ml), followed by the addition of N-methylmorpholine (1.2 ml). To the resulting mixture, a solution of di-tert-butyl dicarbonate (2.51 g) in dichloromethane (dichloromethane: 3 ml) was added under ice cooling. The resulting mixture was stirred at room temperature for 18 hours. After diluted with dichloromethane, the reaction mixture was washed with water and then dried over anhydrous sodium sulfate. The residue obtained by distilling off the solvent under reduced pressure was purified by chromatography on a silica gel column (hexane:ethyl acetate=10:1~3:1), followed by recrystallization from a mixed solvent of hexane and ethyl acetate, whereby colorless crystals (2.09 g, 65%) was obtained.

$^1$H-NMR (CDCl$_3$) δ: 0.90–1.10(2H,m), 1.40–1.60(12H, m), 1.80–1.90(2H,m), 2.00–2.10(2H,m), 2.24(1H,m), 2.98 (2H,m), 3.66(3H,s), 4.58(1H,br).

Elementary analysis for C$_{14}$H$_{25}$NO$_4$

Calculated: C, 61.97; H, 9.29; N, 5.16.

Found: C, 62.15; H, 9.42; N, 5.12.

Referential Example 45 trans-4-(N-tert-Butoxycarbonylaminomethyl) cyclohexylmethanol

Methyl N-tert-butoxycarbonyltranexamate (1.00 g) was dissolved in a mixed solvent of tetrahydrofuran (10 ml) and methanol (2 ml). To the resulting solution, sodium borohydride (0.44 g) was added under ice cooling, followed by stirring at room temperature for 24 hours. After the addition of water, the reaction mixture was concentrated under reduced pressure. Ethyl acetate and dilute hydrochloric acid were added to the concentrate. The organic layer so separated was dried over anhydrous sodium sulfate. The residue obtained by distilling off the solvent under reduced pressure was purified by chromatography on a silica gel column in repetition (first time; dichloromethane~dichloromethane:methanol=20:1, second time; hexane:ethyl acetate=3:1), whereby colorless crystals (0.74 g, 82%) were obtained. A portion of the crystals was recrystallized from a mixed solvent of hexane and ethyl acetate, whereby colorless crystals were obtained.

$^1$H-NMR (CDCl$_3$) δ: 0.90–1.10(4H,m), 1.30–1.60(12H, m), 1.80–2.00(4H,m), 2.98(2H,m), 3.45(2H,d.J=6.4 Hz), 4.59(1H,br).

Elementary analysis for C$_{13}$H$_{25}$NO$_3$

Calculated: C, 64.17; H, 10.35, N, 5.76.

Found: C, 64.31; H, 10.03; N, 5.74.

Referential Example 46 trans-4-(N-tert-Butoxycarbonylaminomethyl) cyclohexanecarboxaldehyde

In dichloromethane (5 ml), trans-4-(N-tert-butoxycarbonylaminomethyl)cyclohexylmethanol (0.20 g) was dissolved, followed by the addition of pyridinium chlorochromate (0.23 g). The resulting mixture was stirred at room temperature for 3 hours. The reaction mixture was purified by chromatography on a silica gel column (hexane:ethyl acetate=3:1), whereby the title compound (0.15 g, 76%) was obtained.

$^1$H-NMR (CDCl$_3$) δ: 1.00(2H,m), 1.27(2H,m), 1.40–1.60 (1H,m), 1.44(9H,s), 1.88(2H,m), 2.02(2H,m), 2.18(1H,m), 3.00(2H,t,J=6.4 Hz), 4.61(1H,br), 9.62(1H,s).

MS (FAB) m/z: 242 (M+H)$^+$.

Referential Example 47

1-[trans-4-(N-tert-Butoxycarbonylaminomethyl) cyclohexylmethyl]-4-[(6-chloronaphthalen-2-yl) sulfonyl]piperazine In dichloromethane (7 ml), trans-4-(N-tert-butoxycarbonylaminomethyl)cyclohexane carboxaldehyde (0.13 g) was dissolved, followed by the addition of 1-[(6-chloronaphthalen-2-yl)sulfonyl]piperazine trifluoroacetate (0.24 g), triethylamine (78 µl) and sodium triacetoxyborohydride (0.17 g). The resulting mixture was stirred at room temperature for 11 hours under an argon gas atmosphere. To the reaction mixture, an aqueous solution of sodium bicarbonate was added, followed by dilution with dichloromethane. The organic layer so separated was dried over anhydrous sodium sulfate. The residue obtained by distilling off the solvent under reduced pressure was purified by chromatography on a silica gel column (hexane:ethyl acetate=2:1), whereby the title compound (0.29 g, 100%) was obtained.

$^1$H-NMR (CDCl$_3$) δ: 0.70–0.90(4H,m), 1.30–1.50(2H, m), 1.42(9H,s), 1.70–1.80(4H,m), 2.09(2H,d,J=7.3 Hz), 2.46(4H,m), 2.92(2H,m), 3.08(4H,m), 4.53(1H,br), 7.56 (1H,dd,J=8.8,2.0 Hz), 7.78(1H,dd,J=8.8,2.0 Hz), 7.80–8.00 (3H,m), 8.30(1H,s).

MS (FAB) m/z: 536[(M+H)$^+$, Cl$^{35}$], 538[(M+H)$^+$, Cl$^{37}$].

Referential Example 48

1-[trans-4-(N-tert-Butoxycarbonylaminomethyl) cyclohexylcarbonyl]-4-[(6-chloronaphthalen-2-yl) sulfonyl]piperazine The reaction was conducted as in Referential Examples 11 and 12, whereby the title compound was obtained.

$^1$H-NMR (CDCl$_3$) δ: 0.80–1.00(2H,m), 1.40–1.60(3H, m), 1.42(9H,s), 1.60–1.70(2H,m), 1.70–1.90(2H,m), 2.30 (1H,m), 2.95(2H,m), 3.07(4H,m), 3.58(2H,br), 3.70(2H,br), 4.57(1H,m), 7.58(1H,dd,J=8.8,2.0 Hz), 7.75(1H,dd,J=8.8, 1.5 Hz), 7.90–8.00(3H,m), 8.30(1H,s).

MS (FD) m/z: 549(M$^+$, Cl$^{35}$), 551(M$^+$, Cl$^{37}$).

Referential Example 49

N-[trans-4-(N-tert-Butoxycarbonylaminomethyl) cyclohexylcarbonyl]glycine Benzyl Ester In a similar manner to Referential Examples 11 and 12 except for the use of methyl N-tertbutoxycarbonyltranexamate and glycine benzyl ester as the raw materials, the reaction was conducted, whereby the title compound was obtained.

¹H-NMR (CDCl₃) δ: 0.96(2H,m), 1.44 (9H,s), 1.40–1.60 (3H,m), 1.80–1.90(2H,m), 1.90–2.00(2H,m), 2.10(1H,m), 2.98(2H,m), 4.08(2H,d,J=4.9 Hz), 4.57(1H,br), 5.19(2H,s), 5.97(1H,m), 7.30–7.40(5H,m).

Elementary analysis for C₂₂H₃₂N₂O₅
Calculated: C, 65.32; H, 7.97; N, 6.93.
Found: C, 65.05; H, 7.89; N, 7.16.

Referential Example 50

1-[N-[trans-4-(N-tert-Butoxycarbonylaminomethyl) cyclohexylcarbonyl]glycyl]-4-[(6-chloronaphthalen-2-yl)sulfonyl]piperazine In tetrahydrofuran (11 ml), N-[trans-4-(N-tert-butoxycarbonylaminomethyl)cyclohexylcarbonyl]glycine benzyl ester (0.22 g) was suspended. To the resulting suspension, 10% palladium carbon (water content: about 50%, 50 mg) was added, followed by catalytic reduction at normal pressure and room temperature for 14 hours. After the removal of the catalyst, the solvent was distilled off under reduced pressure. The residue so obtained was reacted as in Referential Example 12, whereby the title compound (0.32 g, 98%) was obtained.

¹H-NMR (CDCl₃) δ: 0.80–1.00(2H,m), 1.30–1.50(3H, m), 1.43(9H,s), 1.80–2.00(4H,m), 2.06(1H,m), 2.95(2H,m), 3.10–3.20(4H,m), 3.52(2H,m), 3.74(2H,m), 3.94(2H,d,J= 4.4 Hz), 4.54(1H,m), 6.40(1H,m), 7.59(1H,dd,J=8.8,2.0 Hz), 7.74(1H,dd,J=8.8,1.5 Hz), 7.80–8.00(3H,m), 8.30(1H, s).

MS (FAB) m/z: 607 [(M+H)⁺, Cl³⁵], 609 [(M+H)⁺, Cl³⁷].

Referential Example 51

1-[(6-Chloronaphthalen-2-yl)sulfonyl] homopiperazine hydrochloride

Homopiperazine (5 g) was dissolved in tetrahydrofuran (100 ml) at room temperature. To the resulting solution, 2-(tert-butoxycarbonyloxyimino)-2-phenylacetonitrile (12.3 g) was added in portions, followed by stirring for 3 hours. After completion of the reaction, the solvent was distilled off. The residue was purified by chromatography on a silica gel column (10 to 20% methanol-dichloromethane), followed by the addition of ethanolic 1N hydrochloric acid. The solvent was then distilled off. The residue was solidified by the addition of ethanol, whereby powders (7.46 g) were obtained. The resulting powders were reacted as in Referential Example 1, whereby the title compound was obtained.

¹H-NMR (DMSO-d₆) δ: 2.00(2H,br s), 3.10–3.30(4H,m), 3.30–3.50(2H,m), 3.55–3.65(2H,m), 7.72(1H,d,J=8.8 Hz), 7.89(1H,d,J=8.3 Hz), 8.17(1H,d,J=8.8 Hz), 8.22–8.28(2H, m), 8.56(1H,s), 9.29(2H,br s).

MS (FAB) m/z: 325 (M+H)⁺.

Elementary analysis for C₁₅H₁₇ClN₂O₂S.HCl
Calculated: C, 49.89; H, 5.02; N, 7.75; Cl, 19.63.
Found: C, 49.94; H, 5.05; N, 7.47; Cl, 19.65.

Referential Example 52

1-[trans-4-(N-tert-Butoxycarbonylaminomethyl) cyclohexylcarbonyl]-4-[(6-chloronaphthalen-2-yl) sulfonyl]homopiperazine In a similar manner to Referential Example 48 except for the use of methyl N-tert-butoxycarbonyltranexamate and 1-[(6-chloronaphthalen-2-yl)sulfonyl]homopiperazine hydrochloride, the reaction was conducted, whereby the title compound was obtained.

¹H-NMR (CDCl₃) δ: 0.80–1.00(2H,m), 1.40–1.60(3H, m), 1.43(9H,s), 1.60–1.90(4H,m), 1.90–2.10(2H,m), 2.30–2.40(1H,m), 2.97(2H,m), 3.30–3.50(4H,m), 3.60–3.80 (4H,m), 4.64(1H,br), 7.50–7.60(1H,m), 7.70–7.80(1H,m), 7.80–8.00(3H,m), 8.33 and 8.35(1H, each s).

MS (FAB) m/z: 564 [(M+H)⁺, Cl³⁵], 566 [(M+H)⁺, Cl³⁷].

Referential Example 53

Methyl 4-(N-tert-butoxycarbonylaminomethyl) benzoate

In a similar manner to Referential Example 44 except for the use of 4-aminomethylbenzoic acid as the raw material, the reaction was conducted, whereby the title compound was obtained.

¹H-NMR (CDCl₃) δ: 1.47(9H,s), 3.91(3H,s), 4.37(2H,d, J=5.4 Hz), 4.92(1H,br), 7.35(2H,d,J=8.3 Hz), 8.00(2H,d,J= 8.3 Hz).

Elementary analysis for C₁₄H₁₉NO₄
Calculated: C, 63.38; H, 7.22; N, 5.28.
Found: C, 63.20; H, 7.02; N, 5.58.

Referential Example 54

1-[4-(N-tert-Butoxycarbonylaminomethyl)benzoyl]-4-[(6-chloronaphthalen-2-yl)sulfonyl]piperazine In a similar manner to Referential Example 48 except for the use of methyl 4-(N-tert-butoxycarbonylaminomethyl) benzoate and 1-[(6-chloronaphthalen-2-yl)sulfonyl] piperazine hydrochloride, the reaction was conducted, whereby the title compound was obtained.

¹H-NMR (CDCl₃) δ: 1.45(9H,s), 3.00–3.30(4H,br), 3.40–4.00(4H,br), 4.31(2H,d,J=5.9 Hz), 4.90(1H,br), 7.27 (4H,m), 7.59(1H,dd,J=8.8,1.5 Hz), 7.75(1H,d,J=8.8 Hz), 7.90–8.00(3H,m), 8.30(1H,s).

MS (FAB) m/z: 544 [(M+H)⁺, Cl³⁵], 546 [(M+H)⁺, Cl³⁷].

Referential Example 55

Methyl 3-(N-tert-butoxycarbonylaminomethyl) benzoate

Methyl 3-methylbenzoate (1.00 g) was dissolved in carbon tetrachloride (10 ml), followed by the addition of N-bromosuccinic imide (1.22 g) and 2,2'-azobisisobutyronitrile (catalytic amount). The resulting mixture was heated under reflux for 1 hour under exposure to a mercury lamp. After the insoluble matter was filtered off, the residue obtained by distilling off the solvent under reduced pressure was purified by chromatography on a silica gel column (hexane:ethyl acetate=20:1), whereby a colorless oil (1.34 g) was obtained.

The colorless oil (0.62 g) so obtained was dissolved in N,N-dimethylformamide (10 ml), followed by the addition of sodium azide (0.38 g). The resulting mixture was stirred at room temperature for 20 hours. After the concentration of the reaction mixture under reduced pressure, the concentrate was diluted with ethyl acetate, washed with water and then dried over anhydrous sodium sulfate. The residue obtained by distilling off the solvent under reduced pressure was dissolved in tetrahydrofuran (15 ml). Triphenylphosphine (0.75 g) was added to the resulting solution, followed by stirring at an external temperature of about 50° C. for 5 hours. After the addition of about 28% aqueous ammonia (7 ml) and stirring for further 2 hours, the reaction mixture was concentrated under reduced pressure. The concentrate was extracted with ether. Dilute hydrochloric acid was added to the extract to make it acidic. To the water layer so separated, a acidic. To the water layer so separated, a dilute aqueous solution of sodium hydroxide was added to make it alkaline, followed by extraction with dichloromethane. The extract was dried over anhydrous sodium sulfate. The residue obtained by distilling off the solvent under reduced pressure was dissolved in dichloromethane (7 ml). To the resulting solution, di-tert-butyl dicarbonate (0.45 g) was added under ice cooling, followed by stirring at room temperature for 3 days. The residue obtained by distilling off the solvent under reduced pressure was purified by chromatography on a silica gel column (hexane:ethyl acetate=5:1), whereby the title compound (0.29 g, 35%) was obtained.

$^1$H-NMR (CDCl$_3$) δ: 1.46(9H,s), 3.91(3H,s), 4.36(2H,d, J=5.9 Hz), 4.97(1H,br), 7.40(1H,t,J=7.8 Hz), 7.49(1H,d,J= 7.8 Hz), 7,90–8,00(2H,m).

MS (FAB) m/z: 266 (M+H)$^+$.

Referential Example 56

Methyl 4-cyanomethylbenzoate

In dichloromethane (20 ml), methyl 4-hydroxymethylbenzoate (1.00 g) was dissolved, followed by the addition of triethylamine (0.9 ml). Under ice cooling, a solution of methanesulfonyl chloride (0.70 g) in dichloromethane (dichloromethane: 5 ml) was added to the resulting solution. The resulting mixture was stirred at room temperature for 15 hours. After dilution with dichloromethane, the reaction mixture was washed with water and was then dried over anhydrous sodium sulfate. The residue obtained by distilling off the solvent under reduced pressure was dissolved in acetonitrile (12 ml). To the resulting solution, potassium cyanide (0.80 g) and 18-Crown-6 (0.16 g) were added, followed by stirring at room temperature for 40 hours. After concentration under reduced pressure, the concentrate was diluted with dichloromethane, washed with water and then, dried over anhydrous sodium sulfate. The residue obtained by distilling off the solvent under reduced pressure was purified by chromatography on a silica gel column (dichloromethane), whereby colorless crystals (0.91 g, 86%) was obtained. A portion of the resulting crystals was recrystallized from a mixed solvent of hexane and ethyl acetate, whereby colorless crystals were obtained.

$^1$H-NMR (CDCl$_3$) δ: 3.82(2H,s), 3.93(3H,s), 7.42(2H,d,= 8.3 Hz), 8.06(2H,d,J=8.3 Hz).

Elementary analysis for C$_{10}$H$_9$NO$_2$

Calculated: C, 68.56; H, 5.18; N, 8.00.

Found: C, 68.39; H, 5.29; N, 8.08.

Referential Example 57

Methyl 4-[2-(tert-butoxycarbonylamino)ethyl]benzoate

Methyl 4-cyanomethylbenzoate (0.20 g) was dissolved in a mixed solvent of methanol (15 ml) and chloroform (0.4 ml). To the resulting solution, platinum dioxide (33 mg) was added, followed by catalytic reduction at room temperature under 3 atmospheric pressure for 3 hours. The catalyst was removed by filtration through Celite and the solvent was distilled off under reduced pressure. The residue was suspended in dichloromethane (5 ml), followed by the addition of triethylamine (160 μl). After the addition of a solution of di-tert-butyl dicarbonate (0.29 g) in dichloromethane (dichloromethane: 2 ml) under ice cooling, the resulting solution was stirred at room temperature for 13 hours. The reaction mixture was diluted with dichloromethane, washed with water and then dried over anhydrous sodium sulfate. The solvent was distilled off under reduced pressure. The residue was purified by chromatography on a silica gel column (hexane:ethyl acetate 10:1~5:1), whereby the title compound (0.28 g, 88%) was obtained.

$^1$H-NMR (CDCl$_3$) δ: 1.43(9H,s), 2.86(2H,t,J=6.8 Hz), 3.39(2H,m), 3.91(3H,s), 4.53(1H,br), 7.27(2H,d,J=8.3 Hz), 7.98(2H,d,J=8.3 Hz).

Elementary analysis for C$_{15}$H$_{21}$NO$_4$

Calculated: C, 64.50; H, 7.58; N, 5.01.

Found: C, 64.43; H, 7.35; N, 4.97.

Referential Example 58

1-[4-[2-(tert-Butoxycarbonylamino)ethyl]benzoyl]-4-[(6-chloronaphthalen-2-yl)sulfonyl]piperazine In a similar manner to Referential Example 48 except for the use of methyl 4-[2-(tert-butoxycarbonylamino)ethyl]benzoate and 1-[(6-chloronaphthalen-2-yl)sulfonyl]piperazine hydrochloride as the raw materials, the title compound was obtained.

$^1$H-NMR (CDCl$_3$) δ: 1.42(9H,s), 2.79(2H,t,J=6.8 Hz), 3.10(4H,br), 3.35(2H,m), 3.40–4.00(4H,br), 4.50(1H,br), 7.18(2H,d,J=8.3 Hz), 7.24(2H,d,J=8.3 Hz), 7.59(1H,dd,J= 8.8,2.0 Hz), 7.75(1H,dd,J=8.8,2.0 Hz), 7.90–8.00(3H,m), 8.30(1H,s).

MS (FAB) m/z: 558 [(M+H)$^+$, Cl$^{35}$], 560 [(M+H)$^+$, Cl$^{37}$].

Referential Example 59

(2RS)-2-(N-tert-Butoxycarbonylaminomethyl)-6-methoxycarbonyl-1,2,3,4-tetrahydronaphthalene In a similar manner to Referential Example 55 except for the use of (2RS)-6-methoxycarbonyl-2-p-toluenesulfonyloxymethyl-1,2,3,4-tetrahydronaphthalene as the raw material, the reaction was conducted, whereby the title compound was obtained.

$^1$H-NMR (CDCl$_3$) δ: 1.40–1.60(1H,m), 1.46(9H,s), 1.90–2.10(2H,m), 2.50(1H,dd,J=17.1,10.7 Hz), 2.70–3.00 (3H,m), 3.10–3.30(2H,m), 3.89(3H,s), 4.68(1H,br), 7.12 (1H,d,J=7.8 Hz), 7.70–7.80(2H,m).

Elementary analysis for C$_{18}$H$_{25}$NO$_4$

Calculated: C, 67.69; H, 7.89; N, 4.39.

Found: C, 67.78; H, 7.61; N, 4.12.

Referential Example 60

1-[[(6RS)-6-(N-tert-Butoxycarbonylaminomethyl)-5,6,7,8-tetrahydronaphthalen-2-yl]carbonyl]-4-[(6-chloronaphthalen-2-yl)sulfonyl]piperazine In a similar manner to Referential Example 48 except for the use of (2RS)-2-(N-tert-butoxycarbonylaminomethyl)-6-methoxycarbonyl-1,2,3,4-tetrahydronaphthalene and 1-[(6-chloronaphthalen-2-yl)sulfonyl]piperazine hydrochloride, the reaction was conducted, whereby the title compound was obtained.

$^1$H-NMR (CDCl$_3$) δ: 1.30–1.60(1H,m), 1.45(9H,s), 1.80–2.00(2H,m), 2.43(1H,dd,J=16.6,10.7 Hz), 2.70–2.90

(3H,m), 3.00–3.20(6H,m), 3.50–3.90(4H,br), 4.69(1H,br), 6.90–7.10(3H,m), 7.59(1H,dd,J=8.8,2.0 Hz), 7.75(1H,dd,J=8.8,2.0 Hz), 7.90–8.00(3H,m), 8.30(1H,s).

MS (FAB) m/z: 598 [(M+H)+, Cl$^{35}$], 600 [(M+H)+, Cl$^{37}$].

Referential Example 61

(2RS)-2-(N-tert-Butoxycarbonylaminomethyl)-6-hydroxymethyl-1,2,3,4-tetrahydronaphthalene In dichloromethane (10 ml), (2RS)-2-(N-tert-butoxycarbonylaminomethyl)-6-methoxycarbonyl-1,2,3,4-tetrahydronaphthalene (0.47 g) was dissolved, followed by the dropwise addition of diisobutylaluminum hydride (a 0.95M hexane solution, 3.6 ml) at an external temperature of −78° C. The resulting mixture was stirred for 90 minutes without changing the temperature. Methanol was added to the reaction mixture, followed by heating to room temperature. The insoluble matter was filtered off through Celite. The filtrate was concentrated under reduced pressure. The concentrate was diluted with dichloromethane, washed with water and dried over anhydrous sodium sulfate. The residue obtained by distilling off the solvent under reduced pressure was purified by chromatography on a silica gel column (hexane:ethyl acetate=3:1), whereby colorless crystals (0.31 g, 72%) were obtained. A portion of the crystals was recrystallized from a mixed solvent of hexane and ethyl acetate, whereby colorless crystals were obtained.

$^1$H-NMR (CDCl$_3$) δ: 1.40–1.60(1H,m), 1.46(9H,s), 1.60–1.70(1H,m), 1.90–2.00(2H,m), 2.45(1H,dd,J=16.6, 10.7 Hz), 2.70–2.90(3H,m), 3.10–3.30(2H,m), 4.62(2H,d,J=5.9 Hz), 4.67(1H,br), 7.00–7.20(3H,m).

Elementary analysis for C$_{17}$H$_{25}$NO$_3$

Calculated: C, 70.07; H, 8.65; N, 4.81.

Found: C, 70.21; H, 8.49; N, 4.75.

Referential Example 62

1-[[(6RS)-6-(N-tert-Butoxycarbonylaminomethyl)-5,6,7,8-tetrahydronaphthalen-2-yl]methyl]-4-[(6-chloronaphthalen-2-yl)sulfonyl]piperazine In a similar manner to Referential Examples 46 and 47 except for the use of (2RS)-2-(N-tert-butoxycarbonylaminomethyl)-6-hydroxymethyl-1,2,3,4-tetrahydronaphthalene as the raw material, the reaction was conducted, whereby the title compound was obtained.

$^1$H-NMR (CDCl$_3$) δ: 1.30–1.50 (1H,m) , 1.44 (9H,s) , 1.80–2.00(2H,m), 2.40(1H,m), 2.51(4H,br), 2.60–2.90(3H,m), 3.09(6H,br), 3.39(2H,s), 4.67(1H,br), 6.90–7.00(3H,m), 7.56(1H,d,J=8.8 Hz), 7.77(1H,d,J=8.8 Hz), 7.80–8.00(3H,m), 8.28(1H,s).

MS (FAB) m/z: 584 [(M+H)+, Cl$^{35}$], 586 (M+H)+, Cl$^{37}$].

Referential Example 63

(2RS)-2-(tert-Butyldimethylsilyloxymethyl)-6-methoxycarbonyl-1,2,3,4-tetrahydronaphthalene In N,N-dimethylformamide (5 ml), (2RS)-2-hydroxymethyl-6-methoxycarbonyl-1,2,3,4-tetrahydronaphthalene (1.71 g) was dissolved, followed by the addition of imidazole (0.81 g) and tert-butyldimethylsilyl chloride (1.81 g) under ice cooling. The resulting mixture was stirred at room temperature for 14 hours. After the addition of methanol, the mixture was concentrated under reduced pressure. The concentrate was diluted with ethyl acetate, washed with water and then dried over anhydrous sodium sulfate. The residue obtained by distilling off the solvent under reduced pressure was purified by chromatography on a silica gel column (hexane:ethyl acetate=50:1), whereby a yellow solid (2.20 g, 85%) was obtained.

$^1$H-NMR (CDCl$_3$) δ: 0.06(6H,s), 0.91(9H,s), 1.40–1.60 (1H,m), 1.90–2.10(2H,m), 2.53(1H,dd,J=17.1,10.3 Hz), 2.80–3.00(3H,m), 3.58(2H,d,J=5.9 Hz), 3.89(3H,s), 7.14 (1H,d,J=7.8 Hz), 7.70–7.80(2H,m).

MS (FAB) m/z: 335 (M+H)+.

Referential Example 64

(2RS)-2-(tert-Butyldimethylsilyloxymethyl)-6-hydroxymethyl-1,2,3,4-tetahydronaphthalene In a similar manner to Referential Example 61 except for the use of (2RS)-2-(tert-butyldimethylsilyloxymethyl)-6-methoxycarbonyl-1,2,3,4-tetrahydronaphthalene as the raw material, the title compound was obtained.

$^1$H-NMR (CDCl$_3$) δ: 0.07(6H,s), 0.91(9H,s), 1.30–1.50 (1H,m), 1.50–1.60(1H,m), 1.90–2.10(2H,m), 2.48(1H,m), 2.70–2.90(3H,m), 3.58(2H,m), 4.62(2H,d,J=5.9 Hz), 7.09 (3H,m).

MS (FAB) m/z: 307 (M+H)+.

Referential Example 65

(2RS)-6-(N-tert-Butoxycarbonylaminomethyl)-2-(tert-butyldimethylsilyloxymethyl)-1,2,3,4-tetrahydronaphthalene In dichloromethane (10 ml), (2RS)-2-(tert-butyldimethylsilyloxymethyl)-6-hydroxymethyl-1,2,3,4-tetrahydronaphthalene (1.00 g) was dissolved. To the resulting solution, triethylamine (0.5 ml). was added, followed by ice cooling. After the addition of a solution of methanesulfonyl chloride (0.39 g) in dichloromethane (dichloromethane: 1 ml), the resulting mixture was stirred at room temperature for 9 hours. The reaction mixture was washed with water and then dried over anhydrous sodium sulfate. The residue obtained by distilling off the solvent under reduced pressure was treated as in Referential Example 59, whereby the title compound (1.10 g, 83%) was obtained.

$^1$H-NMR (CDCl$_3$) δ: 0.06(6H,s), 0.91(9H,s), 1.40–1.60 (1H,m), 1.46(9H,s), 1.90–2.00(2H,m), 2.45(1H,m), 2.70–2.90(3H,m), 3.57(2H,m), 4.24(2H,m), 4.76(1H,br), 7.00–7.10(3H,m).

MS (FAB) m/z: 406 (M+H)+.

Referential Example 66

(2RS)-6-(N-tert-Butoxycarbonylaminomethyl)-2-hydroxymethyl-1,2,3,4-tetrahydronaphthalene In tetrahydrofuran (10 ml), (2RS)-6-(N-tert-butoxycarbonylaminomethyl)-2-(tert-butyldimethylsilyloxymethyl)-1,2,3,4-tetrahydronaphthalene (1.09 g) was dissolved. To the resulting solution, tetra-butylammonium fluoride (a 1.0M tetrahydrofuran solution, 4.0 ml) was added, followed by stirring at room temperature for 2 hours. After concentration under reduced pressure, the concentrate was diluted with dichloromethane, washed with water and dried over anhydrous sodium sulfate. The residue obtained by distilling off the solvent under reduced pressure was purified by chromatography on a silica gel column (hexane:ethyl acetate=

3:1~2:1), whereby a colorless solid (0.77 g, 98%) was obtained. A portion of the solid was recrystallized from a mixed solvent of hexane and ethyl acetate, whereby colorless crystals were obtained.

$^1$H-NMR (CDCl$_3$) δ: 1.40–1.60(2H,m), 1.46(9H,s), 1.90–2.10(2H,m), 2.48(1H,dd,J=16.6,10.7 Hz), 2.70–3.00 (3H,m), 3.6–3.7(2H,m), 4.24(2H,d,J=5.4 Hz), 4.78(1H,br), 7.00–7.10(3H,m).

Elementary analysis for C$_{17}$H$_{25}$NO$_3$

Calculated: C, 70.07; H, 8.65; N, 4.81.

Found: C, 70.02; H, 8.61; N, 4.46.

Referential Example 67

1-[[(2RS)-6-(N-tert-Butoxycarbonylaminomethyl)-1,2,3,4-tetrahydronaphthalen-2-yl]methyl]-4-[(6-chloronaphthalen-2-yl)sulfonyl]piperazine In dichloromethane (5 ml), (2RS)-6-(N-tert-butoxycarbonylaminomethyl)-2-hydroxymethyl-1,2,3,4-tetrahydronaphthalene (0.17 g) was dissolved, followed by the addition of N-methylmorpholine N-oxide (0.13 g) and Molecular Sieves 4A (activated powder, 0.18 g). Under ice cooling, ruthenium tetraoxide tetrapropylammonium salt (10 mg) was added to the resulting mixture under ice cooling, followed by stirring at room temperature for 1 hour. Ether was added to the reaction mixture and the insoluble matter was removed by the filtration through Celite. The filtrate was distilled off under reduced pressure. The residue was purified by chromatography on a silica gel column (dichloromethane), whereby the corresponding aldehyde compound was obtained. In a similar manner to Referential Example 47 except for the use of the resulting aldehyde compound, the reaction was conducted, whereby the title compound (0.14 g, 41%) was obtained.

$^1$H-NMR (CDCl$_3$) δ: 1.20–1.40(1H,m), 1.44(9H,s), 1.80–2.00(2H,m), 2.20–2.40(3H,m), 2.50–2.60(4H,m), 2.60–2.80(3H,m), 3.11(4H,m), 4.20(2H,d,J=5.4 Hz), 4.79 (1H,br), 6.94(3H,m), 7.57(1H,dd,J=8.8,1.5 Hz), 7.79(1H,dd, J=8.8,1.5 Hz), 7.90–8.00(3H,m), 8.31(1H,s).

MS (FAB) m/z: 584 [(M+H)$^+$, Cl$^{35}$], 586 [(M+H)$^+$, Cl$^{37}$].

Referential Example 68

1-[[(2RS)-6-(N-tert-Butoxycarbonylaminomethyl)-1,2,3,4-tetrahydronaphthalen-2-yl]carbonyl]4-[(6-chloronaphthalen-2-yl)sulfonyl]piperazine In carbon tetrachloride (2 ml), acetonitrile (2 ml) and water (3 ml), (2RS)-6-(N-tert-butoxycarbonylaminomethyl)-2-hydroxymethyl-1,2,3,4-tetrahydronaphthalene (0.21 g) was dissolved, followed by the addition of sodium periodate (0.48 g) and ruthenium trichloride hydrate (4 mg). The resulting mixture was stirred for 90 minutes. The reaction mixture was diluted with dichloromethane. The organic layer so separated was dried over anhydrous sodium sulfate. The residue obtained by distilling off the solvent under reduced pressure was added with ether and insoluble matter was filtered off. The filtrate was then distilled under reduced pressure. In a similar manner to Referential Example 12 except for the use of the carboxylic acid compound so obtained, the reaction was conducted, whereby the title compound (0.11 g, 25%) was obtained.

$^1$H-NMR (CDCl$_3$) δ: 1.45(9H,s), 1.70–2.00(2H,m), 2.60–2.90(4H,m), 2.95(1H,m), 3.11(4H,m), 3.64(2H,m), 3.76(2H,m), 4.22(2H,d,J=5.4 Hz), 4.82(1H,br), 6.90–7.10 (3H,m), 7.59(1H,d,J=8.8 Hz), 7.77(1H,d,J=8.8 Hz), 7.90–8.00(3H,m), 8.31(1H,s).

MS (FD) m/z: 597 [M$^{30}$, Cl$^{35}$], 599 [M$^{30}$, Cl$^{37}$].

Referential Example 69

2-(N-tert-Butoxycarbonylaminomethyl)-7-methoxycarbonylnaphthalene

In a similar manner to Referential Example 65 except for the use of 2-hydroxymethyl-7-methoxycarbonylnaphthalene (1.01 g) as the raw material, the reaction was conducted, whereby the title compound was obtained.

$^1$H-NMR (CDCl$_3$) δ: 1.49(9H,s), 3.98(3H,s), 4.50(2H,d, J=5.4 Hz), 4.99(1H,br), 7.53(1H,d,J=8.3 Hz), 7.80–7.90(3H, m), 8.04(1H,dd,J=8.3,1.0 Hz), 8.57(1H,s).

Elementary analysis for C$_{18}$H$_{21}$NO$_4$

Calculated: C, 68.55; H, 6.71; N, 4.44.

Found: C, 68.54; H, 6.70; N, 4.46.

Referential Example 70

1-[[7-(N-tert-Butoxycarbonylaminomethyl)naphthalen-2-yl]carbonyl]-4-[(6-chloronaphthalen-2-yl)sulfonyl]piperazine In a similar manner to Referential Example 48 except for the use of 2-(N-tert-butoxycarbonylaminomethyl)-7-methoxycarbonylnaphthalene as the raw material, the title compound was obtained.

$^1$H-NMR (CDCl$_3$) δ: 1.46(9H,s), 3.12(4H,br), 3.50–4.00. (4H,br), 4.45(2H,d,J=5.9 Hz), 5.01(1H,br), 7.34(1H,d,J=7.8 Hz), 7.45(1H,d,J=8.3 Hz), 7.50–7.60(1H,m), 7.66(1H,s), 7.70–7.80(4H,m), 7.90–8.00(3H,m), 8.30(1H,s).

MS (FAB) m/z: 594 [(M+H)$^+$, Cl$^{35}$], 596 [(M+H)$^+$, Cl$^{37}$].

Referential Example 71

1-[[7-(N-tert-Butoxycarbonylaminomethyl)naphthalene-2-yl]methyl]-4-[(6-chloronaphthalen-2-yl)sulfonyl]piperazine In a similar manner to Referential Examples 61 and 67 except for the use of 2-(N-tert-butoxycarbonylaminomethyl)-7-methoxycarbonylnaphthalene as the raw material, the reaction was conducted, whereby the title compound was obtained.

$^1$H-NMR (CDCl$_3$) δ: 1.47(9H,s), 2.50–2.70(4H,m), 3.10 (4H,br), 3.61(2H,s), 4.44(2H,d,J=5.4 Hz), 4.92(1H,br), 7.30–7.40(2H,m), 7.50–7.70(3H,m), 7.70–7.90(3H,m), 7.90–8.00(3H,m), 8.29(1H,s).

MS (FAB) m/z: 580 [(M+H)$^+$, Cl$^{35}$], 582 [(M+H)$^+$, Cl$^{37}$].

Referential Example 72

2-(N-tert-Butoxycarbonylaminomethyl)-6-methoxycarbonylnaphthalene

In a similar manner to Referential Examples 45 and 65 except for the use of dimethyl 2,6-naphthalenedicarboxylate as the raw material, the reaction was conducted, whereby the title compound was obtained.

$^1$H-NMR (CDCl$_3$) δ: 1.48(9H,s), 3.98(3H,s), 4.50(2H,d, J=5.4 Hz), 4.99(1H,br), 7.47(1H,d,J=8.3 Hz), 7.75(1H,s), 7.84(1H,d,J=8.8 Hz), 7.92(1H,d,J=8.8 Hz), 8.06(1H,d,J=8.3 Hz), 8.58(1H,s).

Elementary analysis for C$_{18}$H$_{21}$NO$_4$

Calculated: C, 68.55; H, 6.71; N, 4.44.

Found: C, 68.93; H, 6.70; N, 4.29.

Referential Example 73

Methyl 4-[[(3S)-1-tert-butoxycarbonyl-3-pyrrolidinyl]oxy]benzoate

In tetrahydrofuran (50 ml), methyl 4-hydroxybenzoate (1.01 g), (3R)-1-tert-butoxycarbonyl-3-pyrrolidinole (1.36 g) and triphenylphosphine (1.73 g) were dissolved, followed by the dropwise addition of a 40% solution (2.87 ml) of diethyl azodicarboxylate in toluene under ice cooling. The resulting mixture was stirred at room temperature for 20 hours. To the reaction mixture, ethyl acetate and a 10% aqueous solution of potassium carbonate were added to separate the organic layer. The organic layer so separated was washed with a 10% aqueous solution of potassium carbonate and water and dried over anhydrous sodium sulfate. The solvent was then distilled off under reduced pressure. The residue was purified by chromatography on a silica gel column (hexane:ethyl acetate=2:1), whereby the title compound (1.60 g, 76%) was obtained.

$^1$H-NMR (CDCl$_3$) δ: 1.48(9H,s), 2.00–2.20(2H,m), 3.40–3.70(4H,m), 3.89(3H,s), 4.96(1H,br s), 6.88(2H,d,J=8.8 Hz), 7.90–8.00(2H,m).

Referential Example 74

4-[[(3S)-1-tert-Butoxycarbony-3-pyrrolidinyl]oxy]benzoic acid

In a similar manner to Referential Example 11 except for the use of methyl 4-[[(3S)-1-tert-butoxycarbonyl-3-pyrrolidinyl]oxy]benzoate as the raw material, the reaction was conducted, whereby the title compound was obtained.

$^1$H-NMR (CD$_3$OD) δ: 1.45 and 1.47(9H, each s), 2.10–2.20(2H,m), 3.40–3.70(4H,m), 5.00–5.10(1H,m), 6.98 (2H,d,J=8.8 Hz), 7.97(2H,d,J=8.8 Hz).

Referential Example 75

1-[4-[[(3S)-1-tert-Butoxycarbonylpyrrolidin-3-yl]oxy]benzoyl]-4-[(6-chloronaphthalen-2-yl)sulfonyl]piperazine In a similar manner to Referential Example 12 except for the use of 4-[[(3S)-1-tert-butoxycarbonyl-3-pyrrolidinyl]oxy]benzoic acid and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 1.46(9H,s), 2.00–2.20(2H,m), 3.00–3.20(4H,m), 3.40–3.80(8H,m), 4.88(1H,br s), 6.82(2H,d,J=8.3 Hz), 7.20–7.30(2H,m), 7.60(1H,dd,J=8.7,1.9 Hz), 7.76(1H,dd,J=8.5,1.7 Hz), 7.90–7.95(3H,m), 8.30(1H,s).

Elementary analysis for C$_{30}$H$_{34}$ClN$_3$O$_6$S

Calculated: C, 60.04; H, 5.71; N, 7.00.

Found: C, 60.05; H, 5.69; N, 6.80.

Referential Example 76

Methyl 3-[[(3S)-1-tert-butoxycarbonyl-3-pyrrolidinyl]oxy]benzoate

In a similar manner to Referential Example 73 except for the use of methyl 3-hydroxybenzoate, the reaction was conducted, whereby the title compound was obtained.

$^1$H-NMR (CDCl$_3$) δ: 1.45 and 1.47(9H, each s), 2.05–2.25(2H,m), 3.40–3.70(4H,m), 3.92(3H,s), 4.96(1H,br s), 7.07(1H,d,J=7.8 Hz), 7.30–7.40(1H,m), 7.53(1H,d,J=2.0 Hz), 7.65(1H,m).

MS (FAB) m/z: 322 (M+H)$^+$.

Referential Example 77

3-[[(3S)-1-tert-Butoxycarbonyl-3-pyrrolidinyl]oxy]benzoic acid

In a similar manner to Referential Example 74 except for the use of methyl 3-[[(3S)-1-tert-butoxycarbonyl-3-pyrrolidinyl]oxy]benzoate as the raw material, the title compound was obtained.

$^1$H-NMR (CD$_3$OD) δ: 1.45 and 1.47(9H, each s), 2.05–2.25(2H,m), 3.35–3.65(4H,m), 5.04(1H,br s), 7.05–7.15(1H,m), 7.30–7.40(1H,m), 7.53(1H,s), 7.62(1H,d, J=7.3 Hz).

MS (FAB) m/z: 308 (M+H)$^+$.

Referential Example 78

1-[3-[[(3S)-1-tert-butoxycarbonylpyrrolidin-3-yl]oxy]benzoyl]-4-[(6-chloronaphthalen-2-yl)sulfonyl]piperazine In a similar manner to Referential Example 75 except for the use of methyl 3-[[(3S)-1-tert-butoxycarbonyl-3-pyrrolidinyl]oxy]benzoic acid as the raw material, the title compound was obtained.

$^1$H-NMR (CDCl$_3$) δ: 1.45 and 1.46(9H, each s), 2.00–2.20(2H,m), 2.95–3.25(4H,m), 3.40–3.90(8H,m), 4.84 (1H,br s), 6.80–6.90(3H,m), 7.20–7.30(1H,m), 7.60(1H,dd, J=8.8,1.5 Hz), 7.76(1H,dd,J=8.5,1.7 Hz), 7.90–7.95(3H,m), 8.30–8.35(1H,m).

MS (FAB) m/z: 600 [(M+H)$^+$, Cl$^{35}$], 602 [(M+H)$^+$, Cl$^{37}$].

Referential Example 79

Methyl 4-[[(3R)-1-tert-butoxycarbonyl-3-pyrrolidinyl]oxy]benzoate

In a similar manner to Referential Example 73 except for the use of methyl 4-hydroxybenzoate and (3S)-1-tert-butoxycarbonyl-3-pyrrolidinole as the raw materials, the title compound was obtained.

$^1$H-NMR (CDCl$_3$) δ: 1.47(9H,s), 2.05–2.25(2H,m), 3.40–3.70(4H,m), 3.89(3H,s), 4.96(1H,br s), 6.88(2H,d,J=8.8 Hz), 7.90–8.00(2H,m).

MS (FAB) m/z: 322 (M+H)$^+$.

Referential Example 80

4-[[(3R)-1-tert-Butoxycarbonyl-3-pyrrolidinyl]oxy]benzoic acid

In a similar manner to Referential Example 74 except for the use of methyl 4-[[(3R)-1-tert-butoxycarbonyl-3-pyrrolidinyl]oxy]benzoate as the raw material, the title compound was obtained.

$^1$H-NMR (CD$_3$OD) δ: 1.47 and 1.48(9H, each s), 2.10–2.25(2H,m), 3.40–3.70(4H,m), 4.98(1H,br s), 6.91 (2H,d,J=8.8 Hz), 8.00–8.10(2H,m).

MS (FAB) m/z: 308 (M+H)$^+$.

Referential Example 81

1-[4-[[(3R)-1-tert-Butoxycarbonylpyrrolidin-3-yl]oxy]benzoyl]-4-[(6-chloronaphthalen-2-yl)sulfonyl]piperazine In a similar manner to Referential Example 75 except for the use of 4-[[(3R)-1-tert-butoxycarbonyl-3-pyrrolidinyl]oxy]benzoic acid as the raw material, the title compound was obtained.

$^1$H-NMR (CDCl$_3$) δ: 1.46(9H,s), 2.00–2.20(2H,m), 3.00–3.20(4H,m), 3.40–3.80(8H,m), 4.89(1H,br s), 6.82 (2H,d,J=8.3 Hz), 7.20–7.30(2H,m), 7.58(1H,dd,J=8.8,2.0 Hz), 7.74(1H,dd,J=8.5,1.7 Hz), 7.90–7.95(3H,m), 8.30(1H, s).

MS (FAB) m/z: 600 [(M+H)$^+$, Cl$^{35}$], 602 [(M+H)$^+$, Cl$^{37}$].

Referential Example 82

Methyl 3-[[(3R)-1-tert-butoxycarbonyl-3-pyrrolidinyl]oxy]benzoate

In a similar manner to Referential Example 73 except for the use of methyl 3-hydroxybenzoate and (3S)-1-tert-butoxycarbonyl-3-pyrrolidinole as the raw materials, the title compound was obtained.

$^1$H-NMR (CDCl$_3$) δ: 1.47(9H,s), 2.05–2.25(2H,m), 3.40–3.70(4H,m), 3.92(3H,s), 4.95(1H,br s), 7.07(1H,d,J=7.8 Hz), 7.30–7.40(1H,m), 7.50–7.55(1H,m), 7.60–7.70(1H,m).

MS (FAB) m/z: 322 (M+H)$^+$.

Referential Example 83

3-[[(3R)-1-tert-butoxycarbonyl-3-pyrrolidinyl]oxy]benzoic acid

In a similar manner to Referential Example 74 except for the use of methyl 3-[[(3R)-1-tert-butoxycarbonyl-3-pyrrolidinyl]oxy]benzoate as the raw material, the title compound was obtained.

$^1$H-NMR (CD$_3$OD) δ: 1.48(9H,s), 2.05–2.25(2H,m), 3.45–3.70(4H,m), 4.97(1H,br s), 7.10–7.15(1H,m), 7.35–7.45(1H,m), 7.58(1H,s), 7.70–7.75(1H,m).

MS (FAB) m/z: 308 (M+H)$^+$.

Referential Example 84

1-[3-[[(3R)-1-tert-butoxycarbonylpyrrolidin-3-yl]oxy]benzoyl]-4-[(6-chloronaphthalen-2-yl)sulfonyl]piperazine In a similar manner to Referential Example 75 except for the use of 3-[[(3R)-1-tert-butoxycarbonyl-3-pyrrolidinyl]oxy]benzoic acid as the raw material, the title compound was obtained.

$^1$H-NMR (CDCl$_3$) δ: 1.45 and 1.46(9H, each s), 2.00–2.20(2H,m), 2.95–3.25(4H,m), 3.40–3.90(8H,m), 4.84 (1H,br s), 6.80–6.90(3H,m), 7.20–7.30(1H,m), 7.60(1H,dd, J=8.5,1.7 Hz), 7.76(1H,dd,J=8.5,2.0 Hz), 7.90–7.95(3H,m), 8.30–8.35(1H,m).

MS (FAB) m/z: 600 [(M+H)$^+$, Cl$^{35}$], 602 [(M+H)$^+$, Cl$^{37}$].

Referential Example 85

4-[2-Amino-5-pyrimidyl)benzoic acid

In a similar manner to Referential Example 2 except for the use of 2-amino-5-bromopyrimidine as the raw material, the title compound was obtained.

$^1$H-NMR (DMSO-d$_6$) δ: 7.81(2H,d,J=8.8 Hz), 8.00(2H, d,J=8.8 Hz), 8.84(2H,s).

MS (FAB) m/z: 216 (M+H)$^+$.

Referential Example 86

1-tert-butoxycarbonyl-4-[(methoxycarbonyl)methylene]piperidine

In tetrahydrofuran (40 ml), methyl dimethylphosphonoacetate (1.8 ml) was dissolved. To the resulting solution, 60% oily sodium hydride (450 mg) was added under ice cooling, followed by stirring under the same condition. After the addition of a solution of 1-(tert-butoxycarbonyl)-4-piperidone (2.05 g) in tetrahydrofuran (tetrahydrofuran: 10 ml) and stirring at room temperature for 30 minutes, the reaction mixture was diluted with ethyl acetate. To the diluted solution, 2N hydrochloric acid was added. The organic layer was separated, washed with a saturated aqueous solution of sodium bicarbonate and saturated aqueous saline, and dried over anhydrous sodium sulfate. The solvent was then distilled off under reduced pressure. The residue was purified by chromatography on a silica gel column (hexane:ethyl acetate=6:1), whereby the title compound (2.35 g, 92%) was obtained.

$^1$H-NMR (CDCl$_3$) δ: 1.47(9H,s), 2.28(2H,t,J=5.9 Hz), 2.94(2H,t,J=5.9 Hz), 3.48(2H,t,J=5.9 Hz), 3.50(2H,t,J=5.9 Hz), 3.70(3H,s), 5.72(1H,s).

Elementary analysis for C$_{13}$H$_{21}$NO$_4$

Calculated: C, 61.16; H, 8.29; N, 5.49.

Found: C, 61.14; H, 8.34; N, 5.20.

Referential Example 87

Methyl (1-tert-butoxycarbonylpiperidin-4-yl)acetate

In ethanol (10 ml), 1-tert-butoxycarbonyl-4-[(methoxycarbonyl)methyl]piperidine (875 mg) was dissolved, followed by the addition of 10% palladium carbon (water content: about 50%, 730 mg). The resulting mixture was subjected to catalytic reduction under normal pressure at room temperature for 3 days. After the removal of the catalyst by filtration, the solvent was distilled off under reduced pressure, whereby the title compound (871 mg, 99%) was obtained.

$^1$H-NMR (CDCl$_3$) δ: 1.16(2H,m), 1.45(9H,s), 1.65(2H, m), 1.93(1H,m), 2.25(2H,d,J=6.8 Hz), 2.72(2H,br), 3.68 (3H,s), 4.08(2H,br).

MS (FAB) m/z: 258 (M+H)$^+$.

Referential Example 88

(1-tert-Butoxycarbonylpiperidin-4-yl)acetic acid

In a similar manner to Referential Example 11 except for the use of methyl (1-tert-butoxycarbonylpiperidin-4-yl)acetate as the raw material, the title compound was obtained.

$^1$H-NMR (CDCl$_3$) δ: 1.18(2H,m), 1.45(9H,s), 1.73(2H, m), 1.94(1H,m), 2.29(2H,d,J=6.8 Hz), 2.72(2H,m), 4.10(2H, br).

MS (EI) m/z: 243 M$^+$.

Referential Example 89

1-[(1-tert-Butoxycarbonylpiperidin-4-yl)acetyl]-4-[(6-chloronaphthalen-2-yl)sulfonyl]piperazine In a similar manner to Referential Example 12 except for the use of (1-tert-butoxycarbonylpiperidin-4-yl)acetic acid and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 1.05(2H,m) , 1.43(9H,s) , 1.63(2H, m), 1.91(1H,m), 2.14(2H,d,J=6.8 Hz), 2.66(2H,m), 3.07(4H, br s), 3.56(2H,br s), 3.67(2H,br s), 4.02(2H,br), 7.58(1H, dd,J=8.8,2.0 Hz), 7.75(1H,d,J=8.8 Hz), 7.91(1H,d,J=8.8 Hz), 7.93(1H,d,J=8.8 Hz), 7.92(1H,s), 8.30(1H,s).

MS (FAB) m/z: 536 [(M+H)$^+$, Cl$^{35}$], 538 (M+H)$^+$, Cl$^{37}$].

Referential Example 90

3-(1-tert-Butoxycarbonylpiperidin-4-yl)propionic acid

In a similar manner to Referential Example 61 except for the use of ethyl 1-tert-butoxycarbonylisonipecotinate as the raw material, the reaction was conducted, whereby the corresponding aldehyde derivative was obtained. The resulting derivative was treated as in Referential Examples 86, 87 and 88, whereby the title compound was obtained.

$^1$H-NMR (CDCl$_3$) δ: 1.10(2H,m), 1.41(1H,m), 1.45(9H, s), 1.60(2H,q,J=7.8 Hz), 1.66(2H,m), 2.39(2H,t,J=7.8 Hz), 2.67(2H,m), 4.09(2H,br).

MS (FAB) m/z: 258 (M+H)$^+$.

Referential Example 91

1-[3-(1-tert-Butoxycarbonylpiperidin-4-yl] propionyl]-4-[(6-chloronaphthalen-2-yl)sulfonyl] piperazine In a similar manner to Referential Example 12 except for the use of 3-(1-tert-butoxycarbonylpiperidin-4-yl)propionic acid and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 1.04(2H,m), 1.35(1H,m), 1.44(9H, s), 1.47(2H,q,J=7.8 Hz), 1.57(2H,m), 2.24(2H,t,J=7.8 Hz), 2.61(2H,m), 3.07(4H,br s), 3.50(2H,br s), 3.71(2H,br s), 4.04(2H,br), 7.58(1H,dd,J=8.8,2.0 Hz), 7.75(1H,dd,J=8.8, 2.0 Hz), 7.90(1H,d,J=8.8 Hz), 7.91(1H,s), 7.92(1H,d,J=8.8 Hz), 8.30(1H,s).

MS (FAB) m/z: 550 [(M+H)$^+$, Cl$^{35}$], 552 [(M+H)$^+$, Cl$^{37}$].

Referential Example 92

(E)-3-(4-Pyridyl)acrylic acid

In a similar manner to Referential Examples 86 and 88 except for the use of isonicotinic aldehyde as the raw material, the title compound was obtained.

$^1$H-NMR (DMSO-d$_6$) δ: 6.79(1H,d,J=16.6 Hz), 7.56(1H, d,J=16.6 Hz), 7.66(2H,d,J=5.9 Hz), 8.62(2H,d,J=5.9 Hz), 12.72(1H,br s).

MS (EI) m/z: 149M$^+$.

Referential Example 93

1-Methoxycarbonyl-3-pyrroline

In dichloromethane (20 ml), 3-pyrroline (1.1 ml) was dissolved, followed by the addition of triethylamine (2.6 ml) and methyl chloroformate (1.2 ml) under ice cooling. The resulting mixture was stirred at room temperature for 17 hours. The residue obtained by distilling the reaction mixture under reduced pressure was purified by chromatography on a silica gel column (hexane:ethyl acetate=4:1), whereby the title compound (0.95 g, 52%) was obtained.

$^1$H-NMR (CDCl$_3$) δ: 3.73(3H,s), 4.00–4.20(4H,m), 5.70–5.90(2H,m).

Referential Example 94

Methyl 4-trifluoromethanesulfonyloxybenzoate

In dichloromethane (20 ml), methyl 4-hydroxybenzoate (1.99 g) was dissolved, followed by the addition of pyridine (2.4 ml) and trifluoromethanesulfonic anhydride (3.0 ml) under ice cooling. After stirring at room temperature for 6 hours, the reaction mixture was added with pyridine (1.5 ml) and trifluoromethanesulfonic anhydride (1.0 ml) again. The resulting mixture was stirred for 5 hours. Dichloromethane and an aqueous solution of sodium bicarbonate were added to the reaction mixture. The organic layer so separated was washed with a 10% aqueous citric acid solution and saturated saline and dried over anhydrous sodium sulfate. The residue obtained by distilling off the solvent under reduced pressure was purified by chromatography on a silica gel column (5% ethyl acetate-hexane), whereby the title compound (3.22 g, 86%) was obtained.

$^1$H-NMR (CDCl$_3$) δ: 3.95(3H,s), 7.36(2H,d,J=8.8 Hz), 8.15(2H,d,J=8.8 Hz).

MS (FAB) m/z: 285 (M+H)$^+$.

Referential Example 95

Methyl 4-(1-methoxycarbonylpyrrolidin-3-yl) benzoate

In N,N-dimethylformamide (25 ml), methyl 4-trifluoromethanesulfonyloxybenzoate (1.05 g), 1-methoxycarbonyl-3-pyrroline (1.0 g), lithium chloride (0.51 g), palladium (II) acetate(53 mg) and tri(2-furyl) phosphine (100 mg) were dissolved, followed by the addition of diisopropylethylamine (2.8 ml). Under an argon gas atmosphere, the resulting mixture was stirred at 90° C. for 11 hours and then, at 100° C. for 7 hours. The residue obtained by distilling off the solvent under reduced pressure was added with dichloromethane and water. The organic layer so separated was washed with water and dried over anhydrous sodium sulfate. The solvent was then distilled off under reduced pressure. The residue was purified by chromatography on a silica gel column (hexane:ethyl acetate=9:1~5:1). The purified product was dissolved in methanol (30 ml), followed by the addition of 10% palladium carbon (water content: about 50%, 186 mg) and ammonium formate (197 mg). The resulting mixture was heated under reflux for 2 hours. After the removal of the catalyst by filtration, the solvent was distilled off under reduced pressure. The residue was purified by chromatography on a silica gel column (10% ethyl acetate-toluene), whereby the title compound (241 mg, 25%) was obtained.

$^1$H-NMR (CDCl$_3$) δ: 1.95–2.10(1H,m), 2.25–2.35(1H, m), 3.30–3.35(4H,m), 3.55–3.75(1H,m), 3.72 and 3.73(3H, each s), 3.80–3.90(1H,m), 3.91(3H,s), 7.30(2H,d,J=3.8 Hz), 8.00(2H,d,J=8.3 Hz).

MS (FAB) m/z: 264 (M+H)$^+$.

Referential Example 96

4-(1-tert-Butoxycarbonylpyrrolidin-3-yl)benzoic acid

In methanol (10 ml), methyl 4-(1-methoxycarbonylpyrrolidin-3-yl)benzoate (0.24 g) was dissolved. The resulting solution was added with 8N hydrochloric acid (30 ml), followed by heating under reflux for 40 hours. The residue obtained by distilling off the solvent under reduced pressure was dissolved in N,N-dimethylformamide (30 ml). To the resulting solution, 2-(tert-butoxycarbonyloxyimino)-2-phenylacetonitrile (0.30 g) and then diisopropylethylamine (0.40 ml) were added, followed by stirring at room temperature for 15 hours. The residue obtained by distilling off the solvent under reduced pressure was distributed in ethyl acetate and a 10% aqueous citric acid solution. The organic layer so separated was washed with saturated saline and dried over anhydrous sodium sulfate. The solvent was then distilled off under reduced pressure. The residue was purified by chromatography on a silica gel column (dichloromethane~10% methanol-dichloromethane), whereby the title compound (234 mg) was obtained.

$^1$H-NMR (CDCl$_3$) δ: 1.48(9H,m), 1.90–2.00(1H,m), 2.20–2.30(1H,m), 3.20–3.90(5H,m), 7.20–7.30(2H,m), 8.00–8.10(2H,m).

MS (EI) m/z: 291M$^+$.

Referential Example 97

1-[4-(3RS)-1-tert-Butoxycarbonylpyrrolidin-3-yl] benzoyl]-4-[(6-chloronaphthalen-2-yl)sulfonyl] piperazine In a similar manner to Referential Example 12 except for the use of 4-(1-tert-butoxycarbonylpyrrolidin-3-yl)benzoic acid and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 1.47 and 1.60(9H, each s), 1.80–2.00(1H,m), 2.10–2.20(1H,m), 3.00–4.00(13H,m), 7.10–7.30(4H,m), 7.55–7.65(1H,m), 7.70–7.80(1H,m), 7.85–8.00(3H,m), 8.30(1H,s).

Referential Example 98

Methyl 5-benzimidazolecarboxylate hydrochloride

In a similar manner to Referential Example 44 except for the use of 5-benzimidazolecarboxylic acid as the raw material, the reaction was conducted, whereby the title compound was obtained.

$^1$H-NMR (DMSO-d$_6$) δ: 3.93(3H,s), 7.96(1H,d,J=8.8 Hz), 8.12(1H,d,J=8.8 Hz), 8.40(1H,s), 9.66(1H,s).

Elementary analysis for C$_9$H$_8$N$_2$O$_2$.HCl
Calculated: C, 50.84; H, 4.27; N, 13.17; Cl, 16.67.
Found: C, 50.64; H, 4.22; N, 13.12; Cl, 16.59.

Referential Example 99

Methyl N-triphenylmethyl-5-benzimidazolecarboxylate

In a similar manner to Referential Example 22 except for the use of methyl 5-benzimidazolecarboxylate hydrochloride as the raw material, the title compound was obtained.

$^1$H-NMR (CDCl$_3$) δ: 3.75(2H,s), 3.89(1H,s), 6.49(1/3H, d,J=8.8 Hz), 7.1–7.4(16H,m), 7.61(1/3H,dd,J=8.8,1.5 Hz), 7.78(2/3H,d,J=8.8 Hz), 7.87(2/3H,dd,J=8.8,1.5 Hz), 7.96(1/3H,s), 8.02(2/3H,s).

MS (FAB) m/z: 419 (M+H)$^+$.

Referential Example 100

Sodium thiazolo[5,4-c]pyridine-2-carboxylate

In tetrahydrofuran (12 ml), ethyl thiazolo[5,4-c]pyridine-2-carboxylate (0.61 g) was dissolved, followed by the addition of a 1N aqueous sodium hydroxide solution (3 ml). After stirring at room temperature for 30 minutes, the insoluble matter was filtered off. Without purification, the filtrate was provided for the subsequent reaction.

$^1$H-NMR (DMSO-d$_6$) δ: 7.95(1H,d,J=5.9 Hz), 8.57(1H, d,J=5.9 Hz), 9.27(1H,s).

Referential Example 101

1-[(5-tert-Butoxycarbonyl-4,5,6,7-tetrahydrothieno [3,2-c]pyridin-2-yl]methyl]-4-[(6-chloronaphthalen-2-yl)sulfonyl]piperazine In a similar manner to Referential Example 47 except for the use of 5-tert-butoxycarbonyl-2-formyl-4,5,6,7-tetrahydrothieno[3,2-c]pyridine and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 1.47(9H,s), 2.53–2.62(4H,m), 2.72 (2H,br s), 3.10(4H,br s), 3.59(2H,s), 3.66(2H,br s), 4.38(2H, s), 6.54(1H,s), 7.57(1H,dd,J=8.8,2.0 Hz), 7.76(1H,dd,J=8.8, 2.0 Hz), 7.87–7.94(3H,m), 8.29(1H,s).

MS (FAB) m/z: 562 [(M+H)$^+$, Cl$^{35}$], 564 [(M+H)$^+$, Cl$^{37}$].

Referential Example 102

3-(5-tert-Butoxycarbonyl-4,5,6,7-tetrahydrothieno[3, 2-c]pyridin-2-yl]propionic acid In a similar manner to Referential Examples 86, 87 and 88 except for the use of 5-tert-butoxycarbonyl-2-formyl-4,5,6, 7-tetrahydrothieno[3,2-c]pyridine as the raw material, the reaction was conducted, whereby the title compound was obtained.

$^1$H-NMR (CDCl$_3$) δ: 1.48(9H,s), 2.70(2H,t,J=7.3 Hz), 2.76(2H,br s), 3.09(2H,t,J=7.3 Hz), 3.70(2H,s), 4.40(2H,s), 6.51(1H,s).

MS (FD) m/z: 311M$^+$.

Referential Example 103

(E)-3-(5-tert-Butoxycarbonyl-4,5,6,7-tetrahydrothieno[3,2-c]pyridin-2-yl]acrylic acid In a similar manner to Referential Examples 86 and 88 except for the use of 5-tert-butoxycarbonyl-2-formyl-4,5,6, 7-tetrahydrothieno[3,2-c]pyridine as the raw material, the reaction was conducted, whereby the title compound was obtained.

$^1$H-NMR (CDCl$_3$) δ: 1.49(9H,s), 2.85(2H,br s), 3.73(2H, br s), 4.47(2H,s), 6.12(1H,d,J=15.4 Hz), 6.98(1H,s), 7.77 (1H,d,J=15.4 Hz).

MS (FD) m/z: 309M$^+$.

Referential Example 104

1-[(E)-3-(5-tert-Butoxycarbonyl-4,5,6,7-tetrahydrothieno[3,2-c]pyridin-2-yl)propenoyl]-4-[(6-chloronaphthalen-2-yl)sulfonyl]piperazine In a similar manner to Referential Example 12 except for the use of (E)-3-(5-tert-butoxycarbonyl-4,5,6,7-tetrahydrothieno[3,2-c]pyridin-2-yl)acrylic acid and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 1.47(9H,s), 2.80(2H,br s), 3.12(4H, t,J=4.9 Hz), 3.46–3.86(6H,m), 4.41(2H,s), 6.39(1H,d,J=15.1 Hz), 6.83(1H,s), 7.55–7.78(3H,m), 7.89–7.92(3H,m), 8.30 (1H,s).

MS (FD) m/z: 601 (M$^+$, Cl$^{35}$), 603 (M$^+$, Cl$^{37}$).

Referential Example 105

1-[3-(5-tert-Butoxycarbonyl-4,5,6,7-tetrahydrothieno [3,2-c]pyridin-2-yl)propionyl]-4-[(6-chloronaphthalen-2-yl)sulfonyl]piperazine In tetrahydrofuran (10 ml), 3-(5-tert-butoxycarbonyl-4,5, 6,7-tetrahydrothieno[3,2-c]pyridin -2-yl)propionic acid (445 mg) was dissolved, followed by the dropwise addition of N-methylmorpholine (170 μl) and isobutyl chloroformate (210 μl) successively at −20° C. After stirring at −20° C. for 10 minutes, 1-[(6-chloronaphthalen-2-yl)sulfonyl] piperazine hydrochloride (607 mg) dissolved in advance in dichloromethane (10 ml) was added to the reaction mixture. The reaction mixture was stirred at −20° C. for 10 minutes and then heated to room temperature. The reaction mixture was concentrated under reduced pressure. The residue was dissolved in dichloroethane. The resulting solution was washed with 1N hydrochloric acid, saturated sodium bicarbonate and saturate saline and dried over anhydrous sodium sulfate. The solvent was distilled off under reduced pressure. The residue was purified by chromatography on a silica gel column (hexane:ethyl acetate=4:1~2:1), whereby the title compound (625 mg, 72%) was obtained.

$^1$H-NMR (CDCl$_3$) δ: 1.47(9H,s), 2.53(2H,t,J=7.5 Hz), 2.68(2H,br s), 2.99–3.10(6H,m), 3.51–3.55(2H,m), 3.64 (2H,br s), 3.72–3.77(2H,m), 4.34(2H,s), 6.43(1H,s), 7.59 (1H,dd,J=8.8,2.0 Hz), 7.74(1H,dd,J=8.8,2.0 Hz), 7.88–7.94 (3H,m), 8.30(1H,s).

MS (FAB) m/z: 604 [(M+H)$^+$, Cl$^{35}$], 606 [(M+H)$^+$, Cl$^{37}$].

Referential Example 106

3-(5-tert-Butoxycarbonyl-4,5,6,7-tetrahydrothieno[3,2-c]pyridin-2-yl)propanal

Ethyl 3-(5-tert-butoxycarbonyl-4,5,6,7-tetrahydrothieno[3,2-c]pyridin-2-yl)propionate (1.68 g) obtained in Referential Example 102 was dissolved in dichloromethane (100 ml). After stirring at −78° C. for 10 minutes, diisobutylaluminum hydride (a 0.98M hexane solution, 7.50 ml) was slowly added dropwise to the reaction mixture. The resulting mixture was stirred at −78° C. for 10 minutes, followed by the addition of methanol (50 ml). The resulting mixture was heated to room temperature. The reaction mixture was concentrated under reduced pressure. To the residue, dichloromethane and a saturated aqueous ammonium chloride solution were added and the resulting mixture was filtered through Celite. The organic layer separated from the filtrate was washed with saturated saline and dried over anhydrous sodium sulfate. The solvent was then distilled off. The residue was purified by chromatography on a silica gel column (hexane:ethyl acetate=5:1), whereby the title compound (935 mg, 55%) was obtained.

$^1$H-NMR (CDCl$_3$) δ: 1.48(9H,s), 2.76(2H,br s), 2.81(2H, t,J=7.3 Hz), 3.09(2H,t,J=7.3 Hz), 3.69(2H,br s), 4.39(2H,s), 6.49(1H,s), 9.81(1H,s).

MS (FAB) m/z: 295M$^+$.

Referential Example 107

1-[3-(5-tert-butoxycarbonyl-4,5,6,7-tetrahydrothieno[3,2-c]pyridin-2-yl)propyl]-4-[(6-chloronaphthalen-2-yl)sulfonyl]piperazine In a similar manner to Referential Example 47 except for the use of 3-(5-tert-butoxycarbonyl-4,5,6,7-tetrahydrothieno[3,2-c]pyridin-2-yl)propanal, 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 1.47(9H,s), 1.69–1.79(2H,m), 2.36 (2H,t,J=7.3 Hz), 2.49–2.54(4H,m), 2.65–2.75(4H,m), 3.10 (4H,br s), 3.67(2H,br s), 4.37(2H,s), 6.39(1H,s), 7.57(1H, dd,J=8.8,2.0 Hz), 7.78(1H,dd,J=8.8,2.0 Hz), 7.88–7.95(3H, m), 8.30(1H,s).

MS (FD) m/z: 589 (M$^+$, Cl$^{35}$) , 591 (M$^+$, Cl$^{37}$).

Referential Example 108

2-Aminomethyl-5-tert-butoxycarbonyl-4,5,6,7-tetrahydrothieno[3,2-c]pyridine

In tetrahydrofuran (100 ml), 5-tert-butoxycarbonyl-2-hydroxymethyl-4,5,6,7-tetrahydrothieno[3,2-c]pyridine (2.10 g) was dissolved, followed by the addition of triphenylphosphine (2.66 g) and phthalimide (1.15 g). After the dropwise addition of diethyl azodicarboxylate (1.28 ml), the resulting mixture was stirred at room temperature for 5 hours. After concentration under reduced pressure, the residue was purified by chromatography on a silica gel column (hexane:ethyl acetate=4:1), whereby a colorless solid was obtained. The resulting solid was dissolved in ethanol (40 ml). To the solution, hydrazine hydrate (0.39 ml) was added, followed by heating under reflux for 5 hours. After the solid so precipitated was filtered off, the filtrate was concentrated under reduced pressure. The residue was purified by chromatography on a silica gel column (dichloromethane~dichloromethane:methanol=25:1), whereby the title compound (448 mg, 21%) was obtained.

$^1$H-NMR (DMSO-d$_6$) δ: 1.42(9H,s), 2.72(2H,m), 3.60 (2H,m), 3.80(2H,s), 4.32(2H,s), 6.64(1H,s).

MS (FD) m/z: 268M$^+$.

Referential Example 109

1-[N-(5-tert-Butoxycarbonyl-4,5,6,7-tetrahydrothieno[3,2-c]pyridin-2-yl)methyl]carbamoyl]-4-[(6-chloronaphthalen-2-yl)sulfonyl]piperazine In tetrahydrofuran (100 ml), 5-tert-butoxycarbonyl-2-aminomethyl-4,5,6,7-tetrahydrothieno[3,2-c]pyridine (150 mg) was dissolved. To the resulting solution, carbonyldiimidazole (136 mg) was added under ice cooling, followed by stirring at room temperature for one hour. After concentration under reduced pressure, the residue was dissolved in toluene (50 ml). To the resulting solution, triethylamine (0.23 ml) and 1-[(6-chloronaphthalen-2-yl)sulfonyl]piperazine hydrochloride (356 mg) were added under ice cooling, followed by stirring overnight at room temperature. The reaction mixture was diluted with ethyl acetate, washed with water and saturated saline and dried over anhydrous sodium sulfate. The solvent was then distilled off under reduced pressure. The residue was purified by chromatography on a silica gel column (hexane:ethyl acetate=3:1~1:1), whereby the title compound (303 mg, 89%) was obtained.

$^1$H-NMR (CDCl$_3$) δ: 1.46(9H,s), 2.70(2H,br s), 3.07(4H, t,J=4.9 Hz), 3.48(4H,t,J=4.9 Hz), 3.66(2H,br s), 4.36(2H,br s), 4.39(2H,d,J=5.4 Hz), 4.69(1H,t,J=5.4 Hz), 6.58(1H,s), 7.58(1H,dd,J=8.8,2.0 Hz), 7.74(1H,dd,J=8.8,2.0 Hz), 7.87–7.93(3H,m), 8.30(1H,s).

MS (FD) m/z: 604 (M$^+$, Cl$^{35}$) , 606 (M$^+$, Cl$^{37}$).

Referential Example 110

1-[(5-tert-Butoxycarbonyl-4,5,6,7-tetrahydrothieno[3,2-c]pyridin-2-yl)carbonyl]-4-[(6-chloronaphthalen-2-yl)sulfonyl]piperazine In a similar manner to Referential Example 12 except for the use of 5-tert-butoxycarbonyl-4,5,6,7-tetrahydrothieno[3,2-c]pyridin-2-carboxylic acid and 1-[(6-chloronaphthalen-2-yl)sulfonyl]piperazine hydrochloride as the raw materials, the title compound was obtained.

$^1$H-NMR (CDCl$_3$) δ: 1.47(9H,s), 2.79(2H,br s), 3.12(4H, t,J=4.9 Hz), 3.68(2H,br s), 3.84(4H,t,J=4.9 Hz), 4.42(2H,br s), 6.91(1H,s), 7.59(1H,dd,J=8.8,2.0 Hz), 7.75(1H,dd,J=8.8, 2.0 Hz), 7.90–7.97(3H,m), 8.30(1H,s).

MS (FD) m/z: 575 (M$^+$, Cl$^{35}$) , 577 (M$^+$, Cl$^{37}$).

Referential Example 111

1-[(5-tert-Butoxycarbonyl-4,5,6,7-tetrahydrothieno[3,2-c]pyridin-2-yl)carbonyl]-4-[(6-chloronaphthalen-2-yl)sulfonyl]-2-ethoxycarbonylpiperazine In a similar manner to Referential Example 12 except for the use of 5-tert-butoxycarbonyl-4,5,6,7-tetrahydrothieno[3, 2-c]pyridin-2-carboxylic acid and 1-[(6-chloronaphthalen-2-yl)sulfonyl]-3-ethoxycarbonylpiperazine hydrochloride as the raw materials, the title compound was obtained.

$^1$H-NMR (CDCl$_3$) δ: 1.32(3H,t,J=7.3 Hz), 1.47(9H,s), 2.35–2.46(1H,m), 2.55–2.64(1H,m), 2.80(2H,br s), 3.15–3.20(1H,m), 3.69(2H,br s), 3.75–3.85(1H,m), 4.12 (2H,q,J=7.3 Hz), 4.20–4.36(2H,m), 4.39–4.48(3H,m), 6.96 (1H,s), 7.59(1H,dd,J=8.8,2.0 Hz), 7.75(1H,dd,J=8.8,2.0 Hz), 7.88–7.94(3H,m), 8.32(1H,s).

MS (FAB) m/z: 648 [(M+H)$^+$, Cl$^{35}$], 650 [(M+H)$^+$, C$^{37}$].

Referential Example 112

1-[(6-Chloronaphthalen-2-yl)sulfonyl]-4-[(5-cyano-4,5,6,7-tetrahydrothieno[3,2-c]pyridin-2-yl)carbonyl]piperazine In ethanol, 1-[(6-chloronaphthalen-2-yl)sulfonyl]-4-[(4,5,6,7-tetrahydrothieno[3,2-c]pyridin-2-yl)carbonyl] piperazine hydrochloride (195 mg), triethylamine (0.2 ml) and sodium acetate (118 mg) were suspended, followed by the addition of cyan bromide (114 mg). The resulting mixture was stirred at room temperature for 2 hours. The residue obtained by concentrating the reaction mixture under reduced pressure was added with dichloromethane, followed by washing with water. After drying over anhydrous sodium sulfate, the residue obtained by distilling off the solvent under reduced pressure was purified by chromatography on a silica gel column (dichloromethane:methanol=100:1), whereby the title compound (51 mg, 28%) was obtained.

$^1$H-NMR (CDCl$_3$) δ: 2.93–2.98(2H,m), 3.11–3.14(4H,m), 3.49–3.55(2H,m), 3.81–3.84(4H,m), 4.29(2H,s), 6.89(1H,s), 7.59(1H,dd,J=8.8,2.0 Hz), 7.75(1H,dd,J=8.8,2.0 Hz), 7.90–7.94(3H,m), 8.30(1H,s).

MS (FAB) m/z: 501 [(M+H)$^+$, Cl$^{35}$], 503 [(M+H)$^+$, Cl$^{37}$].

Referential Example 113

1-[N-(5-tert-Butoxycarbonyl-4,5,6,7-tetrahydrothieno[3,2-c]pyridin-2-yl)carbamoyl]-4-[(6-chloronaphthalen-2-yl)sulfonyl]piperazine In benzene (10 ml), 5-tert-butoxycarbonyl-4,5,6,7-tetrahydrothieno[3,2-c]pyridin-2-carboxylic acid (283 mg) was dissolved, followed by the addition of triethylamine (0.14 ml) and diphenylphosphoryl azide (0.21 g). The resulting mixture was heated under reflux for 2 hours. After cooling to room temperature, the reaction mixture was added with 1-[(6-chloronaphthalen-2-yl)sulfonyl]piperazine hydrochloride (347 mg), followed by heating overnight under reflux. After the reaction mixture was cooled to room temperature, dichloromethane and a 3N aqueous sodium hydroxide solution were added thereto to extract an organic layer. The organic layer so extracted was washed with 0.5N hydrochloric acid, a saturated aqueous solution of sodium bicarbonate and saturated saline and dried over anhydrous sodium sulfate. The solvent was distilled off under reduced pressure. The residue was purified by chromatography on a silica gel column (hexane:ethyl acetate=3:1~2:1), whereby the title compound (284 mg, 48%) was obtained.

$^1$H-NMR (CDCl$_3$) δ: 1.45(9H,s), 2.65(2H,br s), 3.10(4H, t,J=4.9 Hz), 3.57(4H,t,J=4.9 Hz), 3.64(2H,br s), 4.27(2H,s), 6.15(1H,br s), 7.58(1H,dd,J=8.8,2.0 Hz), 7.73(1H,dd,J=8.8, 2.0 Hz), 7.87–7.93(3H,m), 8.28(1H,s).

MS (FAB) m/z: 591 [(M+H)$^+$, Cl$^{35}$], 593 [(M+H)$^+$, Cl$^{37}$].

Referential Example 114

1-[N-(5-tert-Butoxycarbonyl-4,5,6,7-tetrahydrothieno[3,2-c]pyridin-2-yl)-N-methylcarbamoyl]-4-[(6-chloronaphthalen-2-yl)sulfonyl]piperazine In N,N-dimethylformamide (10 ml), 1-[N-(5-tert-butoxycarbonyl-4,5,6,7-tetrahydrothieno[3,2-c]pyridin-2-yl)carbamoyl]-4-[(6-chloronaphthalen-2-yl)sulfonyl] piperazine (147 mg) was dissolved. After the addition of 60% oily sodium hydride (22 mg), the resulting mixture was stirred at room temperature for 30 minutes. Methyl iodide (0.023 ml) was added to the reaction mixture and the resulting mixture was stirred at room temperature for 90 minutes. To the residue obtained by concentrating the reaction mixture under reduced pressure, ethyl acetate was added. The resulting mixture was washed with water and saturated saline and then dried over anhydrous sodium sulfate. The solvent was then distilled off under reduced pressure. The residue was purified by chromatography on a silica gel column (hexane:ethyl acetate=2:1), whereby the title compound (43 mg) was obtained.

$^1$H-NMR (CDCl$_3$) δ: 1.49(9H,s), 2.63(2H,br s), 3.01(4H, t,J=4.9 Hz), 3.13(3H,s), 3.40(4H,t,J=4.9 Hz), 3.67(2H,br s), 4.31(2H,s), 6.21(1H,br s), 7.58(1H,dd,J=8.8,2.0 Hz), 7.72 (1H,dd,J=8.8,2.0 Hz), 7.88–7.95(3H,m), 8.27(1H,s).

MS (FAB) m/z: 605 [(M+H)$^+$, Cl$^{35}$], 607 [(M+H)$^+$, Cl$^{37}$].

(Referential Example 115

1-[(6-tert-Butoxycarbonyl-4,5,6,7-tetrahydrothiazolo[5,4-c]pyridin-2-yl)carbonyl]-4-[(6-chloronaphthalen-2-yl)sulfonyl]piperazine In a similar manner to Referential Example 12 except for the use of 6-tert-butoxycarbonyl-4,5,6,7-tetrahydrothiazolo [5,4-c]pyridine-2-carboxylic acid and 1-[(6-chloronaphthalen-2-yl)sulfonyl]piperazine hydrochloride as the raw materials, the title compound was obtained.

$^1$H-NMR (CDCl$_3$) δ: 1.47(9H,s), 2.84(2H,br s), 3.19(4H, br), 3.72(2H,t,J=5.4 Hz), 3.87(2H,br s), 4.54(2H,s), 4.63 (2H,br s), 7.57(1H,dd,J=8.8,2.0 Hz), 7.76(1H,dd,J=8.8,2.0 Hz), 7.87–7.94(3H,m), 8.30(1H,s).

MS (FAB) m/z: 577 [(M+H)$^+$, Cl$^{35}$], 579 [(M+H)$^+$, Cl$^{37}$].

Referential Example 116

1-[(6-tert-Butoxycarbonyl-4,5,6,7-tetrahydrothiazolo[5,4-c]pyridin-2-yl)carbonyl]-4-[(6-chloronaphthalen-2-yl)sulfonyl]-2-ethoxycarbonylpiperazine In N,N-dimethylformamide (30 ml), 6-tert-butoxycarbonyl-4,5,6,7-tetrahydrothiazo[5,4-c]pyridin-2-carboxylic acid (742 mg), 1-[(6-chloronaphthalen-2-yl) sulfonyl]-3-ethoxycarbonylpiperazine hydrochloride (1.00 g) and benzotriazol-1-yl-oxy-tris(pyrrolidino)phosphonium hexafluorophosphate ("PyBOP", trade name) (1.50 g) were dissolved, followed by the addition of triethylamine (0.40 ml). The resulting mixture was stirred overnight at room temperature. After the reaction mixture was concentrate under reduced pressure, ethyl acetate was added to the residue. The resulting mixture was washed with water and saturated saline and dried over anhydrous sodium sulfate. The solvent was then distilled off under reduced pressure. The residue was purified by chromatography on a silica gel column (hexane:ethyl acetate=4:1), whereby the title compound (505 mg, 30%) was obtained.

$^1$H-NMR (CDCl$_3$) δ: 1.24–1.37(3H,m), 1.47(9H,s), 2.45–2.60(1H,m), 2.62–2.71(1H,m), 2.75–2.90(2H,m), 3.65–3.94(3H,m), 4.19–4.31(2H,m), 4.45–4.72(4H,m), 5.35 (1/2H,br s), 5.71–5.77(1/2H,m), 6.72(1H,br s), 7.58(1H,dd, J=8.8,2.0 Hz), 7.77(1H,dd,J=8.8,2.0 Hz), 7.88–7.92(3H,m), 8.33(1H,s).

MS (FAB) m/z: 649 [(M+H)$^+$, Cl$^{35}$], 651 [(M+H)$^+$, Cl$^{37}$].

Referential Example 117

1-[(6-tert-Butoxycarbonyl-4,5,6,7-tetrahydrothiazolo
[5,4-c]pyridin-2-yl)carbonyl]-2-carbamoyl-4-[(6-
chloronaphthalen-2-yl)sulfonyl]piperazine In tetrahydrofuran (5 ml), 1-[(6-tert-butoxycarbonyl-4,5, 6,7-tetrahydrothiazolo[5,4-c]pyridin-2-yl)carbonyl]-4-[(6-chloronaphthalen-2-yl)sulfonyl]-2-ethoxycarbonylpiperazine (487 mg) was dissolved. After the addition of methanol (5 ml) and a 1N aqueous solution of sodium hydroxide (3 ml), the resulting mixture was stirred at room temperature for 4 hours. To the reaction mixture, 1N hydrochloric acid was added to adjust its pH to 1 to 2, followed by the addition of ethyl acetate. The organic layer so separated was dried over anhydrous sodium sulfate. The residue obtained by distilling off the solvent under reduced pressure was dissolved in tetrahydrofuran (5 ml), followed by the dropwise addition of N-methylmorpholine (0.09 ml) and isobutyl chloroformate (0.11 ml) at −20° C. After stirring at −20° C. for 10 minutes, the reaction mixture was added with an ammonia-dichloromethane solution (0.50 ml). The resulting solution was stirred at −20° C. for 10 minutes, ethanolic 1N hydrochloric acid (10 ml) was added. The reaction mixture was then heated to room temperature and concentrated under reduced pressure. The residue was dissolved in dichloroethane, followed by washing with 1N hydrochloric acid. The organic layer was dried over anhydrous sodium sulfate. The solvent was then distilled off under reduced pressure. The residue was purified by chromatography on a silica gel column (dichloromethane~dichloromethane:methanol=100:1), whereby the title compound (317 mg, 68%) was obtained.

$^1$H-NMR (DMSO-$d_6$) δ: 1.41(9H,s), 2.39–2.86(4H,m), 3.60–3.80(4H,m), 4.25–4.34(1H,m), 4.36–4.44(1/2H,m), 4.62(2H,br s), 4.97(1/2H,br s), 5.44–5.52(1/2H,m), 6.19(1/2H,br s), 7.30–7.39(1H,m), 7.63–7.85(3H,m), 8.15(1H,d,J= 8.8 Hz), 8.20–8.29(2H,m), 8.48(1H,s).

MS (FAB) m/z: 620 [(M+H)$^+$, Cl$^{35}$], 622 [(M+H)$^+$, Cl$^{37}$].

Referential Example 118

1-[(6-tert-Butoxycarbonyl-4,5,6,7-tetrahydrothiazolo
[5,4-c]pyridin-2-yl)carbonyl]-4-[(E)-4-
chlorostyrylsulfonyl]piperazine In a similar manner to Referential Example 12 except for the use of 6-tert-butoxycarbonyl-4,5,6,7-tetrahydrothiazolo [5,4-c]pyridin-2-carboxylic acid and 1-[(E)-4-chlorostyrylsulfonyl]piperazine hydrochloride as the raw materials, the title compound was obtained.

$^1$H-NMR (CDCl$_3$) δ: 1.48(9H,s), 2.87(2H,br s), 3.31(4H, m), 3.75(2H,br s), 3.90(2H,br s), 4.57(2H,br s), 4.68(2H,s), 6.64(1H,d,J=15.6 Hz), 7.28–7.35(5H,m).

MS (FAB) m/z: 553 [(M+H)$^+$, Cl$^{35}$], 555 [(M+H)$^+$, Cl$^{37}$].

Referential Example 119

(3S)-3-Amino-1-tert-butoxycarbonylpyrrolidine

In a similar manner to Referential Example 59 except for the use of (3R)-1-tert-butoxycarbonyl-3-methanesulfonyloxypyrrolidine (1.50 g) as the raw material, the title compound was obtained.

$^1$H-NMR (CDCl$_3$) δ: 1.46(9H,s), 1.98–2.11(2H,m), 2.95–3.10(1H,m), 3.26–3.60(4H,m).

MS (FAB) m/z: 187 (M+H)$^+$.

Referential Example 120

(3S)-3-[(6-Chloronaphthalen-2-yl)sulfonamide]
pyrrolidine trifluoroacetate

In a similar manner to Referential Example 1 except for the use of (3S)-3-amino-1-tert-butoxycarbonylpyrrolidine as the raw material, the reaction was conducted, whereby the title compound was obtained.

$^1$H-NMR (DMSO-$d_6$) δ: 1.69–1.80(1H,m), 1.88-1.99(1H, m), 2.95–3.28(4H,m), 3.75–3.84(1H,m), 7.71(1H,m), 7.91 (1H,m), 8.10–8.30(4H,m), 8.53(1H,s), 8.91(1H,br s), 9.06 (1H,br s).

Referential Example 121

(3S)-1-[(5-tert-Butoxycarbonyl-4,5,6,7-
tetrahydrothieno[3,2-c]pyridin-2-yl)methyl]-3-[(6-
chloronaphthalen-2-yl)sulfonamide]pyrrolidine In a similar manner to Referential Example 47 except for the use of 5-tert-butoxycarbonyl-2-formyl-4,5,6,7-tetrahydrothieno[3,2-c]pyridine and (3S)-3-[(6-chloronaphthalen-2-yl)sulfonamide]pyrrolidine trifluoroacetate as the raw materials, the reaction was conducted, whereby the title compound was obtained.

$^1$H-NMR (CDCl$_3$) δ: 1.49(9H,s), 1.52–1.63(1H,m), 2.03–2.12(1H,m), 2.19–2.27(1H,m), 2.35–2.54(2H,m), 2.73–2.85(3H,m), 3.59(1H,d,J=13.9 Hz), 3,66(1H,d,J=13.9 Hz), 3.70(2H,br s), 3.88–3.95(1H,m), 4.39(2H,s), 4.99(1/2H,s), 5.02(1/2H,s), 6.49(1H,s), 7.55(1H,dd,J=8.8,2.0 Hz), 7.82–7.90(4H,m), 8.40(1H,s).

MS (FD) m/z: 561 (M$^+$, Cl$^{35}$), 563 (M$^+$, Cl$^{37}$).

Referential Example 122

(3S)-1-[(5-tert-Butoxycarbonyl-4,5,6,7-
tetrahydrothieno[3,2-c]pyridin-2-yl)carbonyl]-3-[(6-
chloronaphthalen-2-yl)sulfonamide]pyrrolidine In a similar manner to Referential Example 12 except for the use of 5-tert-butoxycarbonyl-4,5,6,7-tetrahydrothieno[3, 2-c]pyridine-2-carboxylic acid and (3S)-3-[(6-chloronaphthalen-2-yl)sulfonamide]pyrrolidine trifluoroacetate as the raw materials, the title compound was obtained.

$^1$H-NMR (CDCl$_3$) δ: 1.50(9H,s), 1.80–2.08(2H,m), 2.75 (2H,br s), 3.48–3.87(6H,m), 3.88–4.05(1H,m), 4.37(2H,br s), 6.09(1H,br s), 7.05–7.15(1H,m), 7.55(1H,dd,J=8.8,1.5 Hz), 7.79–7.91(4H,m), 8.41(1H,s).

MS (FAB) m/z: 576 [(M+H)$^+$, Cl$^{35}$], 578 [(M+H)$^+$, Cl$^{37}$].

Referential Example 123

(3S)-3-Amino-1-[(6-chloronaphthalen-2-yl)sulfonyl]
pyrrolidine

In trifluoroacetic acid, (3R)-1-tert-butoxycarbonyl-3-methanesulfonyloxypyrrolidine was dissolved. After the resulting solution was concentrated under reduced pressure, diethyl ether was added to the concentrate, followed by the removal of the supernatant. The residue was reacted as in Referential Example 1, whereby the corresponding sulfonamide derivative was obtained as a crude product. The crude product was subjected to azide formation and reduction as in Referential Example 55, whereby the title compound was obtained.

$^1$H-NMR (DMSO-$d_6$) δ: 1.38–1.53(3H,m), 1.72–1.83 (1H,m), 2.81–2.89(1H,m), 3.20–3.39(4H,m), 7.69(1H,dd,J= 8.8,1.9 Hz), 7.87(1H,d,J=8.8 Hz), 8.12(1H,d,J=8.8 Hz), 8.21 (1H,s), 8.26(1H,d,J=8.8 Hz), 8.39(1H,s).

MS (FAB) m/z: 311 [(M+H)$^+$, Cl$^{35}$], 313 [(M+H)$^+$, Cl$^{37}$].

Referential Example 124

(3S)-1-[[(5-tert-Butoxycarbonyl-4,5,6,7-
tetrahydrothieno[3,2-c]pyridin-2-yl)methyl]amino]-
1-[(6-chloronaphthalen-2-yl)sulfonyl]pyrrolidine In a similar manner to Referential Example 47 except for the use of 5-tert-butoxycarbonyl-2-formyl-4,5,6,7- tetrahydrothieno[3,2-c]pyridine and (3S)-3-amino-1-[(6-chloronaphthalen-2-yl)sulfonyl]pyrrolidine as the raw materials, the reaction was conducted, whereby the title compound was obtained.

$^1$H-NMR (CDCl$_3$) δ: 1.48(9H,s) 1.60–1.69(1H,m), 1.95–2.05(1H,m), 2.72(2H,br s), 3.11(1H,dd,J=10.3,4.4 Hz), 3.30–3.46(4H m), 3.68(2H,br s), 3.72(2H,s), 4.36(2H, s), 6.44(1H,s), 7.56(1H,dd,J=8.8,2.0 Hz), 7.86–7.91(4H,m), 8.36(1H,s).

MS (FD) m/z: 561 (M$^+$, Cl$^{35}$), 563 (M$^+$, Cl$^{37}$).

Referential Example 125

(3S)-3-[(5-tert-Butoxycarbonyl-4,5,6,7-tetrahydrothieno[3,2-c]pyridin-2-yl)carbonylamino]-1-[(6-chloronaphthalen-2-yl) sulfonyl]pyrrolidine In a similar manner to Referential Example 12 except for the use of 5-tert-butoxycarbonyl-4,5,6,7-tetrahydrothieno[3,2-c]pyridine-2-carboxylic acid and (3S)-3-amino-1-[(6-chloronaphthalen-2-yl) sulfonyl]pyrrolidine as the raw materials, the title compound was obtained.

$^1$H-NMR (CDCl$_3$) δ: 1.48(9H,s), 1.90–2.00(1H,m), 2.11–2.22(1H,m), 2.80(2H,br s), 3.32–3.42(1H,m), 3.44–3.57(3H,m), 3.71(2H,br s), 4.38(2H,d,J=1.5 Hz), 4.40–4.49(1H,m), 5.80–5.87(1H,m), 6.96(1H,s), 7.54(1H, dd,J=8.8,1.5 Hz), 7.83–7.89(3H,m), 7.90(1H,d,J=8.8 Hz), 8.37(1H,s).

MS (FD) m/z: 576 [(M+H)$^+$, Cl$^{35}$], 578 [(M+H)$^+$, Cl$^{37}$].

Referential Example 126

1-[(5-tert-Butoxycarbonyl-4,5,6,7-tetrahydrothieno[3,2-c]pyridin-2-yl)carbonyl]-4-[(6-chloronaphthalen-2-yl)sulfonyl]homopiperazine In a similar manner to Referential Example 12 except for the use of 5-tert-butoxycarbonyl-4,5,6,7-tetrahydrothieno[3,2-c]pyridine-2-carboxylic acid and 1-[(6-chloronaphthalen-2-yl)sulfonyl]homopiperazine hydrochloride as the raw materials, the title compound was obtained.

$^1$H-NMR (CDCl$_3$) δ: 1.47(9H,s), 2.01(2H,br s), 2.78(2H, br s), 3.37–3.54(4H,m), 3.68(2H,br s), 3.78(2H,t,J=6.1 Hz), 3.86(2H,t,J=6.1 Hz), 4.39(2H,s), 6.88(1H,br s), 7.55(1H,dd, J=8.8,2.0 Hz), 7.75–7.80(1H,m), 7.83–7.90(3H,m), 8.33 (1H,s).

MS (FD) m/z: 589 (M$^+$, Cl$^{35}$), 591 (M$^+$, Cl$^{37}$).

Referential Example 127

4-Benzylamino-1-tert-butoxycarbonylpiperidine

In dichloromethane (500 ml), 1-tert-butoxycarbonyl-4-piperidione (7.00 g) was dissolved, followed by the addition of benzylamine (4.03 ml) and sodium triacetoxyborohydride (11.91 g). The resulting mixture was stirred overnight at room temperature. After the reaction mixture was concentrated under reduced pressure, the residue was dissolved in ethyl acetate. The resulting mixture was washed with water and saturated saline and then dried over anhydrous sodium sulfate. The solvent was then distilled off under reduced pressure. The residue was purified by chromatography on a silica gel column (hexane:ethyl acetate=1:1), whereby the title compound (7.46 g, 76%) was obtained.

$^1$H-NMR (CDCl$_3$) δ: 1.24–1.37(2H,m), 1.45(9H,s), 1.80–1.90(2H,m), 2.62–2.70(1H,m), 2.75–2.85(1H,m), 2.98–3.07(1H,m), 3.78–3.90(3H,m), 3.95–4.10(1H,m), 7.21–7.34(5H,m).

MS (FD) m/z: 290M$^+$.

Referential Example 128

4-Amino-1-tert-butoxycarbonylpiperidine acetate

In methanol (2 ml) and acetic acid (30 ml), 4-benzylamino-1-tert-butoxycarbonylpiperidine (4.04 g) was dissolved, followed by the addition of 10% palladium carbon (water content: about 50%, 3.06 g). The resulting mixture was subjected to catalytic reduction overnight under medium pressure (3 atmospheric pressure). After the removal of the catalyst by filtration, the filtrate was distilled off under reduced pressure. The residue was solidified in ethyl acetate, whereby the title compound (2.23 g, 57%) was obtained.

$^1$H-NMR (DMSO-d$_6$) δ: 1.10–1.23(2H,m), 1.39(9H,s), 1.69–1.77(2H,m), 1.80(3H,s), 2.50(2H,s), 2.67–2.88(2H,m), 3.80–3.90(1H,m).

Elementary analysis for C$_{10}$H$_{20}$N$_2$O$_2$·CH$_3$CO$_2$H
Calculated: C, 53.16; H, 9.37; N, 10.33.
Found: C, 53.51; H, 9.10; N, 9.93.

Referential Example 129

4-[(6-Chloronaphthalen-2-yl)sulfonamido]piperidine trifluoroacetate

In a similar manner to Referential Example 1 except for the use of 4-amino-1-tert-butoxycarbonylpiperidine hydrochloride and 6-chloro-2-naphthylsulfonyl chloride as the raw materials, the title compound was obtained.

$^1$H-NMR (DMSO-d$_6$) δ: 1.47–1.60(2H,m), 1.68–1.78 (2H,m), 2.81–2.95(2H,m), 3.10–3.20(2H,m), 3.29–3.40(1H, m), 7.70(1H,dd,J=8.8,2.0 Hz), 7.91(1H,dd,J=8.8,2.0 Hz), 8.11–8.15(2H,m), 8.21(1H,s), 8.31(1H,br s), 8.50(1H,s), 8.55(1H,br s).

MS (FAB) m/z: 325 [(M+H)$^+$, Cl$^{35}$], 327 [(M+H)$^+$, Cl$^{37}$].

Referential Example 130

1-[(6-Chloronaphthalen-2-yl)sulfonyl]-4-[(6-cyanobenzofuran-2-yl)carbonyl]piperazine In a similar manner to Referential Example 12 except for the use of 6-cyanobenzofuran-2-carboxylic acid and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 3.21(4H,s), 3.95(4H,s), 7.32(1H,d, J=1.0 Hz), 7.55(1H,dd,J=8.3,1.0 Hz), 7.59(1H,dd,J=8.8,2.0 Hz), 7.72(1H,d,J=8.3 Hz), 7.77(1H,dd,J=8.8,2.0 Hz), 7.81 (1H,s), 7.88–7.95(3H,m), 8.32(1H,s).

MS (FAB) m/z: 480 [(M+H)$^+$, Cl$^{35}$], 482 [(M+H)$^+$, Cl$^{37}$].

Referential Example 131

1-[(6-Chloronaphthalen-2-yl)sulfonyl]-4-[(5-cyanobenzothiophen-2-yl)carbonyl]piperazine In a similar manner to Referential Example 12 except for the use of 5-cyanobenzothiophene-2-carboxylic acid and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 3.18(4H,s), 3.89(4H,s), 7.43(1H,d, J=2.0 Hz), 7.60(1H,d,J=8.8 Hz), 7.73–7.80(2H,m), 7.85–7.95(4H,m), 8.10(1H,s), 8.32(1H,s).

MS (FAB) m/z: 496 [(M+H)$^+$, Cl$^{35}$], 498 [(M+H)$^+$, Cl$^{37}$].

Referential Example 132

Ethyl (1RS)-4-trifluoromethanesulfonyloxy-3-cyclohexenecarboxylate

Diisopropylamine (0.99 ml) was dissolved in tetrahydrofuran (50 ml), followed by the dropwise addition of n-butyl lithium (a 1.59M hexane solution, 3.70 ml) at −78° C. After the dropwise addition of ethyl 4-oxocyclohexanecarboxylate (1.00 g) dissolved in tetrahydrofuran (5 ml) to the reaction mixture and stirring for 15 minutes, N-phenyltrifluoromethanesulfonimide (2.10 g) dissolved in tetrahydrofuran (5 ml) was added dropwise to the reaction mixture. The reaction mixture was heated to 0° C., stirred for one hour and then concentrated under reduced pressure. The residue was purified by chromatography on a neutral alumina column (hexane:ethyl acetate=9:1), whereby the title compound (838 mg, 47%) was obtained.

$^1$H-NMR (CDCl$_3$) δ: 1.27(3H,t,J=7.3 Hz), 1.88–1.99(1H, m), 2.10–2.18(1H,m), 2.38–2.50(4H,m), 2.55–2.64(1H,m), 4.16(2H,q,J=7.3 Hz), 5.77(1H,br s).

MS (FAB) m/z: 303 (M+H)$^+$.

Referential Example 133

Ethyl (1RS)-4-(4-pyridyl)-3-cyclohexenecarboxylate

In a similar manner to Referential Example 7 except for the use of ethyl (1RS)-4-trifluoromethanesulfonyloxy-3-cyclohexenecarboxylate as the raw material, the reaction was conducted, whereby the title compound was obtained.

$^1$H-NMR (CDCl$_3$) δ: 1.28(3H,t,J=7.3 Hz), 1.80–1.91(1H, m), 2.19–2.25(1H,m), 2.40–2.57(4H,m), 2.59–2.67(1H,m), 4.17(2H,q,J=7.3 Hz), 6.36(1H,br s), 7.26(2H,dd,J=4.9,1.5 Hz), 8.53(2H,dd,J=4.9,1.5 Hz).

MS (FAB) m/z: 232 (M+H)$^+$.

Referential Example 134

(1RS)-4-(4-Pyridyl)-3-cyclohexenecarboxylic acid

In a similar manner to Referential Example 8 except for the use of ethyl (1RS)-4-(4-pyridyl)-3-cyclohexenecarboxylate as the raw material, the title compound was obtained.

$^1$H-NMR (DMSO-d$_6$) δ: 1.70–1.82(1H,m), 2.10–2.19 (1H,m), 2.42–2.65(5H,m), 6.99(1H,br s), 8.02(2H,d,J=6.8 Hz), 8.80(2H,d,J=6.8 Hz).

MS (FAB) m/z: 204 (M+H)$^+$.

Referential Example 135 cis-, trans-4-(4-Pyridyl)cyclohexanecarboxylic acid

In a similar manner to Referential Example 87 except for the use of (1RS)-4-(4-pyridyl)-3-cyclohexenecarboxylic acid as the raw material, the title compound was obtained.

MS (FAB) m/z: 206 (M+H)$^+$.

Referential Example 136

6-Methoxy-3,4-dihydroisoquinoline

In tetrahydrofuran (100 ml), 3-methoxyphenethylamine (75.0 g) was dissolved, followed by the addition of formic acid (60 ml) and acetic anhydride (108 ml) under ice cooling. The resulting mixture was stirred overnight at room temperature. A saturated aqueous solution of sodium bicarbonate was added to the reaction mixture. The organic lay-layer so separated was washed with saturated saline and dried over anhydrous sodium sulfate. The residue obtained by distilling off the solvent under reduced pressure was dissolved in benzene (200 ml), followed by the dropwise addition of phosphorus oxychloride (140 ml) under ice cooling. After stirring at 70° C. for 15 minutes, ice and then 2N hydrochloric acid were added. The resulting mixture was stirred under ice cooling for one hour. The water layer was separated and neutralized with potassium carbonate. After extraction with dichloromethane, the extract was dried over anhydrous sodium sulfate. The residue obtained by distilling off the solvent under reduced pressure was purified by chromatography on a silica gel column (dichloromethane~dichloromethane:methanol=100:1), the title compound (13.5 g, 17%) was obtained.

$^1$H-NMR (CDCl$_3$) δ: 2.72(2H,t,J=7.3 Hz), 3.72(2H,t,J= 7.3 Hz), 3.83(3H,s), 6.68(1H,d,J=2.4 Hz), 6.79(1H,dd,J= 8.3,2.4 Hz), 7.22(1H,d,J=8.3 Hz), 8.25(1H,s).

MS (FAB) m/z: 162 (M+H)$^+$.

Referential Example 137

6-Methoxy-1,2,3,4-tetrahydroisoquinoline

In methanol (100 ml), 6-methoxy-3,4-dihydroisoquinoline (10.4 g) was dissolved. After the addition of water (10 ml) and then sodium borohydride (6.10 g), the resulting mixture was stirred at room temperature for 15 minutes. The reaction mixture was concentrated under reduced pressure and the residue was dissolved in dichloromethane. The resulting solution was washed with water. The organic layer so separated was dried over anhydrous sodium sulfate. The solvent was then distilled off under reduced pressure. The residue was purified by chromatography on a silica gel column (dichloromethane~dichloromethane:methanol=100:15), whereby the title compound (7.95 g, 76%) was obtained.

$^1$H-NMR (CDCl$_3$) δ: 2.79(2H,t,J=5.9 Hz), 3.12(2H,t,J= 5.9 Hz), 3.76(3H,s), 3.96(2H,s), 6.62(1H,s), 6.70(1H,dd,J= 8.3,2.4 Hz), 6.92(1H,d,J=8.3 Hz).

MS (FAB) m/z: 164 (M+H)$^+$.

Referential Example 138

6-Hydroxy-1,2,3,4-tetrahydroisoquinoline hydrochloride

In dimethylsulfide (20 ml), 6-methoxy-1,2,3,4-tetrahydroisoquinoline (7.75 g) was dissolved, followed by the addition of aluminum chloride (19.0 g) under ice cooling. The resulting mixture was stirred at room temperature for 3 hours. Dichloromethane and dilute hydrochloric acid were added to the reaction mixture. A saturated aqueous solution of sodium bicarbonate was added to the water layer so separated to make it weakly alkaline, followed by the extraction with dichloromethane. After drying over anhydrous sodium sulfate, the solvent was then distilled off under reduced pressure. The residue was dissolved in saturated ethanol hydrochloride (100 ml) and the solvent was distilled off under reduced pressure. Ethyl acetate was added to the residue and the solid so precipitated was collected by filtration, whereby the title compound (7.91 g, 90%) was obtained.

$^1$H-NMR (DMSO-d$_6$) δ: 3.06(2H,t,J=5.9 Hz), 3.43(2H, m), 4.25(2H,s), 6.76(1H,d,J=2.0 Hz), 6.83(1H,dd,J=8.3,2.0 Hz), 7.15(1H,d,J=8.3 Hz), 9.71(3H,br s).

MS (FAB) m/z: 150 (M+H)$^+$.

Referential Example 139

2-tert-Butoxycarbonyl-6-hydroxy-1,2,3,4-tetrahydroisoquinoline

In methanol (100 ml), 6-hydroxy-1,2,3,4-tetrahydroisoquinoline hydrochloride (7.87 g) was dissolved, followed by the addition of triethylamine (4.67 ml) and di-tert-butyl dicarbonate (13.95 g). The resulting mixture was stirred at room temperature for 3 hours. To the residue obtained by concentrating the reaction mixture under reduced pressure, ethyl acetate was added. The resulting mixture was washed with 1N hydrochloric acid and dried over anhydrous sodium sulfate. The solvent was then distilled off under reduced pressure. The residue was purified by chromatography on a silica gel column (hexane:ethyl acetate=10:1~3:1), whereby the title compound (9.96 g, 94%) was obtained.

$^1$H-NMR (CDCl$_3$) δ: 1.49(9H,s), 2.75(2H,t,J=5.9 Hz), 3.61(2H,t,J=5.9 Hz), 4.48(2H,s), 6.25(1H,br s), 6.64(1H,d, J=2.4 Hz), 6.70(1H,br s), 6.93(1H,d,J=7.8 Hz).

Referential Example 140

2-tert-Butoxycarbonyl-6-trifluoromethanesulfonyloxy-1,2,3,4-tetrahydroisoquinoline In a similar manner to Referential Example 94 except for the use of 2-tert-butoxycarbonyl-6-hydroxy-1,2,3,4-tetrahydroisoquinoline as the raw material, the title compound was obtained.

$^1$H-NMR (CDCl$_3$) δ: 1.49(9H,s), 2.87(2H,t,J=5.9 Hz), 3.66(2H,t,J=5.9 Hz), 4.59(2H,s), 7.06(1H,br s), 7.08(1H,d, J=8.3 Hz), 7.17(1H,d,J=8.3 Hz).

Elementary analysis for C$_{15}$H$_{18}$F$_3$NO$_5$S

Calculated: C, 47.24; H, 4.76; F, 14.94; N, 3.67; S, 8.41.

Found: C, 47.34; H, 4.72; F, 15.25; N, 3.42; S, 8.65.

Referential Example 141

2-tert-Butoxycarbonyl-6-methoxycarbonyl-1,2,3,4-tetrahydroisoquinoline

In methanol (50 ml), 2-tert-butoxycarbonyl-6-trifluoromethanesulfonyloxy-1,2,3,4-tetrahydroisoquinoline (1.34 g) was dissolved, followed by the addition of triethylamine (0.73 ml), palladium (II) acetate (40 mg) and 1,3-(diphenylphosphino)propane (145 mg). The resulting mixture was stirred overnight at 70° C. under a carbon monoxide gas stream. After the reaction mixture was concentrated under reduced pressure, the residue was purified by chromatography on a silica gel column (hexane:ethyl acetate= 15:1), whereby the title compound (665 mg, 65%) was obtained.

$^1$H-NMR (CDCl$_3$) δ: 1.50(9H,s), 2.88(2H,m), 3.66(2H,br s), 3.91(3H,s), 4.62(2H,s), 7.17(1H,d,J=7.8 Hz), 7.83(1H,s), 7.84(1H,d,J=7.8 Hz).

Referential Example 142

1-[(2-tert-Butoxycarbonyl-1,2,3,4-tetrahydroisoquinolin-6-yl)carbonyl]-4-[(6-chloronaphthalen-2-yl)sulfonyl]piperazine In a similar manner to Referential Example 48 except for the use of 2-tert-butoxycarbonyl-6-methoxycarbonyl-1,2,3,4-tetrahydroisoquinoline and 1-[(6-chloronaphthalen-2-yl)sulfonyl]piperazine hydrochloride as the raw materials, the title compound was obtained.

$^1$H-NMR (CDCl$_3$) δ: 1.48(9H,s), 2.76(2H,t,J=5.4 Hz), 3.09(4H,br), 3.60(2H,t,J=5.4 Hz), 3.77(4H,br), 4.52(2H,s), 7.12–7.25(3H,m), 7.59(1H,dd,J=8.8,2.0 Hz), 7.75(1H,dd,J= 8.8,2.0 Hz), 7.88–7.95(3H,m), 8.30(1H,s).

MS (FAB) m/z: 570 [(M+H)$^+$, Cl$^{35}$], 572 [(M+H)$^+$, Cl$^{37}$].

Referential Example 143

4-(1-tert-Butoxycarbonyl-1,2,3,6-tetrahydropyridin-4-yl)benzoic acid

In 1,2-dimethoxyethane (30 ml), 4-(1-tert-butoxycarbonyl-4-trifluoromethanesulfonyloxy-1,2,3,6-tetrahydropyridine (3.59 g) was dissolved, followed by the addition of 4-carboxyphenylboric acid (3.60 g), lithium chloride (1.38 g), tetrakistriphenylphosphine palladium (0.62 g) and an aqueous solution of sodium carbonate (2M, 16.3 ml). The resulting mixture was heated under reflux for 2 hours under an argon gas atmosphere. To the reaction mixture, 1N hydrochloric acid was added. The resulting mixture was extracted with ethyl acetate. The extract was dried over anhydrous sodium sulfate. The residue obtained by distilling off the solvent under reduced pressure was purified by chromatography on a silica gel column (dichloromethane~dichloromethane:methanol 100:1). The purified product was pulverized and washed in a mixed solvent of hexane and ethyl acetate (hexane:ethyl acetate 5:1), whereby the title compound (462 mg, 14%) was obtained.

$^1$H-NMR (CDCl$_3$) δ: 1.50(9H,s), 2.56(2H,br s), 3.66(2H, m), 4.12(2H,br s), 6.19(1H,br s), 7.47(2H,d,J=8.3 Hz), 8.07 (2H,d,J=8.3 Hz).

MS (FAB) m/z: 304 (M+H)$^+$.

Referential Example 144

4-(1-tert-Butoxycarbonylpiperidin-4-yl)benzoic acid

In a similar manner to Referential Example 87 except for the use of 4-(1-tert-butoxycarbonyl-1,2,3,6-tetrahydropyridin-4-yl)benzoic acid as the raw material, the title compound was obtained.

$^1$H-NMR (CDCl$_3$) δ: 1.48(9H,s), 1.60–1.71(2H,m), 1.80–1.89(2H,m), 2.69–2.90(3H,m), 4.20–4.35(2H,m), 7.31 (2H,d,J=8.3 Hz), 8.05(2H,d,J=8.3 Hz).

MS (FAB) m/z: 306 (M+H)$^+$.

Referential Example 145

1-[4-(1-tert-butoxycarbonyl-1,2,3,6-tetrahydropyridin-4-yl)benzoyl]-4-[(6-chloronaphthalen-2-yl)sulfonyl]piperazine In a similar manner to Referential Example 12 except for the use of 4-(1-tert-butoxycarbonyl-1,2,3,6-tetrahydropyridin-4-yl)benzoic acid and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 1.49(9H,s), 2.48(2H,br s), 3.10(4H, br), 3.62(2H,t,J=5.9 Hz), 3.70(4H,br), 4.08(2H,br s), 6.05 (1H,br s), 7.25(2H,d,J=8.3 Hz), 7.34(2H,d,J=8.3 Hz), 7.59 (1H,dd,J=8.8,2.0 Hz), 7.75(1H,dd,J=8.8,2.0 Hz), 7.90–7.96 (3H,m), 8.30(1H,s).

MS (FAB) m/z: 596 [(M+H)$^+$, Cl$^{35}$], 598 [(M+H)$^+$, Cl$^{37}$].

Referential Example 146

1-[4-(1-tert-Butoxycarbonylpiperidin-4-yl)benzoyl]-4-[(6-chloronaphthalen-2-yl)sulfonyl]piperazine In a similar manner to Referential Example 12 except for the use of 4-(1-tert-butoxycarbonylpiperidin-4-yl)benzoic acid and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 1.47(9H,s), 1.49–1.63(2H,m), 1.72–1.80(2H,m), 2.59–2.68(1H,m), 2.71–2.86(2H,m), 2,92–3.30(4H,m), 3.45–4.95(4H,m), 4.16–4.31(2H,m), 7.18 (2H,d,J=8.3 Hz), 7.24(2H,d,J=8.3 Hz), 7.59(1H,dd,J=8.8, 2.0 Hz), 7.75(1H,dd,J=8.8,2.0 Hz), 7.90–7.94(3H,m), 8.30 (1H,s).

MS (FAB) m/z: 598 [(M+H)$^+$, Cl$^{35}$], 600 [(M+H)$^+$, Cl$^{37}$].

Referential Example 147

(3RS)-3-Amino-1-tert-butoxycarbonylpyrrolidine

In methanol (30 ml), 3-aminopyrrolidine (0.54 g) was dissolved under ice cooling, followed by the addition of diisopropylethylamine (720 μl) and 2-(tert-butoxycarbonyloxyimino)-2-phenylacetonitrile (0.84 g). The resulting mixture was gradually heated to room temperature and stirred for 11 hours. The residue obtained by distilling off the solvent under reduced pressure was purified by chromatography on a silica gel column (dichloromethane~5% methanol-dichloromethane), whereby the title compound (0.59 g, 94%) was obtained.

$^1$H-NMR (CDCl$_3$) δ: 1.45(9H,s), 2.00–2.30(2H,m), 3.10–4.00(5H,m).

Referential Example 148

(3RS)-1-tert-Butoxycarbonyl-3-[(6-chloronaphthalen-2-yl)sulfonamido]pyrrolidine

In a similar manner to Referential Example 1 except for the use of (3RS)-3-amino-1-tert-butoxycarbonylpyrrolidine as the raw material, the title compound was obtained.

$^1$H-NMR (CDCl$_3$) δ: 1.37(9H,s), 1.60–2.10(2H,m), 3.00–3.50(4H,m), 3.88(1H,br), 4.96(1H,br), 7.50–7.60(1H, m), 7.80–7.90(4H,m), 8.43(1H,s).

MS (FAB) m/z: 411 [(M+H)$^+$, Cl$^{35}$], 413 [(M+H)$^+$, Cl$^{37}$].

Referential Example 149

(3RS)-1-tert-Butoxycarbonyl-3-[4-(4-pyridyl)benzamido]pyrrolidine

In a similar manner to Referential Example 12 except for the use of (3RS)-3-amino-1-tert-butoxycarbonylpyrrolidine and 4-(4-pyridyl)benzoic acid as the raw materials, the title compound was obtained.

$^1$H-NMR (CDCl$_3$) δ: 1.48(9H,s), 1.90–2.10(1H,m) , 2.20–2.30(1H,m), 3.30–3.40(1H,m), 3.40–3.60(2H,m), 3.70–3.80(1H,m), 4.65–4.75(1H,m), 6.25–6.35(1H,m), 7.52 (2H,d,J=5.9 Hz), 7.71(2H,d,J=8.3 Hz), 7.88(2H,d,J=8.3 Hz), 8.70(2H,d,J=5.4 Hz).

MS (FAB) m/z: 368 (M+H)$^+$.

Referential Example 150

6-Chloro-N-methoxy-N-methylnicotinamide

Under ice cooling, 6-chloronicotinic acid (5.00 g) was suspended in dichloromethane (150 ml), followed by the addition of a catalytic amount of N,N-dimethylformamide and oxalyl chloride (5.30 ml). The resulting mixture was stirred at room temperature for 23 hours. The residue obtained by concentrating the reaction mixture was dissolved in dichloromethane (100 ml), followed by the addition of N,O-dimethylhydroxylamine hydrochloride (6.18 g) and triethylamine (13.3 ml) under ice cooling. After stirring at room temperature for 6 hours, the reaction mixture was diluted with dichloromethane (150 ml), washed with a saturated aqueous solution of sodium bicarbonate, water and saturated saline and then dried over anhydrous magnesium sulfate. The residue obtained by distilling off the solvent under reduced pressure was purified by chromatography on a silica gel column (hexane:ethyl acetate=2:1), whereby the title compound (6.08 g, 96%) was obtained.

$^1$H-NMR (CDCl$_3$) δ: 3.39(3H,s), 3.56(3H,s), 7.39(1H,d, J=8.3 Hz), 8.03(1H,dd,J=8.3,2.4 Hz), 8.78(1H,d,J=2.4 Hz).

Referential Example 151

6-Chloronicotinaldehyde

In tetrahydrofuran (8 ml), 6-chloro-N-methoxy-N-methylnicotinamide (500 mg) was dissolved, followed by the dropwise addition of diisobutylaluminum hydride (a 0.95M hexane solution, 2.88 ml) at −78° C. in an argon gas atmosphere. The resulting mixture was stirred for 3 hours and then, at room temperature, for 2 hours. After the reaction mixture was cooled to −20° C., saturated saline (2 ml) was added thereto, followed by stirring for 30 minutes. The insoluble matter was filtered off. The residue was washed with ethyl acetate. The filtrate and the washing were combined together. The mixture was washed with saturated saline and dried over anhydrous sodium sulfate. The solvent was then distilled off under reduced pressure, whereby the title compound (346 mg, 98%) was obtained as a crude product. The product was provided for the subsequent reaction without purification.

$^1$H-NMR (CDCl$_3$) δ: 7.52(1H,d,J=8.3 Hz), 8.14(1H,dd, J=8.3,2.2 Hz), 8.87(1H,d,J=2.2 Hz), 10.10(1H,s).

Referential Example 152

1-tert-Butoxycarbonyl-4-methanesulfonylpiperazine

In dichloromethane (40 ml), N-tert-butoxycarbonylpiperazine (2.00 g) was dissolved, followed by the addition of triethylamine (1.78 ml). To the resulting solution, methanesulfonyl chloride (0.91 ml) was added dropwise under ice cooling. After stirring for one hour under ice cooling, the reaction mixture was diluted with dichloromethane (20 ml), washed with a 5% aqueous citric acid solution, water and saturated saline and dried over anhydrous magnesium sulfate. The residue obtained by distilling off the solvent under reduced pressure was recrystallized from a mixed solvent of ethyl acetate and hexane, whereby the title compound (2.58 g, 91%) was obtained.

$^1$H-NMR (CDCl$_3$) δ: 1.47(9H,s), 2.79(3H,s), 3.19(4H,t, J=5.1 Hz), 3.55(4H,t,J=5.1 Hz).

Referential Example 153

1-tert-Butoxycarbonyl-4-[[(2RS)-2-(6-chloropyridin-3-yl)-2-hydroxyethyl]sulfonyl]piperazine In tetrahydrofuran (8 ml), 1-tert-butoxycarbonyl-4-methanesulfonylpiperazine (838 mg) was dissolved, followed by the addition of tert-butyl lithium (a 1.7M pentane solution, 1.72 ml) at −78° C. in an argon gas atmosphere. The resulting mixture was stirred for 2 hours. After the dropwise addition of a solution of 6-chloronicotinaldehyde (346 mg) in tetrahydrofuran (tetrahydrofuran: 4 ml) and stirring at −78° C. for 3 hours, the reaction mixture was added with isopropanol (1 ml). The resulting mixture was heated to room temperature and diluted with ethyl acetate. The diluted solution was washed with water and saturated saline and dried over anhydrous sodium sulfate. The residue obtained by distilling off the solvent under reduced pressure was recrystallized from ethyl acetate, whereby the title compound (532 mg, 54%) was obtained.

$^1$H-NMR (CDCl$_3$) δ: 1.46(9H,s), 3.11(1H,dd,J=14.1,2.2 Hz), 3.21(1H,dd,J=14.1,9.8 Hz), 3.23–3.33(4H,m), 3.52–3.57(4H,m), 3.70(1H,br s), 5.37(1H,br), 7.36(1H,d,J= 8.3 Hz), 7.72(1H,dd,J=8.3,2.4 Hz), 8.41(1H,d,J=2.4 Hz).

MS (FAB) m/z: 405 (M+H)$^+$.

Referential Example 154

1-tert-Butoxycarbonyl-4-[[(E)-2-(6-chloropyridin-3-yl)ethyl]sulfonyl]piperazine

In dichloromethane (10 ml), 1-tert-butoxycarbonyl-4-[[(2RS)-2-(6-chloropyridin-3-yl)-2-hydroxyethyl]sulfonyl] piperazine (465 mg) was dissolved, followed by the addition of N-methylmorpholine (0.152 ml) and N,N-dimethyl-4-aminopyridine (14.1 mg). Under an argon atmosphere, p-toluenesulfonyl chloride (263 mg) was added under ice cooling. After stirring at room temperature for 2 hours, N,N-dimethyl-4-aminopyridine (141 mg) was added further and the resulting mixture was stirred at room temperature for 3 hours. After dilution with dichloromethane (20 ml), the reaction mixture was washed with a saturated aqueous solution of sodium bicarbonate, water and saturated saline and then dried over anhydrous sodium sulfate. The residue obtained by distilling off the solvent under reduced pressure was purified by chromatography on a silica gel column (dichloromethane:methanol=100:1), whereby the title compound (414 mg, 93%) was obtained.

$^1$H-NMR (CDCl$_3$) δ: 1.45(9H,s), 3.19(4H,br), 3.55(4H, br), 6.73(1H,d,J=15.6 Hz), 7.40(1H,d,J=8.3 Hz), 7.43(1H, d,J=15.6 Hz), 7.76(1H,dd,J=8.3,2.5 Hz), 8.50(1H,d,J=2.5 Hz).

Elementary analysis for C$_{16}$H$_{22}$ClN$_3$O$_3$S

Calculated: C, 49.54; H, 5.72; N, 10.83; Cl, 9.14; S,8.27.
Found: C, 49.54; H, 5.73; N, 10.63; Cl, 9.44; S,8.15.

Referential Example 155

1-(4-Bromo-2-methylbenzoyl)-4-[(6-chloronaphthalen-2-yl)sulfonyl]piperazine

In a similar manner to Referential Example 12 except for the use of 4-bromo-2-methylbenzoic acid and 1-[(6-chloronaphthalen-2-yl)sulfonyl]piperazine hydrochloride as the raw materials, the reaction was conducted, whereby the title compound was obtained.

$^1$H-NMR (CDCl$_3$) δ: 2.13(3H,s), 2.80–4.10(8H,m), 6.89 (1H,d,J=8.3 Hz), 7.30(1H,dd,J=8.3,2.0 Hz), 7.35(1H,d,J= 2.0 Hz), 7.60(1H,dd,J=8.8,2.0 Hz), 7.74(1H,dd,J=8.8,2.0 Hz), 7.90–7.95(3H,m), 8.30(1H,br s).

MS (FAB) m/z: 507 [(M+H)$^+$, Br$^{79}$], 509 [(M+H)$^+$, Br$^{81}$].

Referential Example 156

3-Methyl-4-(4-pyridyl)benzoic acid hydrochloride

In a similar manner to Referential Example 6 except for the use of 4-bromo-3-methylbenzoic acid as the raw material, the reaction was conducted, whereby the title compound was obtained.

$^1$H-NMR (DMSO-d$_6$) δ: 2.36(3H,s), 7.50(1H,d,J=7.8 Hz), 7.92(1H,d,J=7.8 Hz), 7.97(1H,s), 8.08(2H,d,J=6.4 Hz), 8.99(2H,d,J=6.4 Hz).

MS (FAB) m/z: 214 (M+H)$^+$.

Referential Example 157

4-(2-Methyl-4-pyridyl)benzoic acid hydrochloride

In a similar manner to Referential Example 2 except for the use of 4-bromo-2-methylpyridine as the raw material, the reaction was conducted, whereby the title compound was obtained.

$^1$H-NMR (DMSO-d$_6$) δ: 2.81(3H,s), 8.10–8.16(4H,m), 8.23(1H,dd,J=6.4,1.5 Hz), 8.36(1H,d,J=1.5 Hz), 8.85(1H,d, J=6.4 Hz).

MS (FAB) m/z: 214 (M+H)$^+$.

Referential Example 158

1,4-Dibenzyl-2-methoxycarbonylmethylpiperazine

In toluene (250 ml), N,N'-dibenzylethylenediamine (12 ml) and triethylamine (12 ml) were dissolved, followed by the dropwise addition of methyl 3-bromocrotonate (7.0 ml) under ice cooling. The resulting mixture was stirred at room temperature for 24 hours. After the addition of triethylamine (2.0 ml), the resulting mixture was stirred at room temperature for 71 hours. The insoluble matter was filtered off and the filtrate was distilled under reduced pressure. The residue was added with 10% hydrochloric acid (300 ml) and crystals so precipitated were removed by filtration. Ethyl acetate was added to the filtrate. Potassium carbonate was added to the water layer so separated to make it alkaline. Ethyl acetate was added to the resulting mixture. The organic layer so separated was washed with saturated saline and dried over anhydrous potassium carbonate. The solvent was then distilled off under reduced pressure. The residue was purified by chromatography on a silica gel column (hexane:ethyl acetate=4:1), whereby the title compound (1.07 g, 62%) was obtained.

$^1$H-NMR (CDCl$_3$) δ: 2.30–2.70(8H,m), 3.11(1H,br s), 3.40–3.80(4H,m), 3.60(3H,s), 7.20–7.40(10H,m).

MS (FAB) m/z: 339 (M+H)$^+$.

Referential Example 159

1-[(6-Chloronaphthalen-2-yl)sulfonyl]-3-methoxycarbonylmethylpiperazine

In acetic acid (40 ml), 1,4-dibenzyl-2-methoxycarbonylmethylpiperazine (2.04 g) was dissolved, followed by the addition of 10% palladium carbon (water content: about 50%, 2.00 g). The resulting mixture was subjected to catalytic reduction at room temperature for 4 hours under 4 atmospheric pressure. After removal of the catalyst by filtration, the residue obtained by distilling the filtrate under reduced pressure was added with dichloromethane and a saturated aqueous solution of sodium bicarbonate. The insoluble matter so precipitated was filtered off. The organic layer so separated was washed with saturated saline and dried over anhydrous sodium sulfate. The solvent was then distilled off under reduced pressure. The residue was dissolved in dichloromethane (30 ml), followed by the addition of 6-chloro-2-naphthylsulfonyl chloride (782 mg). The resulting mixture was stirred at 0° C. for 2 hours. To the reaction mixture, triethylamine (410 µl) was added, followed by stirring at 0° C. for further three hours. The residue obtained by distilling off the solvent under reduced pressure was purified by chromatography on a silica gel column (dichloromethane~3% methanol-dichloromethane), whereby the title compound (759 mg, 33%) was obtained.

$^1$H-NMR (CDCl$_3$) δ: 1.71(1H,br s), 2.15–2.55(4H,m), 2.90–3.05(2H,m), 3.15–3.25(1H,m), 3.60–3.70(5H,m), 7.55–7.60(1H,m), 7.75–7.80(1H,m), 7.85–7.95(3H,m), 8.30 (1H,s).

MS (FAB) m/z: 383 [(M+H)$^+$, Cl$^{35}$], 385 [(M+H)$^+$, Cl$^{37}$].

Referential Example 160

4-tert-Butoxycarbonyl-1-[(3-chloro-1-propyl)sulfonyl]piperazine

Under an argon gas atmosphere, 1-tert-butoxycarbonylpiperazine (3.00 g) and triethylamine (2.24 ml) were dissolved in dichloromethane (40 ml) under ice cooling, followed by the addition of 3-chloro-1-propanesulfonic acid chloride (1.96 g). The resulting mixture was stirred for 20 minutes under ice cooling and then, at room temperature for 10 minutes. The reaction mixture was diluted with dichloromethane, washed with water and saturated saline and then dried over anhydrous sodium sulfate. The solvent was then distilled off under reduced pressure. The residue was recrystallized from a mixed solvent of ethyl acetate and hexane, whereby the title compound (4.36 g, 83%) was obtained.

$^1$H-NMR (CDCl$_3$) δ: 1.41(9H,s), 2.27–2.33(2H,m), 3.08 (2H,t,J=7.3 Hz), 3.26(4H,t,J=4.9 Hz), 3.53(4H,t,J=4.9 Hz), 3.69(2H,t,J=6.1 Hz).

MS (FAB) m/z: 327 (M+H)$^+$

Elementary analysis for C$_{12}$H$_{23}$ClN$_2$O$_4$S

Calculated: C, 44.10; H, 7.09, Cl, 10.85; N, 8.57; S, 9.81.

Found: C, 44.18; H, 7.11; Cl, 10.69; N, 8.23; S, 9.76.

Referential Example 161

4-tert-Butoxycarbonyl-1-[(3-hydroxy-1-propyl)sulfonyl]piperazine

In N,N-dimethylformamide (10 ml), 4-tert-butoxycarbonyl-1-[(3-chloro-1-propyl)sulfonyl]piperazine (1.18 g) was dissolved, followed by the addition of potassium acetate (1.06 g). After stirring at room temperature for 2 hours, the reaction mixture was stirred under heat at 100° C. for 3 hours. The reaction mixture was diluted with ethyl acetate, followed by the addition of water and a saturated aqueous solution of sodium bicarbonate. After stirring, the organic layer so separated was washed with a 5% aqueous citric acid solution, water and saturated saline. After drying over anhydrous sodium sulfate, the residue obtained by distilling off the solvent under reduced pressure was dissolved in tetrahydrofuran (20 ml). To the resulting solution, water and lithium hydroxide monohydrate (221 mg) were added, followed by stirring at room temperature for 18 hours. Ethyl acetate and saturated saline were added to the reaction mixture to separated an organic layer. From the water layer, another organic layer was extracted with ethyl acetate. The organic layers were combined together, washed with saturated saline and dried over anhydrous sodium sulfate. The solvent was then distilled off under reduced pressure. The residue was recrystallized from a mixed solvent of ethyl acetate an hexane, whereby the title compound (944 mg, 84%) was obtained.

$^1$H-NMR (CDCl$_3$) δ: 1.47(9H,s), 2.04–2.11(2H,m), 3.06 (2H,t,J=7.6 Hz), 3.25(4H,t,J=4.9 Hz), 3.53(4H,t,J=4.9 Hz), 3.80(2H,q,J=5.4 Hz).

MS (FAB) m/z: 309 (M+H)$^+$.

Elementary analysis for C$_{12}$H$_{24}$N$_2$O$_5$S

Calculated: C, 46.74; H, 7.84; N, 9.08; S, 10.40.

Found: C, 46.80; H, 7.92; N, 9.05; S, 10.59.

Referential Example 162

4-tert-Butoxycarbonyl-1-[(3-methoxymethyloxy-1-propyl)sulfonyl]piperazine

In dichloromethane (60 ml), 4-tert-butoxycarbonyl-1-[(3-hydroxy-1-propyl)sulfonyl]piperazine (3.00 g) was dissolved. To the resulting solution, diisopropylethylamine (2.72 ml) was added, followed by the addition of methoxymethyl chloride (1.11 ml) under ice cooling. After stirring at room temperature for 20 hours, the reaction mixture was diluted with dichloromethane, washed with water, a 5% aqueous citric acid solution and saturated saline and then dried over anhydrous sodium sulfate. The solvent was then distilled off under reduced pressure. The residue was purified by chromatography on a silica gel column (hexane:ethyl acetate=2:1), whereby the title compound (3.32 g, 97%) was obtained.

$^1$H-NMR (CDCl$_3$) δ: 1.47(9H,s), 2.06–2.13(2H,m), 3.03 (2H,m), 3.25(4H,t,J=4.9 Hz), 3.36(3H,s), 3.52(4H,t,J=4.9 Hz), 3.63(2H,t,J=5.4 Hz), 4.61(2H,s).

MS (FAB) m/z: 353 (M+H)$^+$.

Elementary analysis for C$_{14}$H$_{28}$N$_2$O$_6$S

Calculated: C, 47.71; H, 8.01; N, 7.95; S, 9.10.

Found: C, 47.77; H, 8.18; N, 7.97; S, 9.16.

Referential Example 163

4-tert-Butoxycarbonyl-1-[(E)-4-chloro-β-[2-(methoxymethyloxy)ethyl]-β-styrylsulfonyl]piperazine and 4-tert-butoxycarbonyl-1-[(Z)-4-chloro-β-[2-(methoxymethyloxy)ethyl]-β-styrylsulfonyl]piperazine Under an argon gas atmosphere, 4-tert-butoxycarbonyl-1-[3-methoxymethyloxy-1-propyl)sulfonyl]piperazine (800 mg) was dissolved in tetrahydrofuran (10 ml), followed by the dropwise addition of tert-butyl lithium (a 1.7M hexane solution, 1.47 ml) at −78° C. The resulting mixture was stirred at −78° C. for one hour. After the addition of trimethylsilyl chloride (0.317 ml) and stirring at −78° C. for 90 minutes, tert-butyl lithium (a 1.7M hexane solution, 1.47 ml) was added dropwise to the reaction mixture and stirring was effected at −78° C. for 90 minutes. At −78° C., a solution of p-chlorobenzaldehyde (352 mg) in tetrahydrofuran (tetrahydrofuran: 8 ml) was added dropwise to the reaction mixture. After stirring for 2 hours, the temperature of the reaction mixture was allowed to rise back to room temperature over 15 hours, at which temperature it was stirred for 6 hours. Under ice cooling, a 5% citric acid solution (20 ml) and ethyl acetate (150 ml) were added to the reaction mixture. The organic layer so separated was washed with water and saturated saline and then dried over anhydrous magnesium sulfate. The residue obtained by distilling off the solvent under reduced pressure was purified by chromatography on a silica gel column (hexane:ethyl acetate=3:1~2:1), whereby the title compound was obtained as an E-form (307 mg, 28%) and Z-form (751 mg, 70%). E form:

$^1$H-NMR (CDCl$_3$) δ: 1.42(9H,s), 2.87(2H, t,J=7.3 Hz), 3.21–3.28(4H,m), 3.35(3H,s), 3.46–3.56(4H,m), 3.80(2H,t, J=7.3 Hz), 4.60(2H,s), 7.40(2H,d,J=8.5 Hz), 7.46(2H,d,J= 8.5 Hz), 7.54(1H,s). Z-form:

$^1$H-NMR (CDCl$_3$) δ: 1.43(9H,s), 2.77(2H,dt,J=6.4,1.0 Hz), 2.91–2.98(4H,m), 3.19–3.25(4H,m), 3.38(3H,s), 3.82

(2H,t,J=6.4 Hz), 4.66(2H,s), 7.07(1H,s), 7.32(2H,d,J=8.6 Hz), 7.35(2H,d,J=8.6 Hz).

Example 1

1-[(6-Chloronaphthalen-2-yl)sulfonyl]-4-[4-(pyridin-4-yl)benzoyl]piperazine hydrochloride At room temperature, 1-[4-(4-pyridyl)benzoyl]piperazine ditrifluoroacetate (1.19 g) was suspended in dichloromethane (100 ml), followed by the addition of diisopropylethylamine (1.68 ml) and 6-chloro-2-naphthylsulfonyl chloride (691 mg). After stirring at room temperature for 2 hours, the reaction mixture was purified by chromatography on a silica gel column (2% methanol-dichloromethane). To the resulting fraction, ethanolic 1N hydrochloric acid was added to make it weakly acidic. The solvent was then distilled off. The resulting colorless solid was washed with tetrahydrofuran, whereby the title compound (1.05 g, 81%) was obtained as a colorless solid.

$^1$H-NMR (DMSO-$d_6$) δ: 2.95–3.25(4H,m), 3.43(2H,br s), 3.60(2H,br s), 7.56(2H,d,J=8.3 Hz), 7.74(1H,dd,J=8.8,2.5 Hz), 7.83(1H,dd,J=8.8,2.0 Hz), 8.01(2H,d,J=8.3 Hz), 8.19 (1H,d,J=8.8 Hz), 8.25–8.40(4H,m), 8.51(1H,s), 8.94(2H,d, J=6.8 Hz).

MS (FAB) m/z: 492 [(M+H)$^+$, Cl$^{35}$], 494 [(M+H)$^+$, Cl$^{37}$].
Elementary analysis for $C_{26}H_{22}N_3O_3ClS \cdot HCl \cdot 0.5H_2O$
Calculated: C, 58.10; H, 4.50; N, 7.82; Cl, 13.19; S, 5.97.
Found: C, 58.12; H, 4.67; N, 7.66; Cl, 13.12; S, 6.10.

Example 2

4-[(6-Chloronaphthalen-2-yl)sulfonyl]-2-ethoxycarbonyl-1-[4-(pyridin-4-yl)benzoyl]piperazine hydrochloride In dichloromethane (30 ml), 4-tert-butoxycarbonyl-2-ethoxycarbonyl-1-[4-(4-pyridyl)benzoyl]piperazine (514 mg) was dissolved, followed by the addition of trifluoroacetic acid (30 ml) under ice cooling. After stirring at room temperature for 45 minutes, the residue obtained by distilling off the solvent was suspended in dichloromethane (100 ml) under ice cooling, followed by the addition of diisopropylethylamine (1.02 ml) and 6-chloro-2-naphthylsulfonyl chloride (366 mg). After stirring at room temperature for one hour, the reaction mixture was purified as was by chromatography on a silica gel column (1% methanol-dichloromethane). To the resulting fraction, ethanolic 1N hydrochloric acid was added to make it weakly acidic. The solvent was then distilled off. The resulting colorless solid was washed with ethanol, whereby the title compound (308 mg, 43%) was obtained as a colorless solid.

$^1$H-NMR (DMSO-$d_6$) δ: 1.15–1.30(3H,m), 2.60–5.40 (9H,m), 7.50(2/3H,d,J=8.3 Hz), 7.57(4/3H,d,J=7.8 Hz), 7.74.(1H,dd,J=9.0,1.7 Hz), 7.83(1H,d,J=8.8 Hz), 8.00(2/3H, d,J=7.8 Hz), 8.04(4/3H,d,J=8.3 Hz), 8.19(1H,d,J=8.8 Hz), 8.25–8.35(4H,m), 8.55(1H,s), 8.92(2H,d,J=4.9 Hz).

MS (FAB) m/z: 564 [(M+H)$^+$, Cl$^{35}$], 566 [(M+H)$^+$, Cl$^{37}$].
Elementary analysis for $C_{29}H_{26}N_3O_5ClS \cdot HCl \cdot 0.5H_2O$
Calculated: C, 57.15; H, 4.63; N, 6.89; Cl, 11.63; S, 5.26.
Found: C, 56.95; H, 4.68; N, 6.70; Cl, 11.36; S, 5.30.

Example 3

4-[(6-Chloronaphthalen-2-yl)sulfonyl]-1-[4-(pyridin-4-yl)benzoyl]piperazine-2-carboxylic acid hydrochloride In a mixed solvent of ethanol (1 ml), tetrahydrofuran (1 ml) and water (1 ml), 4-[(6-chloronaphthalen-2-yl) sulfonyl]-2-ethoxycarbonyl-1-[4-(pyridin-4-yl)benzoyl] piperazine hydrochloride (152 mg) obtained in Example 2 was dissolved under ice cooling, followed by the dropwise addition of a 1N aqueous solution of sodium hydroxide. The reaction mixture was stirred at room temperature for 90 minutes. After concentration under reduced pressure, 1N hydrochloric acid was added to the reaction mixture to make it weakly acidic. The colorless solid so precipitated was collected by filtration, followed by drying, whereby the title compound (62 mg, 42%) was obtained as a colorless solid.

$^1$H-NMR (DMSO-$d_6$) δ: 2.65–5.30(7H,m), 7.49(4/5H,d, J=7.7 Hz), 7.56(6/5H,d,J=8.3 Hz), 7.74(1H,dd,J=8.8,2.0 Hz), 7.82(1H,d,J=8.3 Hz), 7.95–8.05(2H,m), 8.19(1H,d,J= 8.3 Hz), 8.20–8.35(4H,m), 8.53(1H,s), 8.92(2H,d,J=5.4 Hz).

MS (FAB) m/z: 536 [(M+H)$^+$, Cl$^{35}$], 538 [(M+H)$^+$, Cl$^{37}$].
Elementary analysis for $C_{27}H_{22}N_3O_5ClS \cdot 0.9HCl \cdot 1.2H_2O$
Calculated: C, 54.92; H, 4.32; N, 7.12; Cl, 11.41; S, 5.43.
Found: C, 54.94; H, 4.42; N, 6.83; Cl, 11.31; S, 5.33.

Example 4

1-[(6-Chloronaphthalen-2-yl)sulfonyl]-4-[4-(pyridin-4-yl)nicotinyl]piperazine hydrochloride In dichloromethane (10 ml), 6-(4-pyridyl)nicotinic acid hydrochloride (96 mg) and 1-[(6-chloronaphthalen-2-yl) sulfonyl]piperazine trifluoroacetate (150 mg) were suspended, followed by the addition of 1-hydroxybenzotriazole (48 mg) and N-methylmorpholine (155 μl). After the addition of 1-(3-dimethylaminopropyl)-3-ethylcarbodiimide hydrochloride (102 mg) under ice cooling, the resulting mixture was stirred at room temperature for 16 hours. Owing to the slow reaction, N,N-dimethylformamide (10 ml) was added to the reaction mixture and the resulting mixture was stirred for 3 days. After completion of the reaction, the solvent was distilled off. The residue was purified by chromatography on a silica gel column (1% methanol-di-chloromethane). The solvent was then distilled off. To the residue, tetrahydrofuran and ethanolic 1N hydrochloric acid were added and the solid so precipitated was collected by filtration and dried, whereby the title compound (105 mg, 55%) was obtained as a colorless solid.

$^1$H-NMR (DMSO-$d_6$) δ: 3.00–3.25(4H,m), 3.46(2H,br s), 3.76(2H,br s), 7.74(1H,dd,J=8.5,1.7 Hz), 7.83(1H,d,J=8.8 Hz), 8.07(1H,dd,J=7.8,1.5 Hz), 8.19(1H,d,J=8.8 Hz), 8.28 (1H,s), 8.29(1H,d,J=8.8 Hz), 8.42(1H,d,J=8.3 Hz), 8.51(1H, s), 8.65(2H,d,J=6.4 Hz), 8.80(1H,m), 9.01(2H,d,J=5.9 Hz).

MS (FAB) m/z: 493 [(M+H)$^+$, Cl$^{35}$], 495 [(M+H)$^+$, Cl$^{37}$].
Elementary analysis for $C_{25}H_{21}N_4O_3ClS \cdot HCl \cdot 1H_2O$
Calculated: C, 54.85; H, 4.42; N, 10.23; Cl, 12.95; S, 5.86.
Found: C, 54.57; H, 4.51; N, 10.06; Cl, 13.08; S, 5.87.

Example 5

1-[(6-Chloronaphthalen-2-yl)sulfonyl]-4-[4-(pyridin-3-yl)benzoyl]piperazine hydrochloride In a similar manner to Example 4 except for the use of 4-(3-pyridyl)benzoic acid hydrochloride and 1-[(6-chloronaphthalen-2-yl)sulfonyl]piperazine trifluoroacetate as the raw materials, the reaction was conducted, whereby the title compound was obtained as a colorless solid.

$^1$H-NMR (DMSO-$d_6$) δ: 3.00–3.25(4H,m), 3.47(2H,br s), 3.73(2H,br s), 7.51(2H,d,J=8.3 Hz), 7.73(1H,dd,J=8.8,2.0

Hz), 7.8–7.9(3H,m), 7.92(1H,dd,J=7.8,5.4 Hz), 8.19(1H,d, J=8.8 Hz), 8.25–8.30(2H,m), 8.50(1H,s), 8.55–8.65(1H,m), 8.75–8.85(1H,m), 9.14(1H,d,J=2.0 Hz).

MS (FAB) m/z: 492 [(M+H)$^+$, Cl$^{35}$], 494 [(M+H)$^+$, Cl$^{37}$].
Elementary analysis for $C_{26}H_{22}N_3O_3Cl S.0.85HCl.H_2O$
Calculated: C, 57.72; H, 4.63; N, 7.77; Cl, 12.12; S, 5.93.
Found: C, 57.44; H, 4.62; N, 7.68; Cl, 11.99; S, 5.83.

Example 6

4-[4-[[4-[(6-Chloronaphthalen-2-yl)sulfonyl]piperazin-1-yl]carbonyl]phenyl]pyridine N-oxide In dichloromethane (10 ml), 1-[(6-chloronaphthalen-2-yl)sulfonyl]-4-[4-(pyridin-4-yl)benzoyl]piperazine (300 mg) obtained in Example 1 was dissolved, followed by the addition of 3-chloroperbenzoic acid (382 g) at −20° C. The resulting mixture was stirred at −20° C. for 21 hours. An aqueous solution of sodium sulfite was added to decompose an excess peroxide. Dichloromethane and a saturated aqueous solution of sodium bicarbonate were added to separate an organic layer. After drying the organic layer over anhydrous magnesium sulfate, the residue obtained by distilling off the solvent was purified by chromatography on a silica gel column (2–5% methanol-dichloromethane). After the solvent was distilled off, ether was added to the residue to solidify it, followed by collection through filtration, whereby the title compound (200 mg, 63%) was obtained as a colorless solid.

$^1$H-NMR (CDCl$_3$) δ: 2.90–3.40(4H,m), 3.40–4.20(4H, m), 7.43(2H,d,J=8.3 Hz), 7.47(2H,d,J=7.3 Hz), 7.55–7.65 (3H,m), 7.76(1H,dd,J=8.8,1.5 Hz), 7.90–8.00(3H,m), 8.26 (2H,d,J=7.3 Hz), 8.31(1H,s).

MS (FAB) m/z: 508 [(M+H)$^+$, Cl$^{35}$], 510 [(M+H)$^+$, Cl$^{37}$].
Elementary analysis for $C_{26}H_{22}N_3O_4Cl S.0.8H_2O$
Calculated: C, 59.78; H, 4.55; N, 8.04; Cl, 6.79; S, 6.14.
Found: C, 59.82; H, 4.45; N, 7.94; Cl, 6.85; S, 6.29.

Example 7

1-[4-(2-Aminopyridin-5-yl)benzoyl]-4-[(6-chloronaphthalen-2-yl)sulfonyl]piperazine hydrochloride In a mixed solvent of dichloromethane (1 ml) and ethanol (1 ml), 1-[4-[2-tert-butoxycarbonylamino)pyridin-5-yl)benzoyl]-4-[(6-chloronaphthalen-2-yl)sulfonyl]piperazine (128 mg) was dissolved, followed by the addition of a saturated ethanol hydrochloride solution (10 ml) under ice cooling. After stirring at room temperature for 1 minute, the solvent was distilled off. Isopropanol was added to the residue for crystallization. The crystals so obtained were collected by filtration and dried, whereby the title compound (88 mg, 68%) was obtained as a colorless solid.

$^1$H-NMR (DMSO-d$_6$) δ: 3.00–3.20(4H,m), 3.30–3.90 (4H,m), 7.05(1/2H,d,J=8.8 Hz), 7.06(1/2H,d,J=8.8 Hz), 7.43 (2H,d,J=8.3 Hz), 7.67(2H,d,J=8.3 Hz), 7.73(1H,d,J=8.3 Hz), 7.82(1H,d,J=8.8 Hz), 7.90–8.10(2H,br), 8.18(1H,d,J=8.3 Hz), 8.25–8.35(4H,m), 8.50(1H,s).

MS (FAB) m/z: 507 [(M+H)$^+$, Cl$^{35}$], 509 [(M+H)$^+$, Cl$^{37}$].
Elementary analysis for $C_{26}H_{23}ClN_4O_3S.HCl.1.2H_2O.0.8iPrOH$
Calculated: C, 55.56; H, 5.52; N, 9.13; Cl, 11.55; S, 5.22.
Found: C, 55.40; H, 5.24; N, 8.85; Cl, 11.79; S, 5.50.

Example 8

1-[4-(4-Aminophenyl)benzoyl]-4-[(6-chloronaphthalen-2-yl)sulfonyl]piperazine hydrochloride In a similar manner to Example 7 except for the use of 1-[4-[4-(tert-butoxycarbonylamino)phenyl]benzoyl]-4-[(6-chloronaphthalen-2-yl)sulfonyl]piperazine as the raw material, the reaction was conducted, whereby the title compound was obtained as a colorless solid.

$^1$H-NMR (DMSO-d$_6$) δ: 2.90–3.20(4H,m), 3.25–3.80 (4H,m), 6.68(2H,d,J=8.3 Hz), 7.32(2H,d,J=8.3 Hz), 7.39 (2H,d,J=8.3 Hz), 7.54(2H,d,J=8.3 Hz), 7.73(1H,dd,J=8.8, 2.0 Hz), 7.82(1H,dd,J=8.8,2.0 Hz), 8.18(1H,dd,J=8.8 Hz), 8,25–8.40(2H,m), 8.50(1H,br s).

MS (FAB) m/z: 506 [(M+H)$^+$, Cl$^{35}$], 508 [(M+H)$^+$, Cl$^{37}$].
Elementary analysis for $C_{27}H_{24}ClN_3O_3S.0.2HCl$
Calculated: C, 63.18; H, 4.75; N, 8.19; Cl, 8.29; S, 6.25.
Found: C, 62.93; H, 4.93; N, 7.91; Cl, 7.99; S, 6.36.

Example 9

1-[4-(2-Aminothiazol-4-yl)benzoyl]-4-[(6-chloronaphthalen-2-yl)sulfonyl]piperazine hydrochloride In a similar manner to Example 4 except for the use of 4-(2-aminothiazol-4-yl)benzoic acid and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 2.90–3.20(4H,m), 3.30–3.90 (4H,m), 7.26(1H,s), 7.41(2H,d,J=8.3 Hz), 7.73(1H,dd,J=8.8, 2.0 Hz), 7.79(2H,d,J=8.3 Hz), 7.82(1H,dd,J=8.8,2.0 Hz), 8.18(1H,d,J=8.8 Hz), 8.25–8.30(2H,m), 8.50(1H,br s).

MS (FAB) m/z: 513 [(M+H)$^+$, Cl$^{35}$], 515 [(M+H)$^+$, Cl$^{37}$].
Elementary analysis for $C_{24}H_{21}N_4O_3ClS_2.HCl.0.3H_2O$
Calculated: C, 51.95; H, 4.11; N, 10.10; Cl, 12.78; S, 11.56.
Found: C, 51.99; H, 4.19; N, 10.03; Cl, 12.61; S, 11.45.

Example 10

1-[(6-Chloronaphthalen-2-yl)sulfonyl]-4-[4-[imidazol-4(5)-yl]benzoyl]piperazine hydrochloride In dichloromethane (5 ml), 1-[(6-chloronaphthalen-2-yl)sulfonyl]-4-[4-[1-triphenylmethylimidazol-4(5)-yl]benzoyl]piperazine (303 mg) was dissolved, followed by the addition of a saturated ethanol hydrochloride solution (30 ml) under ice cooling. After stirring at room temperature for 3 hours, the solvent was distilled off. Ether was added to the residue for crystallization and the resulting crystals were collected by filtration, whereby the title compound (307 mg, 76%) was obtained as a colorless solid.

$^1$H-NMR (DMSO-d$_6$) δ: 2.90–3.20(4H,m), 3.30–3.90 (4H,m), 7.47(2H,d,J=8.3 Hz), 7.74(1H,dd,J=8.8,2.0 Hz), 7.82(1H,dd,J=8.8,2.0 Hz), 7.89(2H,d,J=8.3 Hz), 8.19(1H,d, J=8.8 Hz), 8.22(1H,d,J=1.0 Hz), 8.25–8.30(2H,m), 8.50(1H, m), 9.22(1H,d,J=1.0 Hz).

MS (FAB) m/z: 481 [(M+H)$^+$, Cl$^{35}$], 483 [(M+H)$^+$, Cl$^{37}$].
Elementary analysis for $C_{24}H_{21}ClN_4O_3S.HCl.0.4H_2O$
Calculated: C, 54.94; H, 4.38; N, 10.68; Cl, 13.52; S, 6.11.
Found: C, 54.98; H, 4.29; N, 10.62; Cl, 13.56; S, 6.14.

Example 11

1-[4-(2-Aminoimidazol-4-yl)benzoyl]-4-[(6-chloronaphthalen-2-yl)sulfonyl]piperazine hydrochloride In a similar manner to Example 4 except for the use of 4-(2-aminoimidazol-4-yl)benzoic acid hydrochloride and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 2.90–3.20(4H,m), 3.30–3.90 (4H,m), 7.39(2H,d,J=8.3 Hz), 7.47(1H,s), 7.49(2H,br s), 7.67(2H,d,J=8.3 Hz), 7.73(1H,dd,J=8.8,2.5 Hz), 7.82(1H, dd,J=8.8,2.0 Hz), 8.18(1H,d,J=8.8 Hz), 8.25–8.30(2H,m), 8.50(1H,br s).

MS (FAB) m/z: 496 [(M+H)$^+$, Cl$^{35}$], 498 [(M+H)$^+$, Cl$^{37}$].

Elementary analysis for C$_{24}$H$_{22}$N$_5$O$_3$ClS.HCl

Calculated: C, 54.14; H, 4.35; N, 13.15; Cl, 13.32; S, 6.02.

Found: C, 53.94; H, 4.39; N, 12.82; Cl, 13.27; S, 6.07.

Example 12

4-[4-[[4-[(6-Chloronaphthalen-2-yl)sulfonyl] piperazin-1-yl]carbonyl]phenyl]-1-methylpyridinium iodide In a mixed solvent of benzene (10 ml) and methanol (10 ml), 1-[(6-chloronaphthalen-2-yl)sulfonyl]-4-[4-(pyridin-4-yl)benzoyl]piperazine (300 mg) obtained in Example 1 was dissolved at room temperature, followed by the addition of methyl iodide (1 ml). To the resulting mixture, the same amount of methyl iodide was added three times at intervals of 24 hours, followed by heating under reflux for 4 days. The reaction mixture was distilled under reduced pressure and the residue was washed with methanol, collected by filtration and dried, whereby the title compound (229 mg, 58%) was obtained as a yellow solid.

$^1$H-NMR (DMSO-d$_6$) δ: 3.03(2H,br s), 3.13(2H,br s), 3.43(2H,br s), 3.75(2H,br s), 4.34(3H,s), 7.59(2H,d,J=8.8 Hz), 7.74(1H,dd,J=8.8,2.4 Hz), 7.85(1H,dd,J=8.8,2.0 Hz), 8.08(2H,d,J=8.8 Hz), 8.19(1H,d,J=8.8 Hz), 8.25–8.30(2H, m), 8.45–8.55(3H,m), 9.03(2H,d,J=6.8 Hz).

Elementary analysis for C$_{27}$H$_{25}$N$_3$O$_3$ClIS.H$_2$O

Calculated: C, 49.74; H, 4.17; N, 6.45.

Found: C, 49.60; H, 4.09; N, 6.23.

Example 13

3-[4-[[4-[(6-chloronaphthalen-2-yl)sulfonyl] piperazin-1-yl]carbonyl]phenyl]pyridine N-oxide In a similar manner to Example 6 except for the use of 1-[(6-chloronaphthalen-2-yl)sulfonyl]-4-[4-(pyridin-3-yl) benzoyl]piperazine, which had been obtained in Example 6, as the raw material, the reaction was conducted, whereby the title compound was obtained.

$^1$H-NMR (CDCl$_3$) δ: 2.90–3.40(4H,m), 3.40–4.20(4H, m), 7.50–7.60(1H,m), 7.40–7.45(3H,m), 7.54(2H,d,J=8.3 Hz), 7.60(1H,dd,J=8.8,2.0 Hz), 7.76(1H,dd,J=8.8,2.0 Hz), 7.90–8.00(3H,m), 8.22(1H,d,J=5.9 Hz), 8.31(1H,d,J=2.0 Hz), 8.43(1H,br s).

MS (FAB) m/z: 508 [(M+H)$^+$, Cl$^{35}$], 510 [(M+H)$^+$, Cl$^{37}$].

Elementary analysis for C$_{26}$H$_{22}$N$_3$O$_4$ClS.H$_2$O

Calculated: C, 59.37; H, 4.60; N, 7.99; Cl, 6.74; S, 6.10.

Found: C, 59.48; H, 4.69; N, 7.74; Cl, 6.73; S, 6.07.

Example 14

1-[2-Carboxy-4-(pyridin-4-yl)benzoyl]-4-[(6-chloronaphthalen-2-yl)sulfonyl]piperazine In dichloromethane (50 ml), 1-[2-tert-butoxycarbonyl-4-(pyridin-4-yl)benzoyl]-4-[(6-chloronaphthalen-2-yl) sulfonyl]piperazine hydrochloride (250 mg) was dissolved, followed by the dropwise addition of trifluoroacetic acid (50 ml) under ice cooling. After stirring at room temperature for 5 hours, the solvent was distilled off. The residue was dissolved in methanol and the resulting solution was allowed to stand in a refrigerator for one day. The colorless solid so precipitated was collected by filtration and dried, whereby the title compound (550 mg, 28%) was obtained as a colorless solid.

$^1$H-NMR (DMSO-d$_6$) δ: 2.90–3.40(6H,m), 3.65–3.75 (2H,m), 7.41(1H,d,J=7.8 Hz), 7.70–7.75(3H,m), 7.82(1H, dd,J=8.8,2.0 Hz), 8.00(1H,dd,J=7.8,1.5 Hz), 8.15–8.30(4H, m), 8.50(1H,br s), 8.67(2H,d,J=5.9 Hz), 13.29(1H,br s).

MS (FAB) m/z: 536 [(M+H)$^+$, Cl$^{35}$], 538 [(M+H)$^+$, Cl$^{37}$].

Elementary analysis for C$_{27}$H$_{22}$ClN$_3$O$_5$S.0.5H$_2$O

Calculated: C, 59.50; H, 4.25; N, 7.71; Cl, 6.50; S, 5.88.

Found: C, 59.54; H, 4.30; N, 7.37; Cl, 6.35; S, 5.89.

Example 15

1-[(6-Chloronaphthalen-2-yl)sulfonyl]-4-[(5-(pyridin-4-yl)thiophen-2-yl]carbonyl]piperazine hydrochloride In a similar manner to Example 4 except for the use of 5-(pyridin-4-yl)thiophene-2-carboxylic acid hydrochloride obtained in Referential Example 28 and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 3.11(4H,br s), 3.74(4H,br s), 7.52(1H,d,J=3.9 Hz), 7.73(1H,dd,J=8.8,2.5 Hz), 7.83(1H, dd,J=8.8,2.0 Hz), 8.03(1H,d,J=3.9 Hz), 8.10–8.15(2H,m), 8.18(1H,d,J=8.8 Hz), 8.25–8.30(2H,m), 8.51(1H,s), 8.88 (2H,d,J=6.8 Hz).

MS (FAB) m/z: 498 [(M+H)$^+$, Cl$^{35}$], 500 [(M+H)$^+$, Cl$^{37}$].

Elementary analysis for C$_{24}$H$_{20}$ClN$_3$O$_3$S$_2$.HCl.H$_2$O

Calculated: C, 52.17; H, 4.20; N, 7.61; Cl, 12.83; S, 11.61.

Found: C, 52.04; H, 4.22; N, 7.22; Cl, 12.74; S, 11.57.

Example 16

1-[(6-Chloronaphthalen-2-yl)sulfonyl]-4-[[5-(pyridin-4-yl)furan-2-yl]carbonyl]piperazine hydrochloride In a similar manner to Example 4 except for the use of 5-(pyridin-4-yl)furan-2-carboxylic acid hydrochloride obtained in Referential Example 29 and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 3.13(4H,br s), 3.30–4.00(4H,m), 7.21(1H,d,J=3.9 Hz), 7.71(1H,d,J=8.8 Hz), 7.75–7.80(1H, m), 7.83(1H,d,J=8.8 Hz), 8.10–8.30(5H,m), 8.51(1H,s), 8.85–8.90(2H,m).

MS (FAB) m/z: 482 [(M+H)$^+$, Cl$^{35}$], 484 [(M+H)$^+$, Cl$^{37}$].

Elementary analysis for C$_{24}$H$_{20}$ClN$_3$O$_4$S.HCl.H$_2$O

Calculated: C, 53.74; H, 4.32; N, 7.83; Cl, 13.22; S, 5.98.

Found: C, 53.51; H, 4.36; N, 7.57; Cl, 13.21; S, 5.97.

Example 17

1-[(6-Chloronaphthalen-2-yl)sulfonyl]-4-[4-(pyridin-2-yl)benzoyl]piperazine hydrochloride In a similar manner to Example 4 except for the use of 4-(pyridin-2-yl)benzoic acid hydrochloride obtained in Referential Example 30 and 1-[(6-chloronaphthalen-2-yl)sulfonyl]piperazine hydrochloride as the raw materials, the reaction was conducted, whereby the title compound was obtained.

$^1$H-NMR (DMSO-$d_6$) δ: 3.07(4H,br), 3.60–4.00(4H,br), 7.46(3H,br), 7.73(1H,dd,J=8.8,2.0 Hz), 7.82(1H,dd,J=8.8, 2.0 Hz), 7.94–8.05(2H,br), 8.08(2H,d,J=8.8 Hz), 8.18(1H,d,J=8.8 Hz), 8.28(2H,d,J=8.8 Hz), 8.50(1H,s), 8.70(1H,br).

MS (FAB) m/z: 492 [(M+H)$^+$, Cl$^{35}$], 494 [(M+H)$^+$, Cl$^{37}$].

Elementary analysis for $C_{26}H_{22}ClN_3O_3S \cdot 0.9HCl \cdot H_2O$

Calculated: C, 57.53; H, 4.62; Cl, 12.41; N, 7.74; S, 5.91.

Found: C, 57.55; H, 4.52; Cl, 12.64; N, 7.61; S, 6.03.

Example 18

1-[(E)-4-Chlorostyrylsulfonyl]-4-[4-(pyridin-2-yl)benzoyl]piperazine hydrochloride In a similar manner to Example 17 except for the use of 4-(2-pyridyl)benzoic acid hydrochloride and 1-[(E)-4-chlorostyrylsulfonyl]piperazine hydrochloride, which had been obtained in Referential Example 31, as the raw materials, the reaction was conducted, whereby the title compound was obtained.

$^1$H-NMR (DMSO-$d_6$) δ: 3.19(4H,br), 3.46(2H,br), 3.75 (2H,br), 7.36(1H,d,J=15.6 Hz), 7.44(1H,d,J=15.6 Hz), 7.50–7.58(1H,br), 7.53(2H,d,J=7.8 Hz), 7.57(2H,d,J=7.8 Hz), 7.82(2H,d,J=7.8 Hz), 8.13(2H,m), 8.15(2H,d,J=7.8 Hz), 8.75(1H,d,J=4.9 Hz).

MS (FAB) m/z: 468 [(M+H)$^+$, Cl$^{35}$], 470 [(M+H)$^+$, Cl$^{37}$].

Elementary analysis for $C_{24}H_{22}ClN_3O_3S \cdot HCl \cdot 0.3EtOH \cdot 0.3H_2O$ Calculated: C, 56.42 H, 4.89; Cl, 13.54; N, 8.02; S, 6.12.

Found: C, 56.51 H, 4.83; Cl, 13.46; N, 8.10; S, 5.99.

Example 19

2-[4-[[4-[(6-Chloronaphthalen-2-yl)sulfonyl]piperazin-1-yl]carbonyl]phenyl]pyridine N-oxide In a similar manner to Example 6 except for the use of 1-[(6-chloronaphthalen-2-yl)sulfonyl]-4-[4-(pyridin-2-yl)benzoyl]piperazine, which had been obtained in Example 17, as the raw material, the reaction was conducted, whereby the title compound was obtained.

$^1$H-NMR (CDCl$_3$) δ: 3.11(4H,br), 3.63(2H,br), 3.87(2H, br), 7.27(1H,m), 7.33(1H,t,J=8.8 Hz), 7.39–7.41(1H,br), 7.40(2H,d,J=7.8 Hz), 7.60(1H,d,J=8.8 Hz), 7.77(1H,d,J=8.8 Hz), 7.83(2H,d,J=7.8 Hz), 7.93(1H,d,J=3.8 Hz), 7.94(1H,s), 8.31(1H,s), 8.33(1H,d,J=5.9 Hz).

MS (FAB) m/z: 508 [(M+H)$^+$, Cl$^{35}$], 510 [(M+H)$^+$, Cl$^{37}$].

Elementary analysis for $C_{26}H_{22}ClN_3O_4S$

Calculated: C, 61.47; H, 4.37; Cl, 6.98; N, 8.27; S, 6.31.

Found: C, 61.32; H, 4.46; Cl, 7.21; N, 8.13; S, 6.02.

Example 20

2-[4-[[4-[(6-Chloronaphthalen-2-yl)sulfonyl]piperazin-1-yl]carbonyl]phenyl]-1-methylpyridinium iodide In a similar manner to Example 12 except for the use of 1-[(6-chloronaphthalen-2-yl)sulfonyl]-4-[4-(pyridin-2-yl)benzoyl]piperazine, which had been obtained in Example 17, as the raw material, the reaction was conducted, whereby the title compound was obtained.

$^1$H-NMR (DMSO-$d_6$) δ: 2.93–3.23(4H,br), 3.54(2H,br), 3.82(2H,br), 4.30(3H,s), 7.50(2H,d,J=8.8 Hz), 7.53(1H,m), 7.70(2H,d,J=8.8 Hz), 7.70(1H,br), 7.84–7.92(4H,m), 8.15 (1H,t,J=6.8 Hz), 8.26(1H,s), 8.52(1H,t,J=6.8 Hz), 9.29(1H, d,J=5.9 Hz).

Elementary analysis for $C_{27}H_{25}ClIN_3O_3S \cdot 1.6H_2O$

Calculated: C, 48.93; H, 4.29; N, 6.34.

Found: C, 48.81; H, 4.06; N, 6.31.

Example 21

1-[(6-Chloronaphthalen-2-yl)sulfonyl]-4-[4-(2,4-diaminopyrimidin-6-yl)benzoyl]piperazine hydrochloride In a similar manner to Example 4 except for the use of 4-(2,4-diamino-6-pyrimidyl)benzoic acid hydrochloride obtained in Referential Example 32 and 1-[(6-chloronaphthalen-2-yl)sulfonyl]piperazine hydrochloride as the raw materials, the reaction was conducted, whereby the title compound was obtained.

$^1$H-NMR (DMSO-$d_6$) δ: 3.14(4H,br), 3.45(2H,br s), 3.73 (2H,br s), 6.36(1H,s), 7.54(2H,d,J=7.8 Hz), 7.74(1H,dd,J= 8.8,2.0 Hz), 7.82(1H,d,J=8.8 Hz), 7.83(1H,s), 7.84(2H,d,J= 7.8 Hz), 8.18(1H,J=8.8 Hz), 8.18–8.35(3H,br), 8.27(1H,s), 8.28(1H,d,J=8.8 Hz), 8.50(1H,s), 12.64(1H,br s).

MS (FAB) m/z: 523 [(M+H)$^+$, Cl$^{35}$], 525 [(M+H)$^+$, Cl$^{37}$].

Elementary analysis for $C_{25}H_{23}ClN_6O_3S \cdot HCl \cdot 1.4H_2O$

Calculated: C, 51.36; H, 4.62; Cl, 12.13; N, 14.37; S, 5.48.

Found: C, 51.38; H, 4.54; Cl, 12.24; N, 14.23; S, 5.55.

Example 22

1-[(E)-4-Chlorostyrylsulfonyl]-4-[4-(2,4-diaminopyrimidin-6-yl)benzoyl]piperazine hydrochloride In a similar manner to Example 21 except for the use of 4-(2,4-diamino-6-pyrimidyl)benzoic acid hydrochloride obtained in Referential Example 33 and 1-[(E)-4-chlorostyrylsulfonyl)piperazine hydrochloride, which had been obtained in Referential Example 31, as the raw materials, the reaction was conducted, whereby the title compound was obtained.

$^1$H-NMR (DMSO-$d_6$) δ: 3.18(4H,br), 3.43(2H,br), 3.76 (2H,br), 4.0(2H,br), 6.37(1H,s), 7.84(2H,d,J=15.6 Hz), 7.44 (1H,J=15.6 Hz), 7.53(2H,d,J=8.8 Hz), 7.63(2H,d,J=8.8 Hz), 7.82(1H,d,J=8.8 Hz), 7.88(1H,d,J=8.8 Hz), 8.23(1H,br s), 8.32(1H,br s), 12.58(1H,br s).

MS (FAB) m/z: 499 [(M+H)$^+$, Cl$^{35}$], 501 [(M+H)$^+$, Cl$^{37}$].

Elementary analysis for $C_{23}H_{23}ClN_6O_3S \cdot 1.2HCl \cdot 1.4H_2O$

Calculated: C, 48.64; H, 4.79; Cl, 13.73; N, 14.80; S, 5.65.

Found: C, 48.46; H, 4.56; Cl, 13.53; N, 14.54; S, 5.72.

Example 23

2-[4-[[4-(E)-4-Chlorostyrylsulfonyl]piperazin-1-yl]carbonyl]phenyl]pyridine N-oxide In a similar manner to Example 1 except for the use of 2-[4-[(1-piperazyl)carbonyl]phenyl]pyridine N-oxide hydrochloride obtained in Referential Example 35 and (E)-4-chlorostyrylsulfonyl chloride as the raw materials, the reaction was conducted, whereby the title compound was obtained.

$^1$H-NMR (CDCl$_3$) δ: 3.10–3.40(4H,br), 3.66(2H,br), 3.89 (2H,br), 6.65(1H,d,J=15.6 Hz), 7.28(1H,m), 7.34(1H,t,J=7.8 Hz), 7.39–7.48(6H,m), 7.50(2H,d,J=7.8 Hz), 7.88(2H,d,J=7.8 Hz), 8.34(1H,d,J=5.9 Hz).

MS (FD) m/z: 483 (M$^+$, Cl$^{35}$), 485 (M$^+$, Cl$^{37}$).

Elementary analysis for C$_{24}$H$_{22}$ClN$_3$O$_4$S 0.5H$_2$O

Calculated: C, 58.47; H, 4.70; Cl, 7.19; N, 8.52; S, 6.50.

Found: C, 58.49; H, 4.80; Cl, 7.29; N, 8.31; S, 6.34.

Example 24

1-[(E)-4-Chlorostyrylsulfonyl]-4-[4-(pyridin-4-yl)benzoyl]piperazine hydrochloride Under ice cooling, piperazine (727 mg) was dissolved under in dichloromethane (10 ml), followed by the addition of (E)-4-chlorostyrylsulfonyl chloride (500 mg) in portions. After stirring at room temperature for one hour, the reaction mixture was diluted with dichloromethane (100 ml), washed with a saturated aqueous solution of sodium bicarbonate, a 5% aqueous solution of citric acid, water and saturated saline and then dried over anhydrous magnesium sulfate. The residue obtained by distilling off the solvent under reduced pressure was suspended in N,N-dimethylformamide (10 ml), followed by the addition of 4-(4-pyridyl)benzoic acid (420 mg) obtained in Referential Example 2 and N,N-dimethyl-4-aminopyridine (309 mg). Under ice cooling, 1-(3-dimethylaminopropyl)-3-ethylcarbodiimide hydrochloride (405 mg) was added and the resulting mixture was stirred at room temperature for 68 hours. After concentration, the residue was purified by chromatography on a silica gel column (dichloromethane:methanol=70:1). The colorless solid so obtained was recrystallized from a mixed solvent of ethyl acetate and hexane, followed by recrystallization from ethyl acetate to obtain colorless needle crystals (185 mg). To the filtrate, on the other hand, saturated hydrochloric acid-ethanol (4 ml) was added. After concentration, the residue was recrystallized from methanol-ethyl acetate, whereby the title compound (200 mg) was obtained as colorless needle crystals.

$^1$H-NMR (DMSO-d$_6$) δ: 3.17(2H,br s), 3.23(2H,br s), 3.48(2H,br s), 3.77(2H,br s), 7.36(1H,d,J=15.3 Hz), 7.44 (1H,d,J=15.3 Hz), 7.53(2H,d,J=8.8 Hz), 7.64(2H,d,J=8.3 Hz), 7.82(2H,d,J=8.3 Hz), 8.06(2H,d,J=8.8 Hz), 8.32(2H,d,J=6.6 Hz), 8.95(2H,d,J=6.6 Hz).

MS (FAB) m/z: 468 [(M+H)$^+$, Cl$^{35}$], 470 [(M+H)$^+$, Cl$^{37}$].

Elementary analysis for C$_{24}$H$_{22}$ClN$_3$O$_3$S.HCl.0.2H$_2$O.0.22CH$_3$CO$_2$CH$_2$CH$_3$ Calculated: C, 56.66; H, 4.81; Cl, 13.44; N, 7.97; S, 6.08.

Found: C, 56.68; H, 4.79; Cl, 13.43; N, 8.04; S, 6.14.

Example 25

4-[4-[[4-[(E)-4-Chlorostyrylsulfonyl]piperazin-1-yl]carbonyl]phenyl]-1-methylpyridinium iodide In a similar manner to Example 12 except for the use of 1-[(E)-4-chlorostyrylsulfonyl]-4-[4-(pyridin-4-yl)benzoyl]piperazine, which had been obtained in Example 24, as the raw material, the reaction was conducted, whereby the title compound was obtained.

$^1$H-NMR (DMSO-d$_6$) δ: 3.04–3.87(8H,br), 4.35(3H,s), 7.35(1H,d,J=15.6 Hz), 7.44(1H,d,J=15.6 Hz), 7.53(2H,d,J=8.3 Hz), 7.67(2H,d,J=8.3 Hz), 7.82(2H,d,J=8.8 Hz), 8.13 (2H,d,J=8.3 Hz), 8.53(2H,d,J=6.8 Hz), 9.05(2H,d,J=7.3 Hz).

Elementary analysis for C$_{25}$H$_{25}$ClIN$_3$O$_3$S.0.5H$_2$O

Calculated: C, 48.52; H, 4.23; N, 6.79.

Found: C, 48.68; H, 4.13; N, 6.41.

Example 26

3-[4-[[4-[(E)-4-Chlorostyrylsulfonyl]piperazin-1-yl]carbonyl]phenyl]pyridine N-oxide After the protective group was removed by the reaction as in Example 7, the reaction with (E)-4-chlorostyrylsulfonyl chloride was effected in a similar manner to Example 23, whereby the title compound was obtained.

$^1$H-NMR (CDCl$_3$) δ: 3.26(4H,br), 3.52–4.00(4H,br), 6.64 (1H,d,J=15.6 Hz), 7.45–7.52(7H,m), 7.52(2H,d,J=2.0 Hz), 7.57(2H,d,J=2.0 Hz), 8.22(1H,dt,J=6.3,1.6 Hz), 8.44(1H,t,J=1.6 Hz).

MS (FAB) m/z: 484 [(M+H)$^+$, Cl$^{35}$], 486 [(M+H)$^+$, Cl$^{37}$].

Elementary analysis for C$_{24}$H$_{22}$ClN$_3$O$_3$S.0.5H$_2$O

Calculated: C, 58.47; H, 4.70; Cl, 7.19; N, 8.52; S, 6.50.

Found: C, 58.49; H, 4.66; Cl, 7.40; N, 8.54; S, 6.56.

Example 27

1-[(E)-4-Chlorostyrylsulfonyl]-4-[4-(pyridin-3-yl)benzoyl]piperazine hydrochloride In a similar manner to Example 17 except for the use, as the raw materials, of 4-(3-pyridyl)benzoic acid hydrochloride obtained in Referential Example 8 and 1-[(E)-4-chlorostyrylsulfonyl]piperazine hydrochloride obtained in Referential Example 31, the reaction was conducted, whereby the title compound was obtained.

$^1$H-NMR (DMSO-d$_6$) δ: 3.08–3.29(4H,br), 3.42–3.85 (4H,br), 7.35(1H,d,J=15.6 Hz), 7.43(1H,d,J=15.6 Hz), 7.52 (2H,d,J=8.3 Hz), 7.59(2H,d,J=8.3 Hz), 7.80–7.93(5H,m), 8.54(1H,d,J=6.8 Hz), 8.78(1H,d,J=4.5 Hz), 9.13(1H,d,J=2.0 Hz).

MS (FAB) m/z: 468 [(M+H)$^+$, Cl$^{35}$], 470 [(M+H)$^+$, Cl$^{37}$].

Elementary analysis for C$_{24}$H$_{22}$ClN$_3$O$_3$S.HCl.1.3H$_2$O

Calculated: C, 54.61; H, 4.89; N, 7.96; Cl, 13.43; S, 6.07.

Found: C, 54.82; H, 4.80; N, 7.91; Cl, 13.14; S, 6.14.

Example 28

3-[4-[[4-[(6-Chloronaphthalen-2-yl)sulfonyl]piperazin-1-yl]carbonyl]phenyl]-1-methylpyridinium iodide In a similar manner to Example 12 except for the use of 1-[(6-chloronaphthalen-2-yl)sulfonyl]-4-[4-(pyridin-3-yl)benzoyl]piperazine, which had been obtained in Example 5, as the raw material, the reaction was conducted, whereby the title compound was obtained.

$^1$H-NMR (DMSO-d$_6$) δ: 2.50–3.80(8H,m), 4.44(3H,s), 7.57(2H,d,J=8.3 Hz), 7.74(1H,dd,J=8.8,2.0 Hz), 7.84(1H, dd,J=8.8,1.5 Hz), 7.94(2H,d,J=8.3 Hz), 8.10–8.30(4H,m), 8.51(1H,s), 8.90(1H,d,J=7.8 Hz), 9.01(1H,d,J=5.9 Hz), 9.45 (1H,s).

MS (FAB) m/z: 506 [(M+H)$^+$, Cl$^{35}$], 508 [(M+H)$^+$, Cl$^{37}$].

Example 29

1-[(6-Chloronaphthalen-2-yl)sulfonyl]-4-[2-hydroxy-4-(pyridin-4-yl)benzoyl]piperazine hydrochloride In a similar manner to Example 4 except for the use of 2-(hydroxy-4-(4-pyridyl)benzoic acid obtained in Referential Example 38 and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 2.90–3.40(8H,m), 7.25–7.40 (3H,m), 7.70–7.80(1H,m), 7.80–7.90(1H,m), 8.15–8.25(3H, m), 8.25–8.35(2H,m), 8.50–8.60(1H,m), 8.91(2H,d,J=6.4 Hz), 10.41(1H,br s).

MS (FAB) m/z: 535 [(M+H)$^+$, Cl$^{35}$], 537 [(M+H)$^+$, Cl$^{37}$].

Elementary analysis for C$_{26}$H$_{22}$ClN$_3$O$_4$S.1.1HCl.1.7H$_2$O

Calculated: C, 53.96; H, 4.62; N, 7.26; Cl, 12.86; S, 5.54.

Found: C, 53.62; H, 4.58; N, 7.34; Cl, 13.10; S, 5.94.

Example 30

1-[(6-Chloronaphthalen-2-yl)sulfonyl]-4-[3-methoxy-4-(pyridin-4-yl)benzoyl]piperazine hydrochloride In a similar manner to Example 4 except for the use of 3-methoxy-4-(4-pyridyl)benzoic acid obtained in Referential Example 41 and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 3.00–4.00(8H,m), 3.81(3H,s), 7.08(1H,d,J=8.8 Hz), 7.17(1H,s), 7.55(1H,d,J=8.8 Hz), 7.74 (1H,dd,J=8.8,2.0 Hz), 7.83(1H,d,J=8.3 Hz), 8.04(2H,d,J= 6.3 Hz), 8.19(1H,d,J=8.8 Hz), 8.25–8.30(2H,m), 8.52(1H,s), 8.85(2H,d,J=6.3 Hz).

MS (FAB) m/z: 522 [(M+H)$^+$, Cl$^{35}$], 524 [(M+H)$^+$, Cl$^{37}$].

Elementary analysis for C$_{27}$H$_{24}$ClN$_3$O$_4$S.0.8HCl.1.7H$_2$O

Calculated: C, 55.74; H, 4.89; N, 7.22; Cl, 10.97; S, 5.51.

Found: C, 55.59; H, 4.90; N, 7.23; Cl, 10.90; S, 5.52.

Example 31

1-[(6-Chloronaphthalen-2-yl)sulfonyl]-4-[3-hydroxy-4-(pyridin-4-yl)benzoyl]piperazine hydrochloride In dichloromethane (1 ml), boron tribromide (115 μl) was dissolved, followed by the dropwise addition of a solution of 1-[(6-chloronaphthalen-2-yl)sulfonyl]-4-[3-methoxy-4-(pyridin-4-yl)benzoyl]piperazine (105 mg), which had been obtained in Example 30, in dichloromethane (dichloromethane: 4 ml) at an external temperature of about −78° C. While heating gradually to room temperature, the resulting mixture was stirred for 23 hours. After dichloromethane and water were added to the reaction mixture and the resulting mixture was stirred for a while, sodium bicarbonate was added to make alkaline the reaction mixture, which was separated into an organic layer and a water layer. From the water layer, another organic layer was extracted with dichloromethane. These organic layers were combined together, washed with saturated saline and then dried over anhydrous sodium sulfate. The residue obtained by distilling off the solvent under reduced pressure was purified by chromatography on a silica gel column (dichloromethane~3% methanol-dichloromethane). The crudely purified product so obtained was dissolved in tetrahydrofuran. Ethanol hydrochloride was added to the resulting solution to solidify the same. The resulting solid was collected by filtration and then dissolved in a mixed solvent of water and methanol. After the removal of the insoluble matter by filtration, the filtrate was distilled under reduced pressure, whereby the title compound (36 mg, 30%) was obtained.

$^1$H-NMR (DMSO-d$_6$) δ: 3.00–3.80(8H,m), 6.85–6.95 (1H,m), 7.01(1H,d,J=1.4 Hz), 7.49(1H,d,J=8.8 Hz), 7.72 (1H,dd,J=8.8,2.0 Hz), 7.81(1H,dd,J=8.5,1.7 Hz), 7.94(2H, d,J=6.4 Hz), 8.19(1H,d,J=8.8 Hz), 8.25–8.30(2H,m), 8.51 (1H,s), 8.75(2H,d,J=5.9 Hz), 10.67(1H,s).

MS (FAB) m/z: 508 [(M+H)$^+$, Cl$^{35}$], 510 [(M+H)$^+$, Cl$^{37}$].

Example 32

1-[(6-Chloronaphthalen-2-yl)sulfonyl]-2-ethoxycarbonyl-4-[4-(pyridin-4-yl)benzoyl]piperazine In a similar reaction to Example 7 except for the use of 4-tert-butoxycarbonyl-1-[(6-chloronaphthalen-2-yl)sulfonyl]-2-ethoxycarbonylpiperazine as the raw material, the protective group was removed. The residue was then reacted with 4-(4-pyridyl)benzoic acid hydrochloride as in Example 4, whereby the title compound was obtained.

$^1$H-NMR (CDCl$_3$) δ: 0.80–1.10(3H,m), 3.00–4.00(8H, m), 4.60–4.80(1H,m), 7.42(2H,d,J=7.8 Hz), 7.47(2H,d,J= 5.9 Hz), 7.50–7.60(1H,m), 7.64(2H,d,J=8.3 Hz), 7.70–7.80 (1H,m), 7.85–7.95(3H,m), 8.33(1H,s), 8.69(2H,s).

MS (FAB) m/z: 564 [(M+H)$^+$, Cl$^{35}$, 566 [(M+H)$^+$, Cl$^{37}$].

Elementary analysis for C$_{29}$H$_{26}$ClN$_3$O$_5$S.0.3H$_2$O

Calculated: C, 60.78; H, 4.70; N, 7.33; Cl, 6.80; S, 5.60.

Found: C, 60.84; H, 4.84; N, 6.98; Cl, 7.03; S, 5.70.

Example 33

1-[(6-Chloronaphthalen-2-yl)sulfonyl]-4-[4-(pyridin-4-yl)benzoyl]piperazine-2-carboxylic acid In a similar manner to Example 3 except for the use of 1-[(6-chloronaphthalen-2-yl)sulfonyl]-2-ethoxycarbonyl-4-[4-(pyridin-4-yl)benzoyl]piperazine as the raw material, the title compound was obtained.

$^1$H-NMR (DMSO-d$_6$) δ: 2.70–5.00(7H,m), 7.40–7.50 (2H,m), 7.65–7.75(2H,m), 7.85–8.25(8H,m), 8.50–8.60(2H, m), 8.80–8.95(2H,m).

MS (FAB) m/z: 536 [(M+H)$^+$, Cl$^{35}$], 538 [(M+H)$^+$, Cl$^{37}$].

Elementary analysis for C$_{27}$H$_{22}$ClN$_3$O$_5$S.0.3HCl.H$_2$O

Calculated: C, 57.40; H, 4.34; N, 7.44; Cl, 8.16; S, 5.68.

Found: C, 57.16; H, 4.35; N, 7.36; Cl, 7.92; S, 6.08.

Example 34

4-[(6-Chloronaphthalen-2-yl)sulfonyl]-2-ethoxycarbonyl-1-[4-(pyridin-3-yl)benzoyl]piperazine In a similar manner to Example 2, the reaction was conducted, whereby the title compound was obtained.

$^1$H-NMR (CDCl$_3$) δ: 1.15–1.30(3H,m), 2.60–4.60(8H, m), 5.33(1H,br), 7.40–7.55(3H,m), 7.70–7.85(4H,m), 8.05–8.10(1H,m), 8.19(1H,d,J=8.8 Hz), 8.25–8.30(2H,m), 8.50–8.65(2H,m), 8.91(1H,s).

MS (FAB) m/z: 564 [(M+H)$^+$, Cl$^{35}$], 566 [(M+H)$^+$, Cl$^{37}$].

Elementary analysis for C$_{29}$H$_{26}$ClN$_3$O$_5$S.0.1HCl.0.5H$_2$O

Calculated: C, 60.40; H, 4.74; N, 7.29; Cl, 6.76; S, 5.56.

Found: C, 60.67; H, 4.61; N, 7.30; Cl, 6.89; S, 5.51.

Example 35

2-Carbamoyl-4-[(6-chloronaphthalen-2-yl)sulfonyl]-1-[4-(pyridin-3-yl)benzoyl]piperazine hydrochloride In a similar manner to Example 3, with 4-[(6-chloronaphthalen-2-yl)sulfonyl]-2-ethoxycarbonyl-1-[4-

(pyridin-3-yl)benzoyl]piperazine (426 mg) as the raw material, a crude product was obtained by the hydrolysis of the ester, followed by suspension in N,N-dimethylformamide (35 ml). Under ice cooling, di-tert-butyl dicarbonate (646 mg), pyridine (370 µl) and ammonium bicarbonate (196 mg) were added to the resulting suspension. The resulting mixture was stirred at room temperature for 19 hours. The residue obtained by distilling off the solvent under reduced pressure was purified by chromatography on a silica gel column (4% methanol-dichloromethane) and the eluate was dissolved in tetrahydrofuran. Ethanol hydrochloride was added to the resulting solution to solidify the same. The resulting solid was collected by filtration and dissolved in a mixed solvent of water and methanol. The insoluble matter was filtered off and the filtrate was distilled under reduced pressure, whereby the title compound (302 mg, 65%) was obtained.

$^1$H-NMR (DMSO-$d_6$) δ: 2.30–4.50(6H,m), 5.08(1H,br), 7.40–7.60(2H,m), 7.65–7.85(3H,m), 7.92(2H,d,J=7.8 Hz), 8.00–8.10(1H,m), 8.20(2H,d,J=8.8 Hz), 8.25–8.35(2H,m), 8.49(1H,s), 8.80(1H,d,J=7.8 Hz), 8.88(1H,d,J=5.4 Hz), 9.25 (1H,s).

MS (FAB) m/z: 535 [(M+H)$^+$, Cl$^{35}$], 537 [(M+H)$^+$, Cl$^{37}$].

Elementary analysis for $C_{27}H_{23}ClN_4O_4S.1.1HCl.1.7H_2O$

Calculated: C, 53.54; H, 4.58; N, 9.25; Cl, 12.29; S, 5.29.

Found: C, 53.36; H, 4.71; N, 9.07; Cl, 12.17; S, 5.50.

Example 36

2-Carbamoyl-4-[(6-chloronaphthalen-2-yl)sulfonyl]-1-[4-(pyridin-4-yl)benzoyl]piperazine hydrochloride In a similar manner to Example 35 except for the use of 4-[(6-chloronaphthalen-2-yl)sulfonyl]-2-ethoxycarbonyl-1-[4-(pyridin-4-yl)benzoyl]piperazine as the raw material, the title compound was obtained.

$^1$H-NMR (DMSO-$d_6$) δ: 2.30–2.70(2H,m), 3.20–3.80 (2H,m), 4.10–4.50(2H,m), 5.07(1H,br s), 7.40–7.55(2H,m), 7.60–7.65(1H,m), 7.67(1H,s), 7.72(1H,dd,J=8.8,2.4 Hz), 7.78(1H,dd,J=8.8,2.4 Hz), 8.04(2H,d,J=8.8 Hz), 8.20(1H,d, J=8.8 Hz), 8.25–8.35(4H,m), 8.49(1H,s), 8.95(2H,d,J=5.4 Hz).

MS (FAB) m/z: 535 [(M+H)$^+$, Cl$^{35}$], 537 [(M+H)$^+$, Cl$^{37}$].

Elementary analysis for $C_{27}H_{23}ClN_4O_4S.HCl.1.8H_2O$

Calculated: C, 53.70; H, 4.61; N, 9.28; Cl, 11.74; S, 5.31.

Found: C, 53.87; H, 4.40; N, 8.89; Cl, 11.81; S, 5.23.

Example 37

4-[4-[[2-Carbamoyl-4-[(6-chloronaphthalen-2-yl)sulfonyl]piperazin-1-yl]carbonyl]phenyl]pyridine N-oxide In a similar manner to Example 7 except for the use of 2-carbamoyl-4-[(6-chloronaphthalen-2-yl)sulfonyl]-1-[4-pyridin-4-yl)benzoyl]piperazine as the raw material, the reaction was conducted, whereby the title compound was obtained.

$^1$H-NMR (DMSO-$d_6$) δ: 2.30–4.50(6H,m), 5.04(1H,br), 7.30–7.90(10H,m), 8.10–8.30(5H,m), 8.48(1H,s).

MS (FAB) m/z: 551 [(M+H)$^+$, Cl$^{35}$], 553 [(M+H)$^+$, Cl$^{37}$].

Elementary analysis for $C_{27}H_{23}ClN_4O_5S.0.8H_2O$

Calculated: C, 57.35; H, 4.39; N, 9.91; Cl, 6.27; S, 5.67.

Found: C, 57.64; H, 4.50; N, 9.48; Cl, 6.37; S, 5.71.

Example 38

4-[4-[[4-[(6-Chloronaphthalen-2-yl)sulfonyl]-2-ethoxycarbonylpiperazin-1-yl]carbonyl]phenyl]pyridine N-oxide In a similar manner to Example 37, the reaction was conducted, whereby the title compound was obtained.

$^1$H-NMR (CDCl$_3$) δ: 1.30–1.40(3H,m), 2.30–4.70(8H, m), 5.47(1H,br s), 7.40–7.80(8H,m), 7.92(1H,s), 7.94(2H,s), 8.26(2H,d,J=6.8 Hz), 8.48(1H,s).

MS (FAB) m/z: 580 [(M+H)$^+$, Cl$^{35}$], 582 [(M+H)$^+$, Cl$^{37}$].

Elementary analysis for $C_{29}H_{26}ClN_3O_6S.1.3H_2O$

Calculated: C, 57.72; H, 4.78; N, 6.96; Cl, 5.87; S, 5.31.

Found: C, 57.99; H, 4.75; N, 6.56; Cl, 5.98; S, 5.43.

Example 39

4-[4-[[2-Carboxy-4-[(6-chloronaphthalen-2-yl)sulfonyl]piperazin-1-yl]carbonyl]phenyl]pyridine N-oxide In a similar manner to Example 3, the reaction was conducted, whereby the title compound was obtained.

$^1$H-NMR (CDCl$_3$) δ: 2.30–4.50(6H,m), 5.22(1H,br s), 7.35–7.50(2H,m), 7.70–7.90(6H,m), 8.19(1H,d,J=8.8 Hz), 8.25–8.30(4H,m), 8.53(1H,s), 13.42(1H,br).

Elementary analysis for $C_{27}H_{22}ClN_3O_6S.0.2HCl.1.7H_2O$

Calculated: C, 54.97; H, 4.37; N, 7.12; Cl, 7.21; S, 5.44.

Found: C, 55.07; H, 4.40; N, 6.82; Cl, 7.16; S, 5.47.

Example 40

2-Carbamoyl-4-[(E)-4-chlorostyrylsulfonyl]-1-[4-(pyridin-4-yl)benzoyl]piperazine hydrochloride 2-Carbamoyl-4-[[2-(4-chlorophenyl)-2-ethoxyethyl] sulfonyl]-1-[4-(pyridin-4-yl)benzoyl]piperazine hydrochloride In a similar manner to Example 2 and 35, the reaction was conducted, whereby the title compounds were obtained, respectively.

2-Carbamoyl-4-[(E)-4-chlorostyrylsulfonyl]-1-[4-(pyridin-4-yl)benzoyl]piperazine hydrochloride.

$^1$H-NMR (CD$_3$OD) δ: 2.80–4.80(6H,m), 5.32(1H,br), 7.04(1H,d,J=15.6 Hz), 7.40–7.50(3H,m), 7.60–7.80(4H,m), 7.95–8.05(2H,m), 8.20(2H,br), 8.81(2H,br).

MS (FAB) m/z: 511 [(M+H)$^+$, Cl$^{35}$], 513 [(M+H)$^+$, Cl$^{37}$].

Elementary analysis for $C_{25}H_{23}ClN_4O_4S.0.9HCl.1.8H_2O$

Calculated: C, 52.11; H, 4.81; N, 9.72; Cl, 11.69.

Found: C, 52.28; H, 4.83; N, 9.44; Cl, 11.51.

2-Carbamoyl-4-[[2-(4-chlorophenyl)-2-ethoxyethyl] sulfonyl]-1-[4-(pyridin-4-yl)benzoyl]piperazine hydrochloride $^1$H-NMR (CD$_3$OD) δ: 1.10–1.20(3H,m), 2.95–4.70(6H, m), 5.34(1H,br), 7.38(4H,s), 7.65–7.85(2H,m), 8.05–8.15 (2H,m), 8.40–8.50(2H,m), 8.91(2H,d,J=5.9 Hz).

MS (FAB) m/z: 557 [(M+H)$^+$, Cl$^{35}$], 559 [(M+H)$^+$, Cl$^{37}$].

Elementary analysis for $C_{27}H_{29}ClN_4O_5S.HCl.2.5H_2O$

Calculated: C, 50.78; H, 5.52; N, 8.77; Cl, 11.10; S, 5.02.

Found: C, 50.61; H, 5.38; N, 8.68; Cl, 11.27; S, 5.07.

Example 41

1-[trans-4-(Aminomethyl)cyclohexylmethyl]-4-[(6-chloronaphthalen-2-yl)sulfonyl]piperazine hydrochloride In a similar manner to Example 7, the reaction was conducted, whereby the title compound was obtained.

$^1$H-NMR (DMSO-$d_6$) δ: 0.80–1.00(4H,m), 1.48(1H,m), 1.60–1.90(5H,m), 2.60(2H,m), 2.90–3.10(4H,m), 3.14(2H, m), 3.52(2H,m), 3.77(2H,m), 7.75(1H,dd,J=8.8,2.0 Hz), 7.85(1H,d,J=8.8 Hz), 7.99(3H,br), 8.21(1H,d,J=8.8 Hz), 8.30–8.40(2H,m), 8.56(1H,s), 10.46(1H,br).

MS (FAB) m/z: 436 [(M+H)$^+$, Cl$^{35}$], 438 [(M+H)$^+$, Cl$^{37}$].

Elementary analysis for $C_{22}H_{30}ClN_3O_2S.2HCl.3/4H_2O$

Calculated: C, 50.58; H, 6.46; N, 8.04; Cl, 20.36; S, 6.14.

Found: C, 50.74; H, 6.48; N, 7.76; Cl, 20.09; S, 6.19.

Example 42

1-[trans-4-(Aminomethyl)cyclohexylcarbonyl]-4-[(6-chloronaphthalen-2-yl)sulfonyl]piperazine hydrochloride In a similar manner to Example 7 except for the use of 1-[trans-4-(N-tert-butoxycarbonylaminomethyl) cyclohexylcarbonyl]-4-[(6-chloronaphthalen-2-yl)sulfonyl]piperazine as the raw material, the title compound was obtained.

$^1$H-NMR (DMSO-d$_6$) δ: 0.90–1.00(2H,m), 1.20–1.40 (2H,m), 1.48(1H,m), 1.50–1.70(2H,m), 1.70–1.90(2H,m), 2.44(1H,m), 2.59(2H,m), 2.96(4H,m), 3.55(4H,m), 7.72 (1H,dd,J=8.8,2.0 Hz), 7.81(1H,d,J=8.3 Hz), 7.90(3H,br), 8.16(1H,d,J=8.8 Hz), 8.20–8.30(2H,m), 8.49(1H,s).

MS (FAB) m/z: 450 [(M+H)$^+$, Cl$^{35}$], 452 [(M+H)$^+$, Cl$^{37}$].

Elementary analysis for $C_{22}H_{28}ClN_3O_3S.0.9HCl.1.5H_2O$

Calculated: C, 51.83; H, 6.31; N, 8.24; Cl, 13.21; S, 6.29.

Found: C, 51.63; H, 6.22; N, 7.97; Cl, 13.32; S, 6.17.

Example 43

1-[N-[trans-4-(Aminomethyl)cyclohexylcarbonyl] glycyl]]-4-[(6-chloronaphthalen-2-yl)sulfonyl] piperazine hydrochloride In a similar manner to Example 7 except for the use of 1-[N-[trans-4-(N-tert-butoxycarbonylaminomethyl) cyclohexylcarbonyl]glycyl]]-4-[(6-chloronaphthalen-2-yl) sulfonyl]piperazine as the raw material, the reaction was conducted, whereby the title compound was obtained.

$^1$H-NMR (DMSO-d$_6$) δ: 0.80–1.00(2H,m), 1.20–1.40 (2H,m), 1.50(1H,m), 1.60–1.80(4H,m), 2.10(1H,m), 2.62 (2H,m), 2.90–3.10(4H,m), 3.40–3.60(4H,m), 3.83(2H,d,J= 5.4 Hz), 7.70–7.90(3H,m), 7.93(3H,br), 8.17(1H,d,J=8.3 Hz), 8.20–8.30(2H,m), 8.49(1H,s).

MS (FAB) m/z: 507 [(M+H)$^+$, Cl$^{35}$], 509 [(M+H)$^+$, Cl$^{37}$].

Elementary analysis for $C_{24}H_{31}ClN_4O_4S.HCl$

Calculated: C, 53.04; H, 5.93; N, 10.31; Cl, 13.05; S, 5.90.

Found: C, 52.90; H, 5.98; N, 10.29; Cl, 12.98; S, 5.91.

Example 44

1-[trans-4-(Aminomethyl)cyclohexylcarbonyl]-4-[(6-chloronaphthalen-2-yl)sulfonyl]homopiperazine hydrochloride chloride In a similar manner to Example 7 except for the use of 1-[trans-4-(N-tert-butoxycarbonylaminomethyl) cyclohexylcarbonyl]-4-[(6-chloronaphthalen-2-yl)sulfonyl] homopiperazine as the raw material, the title compound was obtained.

$^1$H-NMR (DMSO-d$_6$) δ: 0.90–1.10(2H,m), 1.30–1.50 (2H,m), 1.50–1.90(7H,m), 2.40–2.80(3H,m), 3.20–3.70(8H, m), 7.60–7.70(1H,m), 7.80–8.00(4H,m), 8.10–8.20(1H,m), 8.20–8.30(2H,m), 8.52 and 8.53(1H, each s).

MS (FAB) m/z: 464 [(M+H)$^+$, Cl$^{35}$], 466 [(M+H)$^+$, Cl$^{37}$].

Elementary analysis for $C_{23}H_{30}ClN_3O_3S.HCl$

Calculated: C, 55.20; H, 6.24; N, 8.40; Cl, 14.17; S, 6.41.

Found: C, 55.42; H, 6.18; N, 8.26; Cl, 14.11; S, 6.53.

Example 45

1-[4-(Aminomethyl)benzoyl]-4-[(6-chloronaphthalen-2-yl)sulfonyl]piperazine hydrochloride In a similar manner to Example 7 except for the use of 1-[4-(N-tert-butoxycarbonylaminomethyl)benzoyl]-4-[(6-chloronaphthalen-2-yl)sulfonyl]piperazine as the raw material, the title compound was obtained.

$^1$H-NMR (DMSO-d$_6$) δ: 3.00–3.20(4H,br), 3.30–3.80 (4H,br), 4.03(2H,s), 7.37(2H,d,J=7.3 Hz), 7.50(2H,d,J=7.3 Hz), 7.72(1H,d,J=8.8 Hz), 7.82(1H,d,J=8.8 Hz), 8.18(1H,d, J=8.8 Hz), 8.20–8.40(2H,m), 8.43(3H,br), 8,49(1H,s).

MS (FAB) m/z: 444 [(M+H)$^+$, Cl$^{35}$], 446 [(M+H)$^+$, Cl$^{37}$].

Elementary analysis for $C_{22}H_{22}ClN_3O_3S.HCl.H_2O$

Calculated: C, 53.02; H, 5.06; N, 8.43; Cl, 14.23; S, 6.43.

Found: C, 53.06; H, 5.30; N, 8.32; Cl, 14.20; S, 6.44.

Example 46

1-[3-(Aminomethyl)benzoyl]-4-[(6-chloronaphthalen-2-yl)sulfonyl]piperazine hydrochloride In a similar manner to Example 3 except for the use of methyl 3-(N-tert-butoxycarbonylaminomethyl)benzoate as the raw material, the ester was hydrolyzed. The reaction was then effected as in Examples 4 and 7, whereby the title compound was obtained.

$^1$H-NMR (DMSO-d$_6$) δ: 3.07(4H,br), 3.20–3.80(4H,br), 4.00(2H,s), 7.30–7.60(4H,m), 7.73(1H,d,J=8.8 Hz), 7.83 (1H,d,J=8.8 Hz), 8.10–8.60(7H,m).

MS (FAB) m/z: 444 [(M+H)$^+$, Cl$^{35}$], 446 [(M+H)$^+$, Cl$^{37}$].

Elementary analysis for $C_{22}H_{22}ClN_3O_3S.HCl.1/4H_2O$

Calculated: C, 54.49; H, 4.88; N, 8.67; Cl, 14.62; S, 6.61.

Found: C, 54.64; H, 4.95; N, 8.52; Cl, 14.59; S, 6.70.

Example 47

1-[(6-Chloronaphthalen-2-yl)sulfonyl]-4-[3-[N-(1-pyrrolin-2-yl)aminomethyl]benzoyl]piperazine hydrochloride In dimethylformamide (2 ml), 2-methoxy-1-pyrroline (35 mg) was dissolved, followed by the addition of 1-[3-(aminomethyl)benzoyl]-4-[(6-chloronaphthalen-2-ylsulfonyl]piperazine hydrochloride (0.10 g) and triethylamine (44 µl). The resulting mixture was stirred at room temperature for 3 days. After the reaction mixture was concentrated under reduced pressure, the concentrate was diluted with methanol, followed by the addition of 1N hydrochloric acid. The solvent was then distilled off under reduced pressure. The residue was purified by gel permeation chromatography ("Sephadex LH-20", Ø 15×300 mm, methanol), followed by solidification in a mixed solvent of methanol and ether, whereby a colorless solid (0.11 g, 91%) was obtained.

$^1$H-NMR (DMSO-d$_6$) δ: 2.04(2H,m), 2.81(2H,t,J=7.8 Hz), 3.18(4H,br), 3.20–3.80(5H,m), 4.10(1H,br), 4.51(2H, d,J=5.9 Hz), 7.30–7.50(4H,m), 7.72(1H,dd,J=8.8,2.0 Hz), 7.82(1H,d,J=8.8 Hz), 8.18(1H,d,J=8.8 Hz), 8.20–8.30(2H, m), 8.50(1H,s), 10.01(1H,t,J=5.9 Hz), 10.06(1H,s).

MS (FAB) m/z: 511 [(M+H)+, Cl35], 513 [(M+H)+, Cl37].
Elementary analysis for $C_{26}H_{27}ClN_4O_3S \cdot HCl \cdot CH_3OH \cdot 4/5H_2O$
Calculated: C, 54.60; H, 5.70; N, 9.43; Cl, 11.94; S, 5.40.
Found: C, 54.84; H, 5.47; N, 9.13; Cl, 11.86; S, 5.48.

Example 48

1-[4-(2-Aminoethyl)benzoyl]-4-[(6-chloronaphthalen-2-yl)sulfonyl]piperazine hydrochloride In a similar manner to Example 7 except for the use of 1-[4-(2-(tert-butoxycarbonylamino)ethyl]benzoyl]-4-[(6-chloronaphthalen-2-yl)sulfonyl]piperazine as the raw material, the title compound was obtained.

$^1$H-NMR (DMSO-$d_6$) δ: 2.90–3.20(8H,m), 3.40–3.90 (4H,br), 7.28(4H,s), 7.72(1H,dd,J=8.8,2.4 Hz), 7.81(1H,dd, J=8.8,2.0 Hz), 8.02(3H,br), 8.17(1H,d,J=8.3 Hz), 8.20–8.30 (2H,m), 8.49(1H,s).

MS (FAB) m/z: 458 [(M+H)+, Cl35], 460 [(M+H)+, Cl37].
Elementary analysis for $C_{23}H_{24}ClN_3O_3S \cdot HCl \cdot 1/2CH_3OH \cdot 1/2H_2O$
Calculated: C, 54.34; H, 5.43; N, 8.09; Cl, 13.65; S, 6.17.
Found: C, 54.43; H, 5.26; N, 7.92; Cl, 13.58; S, 6.24.

Example 49

1-[[(6RS)-6-Aminomethyl-5,6,7,8-tetrahydronaphthalen-2-yl]carbonyl]-4-[(6-chloronaphthalen-2-yl)sulfonyl]piperazine hydrochloride In a similar manner to Example 7 except for the use of 1-[[(6RS)-6-(N-tert-butoxycarbonylaminomethyl)-5,6,7,8-tetrahydronaphthalen-2-yl]carbonyl]-4-[(6-chloronaphthalen-2-yl)sulfonyl]piperazine as the raw material, the title compound was obtained.

$^1$H-NMR (DMSO-$d_6$) δ: 1.30–1.50(1H,m), 1.90–2.10 (2H,m), 2.40–2.60(1H,m), 2.60–3.00(5H,m), 3.03(4H,m), 3.40–3.80(4H,br) 7.00–7.10(3H,m), 7.73(1H,dd,J=8.8,2.0 Hz), 7.81(1H,dd,J=8.8,1.5 Hz), 8.05(3H,br), 8.18(1H,d,J=8.3 Hz), 8.20–8.30(2H,m), 8.49(1H,s).

MS (FAB) m/z: 498 [(M+H)+, Cl35], 500 [(M+H)+, Cl37].
Elementary analysis for $C_{26}H_{28}ClN_3O_3S \cdot HCl \cdot 3/2H_2O$
Calculated: C, 55.61; H, 5.74; N, 7.48; Cl, 12.63; S, 5.71.
Found: C, 55.64; H, 5.53; N, 7.77; Cl, 12.79; S, 5.76.

Example 50

1-[[(6RS)-6-Aminomethyl-5,6,7,8-tetrahydronaphthalen-2-yl]methyl]-4-[(6-chloronaphthalen-2-yl)sulfonyl]piperazine hydrochloride In a similar manner to Example 7 except for the use of 1-[[(6RS)-6-(N-tert-butoxycarbonylaminomethyl)-5,6,7,8-tetrahydronaphthalen-2-yl]methyl]-4-[(6-chloronaphthalen-2-yl)sulfonyl]piperazine as the raw material, the title compound was obtained.

$^1$H-NMR (DMSO-$d_6$) δ: 1.30–1.50(1H,m), 2.00–2.10 (2H,m), 2.40–2.60(1H,m), 2.60–3.00(7H,m), 3.00–3.20(2H,m), 3.30–3.50(2H,m), 3.82(2H,m), 4.22(2H,br), 7.00–7.10 (1H,m), 7.25(2H,s), 7.73(1H,dd,J=8.8,2.4 Hz), 7.81(1H,dd, J=8.8,1.5 Hz), 8.00–8.40(6H,m), 8.52(1H,s), 11.08(1H,br).

MS (FAB) m/z: 484 [(M+H)+, Cl35], 486 [(M+H)+, Cl37].
Elementary analysis for $C_{26}H_{30}ClN_3O_2S \cdot 2HCl$
Calculated: C, 56.07; H, 5.79; N, 7.54; Cl, 19.10; S, 5.76.
Found: C, 56.04; H, 5.79; N, 7.52; Cl, 18.95; S, 5.80.

Example 51

1-[[(2RS)-6-Aminomethyl-1,2,3,4-tetrahydronaphthalen-2-yl]methyl]-4-[(6-chloronaphthalen-2-yl)sulfonyl]piperazine hydrochloride In a similar manner to Example 7 except for the use of 1-[[(2RS)-6-(N-tert-butoxycarbonylaminomethyl)-1,2,3,4-tetrahydronaphthalen-2-yl]methyl]-4-[(6-chloronaphthalen-2-yl)sulfonyl]piperazine as the raw material, the title compound was obtained.

$^1$H-NMR (DMSO-$d_6$) δ: 1.30–1.50(1H,m), 2.00–2.20 (1H,m), 2.20–2.40(1H,m), 2.40–2.60(1H,m), 2.75(2H,m), 2.90–3.30(7H,m), 3.60–3.70(2H,m), 3.70–4.00(4H,m), 7.04 (1H,d,J=7.8 Hz), 7.10–7.30(2H,m), 7.74(1H,m), 7.86(1H,d, J=8.8 Hz), 8.20–8.50(6H,m), 8.56(1H,s), 10.69(1H,br).

MS (FAB) m/z: 484 [(M+H)+, Cl35], 486 [(M+H)+, Cl37].
Elementary analysis for $C_{26}H_{30}ClN_3O_2S \cdot 2HCl \cdot 1/2H_2O$
Calculated: C, 55.18; H, 5.88; N, 7.42; Cl, 18.79; S, 5.66.
Found: C, 55.34; H, 5.70; N, 7.31; Cl, 18.76; S, 5.85.

Example 52

1-[[(2RS)-6-Aminomethyl-1,2,3,4-tetrahydronaphthalen-2-yl]carbonyl]-4-[(6-chloronaphthalen-2-yl)sulfonyl]piperazine hydrochloride In a similar manner to Example 7 except for the use of 1-[[(2RS)-6-(N-tert-butoxycarbonylaminomethyl)-1,2,3,4-tetrahydronaphthalen-2-yl]carbonyl]-4-[(6-chloronaphthalen-2-yl)sulfonyl]piperazine as the raw material, the title compound was obtained.

$^1$H-NMR (DMSO-$d_6$) δ: 1.55(1H,m), 1.80–1.90(1H,m), 2.60–2.90(4H,m), 2.90–3.10(5H,m), 3.50–3.80(4H,m), 3.90 (2H,s), 7.05(1H,d,J=7.8 Hz), 7.10–7.20(2H,m), 7.71(1H,d, J=8.8 Hz), 7.82(1H,d,J=8.3 Hz), 8.10–8.40(6H,m), 8.50(1H, s).

MS (FAB) m/z: 498 [(M+H)+, Cl35], 500 [(M+H)+, Cl37].
Elementary analysis for $C_{26}H_{28}ClN_3O_3S \cdot 1.2HCl \cdot 0.8H_2O$
Calculated: C, 56.15; H, 5.58; N, 7.55; Cl, 14.02; S, 5.76.
Found: C, 55.93; H, 5.22; N, 7.37; Cl, 14.26; S, 5.70.

Example 53

1-[(7-Aminomethylnaphthalen-2-yl)carbonyl]-4-[(6-chloronaphthalen-2-yl)sulfonyl]piperazine hydrochloride In a similar manner to Example 7 except for the use of 1-[[7-N-tert-butoxycarbonylaminomethyl)naphthalen-2-yl] carbonyl]-4-[(6-chloronaphthalen-2-yl)sulfonyl]piperazine as the raw material, the title compound was obtained.

$^1$H-NMR (DMSO-$d_6$) δ: 3.10(4H,br), 3.30–3.90(4H,br), 4.18(2H,s), 7.46(1H,d,J=8.8 Hz), 7.69(1H,d,J=8.8 Hz), 7.73 (1H,d,J=8.8 Hz), 7.83(1H,d,J=8.8 Hz), 7.89(1H,s), 7.90–8.00(3H,m), 8.19(1H,d,J=8.8 Hz), 8.20–8.30(2H,m), 8.50(4H,br s).

MS (FAB) m/z: 494 [(M+H)+, Cl35], 496 [(M+H)+, Cl37].
Elementary analysis for $C_{26}H_{24}ClN_3O_3S \cdot HCl \cdot 3/4H_2O$
Calculated: C, 57.41; H, 4.91; N, 7.72; Cl, 13.03; S, 5.89.
Found: C, 57.40; H, 4.87; N, 7.71; Cl, 13.09; S, 5.89.

Example 54

1-[(7-Aminomethylnaphthalen-2-yl)methyl]-4-[(6-chloronaphthalen-2-yl)sulfonyl]piperazine hydrochloride In a similar manner to Example 7 except for the use of 1-[[7-N-tert-butoxycarbonylaminomethyl)naphthalen-2-yl]methyl]-4-[(6-chloronaphthalen-2-yl)sulfonyl]piperazine as the raw material, the title compound was obtained.

$^1$H-NMR (DMSO-d$_6$) δ: 2.92(2H,m), 3.22(2H,m), 3.83 (2H,m), 4.20(2H,d,J=5.4 Hz), 4.51(2H,br), 7.60–7.90(4H, m), 7.90–8.40(7H,m), 8.52(1H,s), 8.57(3H,br), 11.52(1H, br).

MS (FAB) m/z: 480 [(M+H)$^+$, Cl$^{35}$], 482 [(M+H)$^+$, Cl$^{37}$].
Elementary analysis for C$_{26}$H$_{26}$ClN$_3$O$_2$S.2HCl.1/4H$_2$O
Calculated: C, 56.02; H, 5.15; N, 7.54; Cl, 19.08; S, 5.75.
Found: C, 55.88; H, 5.45; N, 7.34; Cl, 18.90; S, 5.69.

Example 55

1-[(6-Aminomethylnaphthalen-2-yl]carbonyl]-4-[(6-chloronaphthalen-2-yl)sulfonyl]piperazine hydrochloride In a similar manner to Examples 3, 4 and 7 except for the use of 2-(N-tert-butoxycarbonylaminomethyl)-6-methoxycarbonylnaphthalene as the raw material, the reaction was conducted, whereby the title compound was obtained.

$^1$H-NMR (DMSO-d$_6$) δ: 3.09(4H,br), 3.40–3.90(4H,br), 4.19(2H,s), 7.47(1H,d,J=8.3 Hz), 7.66(1H,d,J=8.3 Hz), 7.73 (1H,d,J=9.3 Hz), 7.83(1H,d,J=8.8 Hz), 7.90–8.10(4H,m), 8.19(1H,d,J=8.8 Hz), 8.20–8.30(2H,m), 8.40–8.60(4H,m).

MS (FAB) m/z: 494 [(M+H)$^+$, Cl$^{35}$], 496 [(M+H)$^+$, Cl$^{37}$].
Elementary analysis for C$_{26}$H$_{24}$ClN$_3$O$_3$S.HCl.3/4H$_2$O.1/5Et$_2$O
Calculated: C, 57.60; H, 5.14; N, 7.52; Cl, 12.69; S, 5.74.
Found: C, 57.64; H, 5.10; N, 7.12; Cl, 12.69; S, 5.82.

Example 56

1-[(6-Chloronaphthalen-2-yl]sulfonyl]-4-[4-[[(3S)-pyrrolidin-3-yl]oxy]benzoyl]piperazine hydrochloride In a similar manner to Example 7 except for the use of 1-[4 [[(3S)-1-tert-butoxycarbonylpyrrolidin-3-yl]oxy]benzoyl]-4-[(6-chloronaphthalen-2-yl)sulfonyl]piperazine as the raw material, the title compound was obtained.

$^1$H-NMR (DMSO-d$_6$) δ: 2.05–2.25(2H,m), 3.00–3.10 (4H,m), 3.20–3.70(8H,m), 5.16(1H,br s), 6.95(2H,d,J=8.8 Hz), 7.31(2H,d,J=8.3 Hz), 7.70–7.75(1H,m), 7.82(1H,dd,J=8.5,1.7 Hz), 8.18(2H,d,J=8.8 Hz), 8.20–8.30(2H,m), 8.50 (1H,s).

MS (FAB) m/z: 500 [(M+H)$^+$, Cl$^{35}$], 502 [(M+H)$^+$, Cl$^{37}$].

Example 57

1-[(6-Chloronaphthalen-2-yl]sulfonyl]-4-[3-[[(3S)-pyrrolidin-3-yl]oxy]benzoyl]piperazine hydrochloride In a similar manner to Example 56 except for the use of 1-[3-[[(3S)-1-tert-butoxycarbonylpyrrolidin-3-yl]oxy]benzoyl]-4-[(6-chloronaphthalen-2-yl)sulfonyl]piperazine as the raw material, the title compound was obtained.

$^1$H-NMR (DMSO-d$_6$) δ: 2.00–2.20(2H,m), 2.95–3.15 (4H,m), 3.20–3.80(8H,m), 5.11(1H,br s), 6.90–6.95(3H,m), 7.00–7.05(1H,m), 7.30–7.35(1H,m), 7.72(1H,dd,J=8.8,2.0 Hz), 7.81(1H,dd,J=8.5,1.7 Hz), 8.18(2H,d,J=8.8 Hz), 8.25–8.30(2H,m), 8.50(1H,s).

MS (FAB) m/z: 500 [(M+H)$^+$, Cl$^{35}$], 502 [(M+H)$^+$, Cl$^{37}$].
Elementary analysis for C$_{25}$H$_{26}$ClN$_3$O$_4$S.HCl.H$_2$O
Calculated: C, 54.15; H, 5.27; N, 7.58; Cl, 12.79; S, 5.78.
Found: C, 53.84; H, 5.19; N, 7.33; Cl, 12.72; S, 5.86.

Example 58

1-[(6-Chloronaphthalen-2-yl]sulfonyl]-4-[4-[[(3R)-pyrrolidin-3-yl]oxy]benzoyl]piperazine hydrochloride In a similar manner to Example 56 except for the use of 1-[4-[[(3R)-1-tert-butoxycarbonylpyrrolidin-3-yl]oxy]benzoyl]-4-[(6-chloronaphthalen-2-yl)sulfonyl]piperazine as the raw material, the title compound was obtained.

$^1$H-NMR (DMSO-d$_6$) δ: 2.05–2.25(2H,m), 3.00–3.10 (4H,m), 3.20–3.70(8H,m), 5.16(1H,br s), 6.96(2H,d,J=8.8 Hz), 7.31(2H,d,J=8.8 Hz), 7.74(1H,dd,J=8.8,2.0 Hz), 7.82 (1H,dd,J=8.8,1.5 Hz), 8.18(1H,d,J=8.8 Hz), 8.25–8.30(2H, m), 8.50(1H,s).

MS (FAB) m/z: 500 [(M+H)$^+$, Cl$^{35}$], 502 [(M+H)$^+$, Cl$^{37}$].
Elementary analysis for C$_{25}$H$_{26}$ClN$_3$O$_4$S.1.2HCl.0.8H$_2$O
Calculated: C, 53.80; H, 5.20; N, 7.53; Cl, 13.97; S, 5.74.
Found: C, 53.84; H, 5.05; N, 7.51; Cl, 13.79; S, 5.74.

Example 59

1-[(6-Chloronaphthalen-2-yl]sulfonyl]-4-[3-[[(3R)-pyrrolidin-3-yl]oxy]benzoyl]piperazine hydrochloride In a similar manner to Example 56 except for the use of 1-[3-[[(3R)-1-tert-butoxycarbonylpyrrolidin-3-yl]oxy]benzoyl]-4-[(6-chloronaphthalen-2-yl)sulfonyl]piperazine as the raw material, the title compound was obtained.

$^1$H-NMR (DMSO-d$_6$) δ: 2.00–2.20(2H,m), 2.95–3.15 (4H,m), 3.20–3.80(8H,m), 5.11(1H,br s), 6.90–6.95(2H,m), 7.00–7.05(1H,m), 7.30–7.35(1H,m), 7.74(1H,dd,J=8.8,2.0 Hz), 7.82.(1H,dd,J=8.8,1,5 Hz), 8.18(2H,d,J=8.8 Hz), 8.25–8.30(2H,m), 8.50(1H,s).

MS (FAB) m/z: 500 [(M+H)$^+$, Cl$^{35}$], 502 [(M+H)$^+$, Cl$^{37}$].
Elementary analysis for C$_{25}$H$_{26}$ClN$_3$O$_4$S.HCl.H$_2$O
Calculated: C, 54.15; H, 5.27; N, 7.58; Cl, 12.79; S, 5.78.
Found: C, 53.91; H, 5.14; N, 7.37; Cl, 12.62; S, 5.67.

Example 60

1-[4-(2-Aminopyrimidin-5-yl)benzoyl]-4-[(6-chloronaphthalen-2-yl]sulfonyl]piperazine hydrochloride In a similar manner to Example 4 except for the use of 4-(2-amino-5-pyrimidyl)benzoic acid and 1-[(6-chloronaphthalen-2-yl]sulfonyl]piperazine hydrochloride as the raw materials, the reaction was conducted, whereby the title compound was obtained.

$^1$H-NMR (DMSO-d$_6$) δ: 3.06(4H,br), 3.56 and (each 2H,br), 4.70–5.45(3H,br), 7.40(2H,d,J=8.8 Hz), 7.67(2H,d, J=8.8 Hz), 7.73(1H,dd,J=8.8,2.0 Hz), 7.82(1H,d,J=8.8 Hz), 8.18(1H,d,J=8.8 Hz), 8.27(1H,s), 8.28(1H,d,J=8.8 Hz), 8.50 (1H,s), 8.72(1H,s).

MS (FAB) m/z: 508 [(M+H)$^+$, Cl$^{35}$], 510 [(M+H)$^+$, Cl$^{37}$].
Elementary analysis for C$_{25}$H$_{22}$ClN$_5$O$_3$S.1HCl.0.7H$_2$O
Calculated: C, 53.55; H, 4.40; Cl, 13.28; N, 12.49; S, 5.72.
Found: C, 53.59; H, 4.58; Cl, 13.02; N, 12.58; S, 5.89.

Example 61

1-[(6-Chloronaphthalen-2-yl]sulfonyl]-4-[(piperidin-4-yl)acetyl]piperazine hydrochloride In a similar manner to Example 7 except for the use of 1-[(1-tert-butoxycarbonylpiperidin-4-yl)acetyl]-4-[(6-chloronaphthalen-2-yl]sulfonyl]piperazine as the raw material, the title compound was obtained.

$^1$H-NMR (DMSO-d$_6$) δ: 1.25(2H,m), 1.71(2H,m), 1.87 (1H,m), 2.20(2H,d,J=6.8 Hz), 2.78(2H,br), 2.96(4H,br s), 3.14(2H,m), 3.52(4H,br s), 4.02(2H,br), 7.73(1H,dd,J=88, 2.0 Hz), 7.81(1H,d,J=8.8 Hz), 8.17(1H,d,J=8.8 Hz), 8.28 (1H,d,J=8.8 Hz), 8.26(1H,s), 8.50(1H,s), 8.54(1H,br), 8.75 (1H,br).

MS (FAB) m/z: 436 [(M+H)$^+$, Cl$^{35}$], 438 [(M+H)$^+$, Cl$^{37}$].
Elementary analysis for C$_{21}$H$_{26}$ClN$_3$O$_3$S.1.1HCl.1.1H$_2$O
Calculated: C, 50.86; H, 5.96; Cl, 15.01; N, 8.47; S, 6.47.
Found: C, 51.07; H, 5.74; Cl, 14.75; N, 8.36; S, 6.50.

Example 62

1-[(6-Chloronaphthalen-2-yl]sulfonyl]-4-[3-(piperidin-4-yl)propionyl]piperazine hydrochloride In a similar manner to Example 7 except for the use of 1-[3-(1-tert-butoxycarbonylpiperidin-4-yl)propionyl]-4-[(6-chloronaphthalen-2-yl]sulfonyl]piperazine as the raw material, the title compound was obtained.

$^1$H-NMR (CD$_3$OD) δ: 1.29(2H,m), 1.50(1H,m), 1.51(2H, m), 1.89(2H,m), 2.36(2H,m), 2.88(2H,m), 3.08(4H,m), 3.64 (4H,m), 4.04(2H,br), 7.58(1H,dd,J=8.8,2.0 Hz), 7.82(1H,dd, J=8.8,2.0 Hz), 8.05(1H,d,J=8.8 Hz), 8.06(1H,s), 8.09(1H,d, J=8.8 Hz), 8.42(1H,s).

MS (FAB) m/z: 450 [(M+H)$^+$, Cl$^{35}$], 452 [M+H]$^+$, Cl$^{37}$].
Elementary analysis for C$_{22}$H$_{28}$ClN$_3$O$_3$S.1.8HCl.0.9H$_2$O
Calculated: C, 49.68; H, 5.99; Cl, 18.66; N, 7.90; S, 6.03.
Found: C, 49.45; H, 5.70; Cl, 18.63; N, 7.72; S, 6.04.

Example 63

1-[(6-Chloronaphthalen-2-yl]sulfonyl]-4-[(E)-3-(pyridin-3-yl)propenoyl]piperazine hydrochloride In a similar manner to Example 4 except for the use of (E-3-(3-pyridyl)acrylic acid and 1-[(6-chloronaphthalen-2-yl)sulfonyl]piperazine hydrochloride as the raw materials the title compound was obtained.

$^1$H-NMR (DMSO-d$_6$) δ: 3.03(4H,m), 3.69(2H,br), 3.85 (2H,br), 7.51(2H,s), 7.70(1H,dd,J=8.8,2.0 Hz), 7.83(1H,dd, J=8.8,2.0 Hz), 7.89(1H,dd,J=7.8,5.4 Hz), 8.16(1H,d,J=8.8 Hz), 8.22(1H,d,J=2.0 Hz), 8.26(1H,d,J=8.8 Hz), 8.51(1H,s), 8.67(1H,d,J=7.8 Hz), 8.77(1H,d,J=5.4 Hz), 9.13(1H,s).

MS (FAB) m/z: 442 [(M+H)$^+$, Cl$^{35}$], 444 [(M+H)$^+$, Cl$^{37}$].
Elementary analysis for C$_{22}$H$_{20}$ClN$_3$O$_3$S.HCl.1/4H$_2$O
Calculated: C, 54.72; H, 4.49; N, 8.70; Cl, 14.68; S, 6.64.
Found: C, 54.81; H, 4.43; N, 8.54; Cl, 14.68; S, 6.74.

Example 64

1-[(6-Chloronaphthalen-2-yl]sulfonyl]-4-[(E)-3-(pyridin-4-yl)propenoyl]piperazine hydrochloride In a similar manner to Example 4 except for the use of (E)-3-(4-pyridyl)acrylic acid and 1-[(6-chloronaphthalen-2-yl)sulfonyl]piperazine hydrochloride as the raw materials, the title compound was obtained.

$^1$H-NMR (DMSO-d$_6$) δ: 3.03(4H,m), 3.68(2H,br), 3.82 (2H,br), 5.76(1H,s), 7.48(1H,d,J=15.1 Hz), 7.65(1H,d,J= 15.1 Hz), 7.72(1H,dd,J=8.8,2.0 Hz), 7.83(1H,dd,J=8.8,2.0 Hz), 8.11(2H,br s), 8.16(1H,d,J=8.8 Hz), 8.24(1H,s), 8.27 (1H,d,J=8.8 Hz), 8.52(1H,s), 8.82(2H,d,J=5.9 Hz).

MS (FAB) m/z: 442 [(M+H)$^+$, Cl$^{35}$], 444 [(M+H)$^+$, Cl$^{37}$].
Elementary analysis for C$_{22}$H$_{20}$ClN$_3$O$_3$S.HCl.1/5H$_2$O
Calculated: C, 54.82; H, 4.48; Cl, 14.71; N, 8.72; S, 6.65.
Found: C, 54.77; H, 4.41; Cl, 14.71; N, 8.50; S, 6.77.

Example 65

1-[(6-Chloronaphthalen-2-yl]sulfonyl]-4-[(pyridin-4-yl)acetyl]piperazine hydrochloride In a similar manner to Example 4 except for the use of 4-pyridylacetic acid hydrochloride and 1-[(6-chloronaphthalen-2-yl)sulfonyl]piperazine hydrochloride as the raw materials, the title compound was obtained.

$^1$H-NMR (DMSO-d$_6$) δ: 2.99(2H,br), 3.04(2H,br), 3.57 (2H,br), 3.62(2H,br), 4.00(2H,s), 7.71(2H,d,J=5.9 Hz), 7.74 (1H,dd,J=8.8,3.0 Hz), 7.83(1H,dd,J=8.8,2.0 Hz), 8.18(1H, d,J=8.8 Hz), 8.27(1H,s), 8.29(1H,d,J=8.8 Hz), 8.53(1H,s), 8.72(2H,d,J=5.9 Hz).

MS (FAB) m/z: 430 [(M+H)$^+$, Cl$^{35}$], 432 [(M+H)$^+$, Cl$^{37}$].
Elementary analysis for C$_{21}$H$_{20}$ClN$_3$O$_3$S.HCl.0.3H$_2$O
Calculated: C, 53.46; H, 4.61; Cl, 15.03; N, 8.91; S, 6.80.
Found: C, 53.28; H, 4.49; Cl, 15.18; N, 8.91; S, 6.75.

Example 66

1-[(6-Chloronaphthalen-2-yl]sulfonyl]-4-[4-[(3RS)-pyrrolidin-3-yl)benzoyl]piperazine hydrochloride In a similar manner to Example 7 except for the use of 1-[4-[(3RS)-1-tert-butoxycarbonylpyrrolidin-3-yl]benzoyl]-4-[(6-chloronaphthalen-2-yl)sulfonyl]piperazine as the raw materials, the title compound was obtained.

$^1$H-NMR (DMSO-d6) δ: 1.85–1.95(1H,m), 2.30–2.40 (1H,m), 3.00–3.90(13H,m), 7.72(1H,dd,J=8.6,2.2 Hz), 7.80 (1H,dd,J=8.8,2.0 Hz), 7.29(2H,d,J=8.3 Hz), 7.35(2H,d,J= 8.3 Hz), 8.18(1H,d,J=8.8 Hz), 8.25–8.30(2H,m), 8.49(1H,s).

MS (FAB) m/z: 484 [(M+H)$^+$, Cl$^{35}$], 486 [(M+H)$^+$, Cl$^{37}$].
Elementary analysis for C$_{25}$H$_{26}$ClN$_3$O$_3$S.HCl.3/2H$_2$O
Calculated: C, 54.84; H, 5.52; N, 7.67; Cl, 12.95; S, 5.86.
Found: C, 55.00; H, 5.53; N, 7.48; Cl, 13.23; S, 5.97.

Example 67

1-[(6-Chloronaphthalen-2-yl]sulfonyl]-4-[(isoquinolin-7-yl)carbonyl]piperazine hydrochloride In 4N hydrochloric acid, methyl 7-isoquinolinecarboxylate (206 mg) was dissolved, followed by heating under reflux for 4 hours. In a similar manner to Example 4 except for the use of the residue obtained by distilling off the solvent under reduced pressure and 1-[(6-chloronaphthalen-2-yl)sulfonyl]piperazine hydrochloride as the raw materials, the reaction was conducted, whereby the title compound (298 mg, 62%) was obtained.

$^1$H-NMR (DMSO-d$_6$) δ: 2.95–3.25(4H,m), 3.40–3.60 (2H,m), 3.70–3.90(2H,m), 7.73(1H,dd,J=8.8,2.0 Hz), 7.84 (1H,d,J=8.8 Hz), 8.05(1H,d,J=7.3 Hz), 8.20(1H,d,J=8.8 Hz), 8.25–8.35(3H,m), 8.41(1H,d,J=6.4 Hz), 8.45(1H,s), 8.52 (1H,s), 8.71(1H,d,J=6.4 Hz), 9.79(1H,s).

MS (FAB) m/z: 465 [(M+H)$^+$, Cl$^{35}$], 467 [(M+H)$^+$, Cl$^{37}$].

Elementary analysis for C$_{24}$H$_{20}$ClN$_3$O$_3$S.HCl.2.2H$_2$O

Calculated: C, 53.18; H, 4.72; N, 7.75; Cl, 13.08; S, 5.92.

Found: C, 53.11; H, 4.70; N, 7.60; Cl, 13.01; S, 6.16.

Example 68

1-[(6-Chloronaphthalen-2-yl)sulfonyl]-4-[(quinolyl-2-yl)carbonyl]piperazine hydrochloride In a similar manner to Example 4 except for the use of quinoline-2-carboxylic acid and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 3.05(2H,m), 3.17(2H,m), 3.62 (2H,m), 3.83(2H,m), 7.61(1H,d,J=8.3 Hz), 7.60–7.80(2H, m), 7.80–7.90(2H,m), 7.95(1H,d,J=8.3 Hz), 8.00(1H,d,J= 7.3 Hz), 8.18(1H,d,J=8.8 Hz), 8.20–8.40(2H,m), 8.43(1H, d,J=8.3 Hz), 8.51(1H,s).

Elementary analysis for C$_{24}$H$_{20}$ClN$_3$O$_3$S

Calculated: C, 61.87; H, 4.33; N, 9.02; Cl, 7.61; S, 6.88.

Found: C, 61.76; H, 4.20; N, 8.73; Cl, 7.65; S, 6.99.

Example 69

1-[(6-Chloronaphthalen-2-yl)sulfonyl]-4-[(4-hydroxyquinolin-2-yl)carbonyl]piperazine hydrochloride In a similar manner to Example 4 except for the use of 4-hydroxyquinoline-2-carboxylic acid and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 3.00–3.30(4H,br), 3.53(2H,br), 3.77(2H,br), 6.45(1H,s), 7.48(1H,t,J=7.3 Hz), 7.70–7.90 (4H,m), 8.10–8.40(4H,m), 8.52(1H,s).

MS (FAB) m/z: 482 [(M+H)$^+$, Cl$^{35}$], 484 [(M+H)$^+$, Cl$^{37}$].

Elementary analysis for C$_{24}$H$_{20}$ClN$_3$O$_4$S.9/10HCl.1/3CH$_3$OH.3/2H$_2$O Calculated: C, 52.90; H, 4.60; N, 7.61; Cl, 12.19; S, 5.80.

Found: C, 53.17; H, 4.59; N, 7.39; Cl, 12.31; S, 6.07.

Example 70

1-[(6-Chloronaphthalen-2-yl)sulfonyl]-4-[(8-hydroxyquinolin-7-yl)carbonyl]piperazine hydrochloride In a similar manner to Example 4 except for the use of 8-hydroxyquinoline-7-carboxylic acid and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 2.90–3.30(4H,br), 3.35(2H,br), 3.79(2H,br), 7.39(1H,d,J=8.3 Hz), 7.53(1H,d,J=8.3 Hz), 7.60–7.90(3H,m), 8.10–8.40(3H,m), 8.50(1H,s), 8.60(1H,d, J=7.8 Hz), 8.96(1H,d,J=4.4 Hz).

MS (FAB) m/z: 482 [(M+H)$^+$, Cl$^{35}$], 484 [(M+H)$^+$, Cl$^{37}$].

Elementary analysis for C$_{24}$H$_{20}$ClN$_3$O$_4$S.HCl.CH$_3$OH.1/4H$_2$O

Calculated: C, 54.11; H, 4.63; N, 7.57; Cl, 12.78; S, 5.78.

Found: C, 54.40; H, 4.84; N, 7.66; Cl, 13.04; S, 5.99.

Example 71

1-[(Benzimidazol-5-yl)carbonyl]-4-[(6-chloronaphthalen-2-yl)sulfonyl]piperazine hydrochloride In a similar manner to Example 3, 4 or 10 except for the use of methyl N-triphenylmethyl-5-benzimidazolecarboxylate and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 3.08(4H,br), 3.30–4.00(4H,br), 7.48(1H,d,J=8,3 Hz), 7.60–7.90(4H,m), 8.10–8.30(3H,m), 8.50(1H,s), 9.51(1H,s).

MS (FAB) m/z: 455[(M+H)$^+$, Cl$^{35}$], 457 [(M+H)$^+$, Cl$^{37}$].

Elementary analysis for C$_{22}$H$_{19}$ClN$_4$O$_3$S.HCl.5/4H$_2$O

Calculated: C, 51.42; H, 4.41; N, 10.90; Cl, 13.80; S, 6.24.

Found: C, 51.53 H, 4.40; N, 10.71; Cl, 13.61; S, 6.40.

Example 72

1-[(Benzimidazol-5-yl)carbonyl]-4-[(6-chloronaphthalen-2-yl)sulfonyl]homopiperazine hydrochloride In a similar manner to Example 71 except for the use of methyl N-triphenylmethyl-5-benzimidazolecarboxylate and 1-[(6-chloronaphthalen-2-yl)sulfonyl]homopiperazine hydrochloride as the raw materials, the reaction was conducted, whereby the title compound was obtained.

$^1$H-NMR (DMSO-d$_6$) δ: 1.67(1H,m), 1.93(1H,m), 3.20–3.90(8H,m), 7.44(1/2H,m), 7.54(1/2H,m), 7.68(1H, m), 7.80–8.00(3H,m), 8.10–8.30(3H,m), 8.49(1/2H,s), 8.55 (1/2H,s), 9.56 and 9.57(1H, each s).

MS (FAB) m/z: 469 [(M+H)$^+$, Cl$^{35}$], 471 [(M+H)$^+$, Cl$^{37}$].

Elementary analysis for C$_{23}$H$_{21}$ClN$_4$O$_3$S.HCl.0.3CH$_3$OH.H$_2$O

Calculated: C, 52.50; H, 4.76; N, 10.51; Cl, 13.30; S, 6.01.

Found: C, 52.31; H, 4.66; N, 10.50; Cl, 13.34; S, 6.01.

Example 73

1-[(6-Chloronaphthalen-2-yl)sulfonyl]-4-[(thiazolo[5,4-c]pyridin-2-yl)carbonyl]piperazine hydrochloride In a similar manner to Example 4 except for the use of sodium thiazolo[5,4-c]pyridine-2-carboxylate and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 3.10–3.30(4H,m), 3.84(2H,m), 4.32(2H,m), 7.69(1H,dd,J=8.8,2.0 Hz), 7.83(1H,dd,J=8.8, 2.0 Hz), 8.10–8.30(4H,m), 8.51(1H,s), 8.79(1H,d,J=5.9 Hz), 9.62(1H,s).

MS (FAB) m/z: 473 [(M+H)$^+$, Cl$^{35}$], 475 [(M+H)$^+$, Cl$^{37}$].

Elementary analysis for C$_{21}$H$_{17}$ClN$_4$O$_3$S$_2$.HCl

Calculated: C, 49.51; H, 3.56; N, 11.00; Cl, 13.92; S, 12.59.

Found: C, 49.45; H, 3.71; N, 11.20; Cl, 13.67; S, 12.55.

Example 74

1-[(E)-4-Chlorostyrylsulfonyl]-4-[(thiazolo[5,4-c]pyridin-2-yl)carbonyl]piperazine hydrochloride In a similar manner to Example 4 except for the use of sodium thiazolo[5,4-c]pyridine-2-carboxylate and 1-[(E)-4- chlorostyrylsulfonyl)piperazine hydrochloride as the raw materials, the reaction was conducted, whereby the title compound was obtained.

$^1$H-NMR (DMSO-d$_6$) δ: 3.30(4H,m), 3.87(2H,m), 4.35 (2H,m), 7.35(1H,d,J=15.6 Hz), 7.40–7.50(3H,m), 7.79(1H, d,J=8.3 Hz), 8.2(1H,d,J=5.9 Hz), 8.77(1H,d,J=5.9 Hz), 9.59 (1H,s).

MS (FAB) m/z: 449 [(M+H)$^+$, Cl$^{35}$], 451 [(M+H)$^+$, Cl$^{37}$].

Elementary analysis for C$_{19}$H$_{17}$ClN$_4$O$_3$S$_2$.1/2HCl

Calculated: C, 48.85; H, 3.78; N, 11.99; Cl, 11.38; S, 13.73.

Found: C, 49.18; H, 3.80; N, 12.20; Cl, 11.05; S, 13.84.

Example 75

1-[(6-Chloronaphthalen-2-yl)sulfonyl-4-[(4,5,6,7-tetrahydrothieno[3,2-c]pyridin-2-yl)methyl] piperazine hydrochloride In a similar manner to Example 7 except for the use of 1-[(5-tert-butoxycarbonyl-4,5,6,7-tetrahydrothieno[3,2-c]pyridin-2-yl)methyl]-4-[(6-chloronaphthalen-2-yl)sulfonyl]piperazine as the raw material, the title compound was obtained.

$^1$H-NMR (DMSO-d$_6$) δ: 2.82–2.88(4H,m), 2.91–2.99 (4H,m), 3.28–3.36(2H,m), 3.47–3.55(4H,m), 4.02(2H,br s), 6.58(1H,s), 7.71(1H,dd,J=8.8,2.0 Hz), 7.81(1H,dd,J=8.8,2.0 Hz), 7.23–7.28(3H,m), 8.49(1H,s), 9.42(2H,br s).

MS (FAB) m/z: 462 [(M+H)$^+$, Cl$^{35}$], 464 [(M+H)$^+$, Cl$^{37}$].

Elementary analysis for C$_{22}$H$_2$Cl$_4$N$_3$O$_2$S$_2$.2HCl.1.5H$_2$O

Calculated: C, 47.02; H, 5.20; Cl, 18.93; N, 7.48; S, 11.41.

Found: C, 47.18; H, 5.41; Cl, 18.59; N, 7.37; S, 11.33.

Example 76

1-[(6-Chloronaphthalen-2-yl)sulfonyl-4-[trans-3-(4, 5,6,7-tetrahydrothieno[3,2-c]pyridin-2-yl)propenoyl] piperazine hydrochloride In a similar manner to Example 7 except for the use of 1-[trans-3-(5-tert-butoxycarbonyl-4,5,6,7-tetrahydrothieno [3,2-c]pyridin-2-yl)propenoyl]-4-[(6-chloronaphthalen-2-yl)sulfonyl]piperazine as the raw material, the reaction was conducted, whereby the title compound was obtained.

$^1$H-NMR (DMSO-d$_6$) δ: 2.95–3.10(6H,m), 3,32–3.51 (3H,m), 3.60–3.80(3H,m), 4.12(2H,s), 6.75(1H,d,J=15.1 Hz), 7.19(1H,s), 7.50(1H,d,J=15.1 Hz), 7.70(1H,dd,J=8.8, 2.4 Hz), 7.81(1H,dd,J=8.8,2.0 Hz), 8.15(1H,d,J=8.8 Hz), 8.22(1H,d,J=2.0 Hz), 8.50(1H,s), 9.53(2H,br s).

MS (FAB) m/z: 502 [(M+H)$^+$, Cl$^{35}$], 504 [(M+H)$^+$, Cl$^{37}$].

Elementary analysis for C$_{24}$H$_{24}$ClN$_3$O$_3$S$_2$.HCl.0.5H$_2$O

Calculated: C, 52.65; H, 4.79; Cl, 12.95; N, 7.67; S, 11.71.

Found: C, 52.36; H, 4.88; Cl, 12.63; N, 8.01; S, 11.39.

Example 77

1-[(6-Chloronaphthalen-2-yl)sulfonyl]-4-[3-(4,5,6,7-tetrahydrothieno[3,2-c]pyridin-2-yl)propionyl] piperazine hydrochloride In a similar manner to Example 7 except for the use of 1-[3-(5-tert-butoxycarbonyl-4,5,6,7-tetrahydrothieno[3,2-c]pyridin-2-yl)propionyl]-4-[(6-chloronaphthalen-2-yl)sulfonyl]piperazine as the raw material, the reaction was conducted, whereby the title compound was obtained.

$^1$H-NMR (DMSO-d$_6$) δ: 2.80–3.60(16H,m), 4.12(2H,br s), 7.11(1H,br s), 7.74(1H,dd,J=8.8,2.0 Hz), 7.83(1H,dd,J= 8.8,2.0 Hz), 8.20(1H,s), 8.25–8.30(2H,m), 8.53(1H,s), 9.67 (2H,br s).

MS (FAB) m/z: 504 [(M+H)$^+$, Cl$^{35}$], 506 [(M+H)$^+$, Cl$^{37}$].

Elementary analysis for C$_{24}$H$_{26}$ClN$_3$O$_3$S$_2$.1.2HCl.1.3H$_2$O

Calculated: C, 50.46; H, 5.26; Cl, 13.65; N, 7.36.

Found: C, 50.83; H, 5.26; Cl, 13.43; N, 6.97.

Example 78

1-[(6-Chloronaphthalen-2-yl)sulfonyl]-4-[3-(4,5,6,7-tetrahydrothieno[3,2-c]pyridin-2-yl)propyl] piperazine hydrochloride In a similar manner to Example 7 except for the use of 1-[3-(5-tert-butoxycarbonyl-4,5,6,7-tetrahydrothieno[3,2-c]pyridin-2-yl)propyl]-4-[(6-chloronaphthalen-2-yl)sulfonyl]piperazine as the raw material, the title compound was obtained.

$^1$H-NMR (DMSO-d$_6$) δ: 1.90–2.07(2H,m), 2.72–2.80 (2H,m), 2.82–3.21(8H,m), 3.35(2H,br s), 3.51(2H,d,J=11.5 Hz), 3.82(2H,d,J=11.5 Hz), 4.06(2H,s), 6.66(1H,s), 7.74 (1H,dd,J=8.8,1.5 Hz), 7.85(1H,dd,J=8.8,1.5 Hz), 8.20(1H, d,J=8.8 Hz), 8.25–8.39(2H,m), 8.55(1H,s), 9.50(2H,br s), 11.26(1H,br s).

MS (FAB) m/z: 490 [(M+H)$^+$, Cl$^{35}$], 492 [(M+H)$^+$, Cl$^{37}$].

Elementary analysis for C$_{24}$H$_{28}$ClN$_3$O$_2$S$_2$.2HCl.1.6H$_2$O

Calculated: C, 48.71; H, 5.65; Cl, 17.97; N, 7.10; S, 10.84.

Found: C, 49.01; H, 5.77; Cl, 17.62; N, 6.96; S, 10.82.

Example 79

1-[(6-Chloronaphthalen-2-yl)sulfonyl]-4-[N-[(4,5,6, 7-tetrahydrothieno[3,2-c]pyridin-2-yl)methyl] carbamoyl]piperazine hydrochloride In a similar manner to Example 7 except for the use of 1-[N-(5-tert-butoxycarbonyl-4,5,6,7-tetrahydrothieno[3,2-c]pyridin-2-yl)methyl]carbamoyl]-4-[(6-chloronaphthalen-2-yl)sulfonyl]piperazine as the raw material, the title compound was obtained.

$^1$H-NMR (DMSO-d$_6$) δ: 2.78–2.86(2H,br s), 2.88–2.94 (4H,m), 3.29–3.35(2H,m), 3,37–3.42(4H,m), 4.03(2H,br s), 4.19(2H,d,J=5.4 Hz), 6.62(1H,s), 7.25(1H,t,J=5.4 Hz), 7.72 (1H,dd,J=8.8,2.0 Hz), 7.82(1H,dd,J=8.8,2.0 Hz), 8.16(1H, d,J=8.8 Hz), 8.22–8.26(2H,m), 8.50(1H,s), 9.27(2H,br s).

Elementary analysis for C$_{23}$H$_{25}$ClN$_4$O$_3$S$_2$.HCl.1.3H$_2$O

Calculated: C, 48.90; H, 5.10; Cl, 12.55; N, 9.92.

Found: C, 49.02; H, 5.20; Cl, 12.50; N, 9.76.

Example 80

1-[(6-Chloronaphthalen-2-yl)sulfonyl]-4-[(4,5,6,7-tetrahydrothieno[3,2-c]pyridin-2-yl)carbonyl] piperazine hydrochloride In a similar manner to Example 7 except for the use of 1-[(5-tert-butoxycarbonyl-4,5,6,7-tetrahydrothieno[3,2-c]pyridin-2-yl)carbonyl]-4-[(6-chloronaphthalen-2-yl)sulfonyl]piperazine as the raw material, the title compound was obtained.

$^1$H-NMR (DMSO-d6) δ: 2.99–3.05(2H,m), 3.08(4H,t,J= 4.6 Hz), 3.35–3.40(2H,m), 3.71(4H,t,J=4.6 Hz), 4.11(2H,s), 7.17(1H,s), 7.71(1H,dd,J=8.8,2.0 Hz), 7.82(1H,dd,J=8.8,2.0 Hz), 8.22–8.28(3H,m), 8.50(1H,s), 9.38(2H,br s).

MS (FAB) m/z: 476 [(M+H)$^+$, Cl$^{35}$], 478 [(M+H)$^+$, Cl$^{37}$].

Elementary analysis for C$_{22}$H$_{23}$ClN$_3$O$_3$S$_2$.HCl.3/2H$_2$O

Calculated: C, 48.98; H, 4.86; Cl, 13.14; N, 7.79; S, 11.89.
Found: C, 48.96; H, 4.67; Cl, 13.21; N, 7.74; S, 11.93.

Example 81

4-[(6-Chloronaphthalen-2-yl)sulfonyl]-2-ethoxycarbonyl-1-[(4,5,6,7-tetrahydrothieno[3,2-c]pyridin-2-yl)carbonyl]piperazine hydrochloride In a similar manner to Example 7 except for the use of 1-[(5-tert-butoxycarbonyl-4,5,6,7-tetrahydrothieno[3,2-c]pyridin-2-yl)carbonyl]-4-[(6-chloronaphthalen-2-yl)sulfonyl]-2-ethoxycarbonylpiperazine as the raw material, the reaction was conducted, whereby the title compound was obtained.

$^1$H-NMR (DMSO-$d_6$) δ: 1.22(3H,t,J=7.0 Hz), 2.38–2.58 (1H,m), 2.65–2.72(1H,m), 3.04(2H,br s), 3.29–3.43(3H,m), 3.70(1H,br s), 4.01–4.30(6H,m), 5.18(1H,br s), 7.27(1H,s), 7.73(1H,dd,J=8.8,2.0 Hz), 7.82(1H,d,J=8.8 Hz), 8.26(1H,s), 8.29(1H,s), 8.54(1H,s), 9.59(2H,br s).

MS (FAB) m/z: 548 [(M+H)$^+$, Cl$^{35}$], 550 [(M+H)$^+$, Cl$^{37}$].

Elementary analysis for $C_{25}H_{26}N_3ClO_5S_2.1.2HCl.0.6H_2O$

Calculated: C, 49.83; H, 4.75; Cl, 12.94; N, 6.97; S, 10.64.
Found: C, 49.62; H, 4.71; Cl, 13.30; N, 7.19; S, 10.56.

Example 82

2-Carboxy-4-[(6-Chloronaphthalen-2-yl)sulfonyl]-1-[(4,5,6,7-tetrahydrothieno[3,2-c]pyridin-2-yl)carbonyl]piperazine hydrochloride In a similar manner to Example 3 except for the use of 4-[(6-chloronaphthalen-2-yl)sulfonyl]-2-ethoxycarbonyl-1-[(4,5,6,7-tetrahydrothieno[3,2-c]pyridin-2-yl)carbonyl]piperazine hydrochloride as the raw material, the reaction was conducted, whereby the title compound was obtained.

$^1$H-NMR (DMSO-$d_6$) δ: 2.30–2.53(1H,m), 2.58–2.69 (1H,m), 3.04(2H,br s), 3.29–3.83(4H,m), 4.07–4.32(4H,m), 4.90–5.20(1H,m), 7.03–7.30(1H,m), 7.71(1H,dd,J=8.8,2.4 Hz), 7.81(1H,d,J=8.8 Hz), 8.81(1H,d,J=8.8 Hz), 8.20–8.29 (2H,m), 8.52(1H,s), 9.58(2H,br s).

MS (FAB) m/z: 520 [(M+H)$^+$, Cl$^{35}$], 522 [(M+H)$^+$, Cl$^{37}$].

Elementary analysis for $C_{23}H_{22}N_3ClO_5S_2.1.2HCl.0.8H_2O$

Calculated: C, 47.78; H, 4.32; Cl, 13.49; N, 7.27; S, 11.09.
Found: C, 47.41; H, 4.36; Cl, 13.81; N, 7.14; S, 11.01.

Example 83

1-[(6-Chloronaphthalen-2-yl)sulfonyl]-4-[(5-aminohydroxyiminomethyl-4,5,6,7-tetrahydrothieno[3,2-c]pyridin-2-yl)carbonyl]piperazine To methanol (4 ml), a solution of 1-[(6-chloronaphthalen-2-yl)sulfonyl]-4-[(5-cyano-4,5,6,7-tetrahydrothieno[3,2-c]pyridin-2-yl)carbonyl]piperazine (41 mg) in dichloromethane (dichloromethane: 1 ml) was added, followed by the addition of hydroxylamine hydrochloride (28 mg) and triethylamine (0.55 ml). The resulting mixture was stirred at room temperature for 2 hours. The residue obtained by concentrating the reaction mixture under reduced pressure was purified by chromatography on a silica gel column (dichloromethane~dichloromethane : methanol =100:3), whereby the title compound (14 mg, 32%) was obtained.

$^1$H-NMR (DMSO-$d_6$) δ: 2.74–2.79(2H,m), 3.06(4H,s), 3.35–3.38(2H,m), 3.71(4H,s), 4.07(2H,s), 5.32(2H,s), 7.08 (1H,s), 7.71(1H,dd,J=8.8,1.6 Hz), 7.81(1H,dd,J=8.8,1.6 Hz), 8.16(1H,s), 8.23–8.25(2H,m), 8.33(1H,br s), 8.49(1H, s).

MS (FAB) m/z: 534 [(M+H)$^+$, Cl$^{35}$], 536 [(M+H)$^+$, Cl$^{37}$].

Example 84

1-[(6-Chloronaphthalen-2-yl)sulfonyl]-4-[N-(4,5,6,7-tetrahydrothieno[3,2-c]pyridin-2-yl)carbamoyl]piperazine hydrochloride In a similar manner to Example 7 except for the use of 1-[N-(5-tert-butoxycarbonyl-4,5,6,7-tetrahydrothieno[3,2-c]pyridin-2-yl)carbamoyl]-4-[(6-chloronaphthalen-2-yl)sulfonyl]piperazine as the raw material, the reaction was conducted, whereby the title compound was obtained.

$^1$H-NMR (DMSO-$d_6$) δ: 2.83(2H,br s), 2.99(4H,br s), 3.30(2H,br s), 3.54(4H,br s), 4.00(2H,s), 6.33(1H,s), 7.70 (1H,dd,J=8.8,2.0 Hz), 7.82(1H,d,J=8.8 Hz), 8.16(1H,d,J= 8.8 Hz), 8.22(1H,s), 8.26(1H,d,J=8.8 Hz), 8.50(1H,s), 9.18 (2H,br s), 9.82(1H,s).

MS (FAB) m/z: 491 [(M+H)$^+$, Cl$^{35}$], 493 [(M+H)$^+$, Cl$^{37}$].

Elementary analysis for $C_{22}H_{23}N_4ClO_3S_2.HCl.0.3H_2O$

Calculated: C, 49.59; H, 4.65; Cl, 13.31; N, 10.51; S, 12.03.
Found: C, 49.32; H, 4.63; Cl, 13.34; N, 10.81; S, 12.03.

Example 85

1-[(6-Chloronaphthalen-2-yl)sulfonyl]-4-[N-methyl-N-(4,5,6,7-tetrahydrothieno[3,2-c]pyridin-2-yl)carbamoyl]piperazine hydrochloride In a similar manner to Example 7 except for the use of 1-[N-(5-tert-butoxycarbonyl-4,5,6,7-tetrahydrothieno[3,2-c]pyridin-2-yl)-N-methylcarbamoyl]-4-[(6-chloronaphthalen-2-yl)sulfonyl]piperazine as the raw material, the reaction was conducted, whereby the title compound was obtained.

$^1$H-NMR (DMSO-$d_6$) δ: 2.83(2H,t,J=5.4 Hz), 2.97(4H,br s), 3.10(3H,s), 3.28–3.41(6H,m), 4.00(2H,s), 6.35(1H,s), 7.72(1H,dd,J=8.8,2.0 Hz), 7.81(1H,dd,J=8.8,2.0 Hz), 8.17 (1H,d,J=8.8 Hz), 8.23–8.31(2H,m), 8.50(1H,s), 9.28(2H,br s).

MS (FAB) m/z: 505 [(M+H)$^+$, Cl$^{35}$], 507 [(M+H)$^+$, Cl$^{37}$].

Elementary analysis for $C_{23}H_{25}N_4ClO_3S_2.1.1HCl.0.5H_2O$

Calculated: C, 49.85; H, 4.93; Cl, 13.43; N, 10.11; S, 11.57.
Found: C, 49.55; H, 4.92; Cl, 13.23; N, 10.13; S, 11.83.

Example 86

1-[(6-Chloronaphthalen-2-yl)sulfonyl]-4-[[5-(1-pyrrolin-2-yl)-4,5,6,7-tetrahydrothieno[3,2-c]pyridin-2-yl]carbonyl]piperazine hydrochloride In a similar manner to Example 47 except for the use of 1-[(6-chloronaphthalen-2-yl)sulfonyl]-4-[(4,5,6,7-tetrahydrothieno[3,2-c]pyridin-2-yl)carbonyl]piperazine hydrochloride as the raw material, the title compound was obtained.

$^1$H-NMR (DMSO-$d_6$) δ: 2.07–2.18(2H,m), 2.90–3.11(8H, m), 3.62(2H,t,J=6.8 Hz), 3.72(4H,br), 3.80(2H,t,J=5.9 Hz), 3.99(2H,t,J=5.9 Hz), 4.62(1H,br s), 4.73(1H,br s), 7.10(1H, s), 7.50(1H,s), 7.72(1H,dd,J=8.8,2.0 Hz), 7.82(1H,dd,J=8.8, 2.0 Hz), 8.18(1H,d,J=8.8 Hz), 8.22–8.28(2H,m), 8.51(1H,s), 10.37(1H,br s), 10.53(1H,br s).

MS (FAB) m/z: 542 [(M+H)$^+$, Cl$^{35}$], 544 [(M+H)$^+$, Cl$^{37}$].

Elementary analysis for C$_{26}$H$_{27}$ClN$_4$O$_3$S$_2$.1.3HCl.0.4H$_2$O

Calculated: C, 52.25; H, 4.91; Cl, 13.64; N, 9.37; S, 10.73.

Found: C, 52.34; H, 5.03; Cl, 13.56; N, 9.36; S, 10.74.

Example 87

1-[(6-Chloronaphthalen-2-yl)sulfonyl]-4-[(4,5,6,7-tetrahydrothiazolo[5,4-c]pyridin-2-yl)carbonyl] piperazine hydrochloride In a similar manner to Example 7 except for the use of 1-[(6-tert-butoxycarbonyl-4,5,6,7-tetrahydrothiazolo[5,4-c]pyridin-2-yl)carbonyl]-4-[(6-chloronaphthlen-2-yl)sulfonyl]piperazine as the raw material, the title compound was obtained.

$^1$H-NMR (DMSO-d$_6$) δ: 3.01(2H,t,J=5.9 Hz), 3.11(4H,br), 3.44(2H,br s), 3.74(2H,br s), 4.32–4.46(4H,m), 7.71 (1H,dd,J=8.8,2.0 Hz), 7.83(1H,dd,J=8.8 Hz,2.0 Hz), 8.15 (1H,d,J=8.8 Hz), 8.23(1H,s), 8.26(1H,d,J=8.8 Hz), 8.30(1H,s).

MS (FAB) m/z: 477 [(M+H)$^+$, Cl$^{35}$], 479 [(M+H)$^+$, Cl$^{37}$].

Elementary analysis for C$_{21}$H$_{21}$ClN$_4$O$_3$S$_2$.HCl.0.2H$_2$O

Calculated: C, 48.78; H, 4.37; Cl, 13.71; N, 10.84; S, 12.40.

Found: C, 48.60; H, 4.50; Cl, 13.58; N, 10.62; S, 12.29.

Example 88

1-[(6-Chloronaphthalen-2-yl)sulfonyl]-4-[(6-aminohydroxyiminomethyl-4,5,6,7-tetrahydrothiazolo[5,4-c]pyridin-2-yl)carbonyl] piperazine hydrochloride; and 1-[(6-carbamoyl-4,5,6,7-tetrahydrothiazolo[5,4-c]pyridin-2-yl)carbonyl]-4-[(6-chloronaphthalen-2-yl)sulfonyl]piperazine In a similar manner to Referential Example 112 and Example 83 except for the use of 1-[(6-chloronaphthalen-2-yl)sulfonyl]-4-[(4,5,6,7-tetrahydrothiazolo[5,4-c]pyridin-2-yl)carbonyl]piperazine hydrochloride as the raw material, the reaction was effected, whereby 1-[(6-chloronaphthalen-2-yl)sulfonyl]-4-[(6-aminohydroxyiminomethyl-4,5,6,7-tetrahydrothiazolo[5,4-c]pyridin-2-yl]carbonyl]piperazine hydrochloride and 1-[(6-carbamoyl-4,5,6,7-tetrahydrothiazolo[5,4-c]pyridin-2-yl)carbonyl]-4-[(6-chloronaphthalen-2-yl)sulfonyl]piperazine were obtained. 1-[(6-Chloronaphthalen-2-yl)sulfonyl]-4-[(6-aminohydroxyiminomethyl-4,5,6,7-tetrahydrothiazolo[5,4-c]pyridin-2-yl)carbonyl]piperazine hydrochloride $^1$H-NMR (DMSO-d$_6$) δ: 2.77(2H,br s), 3.09(4H,br), 3.48 (2H,t,J=5.4 Hz), 3.73(2H,br s), 4.30–4.50(4H,m), 5.61(1H, br s), 7.71(1H,dd,J=8.8,2.0 Hz), 7.82(1H,dd,J=8.8 Hz,2.0 Hz), 8.15(1H,d,J=8.8 Hz), 8.22(1H,d,J=1.5 Hz), 8.25(1H,d, J=8.8 Hz), 8.50(1H,s), 8.53(1H,br s).

MS (FAB) m/z: 535 [(M+H)$^+$, Cl$^{35}$], 537 [(M+H)$^+$, Cl$^{37}$]. 1-[(6-Carbamoyl-4,5,6,7-tetrahydrothiazolo[5,4-c]pyridin-2-yl)carbonyl]-4-[(6-chloronaphthalen-2-yl)sulfonyl] piperazine $^1$H-NMR (DMSO-d$_6$) δ: 2.75(2H,br s), 3.09(4H,br), 3.63 (2H,t,J=5.9 Hz), 3.73(2H,br s), 4.39(2H,br s), 4.59(2H,s), 6.17(2H,s), 7.70(1H,dd,J=8.8,2.0 Hz), 7.82(1H,dd,J=8.8 Hz,2.0 Hz), 8.14(1H,d,J=8.8 Hz), 8.21(1H,d,J=1.5 Hz), 8.25 (1H,d,J=8.8 Hz), 8.50(1H,s).

MS (FAB) m/z: 520 [(M+H)$^+$, Cl$^{35}$], 522 [(M+H)$^+$, Cl$^{37}$].

Elementary analysis for C$_{22}$H$_{22}$ClN$_5$O$_4$S$_2$.H$_2$O

Calculated: C, 49.11; H, 4.50; N, 13.02.

Found: C, 48.98; H, 4.12; N, 12.83.

Example 89

1-[(6-Chloronaphthalen-2-yl)sulfonyl]-4-[[6-(1-pyrrolin-2-yl)-4,5,6,7-tetrahydrothiazolo[5,4-c] pyridin-2-yl]carbonyl]piperazine hydrochloride In a similar manner to Example 47 except for the use of 1-[(6-chloronaphthalen-2-yl)sulfonyl]-4-[(4,5,6,7-tetrahydrothiazolo[5,4-c]pyridin-2-yl)carbonyl]piperazine hydrochloride as the raw material, the title compound was obtained.

$^1$H-NMR (DMSO-d$_6$) δ: 2.07–2.15(2H,m), 2.94–3.16 (8H,m), 3.63(2H,t,J=7.3 Hz), 3.75(2H,br s), 3.90(2H,br s), 4.39(2H,br s), 4.93(2H,s), 7.70(1H,dd,J=8.8,2.0 Hz), 7.83 (1H,dd,J=8.8 Hz,2.0 Hz), 8.15(1H,d,J=8.8 Hz), 8.22(1H,d, J=2.0 Hz), 8.25(1H,d,J=8.8 Hz), 8.50(1H,s).

MS (FAB) m/z: 544 [(M+H)$^+$, Cl$^{35}$], 546 [(M+H)$^+$, Cl$^{37}$].

Elementary analysis for C$_{25}$H$_{26}$ClN$_5$O$_3$S$_2$.1.4HCl.CH$_3$OH

Calculated: C, 49.79; H, 5.05; Cl, 13.57; N, 11.17; S, 10.23.

Found: C, 49.44; H, 4.78; Cl, 13.63; N, 10.83; S, 10.15.

Example 90

1-[(6-Chloronaphthalen-2-yl)sulfonyl]-4-[(6-formyl-4,5,6,7-tetrahydrothiazolo[5,4-c]pyridin-2-yl) carbonyl]piperazine In a similar manner to Example 4 except for the use of 1-[(6-chloronaphthalen-2-yl)sulfonyl]-4-[(4,5,6,7-tetrahydrothiazolo[5,4-c]pyridin-2-yl)carbonyl]piperazine hydrochloride and formic acid as the raw materials, the reaction was conducted, whereby the title compound was obtained.

$^1$H-NMR (DMSO-d$_6$) δ: 2.74–2.88(2H,m), 3.10(4H,br), 3.31(2H,s), 3.66–3.86(4H,m), 4.64–4.73(2H,m), 7.69(1H, dd,J=8.8,2.0 Hz), 7.82(1H,dd,J=8.8,2.0 Hz), 8.14(1H,d,J= 8.8 Hz), 8.15–8.22(2H,m), 8.24(1H,d,J=8.8 Hz), 8.50(1H,s).

MS (FAB) m/z: 505 [(M+H)$^+$, Cl$^{35}$], 507 [(M+H)$^+$, Cl$^{37}$].

Elementary analysis for C$_{22}$H$_{21}$ClN$_4$O$_4$S$_2$.1/5H$_2$O

Calculated: C, 51.95; H, 4.24; Cl, 6.97; N, 11.02; S, 12.61.

Found: C, 52.18; H, 4.30; Cl, 6.69.; N, 10.71; S, 12.21.

Example 91

1-[(6-Chloronaphthalen-2-yl)sulfonyl]-4-[(6-methyl-4,5,6,7-tetrahydrothiazolo[5,4-c]pyridin-2-yl) carbonyl]piperazine hydrochloride In dichloromethane (10 ml), 1-[(6-chloronaphthalen-2-yl) sulfonyl]-4-[(4,5,6,7-tetrahydrothiazolo[5,4-c]pyridin-2-yl) carbonyl]piperazine hydrochloride (400 mg) was suspended, followed by the addition of triethylamine (0.22 ml) and acetic acid (0.05 ml). The resulting mixture was stirred at room temperature for 5 minutes. To the reaction mixture, a 30% aqueous formaldehyde solution (0.08 ml) and sodium triacetoxyborohydride (264 mg) were added, followed by stirring at room temperature for 10 minutes. After the reaction mixture was concentrated under reduced pressure, the residue was added with ethyl acetate. The resulting mixture was washed with water and saturated saline and then dried over anhydrous sodium sulfate. The solvent was then distilled off under reduced pressure The residue was dissolved in a saturated ethanol hydrochloride solution (1 ml) and then the resulting solution was concentrated under reduced pressure. The residue was crystallized from hexane and ethyl acetate, whereby the title compound (298 mg, 71%) was obtained.

$^1$H-NMR (DMSO-d$_6$) δ: 2.89(3H,s), 3.10(6H,br), 3.32–3.81(4H,m), 4.30–4.81(4H,m), 7.71(1H,dd,J=8.8,2.0 Hz), 7.82(1H,dd,J=8.8,2.0 Hz), 8.15(1H,d,J=8.8 Hz), 8.20–8.28(2H,m), 8.50(1H,s), 11.28(1H,br s).

MS (FAB) m/z: 491 [(M+H)$^+$, Cl$^{35}$], 493 [(M+H)$^+$, Cl$^{37}$].

Elementary analysis for C$_{22}$H$_{23}$ClN$_4$O$_3$S$_2$.HCl.0.6H$_2$O

Calculated: C, 49.09; H, 4.72; Cl, 13.17; N, 10.41; S, 11.91.

Found: C, 48.88; H, 4.78; Cl, 13.26; N, 10.42; S, 12.03.

Example 92

2-[[4-[(6-Chloronaphthalen-2-yl)sulfonyl]piperazin-1-yl]carbonyl]-6,6-dimethyl-4,5,6,7-tetrahydrothiazolo[5,4-c]pyridinium iodide In N,N-dimethylformamide (20 ml), 1-[(6-chloronaphthalen-2-yl)sulfonyl]-4-[(6-methyl-4,5,6,7-tetrahydrothiazolo[5,4-c]pyridin-2-yl)carbonyl]piperazine hydrochloride (200 mg) was dissolved, followed by the addition of methyl iodide (0.05 ml) and potassium carbonate (79 mg). The resulting mixture was stirred overnight at 80° C. After the reaction mixture was concentrated under reduced pressure, the residue was added with water and the resulting precipitate was collected by filtration. The precipitate was then dissolved in a mixed solvent (1:1) of dichloromethane and methanol, followed by the addition of ethyl acetate. The resulting precipitate was collected by filtration, whereby the title compound (144 mg, 56%) was obtained.

$^1$H-NMR (DMSO-d$_6$) δ: 3.05–3.23(12H,m), 3.77(2H,t,J=5.9 Hz), 4.40(2H,br s), 4.79(2H,br s), 7.71(1H,dd,J=8.8,2.0 Hz), 7.83(1H,dd,J=8.8,2.0 Hz), 8.15(1H,d,J=8.8 Hz), 8.20–8.27(2H,m), 8.52(1H,s).

MS (FD) m/z: 505 [(M$^+$, Cl$^{35}$), 507 (M$^+$, Cl$^{37}$).

Elementary analysis for C$_{23}$H$_{26}$ClIN$_4$O$_3$S$_2$.1/2CH$_3$CO$_2$CH$_2$CH$_3$ Calculated: C, 44.35; H, 4.47; N, 8.28.

Found: C, 44.52; H, 4.23; N, 8.01.

Example 93

2-[[4-[(6-Chloronaphthalen-2-yl)sulfonyl]piperazin-1-yl]carbonyl]-6-methyl-4,5,6,7-tetrahydrothiazolo[5,4-c]pyridine N-oxide In acetone (10 ml), 1-[(6-chloronaphthalen-2-yl)sulfonyl]-4-[(6-methyl-4,5,6,7-tetrahydrothiazolo[5,4-c]pyridin-2-yl)carbonyl]piperazine hydrochloride (400 mg) was suspended, followed by the addition of a 1N aqueous solution of sodium hydroxide (0.38 ml) and 30% aqueous hydrogen peroxide (3.50 ml). The resulting mixture was stirred at room temperature for 8 days. After the reaction mixture was concentrated under reduced pressure, the residue was purified by the chromatography through a synthetic adsorbent ("Diaion HP-20", water~water:acetonitrile=2:5), whereby the title compound (84 mg, 39%) was obtained.

$^1$H-NMR (DMSO-d$_6$) δ: 2.83–2.90(1H,m), 3.10(5H,br), 3.20–3.47(4H,m), 3.61–3.83(3H,m), 4.28–4.50(3H,m), 4.78–4.85(1H,m), 7.69(1H,dd,J=8.8,2.0 Hz), 7.82(1H,dd,J=8.8,2.0 Hz), 8.14(1H,d,J=8.8 Hz), 8.19–8.27(2H,m), 8.50(1H,s).

MS (FD) m/z: 506 (M$^+$, Cl$^{35}$), 508 (M$^+$, Cl$^{37}$).

Example 94

2-Carbamoyl-4-[(6-chloronaphthalen-2-yl)sulfonyl]-1-[(4,5,6,7-tetrahydrothiazolo[5,4-c]pyridin-2-yl)carbonyl]piperazine trifluoroacetate To trifluoroacetic acid (1 ml), a solution of 1-[(6-tert-butoxycarbonyl-4,5,6,7-tetrahydrothiazolo[5,4-c]pyridin-2-yl)carbonyl]-2-carbamoyl-4-[(6-chloronaphthalen-2-yl)sulfonyl]piperazine (303 mg) dissolved in dichloromethane (1 ml) was added, followed by concentration under reduced pressure. The resulting precipitate was collected by filtration and washed with diethyl ether, whereby the title compound (263 mg, 83%) was obtained.

$^1$H-NMR (DMSO-d$_6$) δ: 2.39–2.70(2H,m), 2.92–3.06(2H,m), 3.42–3.77(4H,m), 4.25–4.50(7/2H,m), 4.97(1/2H, br s), 5.35–5.44(1/2H,m), 6.14(1/2H,br s), 7.30–7.39(1H, m), 7.66–7.73(2H,m), 7.77–7.82(1H,m), 8.16(1H,d,J=8.8 Hz), 8.21–8.28(2H,m), 8.49(1H,s), 9.26(2H,br s).

MS (FAB) m/z: 520 [(M+H)$^+$, Cl$^{35}$], 522 [(M+H)$^+$, Cl$^{37}$].

Elementary analysis for C$_{22}$H$_{22}$ClN$_5$O$_4$S$_2$.CF$_3$CO$_2$H.0.6H$_2$O Calculated: C, 44.29; H, 3.73; Cl, 5.40; F, 9.55; N, 10.67; S, 9.77.

Found: C, 44.59; H, 3.79; Cl, 5.26; F, 9.54; N, 10.28; S, 9.72.

Example 95

2-Carbamoyl-4-[(6-chloronaphthalen-2-yl)sulfonyl]-1-[(6-methyl-4,5,6,7-tetrahydrothiazolo[5,4-c]pyridin-2-yl)carbonyl]piperazine hydrochloride In a similar manner to Example 91 except for the use of 2-carbamoyl-4-[(6-chloronaphthalen-2-yl)sulfonyl]-1-[(4,5,6,7-tetrahydrothiazolo[5,4-c]pyridin-2-yl)carbonyl]piperazine trifluoroacetate as the raw material, the title compound was obtained.

$^1$H-NMR (DMSO-d$_6$) δ: 2.37–2.70(2H,m), 2.91(3H,s), 3.00–3.78(6H,m), 4.28–4.77(7/2H,m), 4.97(1/2H,br s), 5.40–5.50(1/2H,m), 6.14(1/2H,br 9), 7.32–7.40(1H,m), 7.68–7.75(2H,m), 7.77–7.83(1H,m), 8.15(1H,d,J=8.8 Hz), 8.21–8.28(2H,m), 8.49(1H,s).

MS (FAB) m/z: 534 [(M+H)$^+$, Cl$^{35}$], 536 [(M+H)$^+$, Cl$^{37}$].

Elementary analysis for C$_{23}$H$_{24}$ClN$_5$O$_4$S$_2$.HCl.2.5H$_2$O

Calculated: C, 44.88; H, 4.91; Cl, 11.52; N, 11.38; S, 10.42.

Found: C, 44.83; H, 4.89; Cl, 11.65; N, 11.31; S, 10.46.

Example 96

1-[(6-Chloronaphthalen-2-yl)sulfonyl]-4-[[6-(2-hydroxyethyl)-4,5,6,7-tetrahydrothiazolo[5,4-c]pyridin-2-yl]carbonyl]piperazine hydrochloride In a similar manner to Example 91 except for the use of 1-[(6-chloronaphthalen-2-yl)sulfonyl]-4-[(4,5,6,7-tetrahydrothiazolo[5,4-c]pyridin-2-yl)carbonyl]piperazine hydrochloride (132 mg) and glyoxylic acid hydrate (82 mg) as the raw materials, the reaction was conducted, whereby a crude product was obtained. The product was suspended in tetrahydrofuran (50 ml), followed by the addition of triethylamine (0.22 ml) and ethyl chloroformate (0.03 ml) under ice cooling. After stirring at room temperature for 15 minutes, sodium borohydride (50 mg) and water (10 ml)

were added and the resulting mixture was stirred at room temperature for one hour. The reaction mixture was concentrated under reduced pressure. The concentrate was diluted with dichloromethane, washed with saturated saline and then dried over anhydrous sodium sulfate. The residue obtained by distilling off the solvent under reduced pressure was purified by chromatography on a silica gel column (dichloromethane~dichloromethane:methanol=100:3). The purified product was dissolved in saturated ethanol hydrochloride (1 ml), followed by concentration under reduced pressure. The concentrate was pulverized and washed in ethyl acetate, whereby the title compound (52 mg, 33%) was obtained.

$^1$H-NMR (DMSO-d$_6$) δ: 3.11(4H,br s), 3.20–3.57(6H,m), 3.69–3.87(4H,m), 4.34–4.82(4H,m), 5.38(1H,br s), 7.71 (1H,dd,J=8.8,2.0 Hz), 7.82(1H,dd,J=8.8 Hz,2.0 Hz), 8.15 (1H,d,J=8.8 Hz), 8.22(1H,s), 8.25(1H,d,J=8.8 Hz), 8.50(1H, s), 10.48(1H,br s).

MS (FAB) m/z: 521 [(M+H)$^+$, Cl$^{35}$], 523 [(M+H)$^+$, Cl$^{37}$].

In a similar manner to Example 91 except for the use of 1-[(6-chloronaphthalen-2-yl)sulfonyl]-4-[(4,5,6,7-tetrahydrothiazolo[5,4-c]pyridin-2-yl]carbonyl]piperazine hydrochloride as the raw material, the reaction was conducted, whereby the compounds of Examples 97, 98 and 99 were obtained.

Example 97

1-[(6-Chloronaphthalen-2-yl)sulfonyl]-4-[[6-(pyridin-2-yl)methyl-4,5,6,7-tetrahydrothiazolo[5,4-c]pyridin-2-yl]carbonyl]piperazine hydrochloride $^1$H-NMR (DMSO-d$_6$) δ: 3.07–3.17(6H,m), 3.63(2H,t,J=6.3 Hz), 3.74(2H,br s), 4.39(2H,br s), 4.58(2H,s), 4,61(2H, s), 7.50–7.64(1H,m), 7.67–7.73(2H,m), 7.82(1H,dd,J=8.8, 1.5 Hz), 7.97(1H,m), 8.15(1H,d,J=8.8 Hz), 8.22(1H,d,J=1.5 Hz), 8.25(1H,d,J=8.8 Hz), 8.50(1H,s), 8.69(1H,d,J=4.9 Hz).

MS (FAB) m/z: 568 [(M+H)$^+$, Cl$^{35}$], 570 [(M+H)$^+$, Cl$^{37}$].

Elementary analysis for C$_{27}$H$_{26}$ClN$_5$O$_3$S$_2$.2HCl.0.8H$_2$O

Calculated: C, 49.48; H, 4.55; Cl, 16.23; N, 10.68; S, 9.78.

Found: C, 49.72; H, 4.48; Cl, 16.31; N, 10.86; S, 9.53.

Example 98

1-[(6-Chloronaphthalen-2-yl)sulfonyl]-4-[[6-(pyridin-3-yl)methyl-4,5,6,7-tetrahydrothiazolo[5,4-c]pyridin-2-yl]carbonyl]piperazine hydrochloride $^1$H-NMR (DMSO-d$_6$) δ: 3.03–3.27(6H,m), 3.40–3.81 (4H,m), 3.74(2H,br s), 4.40(2H,br s), 4.50(2H,s), 4,70(2H, s), 7.70(1H,dd,J=8.8,2.4 Hz), 7.82(1H,dd,J=8.8), 8.15(1H, d,J=8.8 Hz), 8.22(1H,s), 8.25(1H,d,J=8.8 Hz), 8.50(1H,s), 8.73(1H,d,j=7.8 Hz), 8.93(1H,d,J=4.4 Hz).

MS (FAB) m/z: 568 [(M+H)$^+$, Cl$^{35}$], 570 [(M+H)$^+$, Cl$^{37}$].

Elementary analysis for C$_{27}$H$_{26}$ClN$_5$O$_3$S$_2$.2.9HCl.4.5H$_2$O

Calculated: C, 42.96; H, 5.06; Cl, 18.32; N, 9.28.

Found: C, 42.97; H, 4.84; Cl, 18.19; N, 9.23.

Example 99

1-[(6-Chloronaphthalen-2-yl)sulfonyl]-4-[[6-(pyridin-4-yl)methyl-4,5,6,7-tetrahydrothiazolo[5, 4c]pyridin-2-yl]carbonyl]piperazine hydrochloride $^1$H-NMR (DMSO-d$_6$) δ: 3.11(4H,br s), 3.19(2H,br s), 3.64(2H,br s), 3.74(2H,br s), 4.41(2H,br s), 4.49(2H,s), 4.80(2H,s), 7.69(1H,dd,J=8.8,2.0 Hz), 7.82(1H,dd,J=8.8,2.0 Hz), 8.15(1H,d,J=8.8 Hz), 8.21(1H,d,J=2.0 Hz), 8.25(1H,d, J=8.8 Hz), 8.41(2H,d,J=6.3 Hz), 8.50(1H,s), 9.04(2H,d,J= 6.3 Hz).

MS (FAB) m/z: 568 [(M+H)$^+$, Cl$^{35}$], 570 [(M+H)$^+$, Cl$^{37}$].

Elementary analysis for C$_{27}$H$_{26}$ClN$_5$O$_3$S$_2$.2.7HCl.6.0H$_2$O

Calculated: C, 41.86; H, 5.30; Cl, 16.93; N, 9.04; S, 8.28.

Found: C, 42.05; H, 4.98; Cl, 16.92; N, 9.37; S, 8.61.

Example 100

1-[(E)-4-Chlorostyrylsulfonyl]-4-[(4,5,6,7-tetrahydrothiazolo[5,4-c]pyridin-2-yl)carbonyl] piperazine hydrochloride In a similar manner to Example 7 except for the use of 1-[(6-tert-butoxycarbonyl-4,5,6,7-tetrahydrothiazolo[5,4-c] pyridin-2-yl]carbonyl]-4-[(E)-4-chlorostyrylsulfonyl] piperazine as the raw material, the title compound was obtained.

$^1$H-NMR (DMSO-d$_6$) δ: 3.04(2H,br s), 3.23(4H,br), 3.47 (2H,br s), 3.77(2H,br s), 4.35–4.50(2H,m), 7.33(1H,d,J= 15.6 Hz), 7.43(1H,d,J=15.6 Hz), 7.49(1H,d,J=8.3 Hz), 7.79 (1H,d,J=8.3 Hz), 9.57(2H,br s).

MS (FAB) m/z: 453 [(M+H)$^+$, Cl$^{35}$], 455 [(M+H)$^+$, Cl$^{37}$].

Elementary analysis for C$_{19}$H$_{21}$ClN$_4$O$_3$S$_2$.HCl.0.3H$_2$O

Calculated: C, 46.12; H, 4.60; Cl, 14.33; N, 11.32; S, 12.96.

Found: C, 46.42; H, 4.66; Cl, 14.38; N, 11.02; S, 13.02.

Example 101

1-[(E)-4-Chlorostyrylsulfonyl]-4-[(6-methyl-4,5,6,7-tetrahydrothiazolo[5,4-c]pyridin-2-yl)carbonyl] piperazine hydrochloride In a similar manner to Example 91 except for the use of [(E)-4-chlorostyrylsulfonyl]-4-[(4,5,6,7-tetrahydrothiazolo [5,4-c]pyridin-2-yl)carbonyl]piperazine hydrochloride as the raw material, the title compound was obtained.

$^1$H-NMR (DMSO-d$_6$) δ: 2.92(3H,s), 3.01–3.32(6H,br), 3.35–3.88(4H,m), 4.29–4.84(4H,m), 7.33(1H,d,J=15.6 Hz), 7.49(1H,d,J=15.6 Hz), 7.49(1H,d,J=8.3 Hz), 7.79(1H,d,J= 8.3 Hz), 11.31(1H,br s).

MS (FAB) m/z: 467 [(M+H)$^+$, Cl$^{35}$], 469 [(M+H)$^+$, Cl$^{37}$].

Elementary analysis for C$_{20}$H$_{23}$ClN$_4$O$_3$S$_2$.HCl.0.2H$_2$O

Calculated: C, 47.37; H, 4.85; Cl, 13.98; N, 11.05; S, 12.65.

Found: C, 47.30; H, 4.92; Cl, 14.05; N, 11.03; S, 12.49.

Example 102

(3S)-3-[(6-Chloronaphthalen-2-yl)sulfonamide]-1-[(4,5,6,7-tetrahydrothieno[3,2-c]pyridin-2-yl)methyl] pyrrolidine hydrochloride In a similar manner to Example 7 except for the use of (3S)-1-[(5-tert-butoxycarbonyl-4,5,6,7-tetrahydrothieno[3, 2-c]pyridin-2-yl)methyl]-3-[(6-chloronaphthalen-2-yl) sulfonamide]pyrrolidine as the raw material, the title compound was obtained.

[α]$_D$=−69.72° (25° C.,c=1.00, CH$_3$OH)

$^1$H-NMR (DMSO-d$_6$ at 100° C.) δ: 1.88–1.89(1H,m), 2.10–2.25(1H,m), 3.02–3.07(2H,m), 3.10–3.50(6H,m), 4.02 (1H,s), 4.12(2H,s), 4.45(2H,s), 7.12(1H,s), 7.65(1H,d,J=8.3

Hz), 7.91(1H,d,J=8.3 Hz), 8.10(1H,d,J=8.3 Hz), 8.14(1H,s), 8.16(1H,d,J=8.3 Hz), 8.18(1H,br s), 8.48(1H,s), 9.65(2H,br s).

MS (FD) m/z: 461 (M$^+$, Cl$^{35}$), 463 (M$^+$, Cl$^{37}$).

Elementary analysis for $C_{22}H_{24}ClN_3O_2S_2$·2.1HCl·$H_2O$

Calculated: C, 47.47; H, 5.09; Cl, 19.74; N, 7.55; S, 11.52.

Found: C, 47.55; H, 5.13; Cl, 19.85; N, 7.45; S, 11.48.

Example 103

(3S)-3-[(6-Chloronaphthalen-2-yl)sulfonamide]-1-[(4,5,6,7-tetrahydrothieno[3,2-c]pyridin-2-yl)carbonyl]pyrrolidine hydrochloride In a similar manner to Example 7 except for the use of (3S)-1-[(5-tert-butoxycarbonyl-4,5,6,7-tetrahydrothieno[3,2-c]pyridin-2-yl)carbonyl]-3-[(6-chloronaphthalen-2-yl)sulfonamide]pyrrolidine as the raw material, the title compound was obtained.

$[\alpha]_D$=−62.70° (25° C.,c=1.00,$CH_3OH$).

$^1$H-NMR (DMSO-$d_6$ at 100° C.) δ: 1.82–1.90(1H,m), 1.96–2.05(1H,m), 3.05(2H,t,J=6.0 Hz), 3.42–3.57(2H,m), 3.60–3.72(2H,m), 3.84–3.90(1H,m), 4.12(2H,s), 4.45(2H,s), 7.25(1H,s), 7.64(1H,dd,J=8.3,1.6 Hz), 7.90(1H,dd,J=8.3,1.6 Hz), 7.97(1H,d,J=5.6 Hz), 8.08(1H,d,J=8.7 Hz), 8.12(1H,s), 8.14(1H,d,J=8.7 Hz), 8.47(1H,s), 9.55(2H,br s).

MS (FAB) m/z: 476 [(M+H)$^+$, Cl$^{35}$], 478 [(M+H)$^+$, Cl$^{37}$].

Elementary analysis for $C_{22}H_{22}ClN_3O_3S_2$·HCl

Calculated: C, 51.56; H, 4.52; Cl, 13.84; N, 8.20; S, 12.51.

Found: C, 51.25; H, 4.61; Cl, 13.68; N, 7.98; S, 12.36.

Example 104

(3S)-1-[(6-Chloronaphthalen-2-yl)sulfonyl]-3-[[(4,5,6,7-tetrahydrothieno[3,2-c]pyridin-2-yl)methyl]amino]pyrrolidine hydrochloride In a similar manner to Example 7 except for the use of (3S)-3-[[(5-tert-butoxycarbonyl-4,5,6,7-tetrahydrothieno[3,2-c]pyridin-2-yl)methyl]amino]-1-[(6-chloronaphthalen-2-yl)sulfonyl]pyrrolidine as the raw material, the title compound was obtained.

$[\alpha]_D$=+34.82° (25° C.,c=1.00,$CH_3OH$).

$^1$H-NMR (DMSO-$d_6$) δ: 1.98–2.20(2H,m), 2.99–3.04(2H,m), 3.19–3.26(1H,m), 3.30–3.50(3H,m), 3.61–3.72(1H,m), 3.52–3.60(1H,m), 4.13(2H,s), 4.29(2H,s), 7.09(1H,s), 7.71(1H,dd,J=8.8,2.0 Hz), 7.89(1H,dd,J=8.8,2.0 Hz), 8.17(1H,d,J=8.8 Hz), 8.25(1H,d,J=2.0 Hz), 8.30(1H,s), 8.57(1H,s), 9.55(2H,br s), 9.7–10.0(1H,m).

MS (FD) m/z: 461 (M$^+$, Cl$^{35}$), 463 (M$^+$, Cl$^{37}$).

Elementary analysis for $C_{22}H_{24}ClN_3O_2S_2$·2HCl·0.2$H_2O$

Calculated: C, 49.06; H, 4.94; Cl, 19.75; N, 7.80; S, 11.91.

Found: C, 48.88; H, 4.97; Cl, 19.65; N, 7.67; S, 11.84.

Example 105

(3S)-3-[(4,5,6,7-tetrahydrothieno[3,2-c]pyridin-2-yl)carbonylamino]-1-[(6-chloronaphthalen-2-yl)sulfonyl]pyrrolidine hydrochloride In a similar manner to Example 7 except for the use of (3S)-3-[(5-tert-butoxycarbonyl-4,5,6,7-tetrahydrothieno[3,2-c]pyridin-2-yl)carbonylamino]-1-[(6-chloronaphthalen-2-yl)sulfonyl]pyrrolidine as the raw material, the title compound was obtained.

$[\alpha]_D$=+33.56° (25°, c=1.00,$CH_3OH$).

$^1$H-NMR (DMSO-$d_6$) δ: 1.85–1.95(1H, m), 1.95–2.05(1H,m), 3.04(2H,m), 3.24–3.40(1H,m), 3.41–3.53(3H,m), 4.04–4.24(3H,m), 7.34(1H,s), 7.67(1H,d,J=8.8 Hz), 7.84(1H,d,J=8.8 Hz), 8.03(1H,d,J=8.8 Hz), 8.17(1H,s), 8.22(1H,d,J=8.8 Hz), 8.27(1H,d,J=5.7 Hz), 8.50(1H,s), 9.59(1H,br s), 9.71(1H,br s).

MS (FAB) m/z: 476 [(M+H)$^+$, Cl$^{35}$], 478 [(M+H)$^+$, Cl$^{37}$].

Example 106

1-[(6-Chloronaphthalen-2-yl)sulfonyl]-4-[(4,5,6,7-tetrahydrothieno[3,2-c]pyridin-2-yl)carbonyl]homopiperazine hydrochloride In a similar manner to Example 7 except for the use of 1-[(5-tert-butoxycarbonyl-4,5,6,7-tetrahydrothieno[3,2-c]pyridin-2-yl)carbonyl]-4-[(6-chloronaphthalen-2-yl)sulfonyl]homopiperazine as the raw material, the title compound was obtained.

$^1$H-NMR (DMSO-$d_6$) δ: 1.83(2H, br s), 3.04(2H, t, J=5.4 Hz), 3.30–3.59(6H,m), 3.60–3.88(4H,m), 4.14(2H,s), 7.20 (1H,br s), 7.69(1H,dd,J=8.8,2.0 Hz), 7.84(1H,d,J=8.8 Hz), 8.10(1H,d,J=8.8 Hz), 8.17–8.21(2H,m), 8.50(1H,s), 9.57(2H,br s).

MS (FAB) m/z: 490 [(M+H)$^+$, Cl$^{35}$], 492 [(M+H)$^+$, Cl$^{37}$].

Elementary analysis for $C_{23}H_{25}ClN_3O_3S_2$·1.1HCl·0.2$H_2O$

Calculated: C, 51.66; H, 4.99; Cl, 13.92; N, 7.86.

Found: C, 51.46; H, 4.61; Cl, 13.55; N, 8.05.

Example 107

4-[(6-Chloronaphthalen-2-yl)sulfonamido]-1-[(4,5,6,7-tetrahydrothieno[3,2-c]pyridin-2-yl)carbonyl]piperidine hydrochloride In a similar manner to Example 4 except for the use of 5-tert-butoxycarbonyl-4,5,6,7-tetrahydrothieno[3,2-c]pyridin-2-carboxylic acid and 4-[(6-chloronaphthalen-2-yl)sulfonamido]piperidine trifluoroacetate as the raw materials, the reaction was conducted, whereby the title compound was obtained.

$^1$H-NMR (DMSO-$d_6$) δ: 1.26–1.38(2H,m), 1.58–1.65(2H,m), 2.93–3.13(4H,m), 3.29–3.40(3H,m), 3.90–4.05(2H,m), 4.11(2H,s), 7.16(1H,s), 7.68(1H,dd,J=8.0,2.0 Hz), 7.92(1H,dd,J=8.8,2.0 Hz), 8.07(1H,d,J=7.3 Hz), 8.13(2H,d,J=8.8 Hz), 8.20(1H,d,J=7.3 Hz), 8.23(1H,s), 8.51(1H,s), 9.71(2H,br s).

MS (FAB) m/z: 490 [(M+H)$^+$, Cl$^{35}$], 492 [(M+H)$^+$, Cl$^{37}$].

Elementary analysis for $C_{23}H_{25}ClN_3O_3S_2$·2.4HCl·3$H_2O$

Calculated: C, 43.67; H, 5.32; Cl, 19.05; N, 6.64.

Found: C, 43.85; H, 5.10; Cl, 19.07; N, 6.63.

Example 108

1-[(6-Chloronaphthalen-2-yl)sulfonyl]-4-[(6-aminohydroxyiminomethylbenzofuran-2-yl)carbonyl]piperazine In a similar manner to Example 83 except for the use of 1-[(6-chloronaphthalen-2-yl)sulfonyl]-4-[(6-cyanobenzofuran-2-yl)carbonyl]piperazine as the raw material, the title compound was obtained.

$^1$H-NMR (DMSO-$d_6$) δ: 3.11(4H,s), 3.83(4H,br), 5.90 (2H,br s), 7.34(1H,s), 7.64–7.75(3H,m), 7.83(1H,dd,J=8.8, 2.0 Hz), 7.89(1H,s), 8.17(1H,d,J=8.8 Hz), 8.23(1H,d,J=1.5 Hz), 8.26(1H,d,J=8.8 Hz), 8.51(1H,s), 9.77(1H,s).

MS (FAB) m/z: 513 [(M+H)$^+$, Cl$^{35}$], 515 [(M+H)$^+$, Cl$^{37}$].

Elementary analysis for C$_{24}$H$_{21}$ClN$_4$O$_5$S.1/5H$_2$O

Calculated: C, 55.80; H, 4.18; Cl, 6.86; N, 10.70; S, 6.21.

Found: C, 55.65; H, 4.25; Cl, 6.81; N, 10.70; S, 6.37.

Example 109

1-[(6-Chloronaphthalen-2-yl)sulfonyl]-4-[(5-aminohydroxyiminomethylbenzothiophen-2-yl)carbonyl]piperazine In a similar manner to Example 83 except for the use of 1-[(6-chloronaphthalen-2-yl)sulfonyl]-4-[(5-cyanobenzothiophen-2-yl)carbonyl]piperazine as the raw material, the title compound was obtained.

$^1$H-NMR (DMSO-d$_6$) δ: 3.11(4H,s), 3.77(4H,s), 5.87(2H, br s), 7.67(1H,s), 7.71(1H,d,J=2.0 Hz), 7.75(1H,d,J=8.8 Hz), 7.83(1H,dd,J=8.8,2.0 Hz), 7.94(1H,d,J=8.8 Hz), 8.15 (1H,s), 8.17(1H,d,J=8.8 Hz), 8.25(1H,d,J=8.8 Hz), 8.29(1H, d,J=8,3 Hz), 8.50(1H,s), 9.68(1H,s).

MS (FAB) m/z: 529 [(M+H)$^+$, Cl$^{35}$], 531 [(M+H)$^+$, Cl$^{37}$].

Elementary analysis for C$_{24}$H$_{21}$N$_4$ClO$_4$S$_2$.0.3H$_2$O

Calculated: C, 53.94; H, 4.07; N, 10.48.

Found: C, 54.22; H, 4.17; N, 10.23.

Example 110

1-[(6-Chloronaphthalen-2-yl)sulfonyl]-4-[[(1RS)-4-(pyridin-4-yl)-3-cyclohexene]carbonyl]piperazine hydrochloride In a similar manner to Example 12 except for the use of (1RS)-4-(4-pyridyl)-3-cyclohexenecarboxylic acid and 1-[(6-chloronaphthalen-2-yl)sulfonyl]piperazine hydrochloride as the raw materials, the reaction was conducted, whereby the title compound was obtained.

$^1$H-NMR (DMSO-d$_6$) δ: 1.50–1.60(1H,m), 1.80–1.90 (1H,m), 2.25–2.58(5H,m), 2.80–2.90(1H,m), 2.91–3.10(1H, m), 3.46–3.72(4H,m), 6.94(1H,br s), 7.71(1H,dd,J=8.8,2.0 Hz), 7.82(1H,dd,J=8.8,2.0 Hz), 7.96(2H,d,J=6.8 Hz), 8.15 (1H,J=8.8 Hz), 8.24(1H,J=2.0 Hz), 8.27(1H,J=8.8 Hz), 8.50 (1H,s), 8.76(2H,d,J=6.8 Hz).

MS (FAB) m/z: 496 [(M+H)$^+$, Cl$^{35}$], 498 [(M+H)$^+$, Cl$^{37}$].

Elementary analysis for C$_{26}$H$_{26}$ClN$_3$O$_3$S.HCl.1.3H$_2$O

Calculated: C, 56.18; H, 5.37; Cl, 12.75; N, 7.56; S, 5.77.

Found: C, 56.03; H, 5.29; Cl, 12.67; N, 7.41; S, 5.77.

Example 111

1-[(E)-4-Chlorostyrylsulfonyl]-4-[[(1RS)-4-(pyridin-4-yl)-3-cyclohexene]carbonyl]piperazine hydrochloride In a similar manner to Referential Example 12 except for the use of (1RS)-4-(4-pyridyl)-3-cyclohexenecarboxylic acid and 1-[(E)-4-chlorostyrylsulfonyl)piperazine hydrochloride as the raw materials, the reaction was conducted, whereby the title compound was obtained.

$^1$H-NMR (DMSO-d$_6$) δ: 1.59–1.70(1H,m), 1.90–1.98 (1H,m), 2.31–2.56(4H,m), 2.90–3.00(1H,m), 3.13(4H,br s), 3.50–3.63(4H,m), 6.98(1H,br s), 7.35(1H,d,J=15.6 Hz), 7.44(1H,d,J=15.6 Hz), 7.51(2H,d,J=8.3 Hz), 7.80(1H,J=8.3 Hz), 7.97(1H,J=6.8 Hz), 8.77(1H,J=6.8 Hz).

MS (FAB) m/z: 472 [(M+H)$^+$, Cl$^{35}$], 474 [(M+H)$^+$, Cl$^{37}$].

Elementary analysis for C$_{24}$H$_{26}$ClN$_3$O$_3$S.0.9HCl.2.3H$_2$O

Calculated: C, 52.77; H, 5.81; Cl, 12.33; N, 7.69; S, 5.87.

Found: C, 52.61; H, 5.80; Cl, 12.54; N, 7.44; S, 6.05.

Example 112 cis-, trans-1-[(6-Chloronaphthalen-2-yl)sulfonyl]-4-[[4-(pyridin-4-yl)cyclohexane]carbonyl]piperazine hydrochloride In a similar manner to Referential Example 12 except for the use of cis-, trans-4-(4-pyridyl)cyclohexanecarboxylic acid and 1-[(6-chloronaphthalen-2-yl)sulfonyl]piperazine hydrochloride as the raw materials, the reaction was conducted, whereby the title compound was obtained.

MS (FAB) m/z: 498 [(M+H)$^+$, Cl$^{35}$], 500 [(M+H)$^+$, Cl$^{37}$].

Elementary analysis for C$_{26}$H$_{28}$ClN$_3$O$_3$S.1.3HCl.2H$_2$O

Calculated: C, 53.71; H, 5.77; Cl, 14.02; N, 7.23; S, 5.51.

Found: C, 53.70; H, 5.70; Cl, 14.21; N, 7.13; S, 5.72.

Example 113 cis-, trans-1-[(E)-4-Chlorostyrylsulfonyl]-4-[[4-(pyridin-4-yl)cyclohexane]carbonyl]piperazine hydrochloride In a similar manner to Referential Example 12 except for the use of cis-, trans-4-(4-pyridyl)cyclohexanecarboxylic acid and 1-[(E)-4-chlorostyrylsulfonyl)piperazine hydrochloride as the raw materials, the reaction was conducted, whereby the title compound was obtained.

MS (FAB) m/z: 474 [(M+H)$^+$, Cl$^{35}$], 476 [(M+H)$^+$, Cl$^{37}$].

Elementary analysis for C$_{24}$H$_{28}$ClN$_3$O$_3$S.1.2HCl.0.8H$_2$O

Calculated: C, 54.17; H, 5.83; Cl, 14.66; N, 7.80; S, 6.03.

Found: C, 54.21; H, 6.20; Cl, 15.03; N, 7.51; S, 6.18.

Example 114

1-[(6-Chloronaphthalen-2-yl)sulfonyl]-4-[(1,2,3,4-tetrahydroisoquinolin-6-yl)carbonyl]piperazine hydrochloride In a similar manner to Example 7 except for the use of 1-[(2-tert-butoxycarbonyl-1,2,3,4-tetrahydroisoquinolin-6-yl)carbonyl]-4-[(6-chloronaphthalen-2-yl)sulfonyl]piperazine as the raw material, the title compound was obtained.

$^1$H-NMR (DMSO-d$_6$) δ: 2.89–3.29(4H,m), 3.20–3.83 (8H,m), 4.25(2H,s), 7.10–7.25(3H,m), 7.71(1H,d,J=8.3 Hz), 7.81(1H,d,J=8.3 Hz), 8.17(1H,d,J=8.8 Hz), 8.15–8.25(2H, m), 8.49(1H,s), 9.54(2H.brs).

MS (FAB) m/z: 470 [(M+H)$^+$, Cl$^{35}$], 472 [(M+H)$^+$, Cl$^{37}$].

Elementary analysis for C$_{24}$H$_{24}$ClN$_3$O$_3$S.HCl.2.0H$_2$O

Calculated: C, 53.14; H, 5.39; Cl, 13.07; N, 7.75; S, 5.91.

Found: C, 53.43; H, 5.43; Cl, 13.15; N, 8.07; S, 5.55.

Example 115

1-[(6-Chloronaphthalen-2-yl)sulfonyl]-4-[(2-methyl-1,2,3,4-tetrahydroisoquinolin-6-yl)carbonyl]piperazine hydrochloride In a similar manner to Example 91 except for the use of 1-[(6-chloronaphthalen-2-yl)sulfonyl]-4-[(1,2,3,4-tetrahydroisoquinolin-6-yl)carbonyl]piperazine hydrochloride as the raw material, the reaction was conducted, whereby the title compound was obtained.

$^1$H-NMR (DMSO-$d_6$) δ: 2.88(3H,s), 2.90–3.80(13H,m), 4.12–4.56(1H,m), 7.19(1H,s), 7.20(2H,d,J=6,8 Hz), 7.72 (1H,dd,J=8.8,2.0 Hz), 7.81(1H,d,J=8.8 Hz), 8.17(1H,d,J= 8.8 Hz), 8.24–8.28(2H,m), 8.49(1H.s), 10.93(1H,brs).

MS (FAB) m/z: 484 [(M+H)$^+$, Cl$^{35}$]486 [(M+H)$^+$, Cl$^{37}$ ].

Elementary analysis for $C_{24}H_{24}ClN_3O_3S.HCl.2.3H_2O$

Calculated: C, 53.44; H, 5.67; Cl, 12.62; N, 7.48; S, 5.71.

Found: C, 53.71; H, 5.81; Cl, 12.37; N, 7.26; S, 5.62.

Example 116

6-[[4-[(6-Chloronaphthalen-2-yl)sulfonyl]piperazin-1-yl]carbonyl]-2, 2-dimethyl-1,2,3,4-tetrahydroisoquinolinium iodide In a similar manner to Example 92 except for the use of 1-[(6-chloronaphthalen-2-yl)sulfonyl]-4-[(2-methyl-1,2,3,4-tetrahydroisoquinolin-6-yl)carbonyl]piperazine hydrochloride as the raw material, the title compound was obtained.

$^1$H-NMR (DMSO-$d_6$) δ: 2.90–3.85(18H,m), 4.61(2H,s), 7.19(1H,d,J=7.8 Hz), 7.24(1H,d,J=7.8 Hz), 7.28(1H,s), 7.72 (1H,dd,J=8.8,1.5 Hz), 7.81(1H,d,J=8.8 Hz), 8.17(1H,d,J= 8.8 Hz), 8.20–8.31(2H,m), 8.50(1H.s).

Elementary analysis for $C_{26}H_{29}ClIN_3O_3S.H_2O$

Calculated: C, 48.49; H, 4.85; N, 6.53.

Found: C, 48.66; H, 4.96; N, 6.39.

Example 117

1-[(6-Chloronaphthalen-2-yl)sulfonyl]-4-[4-(1,2,3,6-tetrahydropyridin-4-yl)benzoyl]piperazine hydrochloride In a similar manner to Referential Example 7 except for the use of 1-[4-(1-tert-butoxycarbonyl-1,2,3,6-tetrahydropyridin-4-yl)benzoyl]-4-[(6-chloronaphthalen-2-yl)sulfonyl]piperazine as the raw material, the title compound was obtained.

$^1$H-NMR (DMSO-$d_6$) δ: 2.67(2H,br s), 3.05(4H,br), 3.30 (2H,br s), 3.35–3.78(6H,m), 6.24(1H,br s), 7.32(2H,d,J=8.3 Hz), 7.47(2H,d,J=8.3 Hz), 7.71(1H,dd,J=8.8,2.0 Hz), 7.81 (1H,dd,J=8.8,2.0 Hz), 8.17(1H,d,J=8.8 Hz), 8.22–8.28(2H, m), 8.49(1H,s), 9.25(2H,br s).

MS (FAB) m/z: 496 [(M+H)$^+$, Cl$^{35}$], 498 [(M+H)$^+$, Cl$^{37}$].

Elementary analysis for $C_{27}H_{26}ClN_3O_3S.HCl.2/5H_2O$

Calculated: C, 57.86; H, 5.19; Cl, 13.14; N, 7.79; S, 5.94.

Found: C, 57.91; H, 5.19; Cl, 12.91; N, 7.75; S, 5.78.

Example 118

1-[(6-Chloronaphthalen-2-yl)sulfonyl]-4-[4-(piperidin-4-yl)benzoyl]piperazine hydrochloride In a similar manner to Referential Example 7 except for the use of 1-[4-(1-tert-butoxycarbonylpiperidin-4-yl) benzoyl]-4-[(6-chloronaphthalen-2-yl)sulfonyl]piperazine as the raw material, the title compound was obtained.

$^1$H-NMR (DMSO-$d_6$) δ: 1.78–1.94(4H,m), 2.80–3.21 (7H,m), 3.30–3.84(6H,m), 7.23(2H,d,J=8.3 Hz), 7.28(2H,d, J=8.3 Hz), 7.71(1H,dd,J=8.8,2.0 Hz), 7.80(1H,dd,J=8.8,2.0 Hz), 8.17(1H,d,J=8.8 Hz), 8.22–8.27(2H,m), 8.49(1H,s), 8.78–9.00(2H,m).

MS (FAB) m/z: 498 [(M+H)$^+$, Cl$^{35}$], 500 [(M+H)$^+$, Cl$^{37}$].

Elementary analysis for $C_{26}H_{28}ClN_3O_3S.HCl.3/5H_2O$

Calculated: C, 57.27; H, 5.58; Cl, 13.00; N, 7.71; S, 5.88.

Found: C, 57.23; H, 5.52; Cl, 12.90; N, 7.60; S, 5.83.

Example 119

(3RS)-3-[(6-Chloronaphthalen-2-yl)sulfonamido]-1-[4-(pyridin-4-yl)benzoyl]pyrrolidine hydrochloride In saturated ethanol hydrochloride, (3RS)-1-tert-butoxycarbonyl-3-[(6-chloronaphthalen-2-yl)sulfonamido] pyrrolidine was dissolved, followed by stirring at room temperature for 8 hours. The solvent was then distilled off under reduced pressure. In a similar manner to Example 4 except for the use of the resulting residue and 4-(4-pyridyl) benzoic acid as the raw materials, the reaction was conducted, whereby the title compound was obtained.

$^1$H-NMR (DMSO-$d_6$) δ: 1.70–2.10(2H,m), 3.00–3.65 (4H,m), 3.75–3.90(1H,m), 7.50–8.40(13H,m), 8.95–9.05 (2H,m).

MS (FAB) m/z: 492 [(M+H)$^+$, Cl$^{35}$], 494 [(M+H)$^+$, Cl$^{37}$].

Elementary analysis for $C_{26}H_{22}ClN_3O_3S.HCl.1.8H_2O$

Calculated: C, 55.68; H, 4.78; N, 7.49; Cl, 12.64; S, 5.72.

Found: C, 55.62; H, 4.94; N, 7.67; Cl, 12.76; S, 5.79.

Example 120

(3RS)-1-[(6-Chloronaphthalen-2-yl)sulfonyl]-3-[4-(pyridin-4-yl)benzamido]pyrrolidine hydrochloride In saturated ethanol hydrochloride, (3RS)-1-tert-butoxycarbonyl-3-[4-(4-pyridyl)benzamido]pyrrolidine was dissolved, followed by stirring at room temperature for 4 hours. The solvent was then distilled off under reduced pressure. In a similar manner to Referential Example 1 except for the use of the resulting residue and 6-chloro-2-naphthylsulfonyl chloride as the raw materials, the reaction was conducted, whereby the title compound was obtained.

$^1$H-NMR (DMSO-$d_6$) δ: 1.90–2.10(2H,m), 3.00–3.60 (4H,m), 4.15–4.25(1H,m), 7.57(1H,dd,J=8.8,2.0 Hz), 7.73 (2H,d,J=8.8 Hz), 7.85(1H,dd,J=8.8,2.0 Hz), 7.90(2H,d,J= 8.8 Hz), 7.95–8.05(2H,m), 8.18(1H,d,J=8.8 Hz), 8.30–8.40 (3H,m), 8.50(1H,s), 8.98(2H,d,J=6.4 Hz).

MS (FAB) m/z: 492 [(M+H)$^+$, Cl$^{35}$], 494 [(M+H)$^+$, Cl$^{37}$].

Elementary analysis for $C_{26}H_{22}ClN_3O_3S.0.8HCl.0.8H_2O$

Calculated: C, 58.31; H, 4.59; N, 7.85; Cl, 11.92; S, 5.99.

Found: C, 58.27; H, 4.68; N, 7.80; Cl, 11.94; S, 6.04.

Example 121

1-[[(E)-2-(6-Chloropyridin-3-yl)ethylene]sulfonyl]-4-[4-(pyridin-4-yl)benzoyl]piperazine In a similar manner to Example 7 except for the use of 1-tert-butoxycarbonyl-4-[[(E)-2-(6-chloropyridin-3-yl) ethylene]sulfonyl]piperazine as the raw material, the tert-butoxycarbonyl group was removed. The residue was subjected to the reaction as in Referential Example 116, whereby the title compound was obtained.

$^1$H-NMR (DMSO-$d_6$) δ: 3.10–3.31(4H,br), 3.40–3.84 (4H,br), 7.50(1H,d,J=15.9 Hz), 7.52(1H,d,J=15.9 Hz), 7.46 (3H,d,J=8.3 Hz), 8.06(2H,d,J=8.3 Hz), 8.28–8.33(3H,m), 8.79(1H,d,J=2.0 Hz), 8.94(2H,d,J=6.4 Hz).

MS (FAB) m/z: 469 [(M+H)$^+$, Cl$^{35}$], 471 [(M+H)$^+$, Cl$^{37}$].

Elementary analysis for $C_{23}H_{21}ClN_4O_3S.HCl.0.4H_2O$

Calculated: C, 53.89; H, 4.48; N, 10.93; Cl, 13.83; S, 6.26.

Found: C, 53.95; H, 4.47; N, 11.02; Cl, 13.91; S, 6.39.

Example 122

1-[(6-Chloronaphthalen-2-yl)sulfonyl]-4-[2-methyl-4-(pyridin-4-yl)benzoyl]piperazine hydrochloride In a similar manner to Referential Example 7 except for the use of 1-(4-bromo-2-methylbenzoyl)-4-[(6-chloronaphthalen-2-yl)sulfonyl]piperazine as the raw material, the reaction was conducted, whereby the title compound was obtained.

$^1$H-NMR (DMSO-$d_6$) δ: 2.20(3H,s), 2.80–4.00(8H,m), 7.36(1H,d,J=8.3 Hz), 7.73(1H,dd,J=8.8,2.4 Hz), 7.75–7.85 (2H,m), 7.88(1H,s), 8.18(1H,d,J=8.8 Hz), 8.20–8.30(4H,m), 8.50(1H,br s), 8.90(2H,d,J=6.8 Hz).

MS (FAB) m/z: 506 [(M+H)$^+$, Cl$^{35}$], 508 [(M+H)$^+$, Cl$^{37}$].

Example 123

4-[4-[[4-[(6-Chloronaphthalen-2-yl)sulfonyl] piperazin-1-yl]carbonyl]-3-methylphenyl]pyridine N-oxide In a similar manner to Example 6 except for the use of 1-[(6-chloronaphthalen-2-yl)sulfonyl]-4-[2-methyl-4-(pyridin-4-yl)benzoyl]piperazine as the raw material, the reaction was conducted, whereby the title compound was obtained.

$^1$H-NMR (CDCl$_3$) δ: 2.27(3H,s), 2.80–4.20(8H,m), 7.16 (1H,d,J=8.3 Hz), 7.38(1H,J=8.3 Hz), 7.41(1H,br s), 7.48 (2H,d,J=6.8 Hz), 7.61(1H,dd,J=8.8,1.5 Hz), 7.75(1H,d,J= 8.8 Hz), 7.91–7.97(3H,m), 8.28(2H,d,J=6.8 Hz), 8.31(1H,br s).

MS (FAB) m/z: 522 [(M+H)$^+$, Cl$^{35}$], 524 [(M+H)$^+$, Cl$^{35}$].

Elementary analysis for $C_{27}H_{24}ClN_3O_4S.H_2O$

Calculated: C, 60.05; H, 4.85; Cl, 6.56; N, 7.78; S, 5.94.

Found: C, 59.98; H, 4.89; Cl, 6.51; N, 7.48; S, 5.92.

Example 124

1-[(6-Chloronaphthalen-2-yl)sulfonyl]-4-[3-methyl-4-(pyridin-4-yl)benzoyl]piperazine hydrochloride In a similar manner to Example 4 except for the use of 3-methyl-4-(4-pyridyl)benzoic acid hydrochloride as the raw material, the reaction was conducted, whereby the title compound was obtained.

$^1$H-NMR (DMSO-$d_6$) δ: 2.27(3H,s), 3.08(4H,br), 3.47 (2H,br), 3.72(2H,br), 7.26–7.37(3H,m), 7.73(1H,dd,J=8.8, 2.0 Hz), 7.83(1H,dd,J=8.8,2.0 Hz), 7.86(2H,d,J=6.8 Hz), 8.18(1H,d,J=8.8 Hz), 8.25–8.29(2H,m), 8.50(1H,br s), 8.87 (2H,d,J=6.8 Hz).

MS (FAB) m/z: 506 [(M+H)$^+$, Cl$^{35}$], 508 [(M+H)$^+$, Cl$^{35}$].

Elementary analysis for $C_{27}H_{24}ClN_3O_3S.0.9HCl.1.7H_2O$

Calculated: C, 56.95; H, 5.01; Cl, 11.83; N, 7.38; S, 5.63.

Found: C, 57.08; H, 5.04; Cl, 11.75; N, 7.37; S, 5.49.

Example 125

4-[4-[[4-[(6-Chloronaphthalen-2-yl)sulfonyl]-piperazin-1-yl]carbonyl]-2-methylphenyl]pyridine N-oxide In a similar manner to Example 6 except for the use of 1-[(6-chloronaphthalen-2-yl)sulfonyl]-4-[3-methyl-4-(pyridin-4-yl)benzoyl piperazine as the raw material, the reaction was conducted, whereby the title compound was obtained.

$^1$H-NMR (CDCl$_3$) δ: 2.28(3H,s), 3.13(4H,br), 3.63(2H, br), 3.86(2H,br), 7.15–7.28(5H,m), 7.60(1H,d,J=8.8 Hz), 7.76(1H,d,J=8.8 Hz), 7.90–7.96(3H,m), 8.26(2H,d,J=6.8 Hz), 8.31(1H,s).

MS (FAB) m/z: 522 [(M+H)$^+$, Cl$^{35}$], 524 [(M+H)$^+$, Cl$^{35}$].

Elementary analysis for $C_{27}H_{24}ClN_3O_4S.H_2O$

Calculated: C, 60.05; H, 4.85; Cl, 6.56; N, 7.78; S, 5.94.

Found: C, 59.71; H, 4.68; Cl, 6.87; N, 7.63; S, 5.91.

Example 126

1-[(6-Chloronaphthalen-2-yl)sulfonyl]-4-[4-(2-methylpyridin-4-yl)benzoyl]piperazine hydrochloride In a similar manner to Example 4 except for the use of 4-(2-methyl-4-pyridyl)benzoic acid hydrochloride as the raw material, the reaction was conducted, whereby the title compound was obtained.

$^1$H-NMR (DMSO-$d_6$) δ: 2.76(3H,s), 3.00–3.90(8H,m), 7.56(2H,d,J=8.3 Hz), 7.74(1H,dd,J=8.8,2.4 Hz), 7.83(1H, dd,J=8.8,2.0 Hz), 8.00(2H,d,J=8.3 Hz), 8.14(1H,d,J=6.4 Hz), 8.19(1H,d,J=8.8 Hz), 8.22–8.29(3H,m), 8.51(1H,br s), 8.80(1H,d,J=6.4 Hz).

MS (FAB) m/z: 506 [(M+H)$^+$, Cl$^{35}$], 508 [(M+H)$^+$, Cl$^{35}$].

Elementary analysis for $C_{27}H_{24}ClN_3O_3S.HCl.2H_2O$

Calculated: C, 56.06; H, 5.05; Cl, 12.26; N, 7.26; S, 5.54.

Found: C, 55.84; H, 5.03; Cl, 12.26; N, 6.87; S, 5.54.

Example 127

4-[4-[[4-[(6-Chloronaphthalen-2-yl)sulfonyl]-piperazin-1-yl]carbonyl]phenyl]-2-methylpyridine N-oxide In a similar manner to Example 6 except for the use of 1-[(6-chloronaphthalen-2-yl)sulfonyl]-4-[4-(2-methylpyridin-4-yl)benzoyl]piperazine as the raw material, the reaction was conducted, whereby the title compound was obtained.

$^1$H-NMR (CDCl$_3$) δ: 2.58(3H,s), 3.13(4H,br), 3.65(2H, br), 3.84(2H,br), 7.34(1H,dd,J=6.8,2.4 Hz), 7.41(2H,d,J=8.3 Hz), 7.45(1H,d,J=2.4 Hz), 7.56–7.62(3H,m), 7.76(1H,dd,J= 8.8,2.0 Hz), 7.91–7.96(3H,m), 8.28–8.32(2H,m).

MS (FAB) m/z: 522 [(M+H)$^+$, Cl$^{35}$], 524 [(M+H)$^+$, Cl$^{37}$].

Elementary analysis for $C_{27}H_{24}ClN_3O4S.H_2O.0.05CH_2Cl_2$

Calculated: C, 59.69; H, 4.83; Cl, 7.16; N, 7.72; S, 5.89.

Found: C, 59.47; H, 4.87; Cl, 6.98; N, 7.48; S, 6.10.

Example 128

4-[4-[[4-[(6-Chloronaphthalen-2-yl)sulfonyl]-2-[[2-(morpholin-4-yl)ethylamino]carbonyl]piperazin-1-yl]carbonyl]phenyl]pyridine N-oxide In a similar manner to Example 4 except for the use of 4-[4-[[2-carboxy-4-[(6-chloronaphthalen-2-yl)sulfonyl] piperazin-1-yl]carbonyl]phenyl]pyridine N-oxide and 4-(2-aminoethyl)morpholine as the raw materials, the reaction was conducted, whereby the title compound was obtained.

$^1$H-NMR (CDCl$_3$) δ: 2.22(4H,s), 2.35–2.80(6H,br), 3.20–3.90(3H,br), 3.74(4H,s), 4.20–4.60(1H,br), 5.25–5.50

(1H,br), 6.80–7.20(1H,br), 7.45–7.70(7H,m), 7.76(1H,d,J= 8.8 Hz), 7.85–7.95(3H,m), 8.26(2H,d,J=6.9 Hz), 8.32(1H,s).

MS (FAB) m/z: 664 [(M+H)$^+$, Cl$^{35}$], 666 [(M+H)$^+$, Cl$^{37}$].

Example 129

4-[4-[[4-[(6-Chloronaphthalen-2-yl)sulfonyl]-2-[[2-(dimethylamino)ethylamino]carbonyl]piperazin-1-yl]carbonyl]phenyl]pyridine N-oxide In a similar manner to Example 4 except for the use of 4-[4-[[2-carboxy-4-[(6-chloronaphthalen-2-yl)sulfonyl]piperazin-1-yl]carbonyl]phenyl]pyridine N-oxide and 2-(dimethylamino)ethylamine as the raw materials, the reaction was conducted, whereby the title compound was obtained.

$^1$H-NMR (CDCl$_3$) δ: 2.29(6H,s), 2.35–2.75(6H,br), 3.35–3.90(3H,br), 4.40–4.60(1H,br), 5.25–5.50(1H,br), 7.00–7.20(1H,br), 7.45–7.65(7H,m), 7.77(1H,dd,J=8.8,1.4 Hz), 7.85–7.95(3H,m), 8.26(2H,d,J=7.3 Hz), 8.34(1H,s).

MS (FAB) m/z: 622 [(M+H)$^+$, Cl$^{35}$], 624 [(M+H)$^+$, Cl$^{37}$].

Elementary analysis for $C_{31}H_{32}N_5O_5S.0.05CH_2Cl_2.2H_2O$

Calculated: C, 56.30; H, 5.49; N, 10.57; Cl, 5.89; S, 4.84.

Found: C, 56.27; H, 5.37; N, 10.39; Cl, 6.01; S, 4.91.

Example 130

4-[(6-Chloronaphthalen-2-yl)sulfonyl]-2-methoxycarbonylmethyl-1-[4-(pyridin-2-yl)benzoyl]piperazine In a similar manner to Referential Example 116 except for the use of 1-[(6-chloronaphthalen-2-yl)sulfonyl]-3-methoxycarbonylmethylpiperazine and 4-(2-pyridyl)benzoic acid hydrochloride as the raw materials, the reaction was conducted, whereby the title compound was obtained.

$^1$H-NMR (DMSO-d$_6$) δ: 2.30–4.50(11H,m), 5.06(1H,br s), 7.30–7.50(3H,m), 7.72(1H,dd,J=8.8,2.0 Hz), 7.80–7.85 (1H,m), 7.85–7.95(1H,m), 7.98(1H,d,J=7.8 Hz), 8.10(2H,d, J=8.3 Hz), 8.18(1H,d,J=8.8 Hz), 8.25–8.30(2H,m), 8.51(1H, s), 8.65–8.70(1H,m).

MS (FAB) m/z: 564 [(M+H)$^+$, Cl$^{35}$], 566 [(M+H)$^+$, Cl$^{37}$].

Elementary analysis for $C_{29}H_{26}ClN_3O_5S.1.1H_2O$

Calculated: C, 59.66; H, 4.87; N, 7.20; Cl, 6.07; S, 5.49.

Found: C, 59.53; H, 4.61; N, 7.05; Cl, 6.33; S, 5.70.

Example 131

4-[(6-Chloronaphthalen-2-yl)sulfonyl]-2-carboxymethyl-1-[4-(pyridin-2-yl)benzoyl]piperazine hydrochloride In a similar manner to Referential Example 3 except for the use of 4-[(6-chloronaphthalen-2-yl)sulfonyl]-2-methoxycarbonylmethyl-1-[4-(pyridin-2-yl)benzoyl]piperazine as the raw material, the reaction was conducted, whereby the title compound was obtained.

$^1$H-NMR (DMSO-d$_6$) δ: 2.30–4.50(8H,m), 5.05(1H,br s), 7.35–7.40(1H,m), 7.43(2H,d,J=8.8 Hz), 7.72(1H,d,J=8.3 Hz), 7.81(1H,d,J=8.8 Hz), 7.85–7.90(1H,m), 7.97(1H,d,J= 7.8 Hz), 8.08(2H,d,J=8.8 Hz), 8.17(1H,d,J=8.8 Hz), 8.25–8.30(2H,m), 8.49(1H,s), 8.65–8.70(1H,m).

MS (FAB) m/z: 550 [(M+H)$^+$, Cl$^{35}$], 552 [(M+H)$^+$, Cl$^{37}$].

Elementary analysis for $C_{28}H_{24}ClN_3O_5S.0.4HCl.0.9H_2O$

Calculated: C, 57.90; H, 4.55; N, 7.23; Cl, 8.55; S, 5.52.

Found: C, 57.76; H, 4.26; N, 7.02; Cl, 8.44; S, 5.27.

Example 132

2-Carbamoylmethyl-4-[(6-chloronaphthalen-2-yl)sulfonyl]-1-[4-(pyridin-2-yl)benzoyl]piperazine hydrochloride In a similar manner to Referential Example 35 except for the use of 4-[(6-chloronaphthalen-2-yl)sulfonyl]-2-carboxymethyl-1-[4-(pyridin-2-yl)benzoyl]piperazine as the raw material, the reaction was conducted, whereby the title compound was obtained.

$^1$H-NMR (DMSO-d$_6$) δ: 2.20–4.50(8H,m), 5.10(1H,br s), 6.96(2H,br s), 7.45–7.55(3H,m), 7.70–7.85(3H,m), 8.05–8.35(6H,m), 8.50(1H,s), 8.81(1H,d,J=4.9 Hz).

MS (FAB) m/z: 549 [(M+H)$^+$, Cl$^{35}$], 551 [(M+H)$^+$, Cl$^{37}$].

Elementary analysis for $C_{28}H_{25}ClN_4O_4S.1.3HCl.1.5H_2O$

Calculated: C, 53.94; H, 4.74; N, 8.99; Cl, 13.08; S, 5.14.

Found: C, 53.85; H, 4.87; N, 8.80; Cl, 13.19; S, 5.27.

Example 133

1-[(Z)-4-Chloro-β-(2-hydroxyethan-1-yl)-β-styrylsulfonyl]-4-[4-(pyridin-2-yl)benzoyl]piperazine hydrochloride Under ice cooling, 4-tert-butoxycarbonyl-1-[(Z)-4-chloro-β-[2-(methoxymethyloxy)ethyl]-β-styrylsulfonyl]piperazine (355 mg) was dissolved in ethanol (3 ml), followed by the addition of saturated ethanol hydrochloride (6 ml). The resulting mixture was stirred at room temperature for 1 hour. After the reaction mixture was concentrated under reduced pressure, the residue was provided for the similar reaction as in Example 4, whereby the title compound (285 mg, 65%) was obtained.

$^1$H-NMR (DMSO-d$_6$) δ: 2.58(2H,t,J=6.6 Hz), 3.06(4H,br s), 3.15–3.60(4H,br), 3.68(2H,t,J=6.6 Hz), 7.24(1H,s), 7.38 (2H,d,J=8.6 Hz), 7.40(2H,d,J=8.6 Hz), 7.47–7.57(3H,m), 8.02–8.10(2H,m), 8.14(2H,d,J=8.3 Hz), 8.74(1H,d,J=4.4 Hz).

MS (FAB) m/z: 512 (M+H)$^+$.

Example 134

1-[(E)-4-chloro-β-(2-hydroxyethan-1-yl)-β-styrylsulfonyl]-4-[4-(pyridin-2-yl)benzoyl]piperazine hydrochloride In a similar manner to Example 133 except for the use of 4-tert-butoxycarbonyl-1-[(E)-4-chloro-β-[2-(methoxymethyloxy)ethyl]-β-styrylsulfonyl]piperazine as the raw material, the title compound was obtained.

$^1$H-NMR (DMSO-d$_6$) δ: 2.74(2H,t,J=7.3 Hz), 3.27(4H,br s), 3.37–3.85(6H,m), 7.45(1H,s), 7.50–7.60(5H,m), 7.68 (2H,d,J=8.3 Hz), 8.06–8.17(4H,m), 8.75(1H,d,J=4.9 Hz).

MS (FAB) m/z: 512 (M+H)$^+$.

Elementary analysis for $C_{26}H_{26}ClN_3O_4S.1.1HCl.0.8H_2O$

Calculated: C, 55.12; H, 5.11; N, 7.42; Cl, 13.14; S, 5.66.

Found: C, 55.22; H, 5.21; N, 7.20; Cl, 12.97; S, 5.66.

Test 1

Measurement of Ki Value Against FXa

In a 96-well microtiter plate, 5 μl of a sample solution, 5 μl of purified water, 40 μl of a 100 mM tris –200 mM sodium chloride −0.2% BSA (pH: 7.4) buffer and 10 μl of 0.05 U/ml human FXa (product of Enzyme Research, dissolved in and diluted with a measuring buffer) were poured, followed by the addition of 40 μl of S2222 (product of Chromogenix, final concentration: 75, 150, 300 and 600 μM). An increase in the absorbance at 405 nm was measured at room temperature for 15 minutes. From a reciprocal of the reaction rate and concentration of the inhibitor, four primary regression equations (Y=aX+b) were found (Dixon Plot). The median of six values available by solving simultaneous equations was designated as a Ki value.

The Ki values of the compounds obtained in Examples 91 and 93 against FXa were 6.6 nM and 10.9 nM, respectively.

Test 2

Measurement of Ki Value Against Thrombin

In a 96-well microtiter plate, 5 μl of a sample solution, 5 μl of purified water, 40 μl of a 100 mM tris −200 mM sodium chloride −0.2% BSA (pH: 7.4) buffer and 10 μl of 5 U/ml human thrombin (product of Sigma Chemical, dissolved in and diluted with a measuring buffer) were poured in portions, followed by the addition of 40 μl of S2226 (product of Chromogenix, final concentration: 50, 100, 200 and 400 μM). An increase in the absorbance at 405 nm was measured at room temperature for 15 minutes. From a reciprocal of the reaction rate and concentration of the inhibitor, four primary regression equations (Y=aX+b) were found (Dixon Plot). The median of six values available by solving simultaneous equations was designated as a Ki value.

The Ki values of the compounds obtained in Examples 91 and 93 against thrombin were 0.4 μM and 3.3 μM, respectively.

Test 3

Measurement of FXa Inhibitory Action ($IC_{50}$)

1) Reaction Rate Method

In a 96-well microtiter plate, 10 μl of a sample solution, 40 μl of a 100 mM tris −200 mM sodium chloride −0.2% BSA (pH: 7.4) buffer and 10 μl of 0.05 U/ml human FXa ("Cosmobio-ERL HFXa-1011", dissolved in and diluted with a measuring buffer) were poured in portions, followed by the addition of 40 ml of S2222 (product of Chromogenix). An increase (mOD/min) in the absorbance at 405 nm was measured at room temperature. From the below-described equation, an inhibitory ratio % of each sample was determined. On a logarithmic probability paper, the final concentration of the sample and inhibitory ratio % were plotted along the abscissa and the ordinate, respectively, whereby a 50% inhibitory concentration ($IC_{50}$) was determined.

Inhibitory ratio (%)=(1−OD of sample÷OD of control)×100

The compound of Example 92 showed a FXa 50% inhibitory concentration of 7.8 nM.

2) End Point Method

A sample solution (100 μl), 280 μl of a 100 mM tris −200 mM sodium chloride (pH 7.4) buffer and 100 μl of a 1 mM S2222 (Chromogenix Corp.) solution were mixed and heated at 37° C. To the resulting mixture, 20 μl of 0.625 U/ml human FXa ("Cosmobio-ERL HFXa-1011", dissolved in and diluted with a measuring buffer) were added, followed by heating at 37° C. for 15 minutes. To the resulting mixture, 100 μl of 1M citric acid were added and then, the absorbance at 405 nm was measured. The mixture to which only the diluting solvent for the sample was added instead of the sample was used as a blank, while the mixture to which 1M citric acid was added prior to the addition of FXa was used as a control. The concentration of the sample ($IC_{50}$) at which 50% of FXa activity was inhibited was determined and it was designated as an index of FXa inhibitory action.

The compounds of Example 6 and 19 exhibited a FXa 50% inhibitory concentration of 125 nM and 72 nM, respectively.

Test 4

Measurement of Thrombin Inhibitory Action ($IC_{50}$)

1) Reaction rate method

In a 96-well microtiter plate, 10 μl of a sample solution, 40 μl of a 100 mM tris −200 mM sodium chloride −0.2% BSA (pH: 7.4) buffer and 10 μl of 4 U/ml human thrombin (Sigma Chemical, dissolved in and diluted with a measuring buffer) were poured, followed by the addition of 40 μl of 500 μM S2266 (product of Chromogenix). An increase (mOD/min) in the absorbance at 405 nm was measured at room temperature. From the below-described equation, an inhibitory ratio % of each sample was determined. On a logarithmic probability paper, the final concentration of the sample and inhibitory ratio were plotted along the abscissa and the ordinate, respectively, whereby a 50% inhibitory concentration ($IC_{50}$) was found.

Inhibitory ratio (%)=(1−OD of sample÷OD of control)×100

The compound of Example 19 showed a thrombin 50% inhibitory concentration of 1.9 μM.

2) End Point Method

A sample solution (100 μl), 280 μl of a 100 mM tris −200 mM sodium chloride (pH 7.4) buffer and 100 μl of 1 mM S2238 (Chromogenix) solution were mixed and heated at 37° C. To the resulting mixture, 20 μl of 1 U/ml human thrombin (Sigma Chemical, dissolved in and diluted with a measuring buffer) were added, followed by heating at 37° C. for 10 minutes. To the resulting mixture, 100 μl of 1M citric acid were added and then, the absorbance at 405 nm was measured. The mixture to which only the diluting solvent was added instead of the sample was used as a blank, while the mixture to which 1M citric acid was added prior to the addition of thrombin was used as a control. The sample concentration ($IC_{50}$) at which 50% of thrombin activity was inhibited was found and it was designated as an index of thrombin inhibitory action.

The compound of Example 92 exhibited a thrombin 50% inhibitory concentration not less than 200 μM.

Test 5

Measurement of Coagulation Extending Action (Measurement of Prothrombin Time)

Plasma (20 μl) and 20 μl of a sample solution were mixed. To the resulting mixture, 40 ml of cynplastin (product of Organon Teknika) were added and the coagulation time was measured. The concentration of the sample (CT2) at which the coagulation time of the plasma was increased twice was found and it was designated as an index of anticoagulant action.

The compound of Example 92 showed CT2 of 0.35 μM.

Test 6

Test of Oral Administration

1) Method

A sample was dissolved or suspended in a 0.5% (w/v) methyl cellulose solution and the resulting solution or suspension was orally administered (10 ml/kg) to a 8 to 11 week-old rat (Wistar male rat (Nippon SLC Co., Ltd.)) which had been fasted overnight. After administration of the sample, the blood to which 1/10 part by weight of 3.13% (w/v) sodium citrate had been added was collected from the cervical vein. The rat was awakened except during the blood collection. Feeding was re-started 6 hours after the blood collection. From each blood sample, the plasma was separated by centrifugal separation and anti-FXa activity in the blood and prothrombin time extending action were measured.

2) Measuring Method 2-1) Measurement of Anti-FXa Activity in the Plasma

In a 96-well plate, 5 µl of the plasma was poured in portions, followed by the addition of 55 µl of a 8:1:2 mixture of 100 mM tris –200 mM sodium chloride –0.2% BSA (pH 7.4) buffer, water and 0.1 U/ml human Factor Xa solution (dissolved in and diluted with a measuring buffer) and 40 µl of 750 µM S-2222. After stirring for 10 seconds in a plate mixer, an increase (mOD/min) of the absorbance at 405 nm was measured at room temperature. The inhibitory ratio was calculated as follows:

An inhibitory ratio (%)=(1–OD of sample÷OD of control on average relative to blood-collecting time of sample)×100

2-2) Measurement of Coagulation Extending Action in Oral Administration (Measurement of Prothrombin Time)

To 20 µl of the plasma, 40 µl of cynplastin (Organon Teknika/USA) were added and the coagulation time was measured. The ratio of the prothrombin time after the administration of the sample relative to the prothrombin time before the administration of the sample was designated as an index of the coagulation extending action.

3) Result

The compound of Example 110 showed an anti-FXa activity of 70% in the plasma one hour after the administration of 30 mg/kg of the sample. It extended the prothrombin time by 1.18 times.

Test 7

Testing Method of Anti-thrombus Effects in a Tissue Thromboplastin-derived Rat DIC Model A rat was anesthetized with halothane. After the collection of the blood (for measurement of the number of platelets, anti-FXa activity and TAT) from its cervical vein by using 1/10 part by weight of 3.13% (w/v) sodium citrate, the sample was administered orally. At an appropriate time after the administration, the rat was intraperioneally anesthetized (1 mg/kg) with Nembutal (50 mg/ml pentobarbital sodium, Abott Laboratories), followed by intravenous drip of 0.2 U/ml of tissue thromboplastin (Thromboplastin C plus, Dade Diagnostics of P. R. Inc.,) from the femoral vein for one minute at a rate of 2.5 to 3.0 ml/kg/min. The blood was collected (for measuring the number of platelets and anti-FXa activity) from the cervical vein 10 minutes after the intravenous drip of the blood was collected (for measuring TAT) from the cervical vein 20 minutes after the blood collection. The number of platelets, anti-FXa activity in the plasma and TAT concentration of each blood sample were measured. The number of the platelets was measured by an automatic cytometer, while the anti-FXa activity in the plasma was measured in a similar manner to that described in Test 7.

For the measurement of TAT (Thrombin-anti Thrombin= complex), EnzygnostR TAT micro kit (Boering Verke) was employed.

As a result of the oral administration of 30 mg/kg of the compound of Example 95, apparent anti-FXa action in the plasma was recognized and a decrease in the number of the platelets and an increase in the TAT concentration were suppressed (the tissue thromboplastin was administered one hour after the administration of the sample).

Capability of Exploitation in Industry

The sulfonyl derivative according to the present invention exhibits anticoagulant action based on excellent FXa inhibitory action so that without acting on a platelet, it can treat or prevent various diseases caused by a thrombus or embolus such as cerebral infarction, cerebral embolism, myocardial infarction, pulmonary infarction, pulmonary embolism, Buerger's disease, deep vein thrombosis, disseminated intravascular coagulation syndrome, thrombus formation after valve replacement, reocclusion after revascularization, formation of a thrombus upon extracorporeal circulation or coagulation upon blood collection.

What is claimed is:

1. A sulfonyl compound represented by the following formula (I):

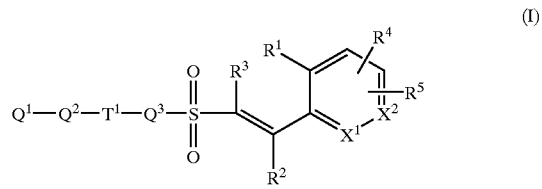

wherein $R^1$ represents a hydrogen atom, a hydroxyl group, a nitro group, a cyano group, a halogen atom, an alkyl group, a hydroxyalkyl group, an alkoxyl group, an alkoxyalkyl group, a carboxyl group, a carboxyalkyl group, an alkylcarbonyl group, an alkoxycarbonyl group, an alkoxycarbonylalkyl group, an alkylcarbonyloxy group or a group $A^1$-$B^1$— (in which $A^1$ represents an amino group which may have one or two substituents, a saturated or unsaturated 5- or 6-membered cyclic hydrocarbon group which may have a substituent or a saturated or unsaturated 5- or 6-membered heterocyclic group which may have a substituent and $B^1$ represents a single bond, a carbonyl group, an alkylene group, a carbonylalkyl group, a carbonylalkyloxy group or an alkylenecarbonyloxy group), $R^2$ and $R^3$ each independently represents a hydrogen atom, a halogen atom, an alkyl group, a hydroxyalkyl group or an alkoxyalkyl group or $R^2$ or $R^3$ may be coupled together with $R^1$ to form a $C_{1-3}$ alkylene or alkenylene group, $R^4$ and $R^5$ each independently represents a hydrogen atom, a hydroxyl group, a halogen atom, an alkyl group or an alkoxyl group (with the proviso that $R^4$ and $R^5$ do not represent a hydrogen atom at the same time), $Q^1$ represents a saturated or unsaturated bicyclic or tricyclic fused ring group which may have a substituent, $Q^2$ represents a single bond, an oxygen atom, a sulfur atom, a linear or branched $C_{1-6}$ alkylene group, a linear or branched $C_{2-6}$ alkenylene group, a linear or branched $C_{2-6}$ alkynylene group, a group —N($R^6$)—CO— (in which $R^6$ represents a hydrogen atom or an alkyl group), a group —N($R^7$)—(CH$_2$)m-(in which $R^7$ represents a hydrogen atom or an alkyl group and m stands for an integer of 0 to 6), $Q^3$ represents any one of the following groups:

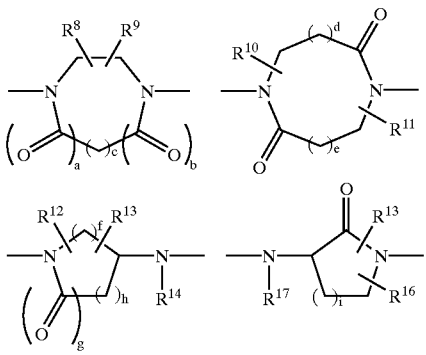

(in which when the carbon atom to which each of $R^8$, $R^9$, $R^{10}$, $R^{11}$, $R^{12}$, $R^{13}$, $R^{15}$ and $R^{16}$ is bonded is not adjacent to a nitrogen atom, $R^8$, $R^9$, $R^{10}$, $R^{11}$, $R^{12}$, $R^{13}$, $R^{15}$, and $R^{16}$ each independently represents:
a hydrogen atom,
a hydroxyl group,
an alkyl group,
an alkoxyl group,
an alkoxyalkyl group,
an alkoxyalkyloxy group,
a hydroxyalkyl group,
a hydroxyalkyloxy group,
a hydroxyalkylsulfonyl group,
a formyl group,
a formylalkyl group,
a formylalkylcarbonyl group,
a formylalkylsulfonyl group,
an alkylcarbonyl group,
an alkylsulfonyl group,
an alkylcarbonylalkyl group,
an alkylsulfonylalkyl group,
a carboxyl group,
a carboxyalkyl group,
a carboxyalkyloxy group,
a carboxyalkylcarbonyl group,
a carboxyalkylsulfonyl group,
a carboxyalkylcarbonylalkyl group,
a carboxyalkylsulfonylalkyl group,
an alkoxycarbonyl group,
an alkoxycarbonylalkyl group,
an alkoxycarbonylalkyloxy group,
an alkoxycarbonylalkylcarbonyl group,
an alkoxycarbonylalkylsulfonyl group,
an amino group which may have one or two substituents,
an aminoalkyl group in which the amino moiety may have one or two substituents,
an aminoalkyloxy group in which the amino moiety may have one or two substituents,
an aminoalkylcarbonyl group in which the amino moiety may have one or two substituents,
an aminoalkylcarbonyloxy group in which the amino moiety may have one or two substituents,
an aminocarbonyl group in which the amino moiety may have one or two substituents,
an aminocarbonylalkyl group in which the amino moiety may have one or two substituents,
an aminocarbonylalkyloxy group in which the amino moiety may have one or two substituents or
a group $A^2$-$B^2$— (in which $A^2$ represents a saturated or unsaturated 5- or 6-membered cyclic hydrocarbon group which may have a substituent or a saturated or unsaturated 5- or 6-membered heterocyclic group which may have a substituent and $B^2$ represents a single bond, a carbonyl group or an alkylene group), when the carbon atom to which each of $R^8$, $R^9$, $R^{10}$, $R^{11}$, $R^{12}$, $R^{13}$, $R^{15}$ and $R^{16}$ is bonded is adjacent to a nitrogen atom, $R^8$, $R^9$, $R^{10}$, $R^{11}$, $R^{12}$, $R^{13}$, $R^{15}$ and $R^{16}$ each independently represents:
a hydrogen atom,
an alkyl group,
a hydroxyalkyl group,
a hydroxyalkylcarbonyl group,
a hydroxyalkylsulfonyl group,
a formyl group,
a formylalkyl group,
a formylalkylcarbonyl group,
a formylalkylsulfonyl group,
an alkylcarbonyl group,
an alkylsulfonyl group,
an alkylcarbonylalkyl group,
an alkylsulfonylalkyl group,
a carboxyl group,
a carboxyalkyl group,
a carboxyalkylcarbonyl group,
a carboxyalkylsulfonyl group,
a carboxyalkylcarbonylalkyl group,
a carboxyalkylsulfonylalkyl group,
an alkoxyalkyl group,
an alkoxycarbonyl group,
an alkoxycarbonylalkyl group,
an alkoxycarbonylalkylcarbonyl group,
an alkoxycarbonylalkylsulfonyl group,
an aminoalkyl group in which the amino moiety may have one or two substituents,
an aminoalkylcarbonyl group in which the amino moiety may have one or two substituents, have one or two substituents,
an aminocarbonyl group in which the amino moiety may have one or two substituents,
an aminocarbonylalkyl group in which the amino moiety may have one or two substituents or
a group $A^3$-$B^3$— (in which $A^3$ represents a saturated or unsaturated 5- or 6-membered cyclic hydrocarbon group which may have a substituent or a saturated or unsaturated 5- or 6-membered heterocyclic group which may have a substituent and $B^3$ represents a single bond, a carbonyl group or an alkylene group), $R^8$ and $R^9$, $R^{10}$ and $R^{11}$, $R^{12}$ and $R^{13}$, and $R^{15}$ and $R^{16}$ may each be coupled together with a carbon atom which constitutes the ring and represent a saturated or unsaturated 5- to 7-membered cyclic hydrocarbon group which may have a substituent or a saturated or unsaturated 5- to 7-membered heterocyclic group which may have a substituent,
$R^{14}$ and $R^{17}$ each independently represents:
a hydrogen atom,
an alkyl group,
a hydroxyalkyl group,
a hydroxyalkylcarbonyl group;
a hydroxyalkylsulfonyl group,
an alkoxyl group,
an alkoxyalkyl group,
an alkoxyalkylcarbonyl group,
an alkoxyalkylsulfonyl group,
a formyl group,
a formylalkyl group,
a formylalkylcarbonyl group, a formylalkylsulfonyl group,
an alkylcarbonyl group,
an alkylcarbonylalkyl group,
an alkylsulfonyl group,
an alkylsulfonylalkyl group,
a carboxyalkyl group,
a carboxyalkylcarbonyl group,
a carboxyalkylsulfonyl group,
a carboxyalkylcarbonylalkyl group,
a carboxyalkylsulfonylalkyl group,
an alkoxycarbonyl group,
an alkoxycarbonylalkyl group,
an alkoxycarbonylalkylcarbonyl group,
an alkoxycarbonylalkylsulfonyl group,
an amino group which may have one or two substituents,
an aminoalkyl group in which the amino moiety may have one or two substituents,
an aminoalkyloxy group in which the amino moiety may have one or two substituents,
an aminoalkylcarbonyl group in which the amino moiety may have one or two substituents,
an aminoalkyloxycarbonyl group in which the amino moiety may have one or two substituents,
an aminocarbonyl group in which the amino moiety may have one or two substituents,
an aminocarbonylalkyl group in which the amino moiety may have one or two substituents, and
an aminocarbonyloxyalkyl group in which the amino moiety may have one or two substituents, $R^{14}$ and $R^{12}$ or $R^{13}$ may be coupled together with a carbon atom constituting a ring and with a nitrogen atom to which $R^{14}$ is bonded to form a saturated or unsaturated 5- to 7-membered heterocyclic group which may have a substituent, $R^{17}$ and $R^{15}$ or $R^{16}$ may be coupled together with a carbon atom constituting a ring and with a nitrogen atom to which $R^{17}$ is bonded to form a saturated or unsaturated 5- to 7-membered heterocyclic group which may have a substituent, and a, b, d, e and g each independently stands for an integer of 0 or 1, c stands for an integer of 0 to 3, f, h and i each independently represents an integer of 1 to 3, with the proviso that the sum of a, b and c stands for an integer of 2 or 3, the sum of d and e stands for an integer of 0 or 1 and the sum of f, g and h stands for an integer of 3 to 5), $T^1$ represents a carbonyl group, or a group —CH($R^{18}$)— (in which $R^{18}$ represents a hydrogen atom, an alkyl group, a hydroxyalkyl group, an alkoxyalkyl group, a carboxyalkyl group, an alkoxycarbonylalkyl group, an aryl group, an aralkyl group, a heteroaryl group, a heteroarylalkyl group or an aminoalkyl group in which the amino moiety may have a substituent), $X^1$ and $X^2$ each independently represents a methine group; salt thereof; or solvate thereof.

2. A sulfonyl compound according to claim 1, wherein the following group:

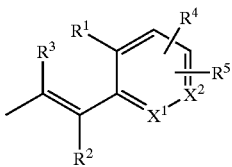

in the formula (I) is a group of the following formula:

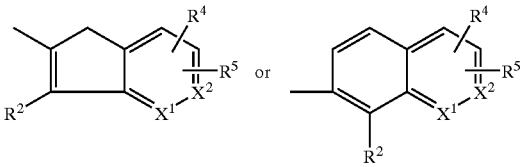

(wherein $R^2$, $R^4$, $R^5$, $X^1$ and $X^2$ have the same meanings as defined above); salt thereof; or solvate thereof.

3. A sulfonyl compound according to claim 1, wherein $R^4$ represents a halogen atom; salt thereof; or solvate thereof.

4. A sulfonyl compound according to claim 1, wherein $Q^1$ represents a tetrahydrothienopyridyl group which may have a substituent or a tetrahydrothiazolopyridyl group which may have a substituent; salt thereof; or solvate thereof.

5. A sulfonyl compound according to claim 1, wherein $Q^2$ represents a single bond; salt thereof; or solvate thereof.

6. A sulfonyl compound according to claim 1, wherein $Q^3$ represents a group of the following formula:

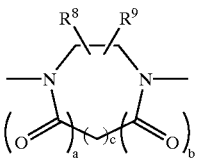

wherein $R^8$, $R^9$, a, b and c have the same meanings as defined above; salt thereof; or solvate thereof.

7. A sulfonyl compound according to claim 1, wherein $T^1$ represents a carbonyl group; salt thereof; or solvate thereof.

8. A pharmaceutical composition comprising a sulfonyl compound, salt thereof or solvate thereof as claimed in any one of claims 1 to 7; and a pharmaceutically acceptable carrier.

9. A method of inhibiting activated coagulation factor X comprising administering to a patient in need thereof a sulfonyl compound, salt thereof or solvate thereof as claimed in any one of claims 1 to 7.

10. A method of inhibiting coagulation comprising administering to a patient in need thereof a sulfonyl compound, salt thereof or solvate thereof as claimed in any one of claims 1 to 7.

11. A method for treating a disease caused by a thrombosis or embolism, which comprises administering, to a patient suffering from the disease, a sulfonyl compound, salt thereof or solvate thereof as claimed in any one of claims 1 to 7.

12. A method for treating cerebral infarction, cerebral embolism, myocardial infarction, pulmonary infarction, pulmonary embolism, Buerger's disease, deep vein thrombosis, disseminated intravascular coagulation syndrome, thrombus formation after valve replacement, reocclusion after revascularization, formation of thrombus upon extracorporeal circulation or coagulation upon blood collection, which comprises administering, to a patient therefrom, an effective amount of sulfonyl compound, salt thereof or solvate thereof as claimed in any one of claims 1 to 7.

* * * * *